(12) United States Patent
Gurney et al.

(10) Patent No.: US 10,112,997 B2
(45) Date of Patent: Oct. 30, 2018

(54) TIGHT-BINDING AGENTS AND USES THEREOF

(71) Applicant: OncoMed Pharmaceuticals, Inc., Redwood City, CA (US)

(72) Inventors: Austin L. Gurney, San Francisco, CA (US); Ming-Hong Xie, Foster City, CA (US)

(73) Assignee: ONCOMED PHARMACEUTICALS, INC., Redwood City, CA (US)

(*) Notice: Subject to any disclaimer, the term of this patent is extended or adjusted under 35 U.S.C. 154(b) by 237 days.

(21) Appl. No.: 15/167,166

(22) Filed: May 27, 2016

(65) Prior Publication Data

US 2016/0376365 A1 Dec. 29, 2016

Related U.S. Application Data

(60) Provisional application No. 62/167,582, filed on May 28, 2015, provisional application No. 62/205,279, filed on Aug. 14, 2015, provisional application No. 62/313,487, filed on Mar. 25, 2016.

(51) Int. Cl.
| | | |
|---|---|---|
| A61K 39/395 | (2006.01) | |
| C07K 16/28 | (2006.01) | |
| A61K 39/00 | (2006.01) | |

(52) U.S. Cl.
CPC .......... *C07K 16/2803* (2013.01); *C07K 16/28* (2013.01); *C07K 16/2818* (2013.01); *C07K 16/2827* (2013.01); *A61K 2039/505* (2013.01); *A61K 2039/507* (2013.01); *C07K 2317/24* (2013.01); *C07K 2317/41* (2013.01); *C07K 2317/732* (2013.01); *C07K 2317/76* (2013.01); *C07K 2317/92* (2013.01); *C07K 2317/94* (2013.01); *Y02A 50/466* (2018.01)

(58) Field of Classification Search
None
See application file for complete search history.

(56) References Cited

U.S. PATENT DOCUMENTS

| | | |
|---|---|---|
| 8,431,350 B2 | 4/2013 | Baldwin et al. |
| 9,499,596 B2 | 11/2016 | Clark et al. |
| 9,713,641 B2 | 7/2017 | Hicklin et al. |
| RE46,534 E | 9/2017 | Baldwin et al. |
| 9,856,318 B2 | 1/2018 | Eisenbach-Schwartz et al. |
| 9,873,740 B2 | 1/2018 | Grogan et al. |
| RE46,805 E | 4/2018 | Baldwin et al. |
| RE46,816 E | 5/2018 | Baldwin et al. |
| 2004/0185040 A1 | 9/2004 | Garcia-Martinez et al. |
| 2006/0105376 A1 | 5/2006 | Isogai et al. |
| 2007/0072797 A1 | 3/2007 | Robinson et al. |
| 2008/0038264 A1 | 2/2008 | Bodary et al. |
| 2008/0050809 A1 | 2/2008 | Abuin et al. |
| 2008/0064049 A1 | 3/2008 | Clarke |
| 2008/0178305 A1 | 7/2008 | Clarke et al. |
| 2009/0258013 A1 | 10/2009 | Clark et al. |
| 2012/0213774 A1 | 8/2012 | Fertig et al. |
| 2013/0251720 A1 | 9/2013 | Clark et al. |
| 2014/0271664 A1 | 9/2014 | Garcia-Martinez et al. |
| 2015/0152160 A1 | 6/2015 | Gao et al. |
| 2015/0216970 A1 | 8/2015 | Grogan et al. |
| 2015/0322119 A1 | 11/2015 | Engelhardt et al. |
| 2016/0000909 A1 | 1/2016 | Eisenbach-Schwartz et al. |
| 2016/0008463 A1 | 1/2016 | Eisenbach-Schwartz et al. |
| 2016/0152720 A1 | 6/2016 | Kim et al. |
| 2016/0176963 A1 | 6/2016 | Maurer et al. |
| 2016/0185863 A1 | 6/2016 | Gao et al. |
| 2016/0355589 A1 | 12/2016 | Williams et al. |
| 2017/0037133 A1 | 2/2017 | Fiedler et al. |
| 2017/0088613 A1 | 3/2017 | Grogan et al. |
| 2017/0107300 A1 | 4/2017 | Kuchroo et al. |
| 2017/0281764 A1 | 5/2017 | Tso et al. |
| 2017/0198042 A1 | 7/2017 | Williams et al. |
| 2017/0209574 A1 | 7/2017 | Cao |
| 2017/0260594 A1 | 9/2017 | Molinero et al. |
| 2017/0340733 A1 | 11/2017 | Cao |

FOREIGN PATENT DOCUMENTS

| | | |
|---|---|---|
| WO | WO 2006/124667 A2 | 11/2006 |
| WO | WO 2008/042236 A2 | 4/2008 |
| WO | WO 2011/100566 A2 | 8/2011 |
| WO | WO 2014/089113 A1 | 6/2014 |
| WO | WO 2014/089169 A2 | 6/2014 |
| WO | WO 2015/009856 A2 | 1/2015 |
| WO | WO 2015/143343 A2 | 9/2015 |
| WO | WO 2016/011264 A2 | 1/2016 |
| WO | WO 2016/028656 A1 | 2/2016 |
| WO | WO 2016/040892 A1 | 3/2016 |

(Continued)

OTHER PUBLICATIONS

White et al. (2001, Ann. Rev. Med., 2001, 52:125-145) (Year: 2001).*
Meibohm (Pharmacokinetics and Pharmacodynamics of Biotech Drugs, Wiley-VHC, 2006, chapter 3, p. 45-91) (Year: 2006).*
Chan, C.J., et al., "Receptors that interact with nectin and nectin-like proteins in the immunosurveillance and immunotherapy of cancer," *Current Opinion in Immunology* 24(2).246-251, Elsevier Ltd., England (2012).
Chauvin, J-M., et al., "TIGIT and PD-1 impair tumor antigen-specific CD8+T cells in melanoma patients," *The Journal of Clinical Investigation* 125(5):2046-2058, American Society for Clinical Investigation, United States (2015).
Johnston, R.J., et al., "The Immunoreceptor TIGIT Regulates Antitumor and Antiviral CD8+T cell Effector Function," *Cancer Cell* 26(6):923-937, Elsevier Inc., United States (2014).

(Continued)

*Primary Examiner* — Laura B Goddard
*Assistant Examiner* — Meera Natarajan
(74) *Attorney, Agent, or Firm* — Sterne, Kessler, Goldstein & Fox P.L.L.C.

(57) ABSTRACT

Agents that specifically bind TIGIT are disclosed. The TIGIT-binding agents may include polypeptides, antibodies, and/or bispecific agents. Also disclosed are methods of using the agents for enhancing the immune response and/or treatment of diseases such as cancer.

17 Claims, 31 Drawing Sheets

Specification includes a Sequence Listing.

(56) References Cited

FOREIGN PATENT DOCUMENTS

| WO | WO 2016/054555 A2 | 4/2016 |
|---|---|---|
| WO | WO 2016/100882 A1 | 6/2016 |
| WO | WO 2016/106302 A1 | 6/2016 |
| WO | WO 2016/109546 A2 | 7/2016 |
| WO | WO 2016/191643 A2 | 12/2016 |
| WO | WO 2016/191643 A3 | 12/2016 |
| WO | WO 2017/030823 A2 | 2/2017 |
| WO | WO 2017/037707 A1 | 3/2017 |
| WO | WO 2017/048824 A1 | 3/2017 |
| WO | WO 2018/102536 A1 | 6/2018 |

OTHER PUBLICATIONS

Johnston, R.J., et al., "The Immunoreceptor TIGIT Regulates Antitumor and Antiviral CD8+T cell Effector Function," *Cancer Cell* 26:S1-S20, Supplemental Data, Elsevier Inc., United States (2014).

Joller, N., et al., "Cutting Edge: TIGIT Has T Cell-Intrinsic Inhibitory Functions," *The Journal of Immunology* 186(3):1338-1342, The American Association of Immunologists, Inc., United States (2011).

Joller, N., et al., "Cutting Edge: TIGIT Has T Cell-Intrinsic Inhibitory Functions," *The Journal of Immunology* 186(3):1338-1342, Supplementary Figures 1-4 and Supplementary Tables 1-2, The American Association of Immunologists, Inc., United States (2011).

Lozano, E., et al., "The TIGIT/CD226 Axis Regulates Human T Cell Function," *The Journal of Immunology* 188(8):3869-3875, The American Association of Immunologists, Inc., United States (2012).

Yu, X., et al., "The surface protein TIGIT suppresses T cell activation by promoting the generation of mature immunoregulatory dendritic cells," *Nature Immunology* 10(1):48-57, Nature Publishing Group, England (2009).

Stanietsky, N., et al., "Mouse TIGIT inhibits NK-cell cytotoxicity upon interaction with PVR," *European Journal of Immunology* 43(8):2138-2150, Weinheim Wiley-VCH, Germany (2013).

Yu, X., et al., "The surface protein TIGIT suppresses T cell activation by promoting the generation of mature immunoregulatory dendritic cells," *Nature Immunology* 10(1):48-57, Supplementary Figures 1-7 and Supplementary Tables 1-3, Nature Publishing Group, England (2009).

Stanietsky, N., et al., "The interaction of TIGIT with PVR and PVRL2 inhibits human NK cell cytotoxicity," *Proc Natl Acad Sci USA* 106(42):17858-17863, National Academy of Sciences, United States (2009).

International Search Report and Written Opinion for International Application No. PCT/US16/34549, ISA/US, Alexandria, Virginia, dated Dec. 5, 2016, 16 pages.

Joller, N., et al., "Treg cells expressing the coinhibitory molecule TIGIT selectively inhibit proinflammatory Th1 and Th17 cell responses," *Immunity* 40(4)569-581, Elsevier Inc., United States (2014).

UniProtKB, "TIGIT_Mouse," Accession No. P86176, accessed at http://www.uniprot.org/uniprot/P86176, accessed on Sep. at 5, 2016, 8 pages.

UniProtKB, "TIGHT_Human" Accession No. Q495A1, accessed at http://www.uniprot.org/uniprot/O495A1, accessed on Sep. 5, 2016, 12 pages.

Stengel, K.F., et al., "Structure of TIGIT immunoreceptor bound to poliovirus receptor reveals a cell-cell adhesion and signaling mechanism that requires *cis-trans* receptor clustering." *Proceedings of the National Academy of Sciences* 109(14):5399-5404, National Academy of Sciences, United States (2012).

International Preliminary Report on Patentability and Written Opinion for International Application No. PCT/US2016/034549, The International Bureau of WIPO, dated Nov. 28, 2017, 8 pages.

International Search Report for International Application PCT/US2017/063918, International Search Report, dated Mar. 7, 2018, 4 pages.

Pauken, K.E., et al., "TIGIT and CD226: Tipping the Balance between Costimulatory and Coinhibitoly Molecules to Augment the Cancer Immunotherapy Toolkit" *Cancer Cell* 26(6):785-787, Cell Press, United States (2014).

\* cited by examiner

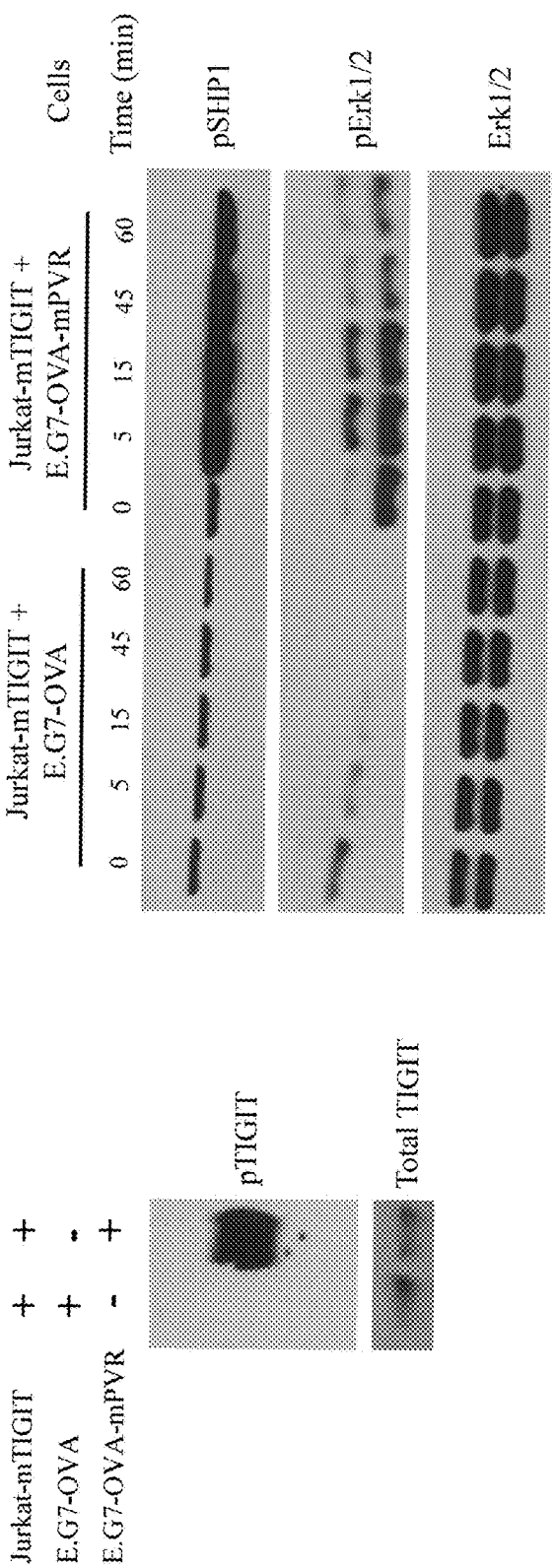

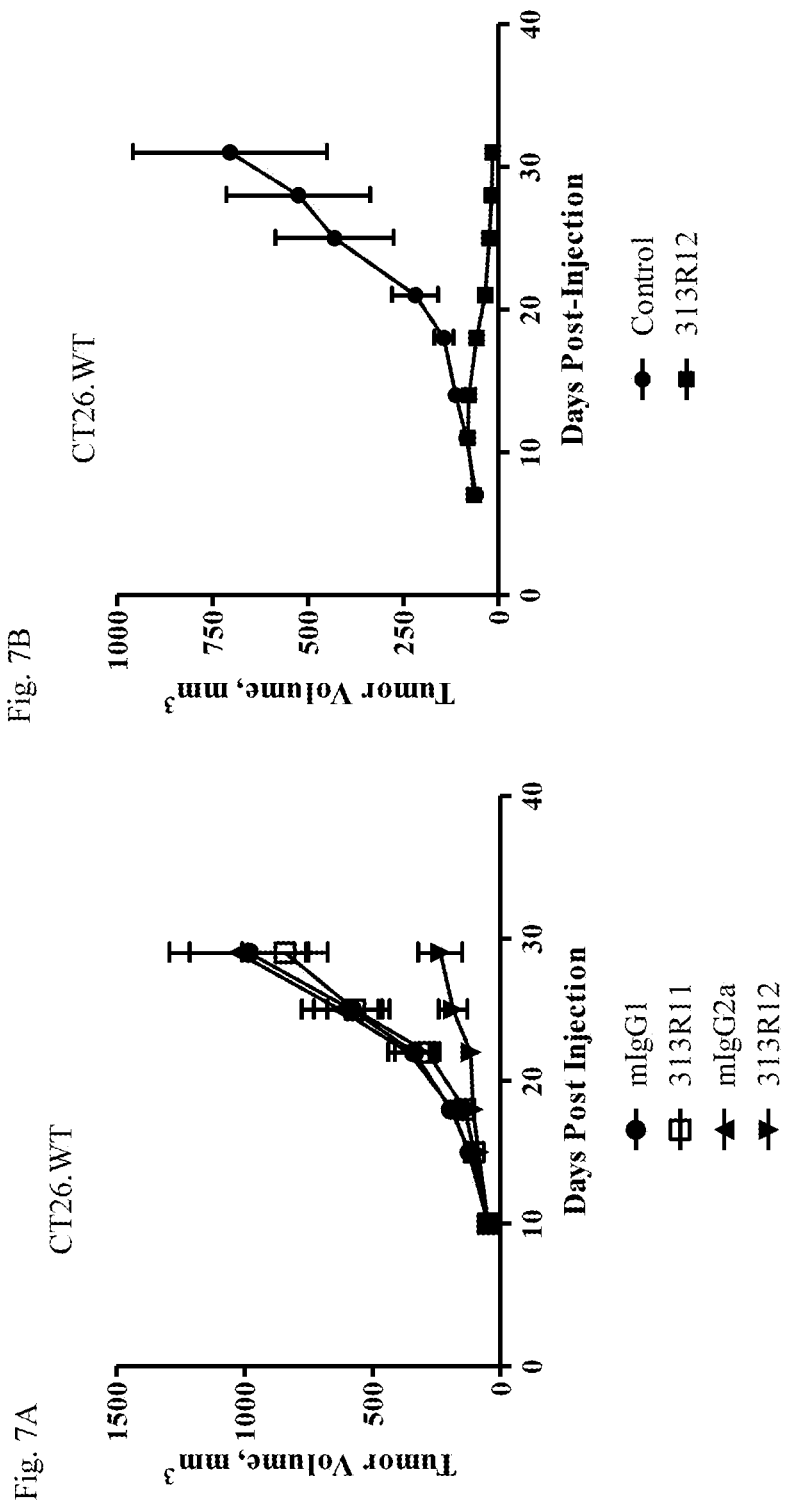

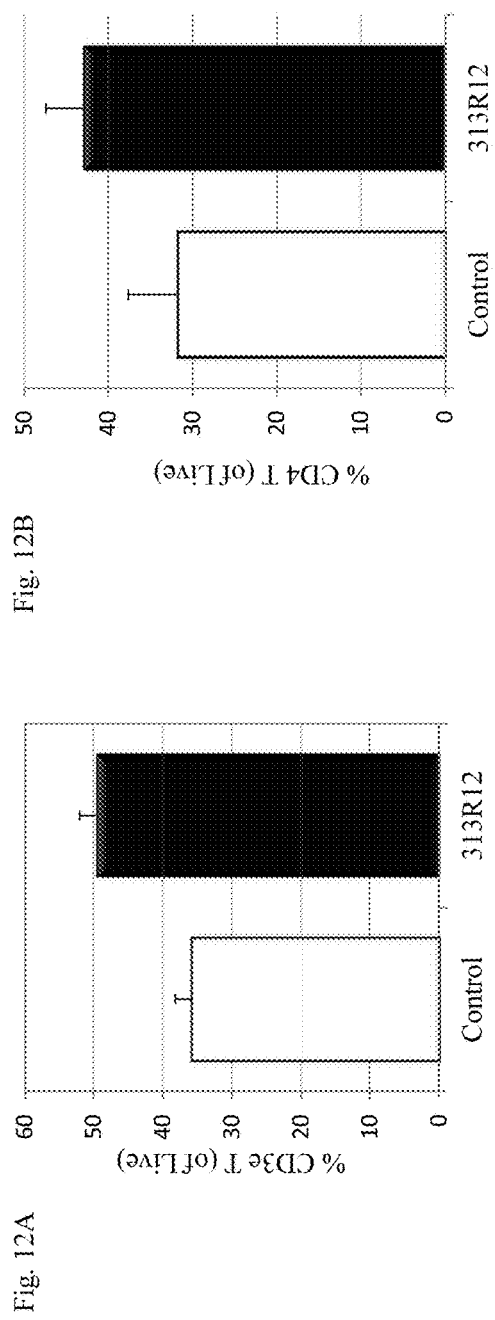
Fig. 12B
Fig. 12A
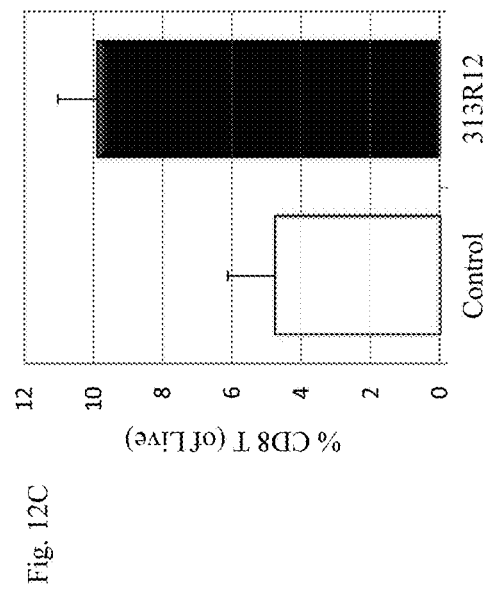
Fig. 12C

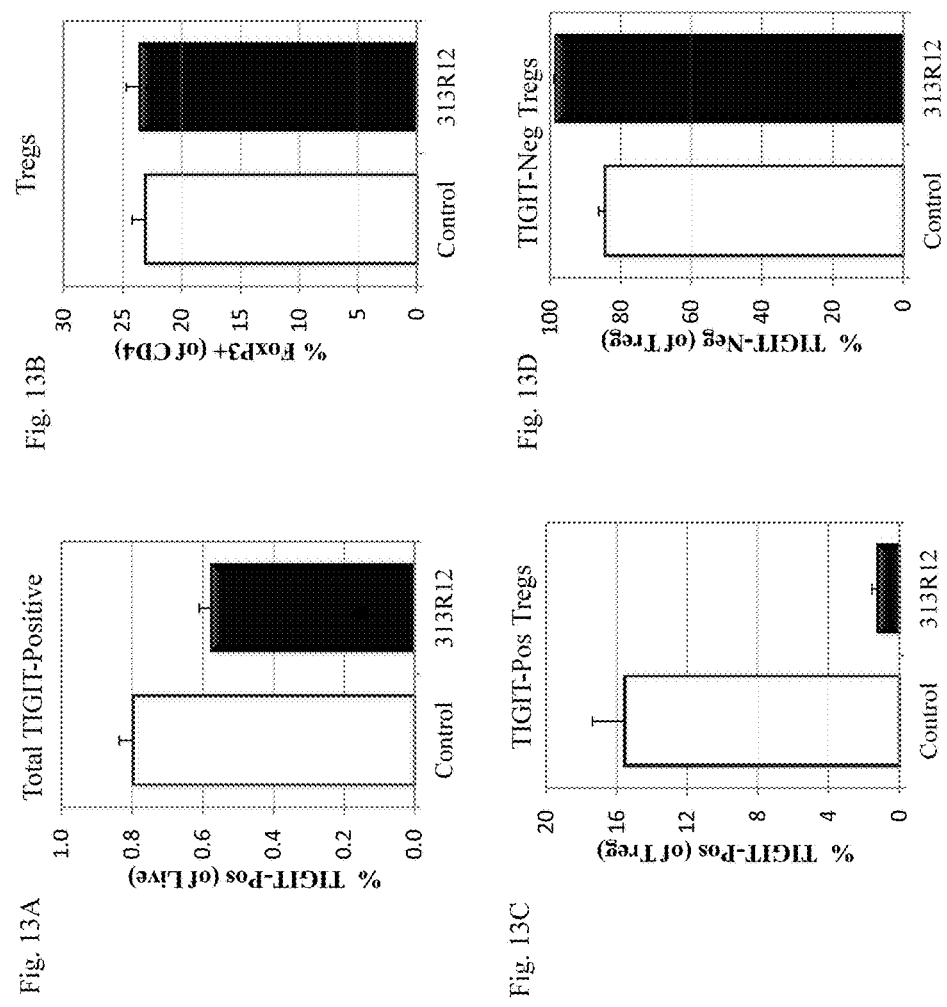

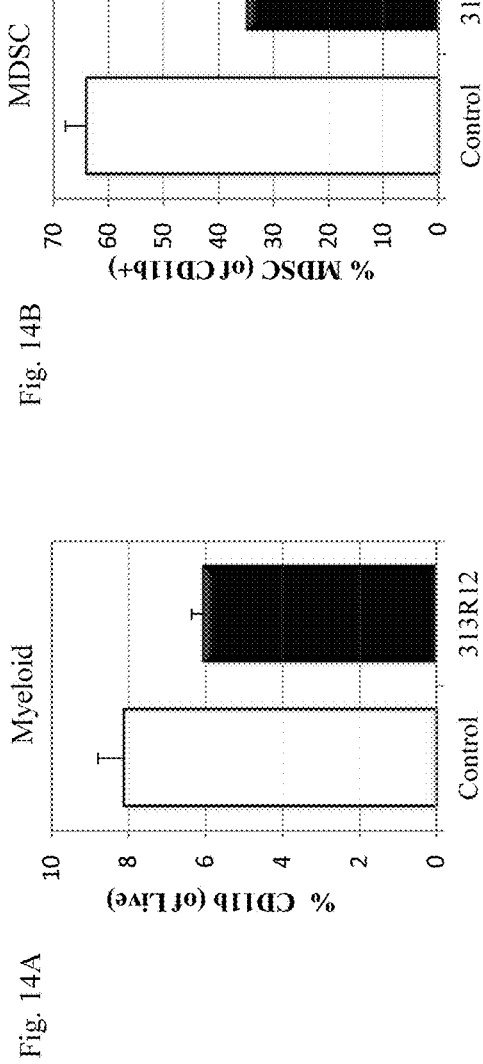
Fig. 14A
Fig. 14B
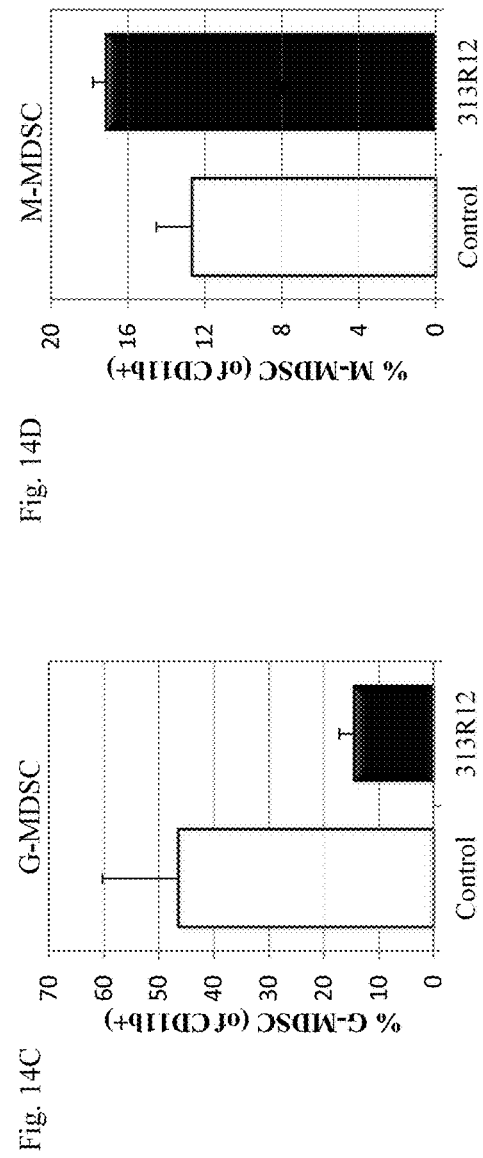
Fig. 14C
Fig. 14D

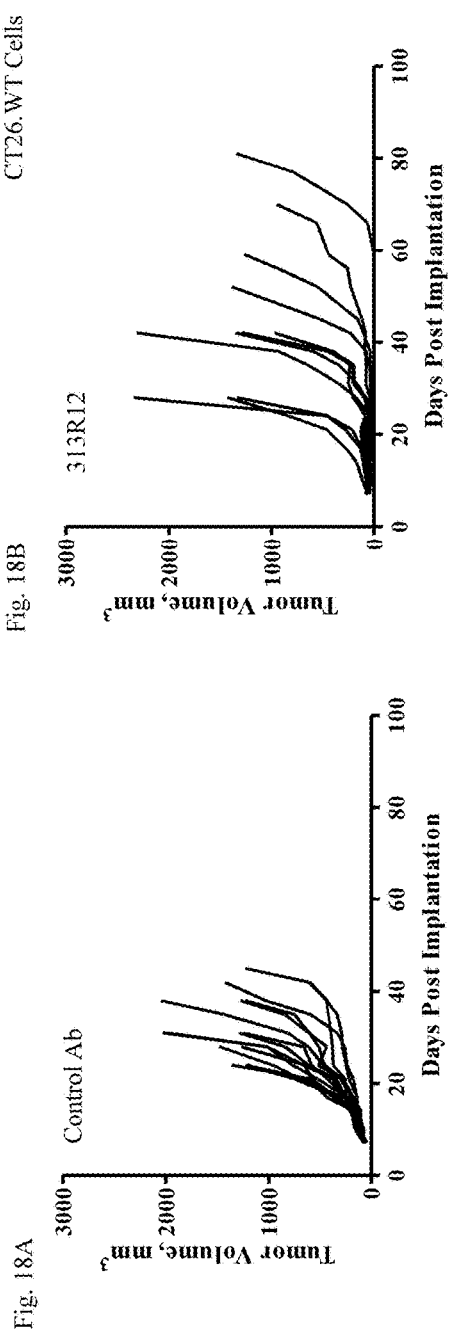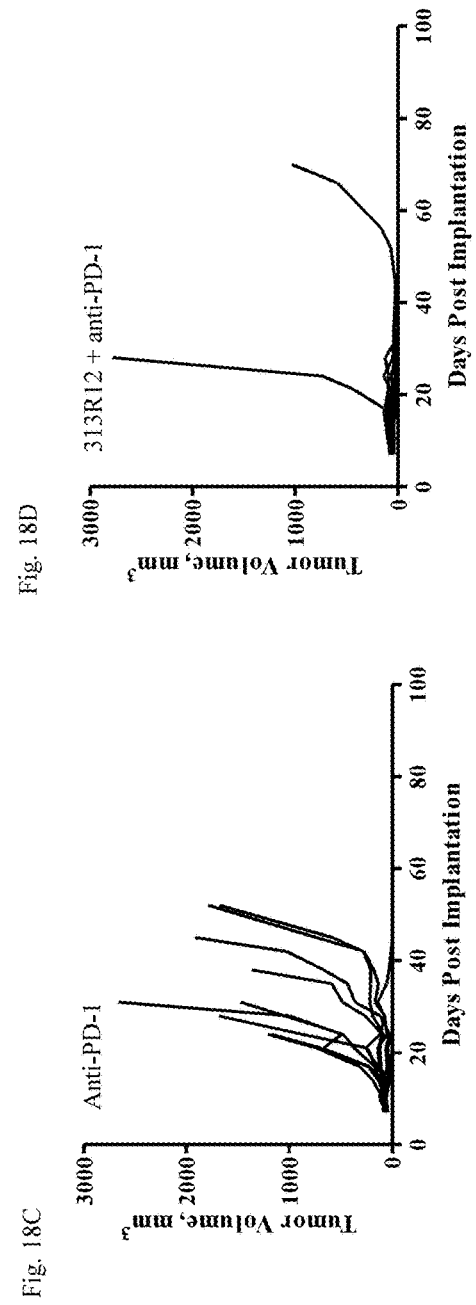
Fig. 18A  Fig. 18B  Fig. 18C  Fig. 18D

Figure 21

```
Human TIGIT      MRWCLLLIWAQGLRQAPLASGMMTGTIETTGNISAEKGGSIILQCHLSSTTAQVTQVNWE
Cynomolgus TIGIT ------F-------------------------K----V--------M------------
Rhesus TIGIT     ------F-------------------------K----V--------M------------

Human TIGIT      QQDQ-LLAICNADLGWHISPSFKDRVAPGPGLGLTLQSLTVNDTGEYFCIYHTYPDGTYT
Cynomolgus TIGIT -H-HS----R----E---Y-A--------------------M------T---------R
Rhesus TIGIT     -H-HS----R----E---Y-A--------------------M------T---------R Human TIGIT      GRIFLEVLESSVAEHGARFQIPLLGAMAATLVVICTAVIVVVALTRKKALRIHSVEGDL
Cynomolgus TIGIT ------------S------------MM--------I------V-A-----S-------SG-
Rhesus TIGIT     ------------S------------MM--------I------V-A-----S-------SG- Human TIGIT      RRKSAGQEEWSPSAPSPPGSCVQAEAAPAGLCGEQRGEDCAELHDYFNVLSYRSLGNCSFFTETG
Cynomolgus TIGIT Q---T-----QI---------------------------Q-D-----------------S-----------
Rhesus TIGIT     Q---T-----QI---------------------------Q-D-----------------S-----------

Human TIGIT      SEQ ID NO:4
Cynomolgus TIGIT SEQ ID NO:77
Rhesus TIGIT     SEQ ID NO:78
```

SEQUENCE LISTING

<160> NUMBER OF SEQ ID NOS: 84

<210> SEQ ID NO 1
<211> LENGTH: 249
<212> TYPE: PRT
<213> ORGANISM: Artificial Sequence
<220> FEATURE:
<223> OTHER INFORMATION: Mouse TIGIT

<400> SEQUENCE: 1

```
Met His Gly Trp Leu Leu Val Trp Val Gln Gly Leu Ile Gln Ala
1               5                   10                  15

Ala Phe Leu Ala Thr Ala Ile Gly Ala Thr Ala Gly Thr Ile Asp Thr
                20                  25                  30

Lys Arg Asn Ile Ser Ala Glu Glu Gly Gly Ser Val Ile Leu Gln Cys
                35                  40                  45

His Phe Ser Ser Asp Thr Ala Glu Val Thr Gln Val Asp Trp Lys Gln
            50                  55                  60

Gln Asp Gln Leu Leu Ala Ile Tyr Ser Val Asp Leu Gly Trp His Val
65                  70                  75                  80

Ala Ser Val Phe Ser Asp Arg Val Val Pro Gly Pro Ser Leu Gly Leu
                85                  90                  95

Thr Phe Gln Ser Leu Thr Met Asn Asp Thr Gly Glu Tyr Phe Cys Thr
                100                 105                 110

Tyr His Thr Tyr Pro Gly Gly Ile Tyr Lys Gly Arg Ile Phe Leu Lys
            115                 120                 125

Val Gln Glu Ser Ser Asp Asp Arg Asn Gly Leu Ala Gln Phe Gln Thr
130                 135                 140

Ala Pro Leu Gly Gly Thr Met Ala Ala Val Leu Gly Leu Ile Cys Leu
145                 150                 155                 160

Met Val Thr Gly Val Thr Val Leu Ala Arg Lys Asp Lys Ser Ile Arg
                165                 170                 175

Met His Ser Ile Glu Ser Gly Leu Gly Arg Thr Glu Ala Glu Pro Gln
            180                 185                 190

Glu Trp Asn Leu Arg Ser Leu Ser Ser Pro Gly Ser Pro Val Gln Thr
            195                 200                 205

Gln Thr Ala Pro Ala Gly Pro Cys Gly Glu Gln Ala Glu Asp Asp Tyr
        210                 215                 220

Ala Asp Pro Gln Glu Tyr Phe Asn Val Leu Ser Tyr Arg Ser Leu Glu
225                 230                 235                 240

Ser Phe Ile Ala Val Ser Lys Thr Gly
                245
```

<210> SEQ ID NO 2
<211> LENGTH: 221
<212> TYPE: PRT
<213> ORGANISM: Artificial Sequence
<220> FEATURE:
<223> OTHER INFORMATION: Mouse TIGIT

<400> SEQUENCE: 2

```
Thr Ile Asp Thr Lys Arg Asn Ile Ser Ala Glu Glu Gly Gly Ser Val
1               5                   10                  15
```

-continued

Ile Leu Gln Cys His Phe Ser Ser Asp Thr Ala Glu Val Thr Gln Val
                20                  25                  30

Asp Trp Lys Gln Gln Asp Gln Leu Leu Ala Ile Tyr Ser Val Asp Leu
            35                  40                  45

Gly Trp His Val Ala Ser Val Phe Ser Asp Arg Val Val Pro Gly Pro
50                  55                  60

Ser Leu Gly Leu Thr Phe Gln Ser Leu Thr Met Asn Asp Thr Gly Glu
65                  70                  75                  80

Tyr Phe Cys Thr Tyr His Thr Tyr Pro Gly Gly Ile Tyr Lys Gly Arg
                85                  90                  95

Ile Phe Leu Lys Val Gln Glu Ser Ser Asp Asp Arg Asn Gly Leu Ala
            100                 105                 110

Gln Phe Gln Thr Ala Pro Leu Gly Gly Thr Met Ala Ala Val Leu Gly
            115                 120                 125

Leu Ile Cys Leu Met Val Thr Gly Val Thr Val Leu Ala Arg Lys Asp
130                 135                 140

Lys Ser Ile Arg Met His Ser Ile Glu Ser Gly Leu Gly Arg Thr Glu
145                 150                 155                 160

Ala Glu Pro Gln Glu Trp Asn Leu Arg Ser Leu Ser Ser Pro Gly Ser
                165                 170                 175

Pro Val Gln Thr Gln Thr Ala Pro Ala Gly Pro Cys Gly Glu Gln Ala
            180                 185                 190

Glu Asp Asp Tyr Ala Asp Pro Gln Glu Tyr Phe Asn Val Leu Ser Tyr
            195                 200                 205

Arg Ser Leu Glu Ser Phe Ile Ala Val Ser Lys Thr Gly
210                 215                 220

<210> SEQ ID NO 3
<211> LENGTH: 120
<212> TYPE: PRT
<213> ORGANISM: Artificial Sequence
<220> FEATURE:
<223> OTHER INFORMATION: Mouse TIGIT extracellular domain

<400> SEQUENCE: 3

Thr Ile Asp Thr Lys Arg Asn Ile Ser Ala Glu Gly Gly Ser Val
1               5                   10                  15

Ile Leu Gln Cys His Phe Ser Ser Asp Thr Ala Glu Val Thr Gln Val
                20                  25                  30

Asp Trp Lys Gln Gln Asp Gln Leu Leu Ala Ile Tyr Ser Val Asp Leu
            35                  40                  45

Gly Trp His Val Ala Ser Val Phe Ser Asp Arg Val Val Pro Gly Pro
50                  55                  60

Ser Leu Gly Leu Thr Phe Gln Ser Leu Thr Met Asn Asp Thr Gly Glu
65                  70                  75                  80

Tyr Phe Cys Thr Tyr His Thr Tyr Pro Gly Gly Ile Tyr Lys Gly Arg
                85                  90                  95

Ile Phe Leu Lys Val Gln Glu Ser Ser Asp Asp Arg Asn Gly Leu Ala
            100                 105                 110

Gln Phe Gln Thr Ala Pro Leu Gly
            115                 120

<210> SEQ ID NO 4
<211> LENGTH: 244
<212> TYPE: PRT
<213> ORGANISM: Artificial Sequence

```
<220> FEATURE:
<223> OTHER INFORMATION: Human TIGIT

<400> SEQUENCE: 4

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
        210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 5
<211> LENGTH: 223
<212> TYPE: PRT
<213> ORGANISM: Artificial Sequence
<220> FEATURE:
<223> OTHER INFORMATION: Human TIGIT

<400> SEQUENCE: 5

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95
```

```
Tyr Thr Gly Arg Ile Phe Leu Glu Val Leu Glu Ser Ser Val Ala Glu
            100                 105                 110

His Gly Ala Arg Phe Gln Ile Pro Leu Leu Gly Ala Met Ala Ala Thr
            115                 120                 125

Leu Val Val Ile Cys Thr Ala Val Ile Val Val Ala Leu Thr Arg
130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
                180                 185                 190

Gln Arg Gly Glu Asp Cys Ala Glu Leu His Asp Tyr Phe Asn Val Leu
                195                 200                 205

Ser Tyr Arg Ser Leu Gly Asn Cys Ser Phe Phe Thr Glu Thr Gly
                210                 215                 220
```

<210> SEQ ID NO 6
<211> LENGTH: 120
<212> TYPE: PRT
<213> ORGANISM: Artificial Sequence
<220> FEATURE:
<223> OTHER INFORMATION: Human TIGIT extracellular domain

<400> SEQUENCE: 6

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
            115                 120
```

<210> SEQ ID NO 7
<211> LENGTH: 10
<212> TYPE: PRT
<213> ORGANISM: Artificial Sequence
<220> FEATURE:
<223> OTHER INFORMATION: 313R11/313R12 Heavy chain CDR1

<400> SEQUENCE: 7

```
Gly Ser Ser Leu Ser Ser Ser Tyr Met Ser
1               5                   10
```

<210> SEQ ID NO 8
<211> LENGTH: 16
<212> TYPE: PRT
<213> ORGANISM: Artificial Sequence
<220> FEATURE:
<223> OTHER INFORMATION: 313R11/313R12/313R14/313R19 Heavy chain CDR2

-continued

<400> SEQUENCE: 8

Ile Ile Gly Ser Asn Gly Asn Thr Tyr Tyr Ala Asn Trp Ala Lys Gly
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: 313R11/313R12/313R14/313R19 Heavy chain CDR3

<400> SEQUENCE: 9

Gly Gly Tyr Arg Thr Ser Gly Met Asp Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: 313R11/313R12 Light chain CDR1

<400> SEQUENCE: 10

Gln Ala Ser Gln Ser Ile Ser Ser Tyr Leu Asn Trp
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 313R11/313R12 Light chain CDR2

<400> SEQUENCE: 11

Asp Ala Leu Lys Leu Ala Ser
1               5

<210> SEQ ID NO 12
<211> LENGTH: 11
<212> TYPE: PRT
<213> ORGANISM: Artificial Sequence
<220> FEATURE:
<223> OTHER INFORMATION: 313R11/313R12 Light chain CDR3

<400> SEQUENCE: 12

Gln Gln Glu His Ser Val Gly Asn Val Asp Asn
1               5                   10

<210> SEQ ID NO 13
<211> LENGTH: 10
<212> TYPE: PRT
<213> ORGANISM: Artificial Sequence
<220> FEATURE:
<223> OTHER INFORMATION: 313R14/313R19 Heavy chain CDR1

<400> SEQUENCE: 13

Gly Phe Ser Leu Ser Ser Ser Tyr Met Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Light chain CDR1 variant1

```
<400> SEQUENCE: 14

Gln Ala Ser Gln Ser Asn Ile Tyr Ser Asp Leu Ala Trp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: 313R14/313R19 Light chain CDR2

<400> SEQUENCE: 15

Arg Ala Ser Thr Leu Ala Ser
1               5

<210> SEQ ID NO 16
<211> LENGTH: 11
<212> TYPE: PRT
<213> ORGANISM: Artificial Sequence
<220> FEATURE:
<223> OTHER INFORMATION: 313R14/313R19 Light chain CDR3

<400> SEQUENCE: 16

Gln Gln Glu His Leu Val Ala Trp Ile Tyr Asn
1               5                   10

<210> SEQ ID NO 17
<211> LENGTH: 115
<212> TYPE: PRT
<213> ORGANISM: Artificial Sequence
<220> FEATURE:
<223> OTHER INFORMATION: 313R11/313R12 Heavy chain variable region

<400> SEQUENCE: 17

Gln Val Gln Leu Glu Ser Glu Gly Gly Leu Phe Lys Pro Thr Asp Thr
1               5                   10                  15

Leu Thr Leu Thr Cys Thr Val Ser Gly Ser Ser Leu Ser Ser Ser Tyr
            20                  25                  30

Met Ser Trp Val Arg Gln Ala Pro Gly Lys Gly Leu Glu Trp Ile Gly
        35                  40                  45

Ile Ile Gly Ser Asn Gly Asn Thr Tyr Tyr Ala Asn Trp Ala Lys Gly
    50                  55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Gly Gly
                85                  90                  95

Tyr Arg Thr Ser Gly Met Asp Pro Trp Gly Pro Gly Thr Leu Val Thr
            100                 105                 110

Val Ser Ser
        115

<210> SEQ ID NO 18
<211> LENGTH: 111
<212> TYPE: PRT
<213> ORGANISM: Artificial Sequence
<220> FEATURE:
<223> OTHER INFORMATION: 313R11/313R12 Light chain variable region

<400> SEQUENCE: 18

Asp Ile Val Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
```

```
                 20                  25                  30

Leu Asn Trp Tyr Gln Gln Lys Pro Gly Gln Pro Pro Lys Leu Leu Ile
            35                  40                  45

Tyr Asp Ala Leu Lys Leu Ala Ser Gly Val Pro Ser Arg Phe Ser Gly
        50                  55                  60

Ser Gly Ser Gly Thr Glu Tyr Thr Leu Thr Ile Ser Gly Val Glu Ser
65                  70                  75                  80

Ala Asp Ala Ala Thr Tyr Tyr Cys Gln Gln Glu His Ser Val Gly Asn
                85                  90                  95

Val Asp Asn Val Phe Gly Gly Gly Thr Glu Val Val Val Lys Arg
            100                 105                 110

<210> SEQ ID NO 19
<211> LENGTH: 116
<212> TYPE: PRT
<213> ORGANISM: Artificial Sequence
<220> FEATURE:
<223> OTHER INFORMATION: 313R14 Heavy chain variable region

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Ser
            20                  25                  30

Tyr Met Ser Trp Ile Arg Gln Pro Pro Gly Lys Gly Leu Glu Trp Ile
        35                  40                  45

Gly Ile Ile Gly Ser Asn Gly Asn Thr Tyr Tyr Ala Asn Trp Ala Lys
50                  55                  60

Gly Arg Val Thr Ile Ser Lys Thr Ser Thr Thr Val Glu Leu Lys Leu
65                  70                  75                  80

Ser Ser Val Thr Ala Ala Asp Thr Ala Val Tyr Tyr Cys Ala Arg Gly
                85                  90                  95

Gly Tyr Arg Thr Ser Gly Met Asp Pro Trp Gly Gln Gly Thr Leu Val
            100                 105                 110

Thr Val Ser Ser
        115

<210> SEQ ID NO 20
<211> LENGTH: 111
<212> TYPE: PRT
<213> ORGANISM: Artificial Sequence
<220> FEATURE:
<223> OTHER INFORMATION: 313R14/313R19/313R20 Light chain variable
      region

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asp
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Leu Val Ala Trp
                85                  90                  95
```

```
Ile Tyr Asn Val Phe Gly Gln Gly Thr Lys Val Glu Ile Lys Arg
            100                 105                 110

<210> SEQ ID NO 21
<211> LENGTH: 458
<212> TYPE: PRT
<213> ORGANISM: Artificial Sequence
<220> FEATURE:
<223> OTHER INFORMATION: 313R11 Heavy chain (mIgG1)
<220> FEATURE:
<221> NAME/KEY: SIGNAL
<222> LOCATION: (1)..(19)

<400> SEQUENCE: 21

Met Lys His Leu Trp Phe Phe Leu Leu Leu Val Ala Ala Pro Arg Trp
1               5                   10                  15

Val Leu Ser Gln Val Gln Leu Glu Ser Gly Gly Leu Phe Lys Pro
            20                  25                  30

Thr Asp Thr Leu Thr Leu Thr Cys Thr Val Ser Gly Ser Ser Leu Ser
            35                  40                  45

Ser Ser Tyr Met Ser Trp Val Arg Gln Ala Pro Gly Lys Gly Leu Glu
        50                  55                  60

Trp Ile Gly Ile Ile Gly Ser Asn Gly Asn Thr Tyr Tyr Ala Asn Trp
65                  70                  75                  80

Ala Lys Gly Arg Phe Thr Ile Ser Lys Thr Ser Thr Thr Val Glu Leu
                85                  90                  95

Lys Ile Thr Ser Pro Thr Thr Glu Asp Thr Ala Thr Tyr Phe Cys Ala
            100                 105                 110

Arg Gly Gly Tyr Arg Thr Ser Gly Met Asp Pro Trp Gly Pro Gly Thr
            115                 120                 125

Leu Val Thr Val Ser Ser Ala Lys Thr Thr Pro Pro Ser Val Tyr Pro
        130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Glu
            180                 185                 190

Ser Asp Leu Tyr Thr Leu Ser Ser Ser Val Thr Val Pro Ser Ser Pro
            195                 200                 205

Arg Pro Ser Glu Thr Val Thr Cys Asn Val Ala His Pro Ala Ser Ser
        210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335
```

```
Ala Ala Phe Pro Ala Pro Ile Glu Lys Thr Ile Ser Lys Thr Lys Gly
            340                 345                 350

Arg Pro Lys Ala Pro Gln Val Tyr Thr Ile Pro Pro Lys Glu Gln
        355                 360                 365

Met Ala Lys Asp Lys Val Ser Leu Thr Cys Met Ile Thr Asp Phe Phe
370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asn Thr Asn Gly Ser Tyr Phe
                405                 410                 415

Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
        435                 440                 445

Glu Lys Ser Leu Ser His Ser Pro Gly Lys
    450                 455

<210> SEQ ID NO 22
<211> LENGTH: 464
<212> TYPE: PRT
<213> ORGANISM: Artificial Sequence
<220> FEATURE:
<223> OTHER INFORMATION: 313R12 Heavy chain (mIgG2)
<220> FEATURE:
<221> NAME/KEY: SIGNAL
<222> LOCATION: (1)..(19)

<400> SEQUENCE: 22

Met Lys His Leu Trp Phe Phe Leu Leu Leu Val Ala Ala Pro Arg Trp
1               5                   10                  15

Val Leu Ser Gln Val Gln Leu Glu Ser Glu Gly Gly Leu Phe Lys Pro
            20                  25                  30

Thr Asp Thr Leu Thr Leu Thr Cys Thr Val Ser Gly Ser Ser Leu Ser
        35                  40                  45

Ser Ser Tyr Met Ser Trp Val Arg Gln Ala Pro Gly Lys Gly Leu Glu
50                  55                  60

Trp Ile Gly Ile Ile Gly Ser Asn Gly Asn Thr Tyr Tyr Ala Asn Trp
65                  70                  75                  80

Ala Lys Gly Arg Phe Thr Ile Ser Lys Thr Ser Thr Thr Val Glu Leu
                85                  90                  95

Lys Ile Thr Ser Pro Thr Thr Glu Asp Thr Ala Thr Tyr Phe Cys Ala
            100                 105                 110

Arg Gly Gly Tyr Arg Thr Ser Gly Met Asp Pro Trp Gly Pro Gly Thr
        115                 120                 125

Leu Val Thr Val Ser Ser Ala Lys Thr Thr Ala Pro Ser Val Tyr Pro
130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
        195                 200                 205

Trp Pro Ser Gln Ser Ile Thr Cys Asn Val Ala His Pro Ala Ser Ser
210                 215                 220
```

```
Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Leu Leu Gly Gly Pro Ser
            245                 250                 255

Val Phe Ile Phe Pro Pro Lys Ile Lys Asp Val Leu Met Ile Ser Leu
        260                 265                 270

Ser Pro Ile Val Thr Cys Val Val Asp Val Ser Glu Asp Asp Pro
    275                 280                 285

Asp Val Gln Ile Ser Trp Phe Val Asn Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Pro Ala Pro Ile Glu Arg Thr
            340                 345                 350

Ile Ser Lys Pro Lys Gly Ser Val Arg Ala Pro Gln Val Tyr Val Leu
        355                 360                 365

Pro Pro Pro Glu Glu Glu Met Thr Lys Lys Gln Val Thr Leu Thr Cys
370                 375                 380

Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
            420                 425                 430

Asn Trp Val Glu Arg Asn Ser Tyr Ser Cys Ser Val Val His Glu Gly
        435                 440                 445

Leu His Asn His His Thr Thr Lys Ser Phe Ser Arg Thr Pro Gly Lys
    450                 455                 460

<210> SEQ ID NO 23
<211> LENGTH: 236
<212> TYPE: PRT
<213> ORGANISM: Artificial Sequence
<220> FEATURE:
<223> OTHER INFORMATION: 313R11/313R12 Light chain
<220> FEATURE:
<221> NAME/KEY: SIGNAL
<222> LOCATION: (1)..(19)

<400> SEQUENCE: 23

Met Lys His Leu Trp Phe Phe Leu Leu Leu Val Ala Ala Pro Arg Trp
1               5                   10                  15

Val Leu Ser Asp Ile Val Met Thr Gln Thr Pro Ala Ser Val Glu Val
            20                  25                  30

Ala Val Gly Gly Thr Val Thr Ile Lys Cys Gln Ala Ser Gln Ser Ile
        35                  40                  45

Ser Ser Tyr Leu Asn Trp Tyr Gln Gln Lys Pro Gly Gln Pro Pro Lys
    50                  55                  60

Leu Leu Ile Tyr Asp Ala Leu Lys Leu Ala Ser Gly Val Pro Ser Arg
65                  70                  75                  80

Phe Ser Gly Ser Gly Ser Gly Thr Glu Tyr Thr Leu Thr Ile Ser Gly
                85                  90                  95

Val Glu Ser Ala Asp Ala Ala Thr Tyr Tyr Cys Gln Gln Glu His Ser
            100                 105                 110
```

```
Val Gly Asn Val Asp Asn Val Phe Gly Gly Gly Thr Glu Val Val Val
        115                 120                 125

Lys Arg Thr Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 24
<211> LENGTH: 465
<212> TYPE: PRT
<213> ORGANISM: Artificial Sequence
<220> FEATURE:
<223> OTHER INFORMATION: 313R14 Heavy chain (hIgG1)
<220> FEATURE:
<221> NAME/KEY: SIGNAL
<222> LOCATION: (1)..(19)

<400> SEQUENCE: 24

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Ser Ser Ser Tyr Met Ser Trp Ile Arg Gln Pro Pro Gly Lys Gly Leu
    50                  55                  60

Glu Trp Ile Gly Ile Ile Gly Ser Asn Gly Asn Thr Tyr Tyr Ala Asn
65                  70                  75                  80

Trp Ala Lys Gly Arg Val Thr Ile Ser Lys Thr Ser Thr Thr Val Glu
                85                  90                  95

Leu Lys Leu Ser Ser Val Thr Ala Ala Asp Thr Ala Val Tyr Tyr Cys
            100                 105                 110

Ala Arg Gly Gly Tyr Arg Thr Ser Gly Met Asp Pro Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220
```

```
Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 25
<211> LENGTH: 237
<212> TYPE: PRT
<213> ORGANISM: Artificial Sequence
<220> FEATURE:
<223> OTHER INFORMATION: 313R14/313R19/313R20 Light chain
<220> FEATURE:
<221> NAME/KEY: SIGNAL
<222> LOCATION: (1)..(20)

<400> SEQUENCE: 25

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asn
            35                  40                  45

Ile Tyr Ser Asp Leu Ala Trp Tyr Gln Gln Lys Pro Gly Lys Ala Pro
        50                  55                  60

Lys Leu Leu Ile Tyr Arg Ala Ser Thr Leu Ala Ser Gly Val Pro Ser
65                  70                  75                  80

Arg Phe Ser Gly Ser Gly Ser Gly Thr Asp Phe Thr Leu Thr Ile Ser
            85                  90                  95
```

```
Ser Leu Gln Pro Glu Asp Phe Ala Thr Tyr Tyr Cys Gln Gln Glu His
            100                 105                 110

Leu Val Ala Trp Ile Tyr Asn Val Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 26
<211> LENGTH: 439
<212> TYPE: PRT
<213> ORGANISM: Artificial Sequence
<220> FEATURE:
<223> OTHER INFORMATION: 313R11 Heavy chain (mIgG1)

<400> SEQUENCE: 26

```
Gln Val Gln Leu Glu Ser Gly Gly Gly Leu Phe Lys Pro Thr Asp Thr
1               5                   10                  15

Leu Thr Leu Thr Cys Thr Val Ser Gly Ser Ser Leu Ser Ser Ser Tyr
            20                  25                  30

Met Ser Trp Val Arg Gln Ala Pro Gly Lys Gly Leu Glu Trp Ile Gly
        35                  40                  45

Ile Ile Gly Ser Asn Gly Asn Thr Tyr Tyr Ala Asn Trp Ala Lys Gly
50                  55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Gly Gly
                85                  90                  95

Tyr Arg Thr Ser Gly Met Asp Pro Trp Gly Pro Gly Thr Leu Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Glu Ser Asp Leu
                165                 170                 175

Tyr Thr Leu Ser Ser Ser Val Thr Val Pro Ser Ser Pro Arg Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220
```

-continued

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
            245                 250                 255

Asp Ile Ser Lys Asp Asp Pro Glu Val Gln Phe Ser Trp Phe Val Asp
        260                 265                 270

Asp Val Glu Val His Thr Ala Gln Thr Gln Pro Arg Glu Glu Gln Phe
    275                 280                 285

Asn Ser Thr Phe Arg Ser Val Ser Glu Leu Pro Ile Met His Gln Asp
290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
            325                 330                 335

Ala Pro Gln Val Tyr Thr Ile Pro Pro Lys Glu Gln Met Ala Lys
        340                 345                 350

Asp Lys Val Ser Leu Thr Cys Met Ile Thr Asp Phe Phe Pro Glu Asp
    355                 360                 365

Ile Thr Val Glu Trp Gln Trp Asn Gly Gln Pro Ala Glu Asn Tyr Lys
370                 375                 380

Asn Thr Gln Pro Ile Met Asn Thr Asn Gly Ser Tyr Phe Val Tyr Ser
385                 390                 395                 400

Lys Leu Asn Val Gln Lys Ser Asn Trp Glu Ala Gly Asn Thr Phe Thr
            405                 410                 415

Cys Ser Val Leu His Glu Gly Leu His Asn His His Thr Glu Lys Ser
        420                 425                 430

Leu Ser His Ser Pro Gly Lys
            435

<210> SEQ ID NO 27
<211> LENGTH: 445
<212> TYPE: PRT
<213> ORGANISM: Artificial Sequence
<220> FEATURE:
<223> OTHER INFORMATION: 313R12 Heavy chain (mIgG2)

<400> SEQUENCE: 27

Gln Val Gln Leu Glu Ser Glu Gly Gly Leu Phe Lys Pro Thr Asp Thr
1               5                   10                  15

Leu Thr Leu Thr Cys Thr Val Ser Gly Ser Ser Leu Ser Ser Ser Tyr
            20                  25                  30

Met Ser Trp Val Arg Gln Ala Pro Gly Lys Gly Leu Glu Trp Ile Gly
        35                  40                  45

Ile Ile Gly Ser Asn Gly Asn Thr Tyr Tyr Ala Asn Trp Ala Lys Gly
    50                  55                  60

Arg Phe Thr Ile Ser Lys Thr Ser Thr Val Glu Leu Lys Ile Thr
65                  70                  75                  80

Ser Pro Thr Thr Glu Asp Thr Ala Thr Tyr Phe Cys Ala Arg Gly Gly
                85                  90                  95

Tyr Arg Thr Ser Gly Met Asp Pro Trp Gly Pro Gly Thr Leu Val Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

```
Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
            165                 170                 175

Tyr Thr Leu Ser Ser Ser Val Val Thr Ser Ser Thr Trp Pro Ser
            180                 185                 190

Gln Ser Ile Thr Cys Asn Val Ala His Pro Ala Ser Ser Thr Lys Val
            195                 200                 205

Asp Lys Lys Ile Glu Pro Arg Gly Pro Thr Ile Lys Pro Cys Pro Pro
            210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Pro Asp Val Gln
            260                 265                 270

Ile Ser Trp Phe Val Asn Asn Val Glu Val His Thr Ala Gln Thr Gln
            275                 280                 285

Thr His Arg Glu Asp Tyr Asn Ser Thr Leu Arg Val Val Ser Ala Leu
290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
            435                 440                 445

<210> SEQ ID NO 28
<211> LENGTH: 217
<212> TYPE: PRT
<213> ORGANISM: Artificial Sequence
<220> FEATURE:
<223> OTHER INFORMATION: 313R11/313R12 Light chain

<400> SEQUENCE: 28

Asp Ile Val Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Asn Trp Tyr Gln Gln Lys Pro Gly Gln Pro Pro Lys Leu Leu Ile
            35                  40                  45

Tyr Asp Ala Leu Lys Leu Ala Ser Gly Val Pro Ser Arg Phe Ser Gly
50                  55                  60
```

```
Ser Gly Ser Gly Thr Glu Tyr Thr Leu Thr Ile Ser Gly Val Glu Ser
 65                  70                  75                  80

Ala Asp Ala Ala Thr Tyr Tyr Cys Gln Gln Glu His Ser Val Gly Asn
                 85                  90                  95

Val Asp Asn Val Phe Gly Gly Gly Thr Glu Val Val Lys Arg Thr
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 29
<211> LENGTH: 446
<212> TYPE: PRT
<213> ORGANISM: Artificial Sequence
<220> FEATURE:
<223> OTHER INFORMATION: 313R14 Heavy chain (hIgG1)

<400> SEQUENCE: 29

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Ser Ser
             20                  25                  30

Tyr Met Ser Trp Ile Arg Gln Pro Pro Gly Lys Gly Leu Glu Trp Ile
         35                  40                  45

Gly Ile Ile Gly Ser Asn Gly Asn Thr Tyr Tyr Ala Asn Trp Ala Lys
     50                  55                  60

Gly Arg Val Thr Ile Ser Lys Thr Ser Thr Thr Val Glu Leu Lys Leu
 65                  70                  75                  80

Ser Ser Val Thr Ala Ala Asp Thr Ala Val Tyr Tyr Cys Ala Arg Gly
                 85                  90                  95

Gly Tyr Arg Thr Ser Gly Met Asp Pro Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

Lys Val Asp Lys Arg Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 30
<211> LENGTH: 217
<212> TYPE: PRT
<213> ORGANISM: Artificial Sequence
<220> FEATURE:
<223> OTHER INFORMATION: 313R14/313R19/313R20 Light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asp
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Leu Val Ala Trp
            85                  90                  95

Ile Tyr Asn Val Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

```
Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 31
<211> LENGTH: 9
<212> TYPE: PRT
<213> ORGANISM: Artificial Sequence
<220> FEATURE:
<223> OTHER INFORMATION: AH-1 peptide

<400> SEQUENCE: 31

Ser Pro Ser Tyr Val Tyr His Gln Phe
1               5

<210> SEQ ID NO 32
<211> LENGTH: 116
<212> TYPE: PRT
<213> ORGANISM: Artificial Sequence
<220> FEATURE:
<223> OTHER INFORMATION: 313R19/313R20 Heavy chain variable region

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Ser
            20                  25                  30

Tyr Met Ser Trp Ile Arg Gln Pro Pro Gly Lys Gly Leu Glu Trp Ile
        35                  40                  45

Gly Ile Ile Gly Ser Asn Gly Asn Thr Tyr Tyr Ala Asn Trp Ala Lys
    50                  55                  60

Gly Arg Val Thr Ile Ser Lys Ser Ser Asn Gln Val Ser Leu Lys Leu
65                  70                  75                  80

Ser Ser Val Thr Ala Ala Asp Thr Ala Val Tyr Tyr Cys Ala Arg Gly
                85                  90                  95

Gly Tyr Arg Thr Ser Gly Met Asp Pro Trp Gly Gln Gly Thr Leu Val
            100                 105                 110

Thr Val Ser Ser
        115

<210> SEQ ID NO 33
<211> LENGTH: 465
<212> TYPE: PRT
<213> ORGANISM: Artificial Sequence
<220> FEATURE:
<223> OTHER INFORMATION: 313R19 Heavy chain (IgG1)
<220> FEATURE:
<221> NAME/KEY: SIGNAL
<222> LOCATION: (1)..(19)

<400> SEQUENCE: 33
```

-continued

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
            35                  40                  45

Ser Ser Ser Tyr Met Ser Trp Ile Arg Gln Pro Pro Gly Lys Gly Leu
        50                  55                  60

Glu Trp Ile Gly Ile Ile Gly Ser Asn Gly Asn Thr Tyr Tyr Ala Asn
65                  70                  75                  80

Trp Ala Lys Gly Arg Val Thr Ile Ser Lys Ser Ser Asn Gln Val Ser
                85                  90                  95

Leu Lys Leu Ser Ser Val Thr Ala Ala Asp Thr Ala Val Tyr Tyr Cys
            100                 105                 110

Ala Arg Gly Gly Tyr Arg Thr Ser Gly Met Asp Pro Trp Gly Gln Gly
        115                 120                 125

Thr Leu Val Thr Val Ser Ser Ala Ser Thr Lys Gly Pro Ser Val Phe
        130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
```

```
                    420                 425                 430
Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 34
<211> LENGTH: 446
<212> TYPE: PRT
<213> ORGANISM: Artificial Sequence
<220> FEATURE:
<223> OTHER INFORMATION: 313R19 Heavy chain (IgG1)

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Ser
            20                  25                  30

Tyr Met Ser Trp Ile Arg Gln Pro Pro Gly Lys Gly Leu Glu Trp Ile
        35                  40                  45

Gly Ile Ile Gly Ser Asn Gly Asn Thr Tyr Tyr Ala Asn Trp Ala Lys
    50                  55                  60

Gly Arg Val Thr Ile Ser Lys Ser Ser Asn Gln Val Ser Leu Lys Leu
65                  70                  75                  80

Ser Ser Val Thr Ala Ala Asp Thr Ala Val Tyr Tyr Cys Ala Arg Gly
                85                  90                  95

Gly Tyr Arg Thr Ser Gly Met Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
```

```
                   305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 35
<211> LENGTH: 8
<212> TYPE: PRT
<213> ORGANISM: Artificial Sequence
<220> FEATURE:
<223> OTHER INFORMATION: Linker

<400> SEQUENCE: 35

Glu Ser Gly Gly Gly Gly Val Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Linker

<400> SEQUENCE: 36

Leu Glu Ser Gly Gly Gly Gly Val Thr
1               5

<210> SEQ ID NO 37
<211> LENGTH: 6
<212> TYPE: PRT
<213> ORGANISM: Artificial Sequence
<220> FEATURE:
<223> OTHER INFORMATION: Linker

<400> SEQUENCE: 37

Gly Arg Ala Gln Val Thr
1               5

<210> SEQ ID NO 38
<211> LENGTH: 6
<212> TYPE: PRT
<213> ORGANISM: Artificial Sequence
<220> FEATURE:
<223> OTHER INFORMATION: Linker

<400> SEQUENCE: 38

Trp Arg Ala Gln Val Thr
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Linker

<400> SEQUENCE: 39

Ala Arg Gly Arg Ala Gln Val Thr
1               5

<210> SEQ ID NO 40
<211> LENGTH: 8
<212> TYPE: PRT
<213> ORGANISM: Artificial Sequence
<220> FEATURE:
<223> OTHER INFORMATION: FLAG Tag

<400> SEQUENCE: 40

Asp Tyr Lys Asp Asp Asp Asp Lys
1               5

<210> SEQ ID NO 41
<211> LENGTH: 330
<212> TYPE: PRT
<213> ORGANISM: Artificial Sequence
<220> FEATURE:
<223> OTHER INFORMATION: Human IgG1 Heavy chain constant region

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 326
<212> TYPE: PRT
<213> ORGANISM: Artificial Sequence
<220> FEATURE:
<223> OTHER INFORMATION: Human IgG2 Heavy chain constant region

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 377
<212> TYPE: PRT
<213> ORGANISM: Artificial Sequence
<220> FEATURE:
<223> OTHER INFORMATION: Human IgG3 Heavy chain constant region

<400> SEQUENCE: 43

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 44
<211> LENGTH: 327
<212> TYPE: PRT
<213> ORGANISM: Artificial Sequence
<220> FEATURE:
<223> OTHER INFORMATION: Human IgG4 Heavy chain constant region

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 45
<211> LENGTH: 227
<212> TYPE: PRT
<213> ORGANISM: Artificial Sequence
<220> FEATURE:
<223> OTHER INFORMATION: Human IgG1 Fc region (13A Version)

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Lys Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 46
<211> LENGTH: 227
<212> TYPE: PRT
<213> ORGANISM: Artificial Sequence
<220> FEATURE:
<223> OTHER INFORMATION: Human IgG1 Fc region (13B Version)

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
                    20                  25                  30
Ile Ser Arg Thr Pro Glu Val Thr Cys Val Val Asp Val Ser His
        35                  40                  45
Glu Asp Pro Glu Val Lys Phe Asn Trp Tyr Val Asp Gly Val Glu Val
50                      55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Glu Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Glu Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 47
<211> LENGTH: 232
<212> TYPE: PRT
<213> ORGANISM: Artificial Sequence
<220> FEATURE:
<223> OTHER INFORMATION: Human IgG1 Fc region (13A Version)

<400> SEQUENCE: 47

Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
                20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Lys Leu Thr
    130                 135                 140
Lys Asn Gln Val Ser Leu Thr Cys Leu Val Lys Gly Phe Tyr Pro Ser
```

```
                145                 150                 155                 160
Asp Ile Ala Val Glu Trp Glu Ser Asn Gly Gln Pro Glu Asn Asn Tyr
                    165                 170                 175

Lys Thr Thr Pro Pro Val Leu Lys Ser Asp Gly Ser Phe Phe Leu Tyr
                    180                 185                 190

Ser Lys Leu Thr Val Asp Lys Ser Arg Trp Gln Gln Gly Asn Val Phe
                    195                 200                 205

Ser Cys Ser Val Met His Glu Ala Leu His Asn His Tyr Thr Gln Lys
                    210                 215                 220

Ser Leu Ser Leu Ser Pro Gly Lys
225                 230

<210> SEQ ID NO 48
<211> LENGTH: 232
<212> TYPE: PRT
<213> ORGANISM: Artificial Sequence
<220> FEATURE:
<223> OTHER INFORMATION: Human IgG1 Fc region (13B Version)

<400> SEQUENCE: 48

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
                130                 135                 140

Lys Asn Gln Val Ser Leu Thr Cys Leu Val Glu Gly Phe Tyr Pro Ser
145                 150                 155                 160

Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                    180                 185                 190

Ser Glu Leu Thr Val Asp Lys Ser Arg Trp Gln Gln Gly Asn Val Phe
                    195                 200                 205

Ser Cys Ser Val Met His Glu Ala Leu His Asn His Tyr Thr Gln Lys
                    210                 215                 220

Ser Leu Ser Leu Ser Pro Gly Lys
225                 230

<210> SEQ ID NO 49
<211> LENGTH: 224
<212> TYPE: PRT
<213> ORGANISM: Artificial Sequence
<220> FEATURE:
<223> OTHER INFORMATION: Human IgG2 Fc region (13A Version)
```

<400> SEQUENCE: 49

```
Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Asp Val Ser His Glu Asp Pro
            35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
                100                 105                 110

Ile Ser Lys Thr Lys Gly Gln Pro Arg Glu Pro Gln Val Tyr Thr Leu
                115                 120                 125

Pro Pro Ser Arg Glu Lys Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Lys
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Gly Lys
                210                 215                 220
```

<210> SEQ ID NO 50
<211> LENGTH: 224
<212> TYPE: PRT
<213> ORGANISM: Artificial Sequence
<220> FEATURE:
<223> OTHER INFORMATION: Human IgG2 Fc region (13B Version)

<400> SEQUENCE: 50

```
Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Asp Val Ser His Glu Asp Pro
            35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
                100                 105                 110

Ile Ser Lys Thr Lys Gly Gln Pro Arg Glu Pro Gln Val Tyr Thr Leu
                115                 120                 125
```

```
Pro Pro Ser Arg Glu Glu Met Thr Lys Asn Gln Val Ser Leu Thr Cys
    130                 135                 140

Leu Val Glu Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Glu Leu Thr Val Asp Lys Ser
            180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Gly Lys
    210                 215                 220
```

<210> SEQ ID NO 51
<211> LENGTH: 235
<212> TYPE: PRT
<213> ORGANISM: Artificial Sequence
<220> FEATURE:
<223> OTHER INFORMATION: Human IgG2 Fc region (13A Version)

<400> SEQUENCE: 51

```
Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235
```

<210> SEQ ID NO 52
<211> LENGTH: 235
<212> TYPE: PRT
<213> ORGANISM: Artificial Sequence
<220> FEATURE:

<223> OTHER INFORMATION: Human IgG2 Fc region (13A Version)

<400> SEQUENCE: 52

```
Thr Lys Val Asp Lys Thr Val Glu Arg Lys Ser Cys Val Glu Cys Pro
1               5                   10                  15
Pro Cys Pro Ala Pro Pro Val Ala Gly Pro Ser Val Phe Leu Phe Pro
            20                  25                  30
Pro Lys Pro Lys Asp Thr Leu Met Ile Ser Arg Thr Pro Glu Val Thr
        35                  40                  45
Cys Val Val Val Asp Val Ser His Glu Asp Pro Glu Val Gln Phe Asn
    50                  55                  60
Trp Tyr Val Asp Gly Val Glu Val His Asn Ala Lys Thr Lys Pro Arg
65                  70                  75                  80
Glu Glu Gln Phe Asn Ser Thr Phe Arg Val Val Ser Val Leu Thr Val
                85                  90                  95
Val His Gln Asp Trp Leu Asn Gly Lys Glu Tyr Lys Cys Lys Val Ser
            100                 105                 110
Asn Lys Gly Leu Pro Ala Pro Ile Glu Lys Thr Ile Ser Lys Thr Lys
        115                 120                 125
Gly Gln Pro Arg Glu Pro Gln Val Tyr Thr Leu Pro Pro Ser Arg Glu
    130                 135                 140
Lys Met Thr Lys Asn Gln Val Ser Leu Thr Cys Leu Val Lys Gly Phe
145                 150                 155                 160
Tyr Pro Ser Asp Ile Ala Val Glu Trp Glu Ser Asn Gly Gln Pro Glu
                165                 170                 175
Asn Asn Tyr Lys Thr Thr Pro Pro Met Leu Lys Ser Asp Gly Ser Phe
            180                 185                 190
Phe Leu Tyr Ser Lys Leu Thr Val Asp Lys Ser Arg Trp Gln Gln Gly
        195                 200                 205
Asn Val Phe Ser Cys Ser Val Met His Glu Ala Leu His Asn His Tyr
    210                 215                 220
Thr Gln Lys Ser Leu Ser Leu Ser Pro Gly Lys
225                 230                 235
```

<210> SEQ ID NO 53
<211> LENGTH: 235
<212> TYPE: PRT
<213> ORGANISM: Artificial Sequence
<220> FEATURE:
<223> OTHER INFORMATION: Human IgG2 Fc region (13B Version)

<400> SEQUENCE: 53

```
Thr Lys Val Asp Lys Thr Val Glu Arg Lys Cys Cys Val Glu Cys Pro
1               5                   10                  15
Pro Cys Pro Ala Pro Pro Val Ala Gly Pro Ser Val Phe Leu Phe Pro
            20                  25                  30
Pro Lys Pro Lys Asp Thr Leu Met Ile Ser Arg Thr Pro Glu Val Thr
        35                  40                  45
Cys Val Val Val Asp Val Ser His Glu Asp Pro Glu Val Gln Phe Asn
    50                  55                  60
Trp Tyr Val Asp Gly Val Glu Val His Asn Ala Lys Thr Lys Pro Arg
65                  70                  75                  80
Glu Glu Gln Phe Asn Ser Thr Phe Arg Val Val Ser Val Leu Thr Val
                85                  90                  95
Val His Gln Asp Trp Leu Asn Gly Lys Glu Tyr Lys Cys Lys Val Ser
            100                 105                 110
```

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
            130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                    165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 54
<211> LENGTH: 235
<212> TYPE: PRT
<213> ORGANISM: Artificial Sequence
<220> FEATURE:
<223> OTHER INFORMATION: Human IgG2 Fc region (13B Version)

<400> SEQUENCE: 54

Thr Lys Val Asp Lys Thr Val Glu Arg Lys Ser Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
        50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
            130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                    165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

```
<210> SEQ ID NO 55
<211> LENGTH: 462
<212> TYPE: PRT
<213> ORGANISM: Artificial Sequence
<220> FEATURE:
<223> OTHER INFORMATION: 313R20 Heavy chain (IgG4)
<220> FEATURE:
<221> NAME/KEY: SIGNAL
<222> LOCATION: (1)..(19)

<400> SEQUENCE: 55
```

| | | | | | | | | | | | | | | | |
|---|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | |
| Val | Leu | Ser | Gln | Val | Gln | Leu | Gln | Glu | Ser | Gly | Pro | Gly | Leu | Val | Lys |
| | | | 20 | | | | | 25 | | | | | 30 | | |
| Pro | Ser | Glu | Thr | Leu | Ser | Leu | Thr | Cys | Thr | Val | Ser | Gly | Phe | Ser | Leu |
| | | | 35 | | | | | 40 | | | | | 45 | | |
| Ser | Ser | Ser | Tyr | Met | Ser | Trp | Ile | Arg | Gln | Pro | Pro | Gly | Lys | Gly | Leu |
| | 50 | | | | | 55 | | | | | 60 | | | | |
| Glu | Trp | Ile | Gly | Ile | Ile | Gly | Ser | Asn | Gly | Asn | Thr | Tyr | Tyr | Ala | Asn |
| 65 | | | | | 70 | | | | | 75 | | | | | 80 |
| Trp | Ala | Lys | Gly | Arg | Val | Thr | Ile | Ser | Lys | Ser | Ser | Asn | Gln | Val | Ser |
| | | | | 85 | | | | | 90 | | | | | 95 | |
| Leu | Lys | Leu | Ser | Ser | Val | Thr | Ala | Ala | Asp | Thr | Ala | Val | Tyr | Tyr | Cys |
| | | | 100 | | | | | 105 | | | | | 110 | | |
| Ala | Arg | Gly | Gly | Tyr | Arg | Thr | Ser | Gly | Met | Asp | Pro | Trp | Gly | Gln | Gly |
| | | | 115 | | | | | 120 | | | | | 125 | | |
| Thr | Leu | Val | Thr | Val | Ser | Ser | Ala | Ser | Thr | Lys | Gly | Pro | Ser | Val | Phe |
| | 130 | | | | | 135 | | | | | 140 | | | | |
| Pro | Leu | Ala | Pro | Cys | Ser | Arg | Ser | Thr | Ser | Glu | Ser | Thr | Ala | Ala | Leu |
| 145 | | | | | 150 | | | | | 155 | | | | | 160 |
| Gly | Cys | Leu | Val | Lys | Asp | Tyr | Phe | Pro | Glu | Pro | Val | Thr | Val | Ser | Trp |
| | | | | 165 | | | | | 170 | | | | | 175 | |
| Asn | Ser | Gly | Ala | Leu | Thr | Ser | Gly | Val | His | Thr | Phe | Pro | Ala | Val | Leu |
| | | | 180 | | | | | 185 | | | | | 190 | | |
| Gln | Ser | Ser | Gly | Leu | Tyr | Ser | Leu | Ser | Ser | Val | Val | Thr | Val | Pro | Ser |
| | | | 195 | | | | | 200 | | | | | 205 | | |
| Ser | Ser | Leu | Gly | Thr | Lys | Thr | Tyr | Thr | Cys | Asn | Val | Asp | His | Lys | Pro |
| | 210 | | | | | 215 | | | | | 220 | | | | |
| Ser | Asn | Thr | Lys | Val | Asp | Lys | Arg | Val | Glu | Ser | Lys | Tyr | Gly | Pro | Pro |
| 225 | | | | | 230 | | | | | 235 | | | | | 240 |
| Cys | Pro | Pro | Cys | Pro | Ala | Pro | Glu | Phe | Leu | Gly | Gly | Pro | Ser | Val | Phe |
| | | | | 245 | | | | | 250 | | | | | 255 | |
| Leu | Phe | Pro | Pro | Lys | Pro | Lys | Asp | Thr | Leu | Met | Ile | Ser | Arg | Thr | Pro |
| | | | 260 | | | | | 265 | | | | | 270 | | |
| Glu | Val | Thr | Cys | Val | Val | Val | Asp | Val | Ser | Gln | Glu | Asp | Pro | Glu | Val |
| | | | 275 | | | | | 280 | | | | | 285 | | |
| Gln | Phe | Asn | Trp | Tyr | Val | Asp | Gly | Val | Glu | Val | His | Asn | Ala | Lys | Thr |
| | 290 | | | | | 295 | | | | | 300 | | | | |
| Lys | Pro | Arg | Glu | Glu | Gln | Phe | Asn | Ser | Thr | Tyr | Arg | Val | Val | Ser | Val |
| 305 | | | | | 310 | | | | | 315 | | | | | 320 |
| Leu | Thr | Val | Leu | His | Gln | Asp | Trp | Leu | Asn | Gly | Lys | Glu | Tyr | Lys | Cys |
| | | | | 325 | | | | | 330 | | | | | 335 | |
| Lys | Val | Ser | Asn | Lys | Gly | Leu | Pro | Ser | Ser | Ile | Glu | Lys | Thr | Ile | Ser |
| | | | 340 | | | | | 345 | | | | | 350 | | |

```
Lys Ala Lys Gly Gln Pro Arg Glu Pro Gln Val Tyr Thr Leu Pro Pro
            355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
                420                 425                 430

Gln Glu Gly Asn Val Phe Ser Cys Ser Val Met His Glu Ala Leu His
            435                 440                 445

Asn His Tyr Thr Gln Lys Ser Leu Ser Leu Ser Leu Gly Lys
    450                 455                 460

<210> SEQ ID NO 56
<211> LENGTH: 443
<212> TYPE: PRT
<213> ORGANISM: Artificial Sequence
<220> FEATURE:
<223> OTHER INFORMATION: 313R20 Heavy chain (IgG4)

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Ser
            20                  25                  30

Tyr Met Ser Trp Ile Arg Gln Pro Pro Gly Lys Gly Leu Glu Trp Ile
        35                  40                  45

Gly Ile Ile Gly Ser Asn Gly Asn Thr Tyr Tyr Ala Asn Trp Ala Lys
    50                  55                  60

Gly Arg Val Thr Ile Ser Lys Ser Ser Asn Gln Val Ser Leu Lys Leu
65                  70                  75                  80

Ser Ser Val Thr Ala Ala Asp Thr Ala Val Tyr Tyr Cys Ala Arg Gly
                85                  90                  95

Gly Tyr Arg Thr Ser Gly Met Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

```
Cys Val Val Asp Val Ser Gln Glu Asp Pro Glu Val Gln Phe Asn
        260             265             270

Trp Tyr Val Asp Gly Val Glu Val His Asn Ala Lys Thr Lys Pro Arg
        275             280             285

Glu Glu Gln Phe Asn Ser Thr Tyr Arg Val Val Ser Val Leu Thr Val
        290             295             300

Leu His Gln Asp Trp Leu Asn Gly Lys Glu Tyr Lys Cys Lys Val Ser
305             310             315             320

Asn Lys Gly Leu Pro Ser Ser Ile Glu Lys Thr Ile Ser Lys Ala Lys
            325             330             335

Gly Gln Pro Arg Glu Pro Gln Val Tyr Thr Leu Pro Pro Ser Gln Glu
            340             345             350

Glu Met Thr Lys Asn Gln Val Ser Leu Thr Cys Leu Val Lys Gly Phe
            355             360             365

Tyr Pro Ser Asp Ile Ala Val Glu Trp Glu Ser Asn Gly Gln Pro Glu
            370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
            405             410             415

Asn Val Phe Ser Cys Ser Val Met His Glu Ala Leu His Asn His Tyr
            420             425             430

Thr Gln Lys Ser Leu Ser Leu Ser Leu Gly Lys
            435             440
```

<210> SEQ ID NO 57
<211> LENGTH: 7
<212> TYPE: PRT
<213> ORGANISM: Artificial Sequence
<220> FEATURE:
<223> OTHER INFORMATION: 313M26/313M32 Heavy chain CDR1

<400> SEQUENCE: 57

```
Thr Ser Asp Tyr Ala Trp Asn
1               5
```

<210> SEQ ID NO 58
<211> LENGTH: 16
<212> TYPE: PRT
<213> ORGANISM: Artificial Sequence
<220> FEATURE:
<223> OTHER INFORMATION: 313M26/313M32 Heavy chain CDR2

<400> SEQUENCE: 58

```
Tyr Ile Ser Tyr Ser Gly Ser Thr Ser Tyr Asn Pro Ser Leu Arg Ser
1               5                   10                  15
```

<210> SEQ ID NO 59
<211> LENGTH: 11
<212> TYPE: PRT
<213> ORGANISM: Artificial Sequence
<220> FEATURE:
<223> OTHER INFORMATION: 313M26/313M32 Heavy chain CDR3

<400> SEQUENCE: 59

```
Ala Arg Arg Gln Val Gly Leu Gly Phe Ala Tyr
1               5                   10
```

<210> SEQ ID NO 60
<211> LENGTH: 11

```
<212> TYPE: PRT
<213> ORGANISM: Artificial Sequence
<220> FEATURE:
<223> OTHER INFORMATION: 313M26/313M32 Light chain CDR1

<400> SEQUENCE: 60

Lys Ala Ser Gln Asp Val Ser Thr Ala Val Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: 313M26/313M32 Light chain CDR2

<400> SEQUENCE: 61

Ser Ala Ser Tyr Arg Tyr Thr
1               5

<210> SEQ ID NO 62
<211> LENGTH: 7
<212> TYPE: PRT
<213> ORGANISM: Artificial Sequence
<220> FEATURE:
<223> OTHER INFORMATION: 313M26/313M32 Light chain CDR3

<400> SEQUENCE: 62

Gln Gln His Tyr Ser Thr Pro
1               5

<210> SEQ ID NO 63
<211> LENGTH: 118
<212> TYPE: PRT
<213> ORGANISM: Artificial Sequence
<220> FEATURE:
<223> OTHER INFORMATION: 313M26 Heavy chain variable region

<400> SEQUENCE: 63

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Val Arg Gln Phe Pro Gly Asn Lys Leu Glu Trp
        35                  40                  45

Met Gly Tyr Ile Ser Tyr Ser Gly Ser Thr Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser
        115

<210> SEQ ID NO 64
<211> LENGTH: 99
<212> TYPE: PRT
<213> ORGANISM: Artificial Sequence
<220> FEATURE:
<223> OTHER INFORMATION: 313M26 Light chain variable region

<400> SEQUENCE: 64
```

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly

<210> SEQ ID NO 65
<211> LENGTH: 354
<212> TYPE: DNA
<213> ORGANISM: Artificial Sequence
<220> FEATURE:
<223> OTHER INFORMATION: 313M26 Heavy chain variable region

<400> SEQUENCE: 65
gatgtgcagc ttcaggagtc aggacctggc ctggtgaaac cttctcagtc tctgtccctc      60
acctgcactg tcactggcta ctcaatcacc agtgattatg cctggaactg ggtccggcag     120
tttccaggaa acaaactgga gtggatgggc tacataagct acagtggtag cactagctac     180
aacccatctc tcagaagtcg aatctctatc actcgagaca catccaagaa ccagttcttc     240
ctgcagttga attctgtgac tactgaggac acagccacat attactgtgc aaggagacag     300
gtcgggctgg ggtttgctta ctggggccaa gggactctgg tcactgtcag ctca           354

<210> SEQ ID NO 66
<211> LENGTH: 297
<212> TYPE: DNA
<213> ORGANISM: Artificial Sequence
<220> FEATURE:
<223> OTHER INFORMATION: 313M26 Light chain variable region

<400> SEQUENCE: 66
gacattgtga tgacccagtc tcacaaattc atgtccacat cagttggaga cagggtcagc      60
atcacctgca aggccagtca ggatgtgagt actgctgtag cctggtatca acagaaacca     120
ggacaatctc ctaaactact gatttactcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctccgtggac gttcggt        297

<210> SEQ ID NO 67
<211> LENGTH: 118
<212> TYPE: PRT
<213> ORGANISM: Artificial Sequence
<220> FEATURE:
<223> OTHER INFORMATION: 313M32 Heavy chain variable region

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
            35                  40                  45

Ile Gly Tyr Ile Ser Tyr Ser Gly Ser Thr Ser Tyr Asn Pro Ser Leu
 50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
                100                 105                 110

Leu Val Thr Val Ser Ser
            115

<210> SEQ ID NO 68
<211> LENGTH: 99
<212> TYPE: PRT
<213> ORGANISM: Artificial Sequence
<220> FEATURE:
<223> OTHER INFORMATION: 313M32 Light chain variable region

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly

<210> SEQ ID NO 69
<211> LENGTH: 467
<212> TYPE: PRT
<213> ORGANISM: Artificial Sequence
<220> FEATURE:
<223> OTHER INFORMATION: 313M32 Heavy chain (IgG1)
<220> FEATURE:
<221> NAME/KEY: SIGNAL
<222> LOCATION: (1)..(19)

<400> SEQUENCE: 69

Met Asp Trp Thr Trp Arg Ile Leu Phe Leu Val Ala Ala Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
            35                  40                  45

Thr Ser Asp Tyr Ala Trp Asn Trp Ile Arg Gln Pro Pro Gly Lys Gly
 50                  55                  60

Leu Glu Trp Ile Gly Tyr Ile Ser Tyr Ser Gly Ser Thr Ser Tyr Asn
65                  70                  75                  80

Pro Ser Leu Arg Ser Arg Val Thr Ile Ser Arg Asp Thr Ser Lys Asn
                85                  90                  95

```
Gln Phe Phe Leu Lys Leu Ser Ser Val Thr Ala Ala Asp Thr Ala Val
                100                 105                 110

Tyr Tyr Cys Ala Arg Arg Gln Val Gly Leu Gly Phe Ala Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 70
<211> LENGTH: 448
<212> TYPE: PRT
<213> ORGANISM: Artificial Sequence
<220> FEATURE:
<223> OTHER INFORMATION: 313M32 Heavy chain (IgG1)
```

<400> SEQUENCE: 70

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Ser Tyr Asn Pro Ser Leu
    50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
```

405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445

<210> SEQ ID NO 71
<211> LENGTH: 234
<212> TYPE: PRT
<213> ORGANISM: Artificial Sequence
<220> FEATURE:
<223> OTHER INFORMATION: 313M32 Light chain
<220> FEATURE:
<221> NAME/KEY: SIGNAL
<222> LOCATION: (1)..(20)

<400> SEQUENCE: 71

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Gln Gln His Tyr
            100                 105                 110

Ser Thr Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 72
<211> LENGTH: 214
<212> TYPE: PRT
<213> ORGANISM: Artificial Sequence
<220> FEATURE:
<223> OTHER INFORMATION: 313M32 Light chain

<400> SEQUENCE: 72

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 73
<211> LENGTH: 354
<212> TYPE: DNA
<213> ORGANISM: Artificial Sequence
<220> FEATURE:
<223> OTHER INFORMATION: 313M32 Heavy chain variable region

<400> SEQUENCE: 73

```
caggtccagc tgcaggagtc tggcccagga ctggtgaagc cttctgagac cctgtccctc      60
acctgcgctg tctctggtta ctccatcacc tccgattatg cctggaactg gattcggcag     120
cccccaggga aggggctgga gtggattggg tacataagct actctggtag cactagctac     180
aacccatctc tccggtcacg ggtcacaata tcacgggaca catccaagaa ccagttcttc     240
ctgaagctgt cctctgtgac cgccgctgac accgccgtgt attactgtgc aaggagacag     300
gtcgggctgg ggtttgctta ctggggccaa ggaaccctgg tcaccgtcag ctca           354
```

<210> SEQ ID NO 74
<211> LENGTH: 297
<212> TYPE: DNA
<213> ORGANISM: Artificial Sequence
<220> FEATURE:
<223> OTHER INFORMATION: 313M32 Light chain variable region

<400> SEQUENCE: 74

```
gacatccaga tgacccagtc tccatcctcc ctgtctgcat ctgttggaga cagagtcacc      60
atcacttgca aggcttctca ggatgtgtct actgctgttg cctggtatca gcagaaacca     120
gggaaagccc ctaagctcct gatctactct gcatcctatc ggtacactgg ggtcccatca     180
aggttctccg gatctggatc tgggacagat tttactttca ccatcagcag cctgcagcct     240
```
gaagatattg caacatatta ctgtcagcaa cattattcta ctccttggac attcggc    297

<210> SEQ ID NO 75
<211> LENGTH: 1404
<212> TYPE: DNA
<213> ORGANISM: Artificial Sequence
<220> FEATURE:
<223> OTHER INFORMATION: 313M32 Heavy chain (IgG1)

<400> SEQUENCE: 75
atggactgga cctggaggat actctttctc gtggctgcag ccacaggagc ccactcccag     60
gtccagctgc aggagtctgg cccaggactg gtgaagcctt ctgagaccct gtccctcacc    120
tgcgctgtct ctggttactc catcacctcc gattatgcct ggaactggat tcggcagccc    180
ccagggaagg gctggagtg gattgggtac ataagctact ctggtagcac tagctacaac    240
ccatctctcc ggtcacgggt cacaatatca cgggacacat ccaagaacca gttcttcctg    300
aagctgtcct ctgtgaccgc cgctgacacc gccgtgtatt actgtgcaag agacaggtc    360
gggctgggggt ttgcttactg gggccaagga acccctggtca ccgtcagctc agccagcaca    420
aagggcccct ccgtgttccc tctggcccct cctccaagt ccacctccgg cggcaccgcc    480
gctctgggct gcctggtgaa ggactacttc cctgagcctg tgaccgtgtc ctggaactct    540
ggcgccctga cctctggcgt gcacaccttc ccagccgtgc tgcagtcctc cggcctgtac    600
tccctgtcct ccgtggtgac cgtgccttcc tcctccctgg gcacccagac ctacatctgc    660
aacgtgaacc acaagccttc caacaccaag gtggacaagc gggtggagcc taagtcctgc    720
gacaagaccc acacctgccc tccctgccct ggccctgagc tgctgggcgg accttccgtg    780
ttcctgttcc ctcctaagcc taaggacacc ctgatgatct cccggacccc tgaggtgacc    840
tgcgtggtgg tggacgtgtc ccacgaggat cctgaggtga agttcaattg gtacgtggac    900
ggcgtggagg tgcacaacgc taagaccaag ccaagggagg agcagtacaa ctccacctac    960
cgggtggtgt ctgtgctgac cgtgctgcac caggactggc tgaacggcaa agaatacaag    1020
tgcaaggtct ccaacaaggc cctgcccgct cccatcgaga aaaccatctc caaggccaag    1080
ggccagcctc gcgagcctca ggtgtacacc ctgccaccca gcgggagga gatgaccaag    1140
aaccaggtgt ccctgacctg tctggtgaag ggcttctacc cttccgatat cgccgtggag    1200
tgggagtcta acggcagcc cgagaacaac tacaagacca cccctcctgt gctggactcc    1260
gacggctcct tcttcctgta ctccaagctg accgtggaca agtcccggtg gcagcagggc    1320
aacgtgttct cctgctccgt gatgcacgag gccctgcaca accactacac ccagaagagc    1380
ctgtctctgt ctcctggcaa gtga    1404

<210> SEQ ID NO 76
<211> LENGTH: 705
<212> TYPE: DNA
<213> ORGANISM: Artificial Sequence
<220> FEATURE:
<223> OTHER INFORMATION: 313M32 Light chain

<400> SEQUENCE: 76
atggtgctcc agacccaggt cttcatttcc ctgctgctct ggatcagcgg agcctacggg     60
gacatccaga tgacccagtc tccatcctcc ctgtctgcat ctgttggaga cagagtcacc    120
atcacttgca aggcttctca ggatgtgtct actgctgttg cctggtatca gcagaaacca    180
gggaaagccc ctaagctcct gatctactct gcatcctatc ggtacactgg ggtcccatca    240
aggttctccg gatctggatc tgggacagat tttactttca ccatcagcag cctgcagcct    300

```
gaagatattg caacatatta ctgtcagcaa cattattcta ctccttggac attcggccaa    360
gggaccaagg tggaaatcaa acgtacggtg gctgcaccat ctgtcttcat cttccctcca    420
tctgatgagc agctcaaatc tggaactgcc tctgttgtgt gcctgctgaa taacttctat    480
cccagagagg ccaaagtcca gtggaaggtg gataacgccc tccaatccgg caactcccag    540
gagagtgtca cagagcagga cagcaaggac agcacctaca gcctcagcaa caccctgaca    600
ctgagcaaag cagactacga aaacacaaa gtctatgcct gcgaagtcac ccatcagggc    660
ctgtcttccc ccgtcacaaa gagcttcaac aggggagagt gctaa                  705
```

<210> SEQ ID NO 77
<211> LENGTH: 245
<212> TYPE: PRT
<213> ORGANISM: Artificial Sequence
<220> FEATURE:
<223> OTHER INFORMATION: Cynomolgus monkey TIGIT

<400> SEQUENCE: 77

```
Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile Pro Leu Leu
    130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Glu Gln Ile Pro
            180                 185                 190

Ser Ala Pro Ser Pro Gly Ser Cys Val Gln Ala Glu Ala Ala Pro
        195                 200                 205

Ala Gly Leu Cys Gly Glu Gln Gln Gly Asp Asp Cys Ala Glu Leu His
    210                 215                 220

Asp Tyr Phe Asn Val Leu Ser Tyr Arg Ser Leu Gly Ser Cys Ser Phe
225                 230                 235                 240

Phe Thr Glu Thr Gly
            245
```

<210> SEQ ID NO 78
<211> LENGTH: 245
<212> TYPE: PRT
<213> ORGANISM: Artificial Sequence
<220> FEATURE:

<223> OTHER INFORMATION: Rhesus monkey TIGIT

<400> SEQUENCE: 78

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile Pro Leu Leu
130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Glu Gln Ile Pro
            180                 185                 190

Ser Ala Pro Ser Pro Pro Gly Ser Cys Val Gln Ala Glu Ala Ala Pro
        195                 200                 205

Ala Gly Leu Cys Gly Glu Gln Gln Gly Asp Asp Cys Ala Glu Leu His
210                 215                 220

Asp Tyr Phe Asn Val Leu Ser Tyr Arg Ser Leu Gly Ser Cys Ser Phe
225                 230                 235                 240

Phe Thr Glu Thr Gly
            245

<210> SEQ ID NO 79
<211> LENGTH: 16
<212> TYPE: PRT
<213> ORGANISM: Artificial Sequence
<220> FEATURE:
<223> OTHER INFORMATION: Human TIGIT amino acids 55-70

<400> SEQUENCE: 79

Thr Gln Val Asn Trp Glu Gln Gln Asp Gln Leu Leu Ala Ile Cys Asn
1               5                   10                  15

<210> SEQ ID NO 80
<211> LENGTH: 18
<212> TYPE: PRT
<213> ORGANISM: Artificial Sequence
<220> FEATURE:
<223> OTHER INFORMATION: Human TIGIT amino acids 105-122

<400> SEQUENCE: 80

Glu Tyr Phe Cys Ile Tyr His Thr Tyr Pro Asp Gly Thr Tyr Thr Gly
1               5                   10                  15

Arg Ile

<210> SEQ ID NO 81
<211> LENGTH: 12
<212> TYPE: PRT
<213> ORGANISM: Artificial Sequence
<220> FEATURE:
<223> OTHER INFORMATION: 313R14/313R19 Light chain CDR1

<400> SEQUENCE: 81

Gln Ala Ser Gln Asn Ile Tyr Ser Asp Leu Ala Trp
1               5                   10

<210> SEQ ID NO 82
<211> LENGTH: 445
<212> TYPE: PRT
<213> ORGANISM: Artificial Sequence
<220> FEATURE:
<223> OTHER INFORMATION: 313M33 Heavy chain (IgG4) without signal
      sequence

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Tyr Asn Pro Ser Leu
    50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 83
<211> LENGTH: 464
<212> TYPE: PRT
<213> ORGANISM: Artificial Sequence
<220> FEATURE:
<223> OTHER INFORMATION: 313M33 Heavy chain (IgG4) with signal sequence

<400> SEQUENCE: 83

Met Asp Trp Thr Trp Arg Ile Leu Phe Leu Val Ala Ala Ala Thr Gly
1               5                   10                  15
Ala His Ser Gln Val Gln Leu Gln Glu Ser Gly Pro Gly Leu Val Lys
            20                  25                  30
Pro Ser Glu Thr Leu Ser Leu Thr Cys Ala Val Ser Gly Tyr Ser Ile
        35                  40                  45
Thr Ser Asp Tyr Ala Trp Asn Trp Ile Arg Gln Pro Pro Gly Lys Gly
    50                  55                  60
Leu Glu Trp Ile Gly Tyr Ile Ser Tyr Ser Gly Ser Thr Ser Tyr Asn
65                  70                  75                  80
Pro Ser Leu Arg Ser Arg Val Thr Ile Ser Arg Asp Thr Ser Lys Asn
                85                  90                  95
Gln Phe Phe Leu Lys Leu Ser Ser Val Thr Ala Ala Asp Thr Ala Val
            100                 105                 110
Tyr Tyr Cys Ala Arg Arg Gln Val Gly Leu Gly Phe Ala Tyr Trp Gly
        115                 120                 125
Gln Gly Thr Leu Val Thr Val Ser Ser Ala Ser Thr Lys Gly Pro Ser
    130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205

Pro Ser Ser Leu Gly Thr Lys Thr Tyr Thr Cys Asn Val Asp His
    210             215                 220

Lys Pro Ser Asn Thr Lys Val Asp Lys Arg Val Glu Ser Lys Tyr Gly
225             230                 235                 240

Pro Pro Cys Pro Pro Cys Pro Ala Pro Glu Phe Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser Gln Glu Asp Pro
        275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305             310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Arg Leu Thr Val Asp Lys Ser
        420                 425                 430

Arg Trp Gln Glu Gly Asn Val Phe Ser Cys Ser Val Met His Glu Ala
    435                 440                 445

Leu His Asn His Tyr Thr Gln Lys Ser Leu Ser Leu Ser Leu Gly Lys
        450                 455                 460

<210> SEQ ID NO 84
<211> LENGTH: 1395
<212> TYPE: DNA
<213> ORGANISM: Artificial Sequence
<220> FEATURE:
<223> OTHER INFORMATION: 313M33 Heavy chain (IgG4)

<400> SEQUENCE: 84
atggactgga cctggaggat actctttctc gtggctgcag ccacaggagc ccactcccag    60
gtccagctgc aggagtctgg cccaggactg gtgaagcctt ctgagaccct gtccctcacc   120
tgcgctgtct ctggttactc catcacctcc gattatgcct ggaactggat tcggcagccc   180
ccagggaagg gctggagtg gattgggtac ataagctact ctggtagcac tagctacaac   240
ccatctctcc ggtcacgggt cacaatatca cgggacacat ccaagaacca gttcttcctg   300
aagctgtcct ctgtgaccgc cgctgacacc gccgtgtatt actgtgcaag agacaggtc   360 gggctggggt ttgcttactg gggccaagga accctggtca ccgtcagctc agccagcaca   420
aagggcccat ccgtcttccc cctggcaccc tgctcccgga gcacctccga gagcacagcc   480
gccctgggct gcctggtcaa ggactacttc cccgaacccg ttaccgtgtc ttggaactcc   540
ggcgcactga ccagcggcgt gcacaccttc cctgctgtcc tccaatcctc tggactctac   600
tccctctcct ccgtggtgac agtgccctcc agcagcctgg gcactaagac ctacacctgc   660

```
aacgtcgatc acaagcccag caacaccaag gtggacaaga gagttgagtc caaatatgga      720
cccccatgcc caccttgccc agcacctgag ttcctggggg gaccatcagt cttcctgttc      780
cccccaaaac ccaaggacac tctcatgatc tcccggaccc ctgaggtcac ttgcgtggtg      840
gtggacgtga gccaggaaga ccccgaggtc cagttcaact ggtatgtgga tggcgtggag      900
gttcataatg ccaagacaaa gcctcgggag gagcagttca acagcaccta ccgggtggtc      960
agcgtcctca ccgtcctgca ccaagactgg ctgaacggca aggagtacaa gtgcaaggtc     1020
tccaacaaag gctcccatc ctccatcgag aaaaccatct ccaaagccaa agggcagccc     1080
cgggagccac aggtgtacac cctgccccca tccaagagg agatgaccaa gaaccaagtg     1140
tccctgacct gcctggtcaa aggcttctac cccagcgaca tcgccgtgga gtgggagagc     1200
aatgggcagc ctgagaacaa ctacaagacc actcctcccg tgctggactc cgacggctcc     1260
ttcttcctct actcccggct caccgtggac aagagcaggt ggcaggaggg caatgtcttc     1320
tcctgctccg tgatgcatga ggctctgcac aaccactaca cacagaagag cctctccctg     1380
tctctgggca aatga                                                      1395
```

US 10,112,997 B2

TIGHT-BINDING AGENTS AND USES THEREOF

CROSS-REFERENCE TO RELATED APPLICATIONS

This application claims the priority benefit of U.S. Provisional Application No. 62/167,582, filed May 28, 2015, U.S. Provisional Application No. 62/205,279, filed Aug. 14, 2015, and U.S. Provisional Application No. 62/313,487, filed Mar. 25, 2016, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 2293_1400003_SL; Size: 139,587 bytes; and Date of Creation: Sep. 5, 2016) is herein incorporated by reference in its entirety.

FIELD OF THE INVENTION

The present invention generally relates to agents that bind TIGIT, particularly antibodies that specifically bind the extracellular domain of TIGIT, as well as to methods of using the agents for the modulation of immune responses and/or the treatment of diseases such as cancer.

BACKGROUND OF THE INVENTION

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include agents and methods to induce or enhance specific immune responses or to inhibit or reduce specific immune responses.

The immune system is a highly complex system made up of a great number of cell types, including but not limited to, T-cells, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases).

The concept of cancer immunosurveillance is based on the theory that the immune system can recognize tumor cells, mount an immune response, and suppress the development and/or progression of a tumor. However, it is clear that many cancerous cells have developed mechanisms to evade the immune system which can allow for uninhibited growth of tumors. Cancer/tumor immunotherapy focuses on the development of new and novel agents that can activate and/or boost the immune system to achieve a more effective attack against tumor cells resulting in increased killing of tumor cells and/or inhibition of tumor growth.

BRIEF SUMMARY OF THE INVENTION

The present invention provides a variety of agents that bind T-cell immunoreceptor with Ig and ITIM domains (TIGIT), including, but not limited to, antibodies that specifically bind the extracellular domain of TIGIT. In certain embodiments, the agent is a TIGIT antagonist. The invention provides methods of using the agents. In some embodiments, the invention provides methods of using the agents for immunotherapy. In some embodiments, the invention provides methods of using the agents for cancer immunotherapy. In some embodiments, the agents are used in methods of inducing, activating, promoting, increasing, enhancing, or prolonging an immune response. In some embodiments, the agents are used in methods of inducing, activating, promoting, increasing, enhancing, or prolonging an immune response to cancer and/or a tumor. In some embodiments, the agents are used in methods of inhibiting the growth of a tumor or tumor cells. In some embodiments, the agents are used in methods for the treatment of cancer. In some embodiments, the methods comprise inhibiting the growth of cancer cells. In some embodiments, the agents are used in combination with at least one additional therapeutic agent.

The invention also provides compositions, such as pharmaceutical compositions, comprising the agents described herein. Polynucleotides and/or vectors encoding the agents and methods of making the agents are also provided. Cells comprising or producing the agents described herein are provided as well as cells comprising the polynucleotides and/or the vectors described herein.

In one aspect, the present invention provides agents that bind TIGIT. In some embodiments, the agent binds mouse TIGIT. In some embodiments, the agent binds human TIGIT. In some embodiments, the agent binds mouse TIGIT and human TIGIT. In some embodiments, the agent is an antibody. In some embodiments, the agent is an antibody that binds mouse TIGIT. In some embodiments, the agent is an antibody that binds human TIGIT. In some embodiments, the agent is an antibody that binds mouse TIGIT and human TIGIT. In some embodiments, the agent is an antibody that binds human TIGIT and does not bind mouse TIGIT.

In some embodiments, the agent is an antibody that specifically binds the extracellular domain of TIGIT, which comprises a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9), and/or a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16). In some embodiments, the agent is an antibody that comprises a heavy chain CDR1 comprising GSSLSSSYMS (SEQ ID NO:7), a heavy chain CDR2 comprising IIGSNGNTYYANWAKG (SEQ ID NO:8), and a heavy chain CDR3 comprising GGYRTSGMDP (SEQ ID NO:9), and/or a light chain CDR1 comprising QASQSISSYLNW (SEQ ID NO:10), a light chain CDR2 comprising DALKLAS (SEQ ID NO:11), and a light chain CDR3 comprising QQEHSVGNVDN (SEQ ID NO:12). In other embodiments, the agent is an antibody that comprises a heavy chain CDR1 comprising GFSLSSSYMS (SEQ ID NO:13), a heavy chain CDR2 comprising IIGSNGNTYYANWAKG (SQ ID NO:8), and a heavy chain CDR3 comprising GGYRTSGMDP (SEQ ID NO:9); and/or a light chain CDR1 comprising QASQSNIYSDLAW (SEQ ID NO:14), a light chain CDR2 comprising RASTLAS (SEQ ID NO:15), and a light chain CDR3 comprising QQEHLVAWIYN (SEQ ID NO:16). In other embodiments, the agent is an antibody that comprises a heavy chain CDR1 comprising GFSLSSSYMS (SEQ ID NO:13), a heavy chain CDR2 comprising IIGSNGNTYYANWAKG (SQ ID NO:8), and a heavy chain CDR3 comprising GGYRTSGMDP (SEQ ID NO:9); and/or a light chain CDR1 comprising QASQNIYSDLAW (SEQ ID NO:81), a light chain CDR2 comprising RASTLAS (SEQ ID NO:15), and a light chain CDR3 comprising QQEHLVAWIYN (SEQ ID NO:16).

In some embodiments, the agent is an antibody that specifically binds the extracellular domain of TIGIT, wherein the antibody comprises a heavy chain variable region having at least 90% sequence identity to SEQ ID NO:17, SEQ ID NO:19, or SEQ ID NO:32; and/or a light chain variable region having at least 90% sequence identity to SEQ ID NO:18 or SEQ ID NO:20. In some embodiments, the antibody comprises a heavy chain variable region having at least 95% sequence identity to SEQ ID NO:17, SEQ ID NO:19, or SEQ ID NO:32; and/or a light chain variable region having at least 95% sequence identity to SEQ ID NO:18 or SEQ ID NO:20. In some embodiments, the antibody comprises a heavy chain variable region comprising SEQ ID NO:17 and a light chain variable region comprising SEQ ID NO:18; a heavy chain variable region comprising SEQ ID NO:19 and a light chain variable region comprising SEQ ID NO:20; or a heavy chain variable region comprising SEQ ID NO:32 and a light chain variable region comprising SEQ ID NO:20.

In some embodiments, the agent is an antibody that specifically binds the extracellular domain of human TIGIT, which comprises a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59), and/or a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

In some embodiments, the agent is an antibody that specifically binds the extracellular domain of TIGIT, wherein the antibody comprises a heavy chain variable region having at least 90% sequence identity to SEQ ID NO:63 or SEQ ID NO:67; and/or a light chain variable region having at least 90% sequence identity to SEQ ID NO:64 or SEQ ID NO:68. In some embodiments, an antibody comprises a heavy chain variable region having at least 95% sequence identity to SEQ ID NO:63 or SEQ ID NO:67; and/or a light chain variable region having at least 95% sequence identity to SEQ ID NO:64 or SEQ ID NO:68. In some embodiments, an antibody comprises a heavy chain variable region comprising SEQ ID NO:63 and a light chain variable region comprising SEQ ID NO:64, or a heavy chain variable region comprising SEQ ID NO:67 and a light chain variable region comprising SEQ ID NO:68.

In some embodiments, the agent is an antibody which is a monoclonal antibody, a humanized antibody, a human antibody, a recombinant antibody, a chimeric antibody, a bispecific antibody, an antibody fragment comprising an antigen-binding site, an IgG antibody, an IgG1 antibody, an IgG2 antibody, or an IgG4 antibody. In some embodiments, the antibody is monovalent. In some embodiments, the antibody is bivalent. In some embodiments, the antibody is monospecific. In some embodiments, the antibody is bispecific.

In some embodiments, the agent is an antibody that specifically binds TIGIT, wherein the antibody comprises a heavy chain amino acid sequence selected from the group consisting of: SEQ ID NO:26, SEQ ID NO:27, SEQ ID NO:29, SEQ ID NO:34, and SEQ ID NO:56; and a light chain amino acid sequence selected from the group consisting of: SEQ ID NO:28 and SEQ ID NO:30. In some embodiments, the antibody comprises a heavy chain amino acid sequence of SEQ ID NO:26 and a light chain amino acid sequence of SEQ ID NO:28; a heavy chain amino acid sequence of SEQ ID NO:27 and a light chain amino acid sequence of SEQ ID NO:28; a heavy chain amino acid sequence of SEQ ID NO:29 and a light chain amino acid sequence of SEQ ID NO:30; a heavy chain amino acid sequence of SEQ ID NO:34 and a light chain amino acid sequence of SEQ ID NO:30; or a heavy chain amino acid sequence of SEQ ID NO:56 and a light chain amino acid sequence of SEQ ID NO:30.

In some embodiments, an antibody that specifically binds human TIGIT comprises a heavy chain amino acid sequence of SEQ ID NO:70 and a light chain amino acid sequence of SEQ ID NO:72. In some embodiments, an antibody that specifically binds human TIGIT comprises a heavy chain amino acid sequence of SEQ ID NO:82 and a light chain amino acid sequence of SEQ ID NO:72.

In some embodiments an antibody that specifically binds human TIGIT, does not bind mouse TIGIT. In some embodiments an antibody that specifically binds human TIGIT, does not bind rat TIGIT. In some embodiments an antibody that specifically binds human TIGIT, does not bind rabbit TIGIT. In some embodiments an antibody that specifically binds human TIGIT, does not bind marmoset TIGIT. In some embodiments an antibody that specifically binds human TIGIT, does not bind dog TIGIT. In some embodiments an antibody that specifically binds human TIGIT, does not bind pig TIGIT. In some embodiments an antibody that specifically binds human TIGIT, does not bind cynomolgus monkey TIGIT. In some embodiments an antibody that specifically binds human TIGIT, does not bind rhesus monkey TIGIT.

In some embodiments, the agent is an antibody that specifically binds TIGIT, wherein the antibody comprises the heavy chain variable region and the light chain variable region from an antibody selected from the group consisting of: 313R11, 313R12, 313R14, 313R19, and 313R20. In some embodiments, the antibody is selected from the group consisting of: 313R11, 313R12, 313R14, 313R19, and 313R20. In some embodiments, the antibody is 313R19. In some embodiments, the antibody comprises the heavy chain variable region encoded by the plasmid deposited with ATCC as PTA-122180. In some embodiments, the antibody comprises the light chain variable region encoded by the plasmid deposited with ATCC as PTA-122181. In some embodiments, the antibody comprises a heavy chain comprising the heavy chain variable region encoded by the plasmid deposited with ATCC as PTA-122180. In some embodiments, the antibody comprises a light chain comprising the light chain variable region encoded by the plasmid deposited with ATCC as PTA-122181. In some embodiments, the antibody comprises the heavy chain variable region encoded by the plasmid deposited with ATCC as PTA-122180 and the light chain variable region encoded by the plasmid deposited with ATCC as PTA-122181. In some embodiments, the antibody comprises a polypeptide encoded by the plasmid deposited with ATCC as PTA-122180 and a polypeptide encoded by the plasmid deposited with ATCC as PTA-122181.

In another aspect, the invention provides a plasmid deposited with ATCC and assigned designation number PTA- 122180 and a plasmid deposited with ATCC and assigned designation number PTA-122181.

In some embodiments, an antibody that specifically binds human TIGIT comprises the heavy chain variable region and the light chain variable region from antibody 313M32. In some embodiments, the antibody comprises the heavy chain variable region encoded by the plasmid deposited with ATCC as PTA-122346. In some embodiments, the antibody comprises a polypeptide comprising the heavy chain variable region encoded by the plasmid deposited with ATCC as PTA-122346. In some embodiments, the antibody comprises the light chain variable region encoded by the plasmid deposited with ATCC as PTA-122347. In some embodiments, the antibody comprises the light chain encoded by the plasmid deposited with ATCC as PTA-122347. In some embodiments, the antibody comprises the heavy chain variable region encoded by the plasmid deposited with ATCC as PTA-122346 and the light chain variable region encoded by the plasmid deposited with ATCC as PTA-122347. In some embodiments, the antibody comprises a polypeptide encoded by the plasmid deposited with ATCC as PTA-122346 and a polypeptide encoded by the plasmid deposited with ATCC as PTA-122347.

In another aspect, the invention provides a plasmid deposited with ATCC and assigned designation number PTA-122346 and a plasmid deposited with ATCC and assigned designation number PTA-122347.

In some embodiments of each of the aforementioned aspects and embodiments, as well as other aspects and embodiments described herein, the agent is monovalent. In some embodiments, the agent is bivalent. In some embodiments, the agent is monospecific. In some embodiments, the agent is bispecific. In some embodiments, the bispecific agent is a heterodimeric agent or heterodimeric molecule. In some embodiments, a heterodimeric agent comprises an antibody described herein that specifically binds TIGIT.

In another aspect, the invention provides an isolated antibody that competes for specific binding to human TIGIT with an agent (e.g., antibody) described herein. In some embodiments, an isolated antibody binds the same epitope on human TIGIT as an agent (e.g., antibody) described herein. In some embodiments, an isolated antibody binds an epitope on human TIGIT that overlaps with the epitope on TIGIT bound by an agent (e.g., antibody) described herein. In some embodiments, an antibody that specifically binds human TIGIT binds an epitope comprising amino acids within SEQ ID NO:79. In some embodiments, an antibody that specifically binds human TIGIT binds an epitope comprising amino acids within SEQ ID NO:80. In some embodiments, an antibody that specifically binds human TIGIT binds an epitope comprising amino acids within SEQ ID NO:79 and SEQ ID NO:80. In some embodiments, an antibody that specifically binds human TIGIT binds an epitope comprising amino acids Q62 and I109 of SEQ ID NO:4. In some embodiments, an antibody that specifically binds human TIGIT binds an epitope comprising amino acids Q62 and T119 of SEQ ID NO:4. In some embodiments, an antibody that specifically binds human TIGIT binds an epitope comprising amino acids Q64 and I109 of SEQ ID NO:4. In some embodiments, an antibody that specifically binds human TIGIT binds an epitope comprising amino acids Q64 and T119 of SEQ ID NO:4. In some embodiments, an antibody that specifically binds human TIGIT binds an epitope comprising amino acids Q62, Q64, and I109 of SEQ ID NO:4. In some embodiments, an antibody that specifically binds human TIGIT binds an epitope comprising amino acids Q62, Q64, and T119 of SEQ ID NO:4. In some embodiments, an antibody that specifically binds human TIGIT binds an epitope comprising amino acids Q62, I109, and T119 of SEQ ID NO:4. In some embodiments, an antibody that specifically binds human TIGIT binds an epitope comprising amino acids Q64, I109, and T119 of SEQ ID NO:4. In some embodiments, an antibody that specifically binds human TIGIT binds an epitope comprising amino acids Q62, Q64, I109, and T119 of SEQ ID NO:4. In some embodiments, an antibody that specifically binds human TIGIT binds an epitope comprising at least one amino acid selected from the group consisting of: N58, E60, Q62, Q64, L65, F107, I109, H111, T117, T119, G120, and R121 of SEQ ID NO:4. In some embodiments, the epitope is a conformational epitope. In some embodiments, an antibody that specifically binds human TIGIT binds an epitope that does not comprise amino acid V100 of SEQ ID NO:4.

In some embodiments of each of the aforementioned aspects and embodiments, as well as other aspects and embodiments described herein, the agent that specifically binds TIGIT is an antibody, wherein the antibody is part of a bispecific agent. In some embodiments, a bispecific agent comprises a first arm which binds TIGIT and a second arm which binds a second target. In some embodiments, a bispecific agent comprises a first arm that specifically binds TIGIT and a second arm, wherein the first arm comprises an anti-TIGIT antibody described herein. In some embodiments, a bispecific agent comprises a first arm that binds TIGIT and a second arm which comprises an antigen-binding site from an antibody. In some embodiments, a bispecific agent comprises a first arm that binds TIGIT and a second arm that specifically binds PD-1, PD-L1, CTLA4, TIM-3, LAG-3, OX-40, or GITR. In some embodiments, a bispecific agent comprises a first arm that binds TIGIT and a second arm that specifically binds a tumor antigen. In some embodiments, a bispecific agent comprises a first arm that binds TIGIT and a second arm that comprises an immune response stimulating agent. In some embodiments, the immune response stimulating agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA4 antibody, anti-PD-1 antibody, anti-PD-L1 antibody, anti-GITR antibody, anti-OX-40 antibody, anti-LAG-3 antibody, and anti-TIM-3 antibody.

In some embodiments, the bispecific agent is a heterodimeric agent or heterodimeric molecule. In some embodiments, the bispecific agent is a homodimeric agent or homodimeric molecule. In some embodiments, a heterodimeric molecule comprises a first arm which binds human TIGIT and a second arm which binds a second target. In some embodiments, a heterodimeric molecule comprises a first arm that specifically binds human TIGIT and a second arm, wherein the first arm comprises an anti-TIGIT antibody described herein. In some embodiments, a heterodimeric molecule comprises a first arm that binds human TIGIT and a second arm which comprises an antigen-binding site from an antibody that specifically binds a second target. In some embodiments, a heterodimeric molecule is a bispecific antibody. In some embodiments, a heterodimeric molecule comprises a first arm that binds human TIGIT and a second arm that specifically binds a tumor antigen. In some embodiments, a heterodimeric molecule comprises a first arm that binds human TIGIT and a second arm that specifically binds PD-1, PD-L1, CTLA-4, TIM-3, LAG-3, OX-40, 4-1BB, or GITR. In some embodiments, a heterodimeric molecule comprises a first arm that binds TIGIT and a second arm that comprises an immunotherapeutic agent. In some embodiments, the immunotherapeutic agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA-4 antibody, anti-PD-1 antibody, anti-PD-L1 antibody, anti-4-1BB antibody, anti-GITR antibody, anti-OX-40 antibody, anti-LAG-3 antibody, and anti-TIM-3 antibody.

In some embodiments, a heterodimeric molecule described herein comprises a first arm comprising a first CH3 domain and a second arm comprising a second CH3 domain wherein each CH3 domain is modified to promote formation of heterodimers. In some embodiments, the CH3 domains are modified based upon electrostatic effects. In some embodiments, the CH3 domains are modified using a knobs-into-holes technique.

In some embodiments, a bispecific agent described herein comprises a first arm comprising a first CH3 domain and a second arm comprising a second CH3 domain wherein each CH3 domain is modified to promote formation of heterodimers. In some embodiments, the CH3 domains are modified based upon electrostatic effects. In some embodiments, the CH3 domains are modified using a knobs-into-holes technique.

In some embodiments of each of the aforementioned aspects and embodiments, as well as other aspects and embodiments described herein, an agent described herein specifically binds TIGIT and inhibits binding of TIGIT to poliovirus receptor (PVR). In some embodiments, an agent specifically binds TIGIT and inhibits or blocks the interaction between TIGIT and PVR. In some embodiments, an agent specifically binds TIGIT and inhibits binding of TIGIT to PVR-L2. In some embodiments, an agent specifically binds TIGIT and inhibits or blocks the interaction between TIGIT and PVR-L2. In some embodiments, an agent specifically binds TIGIT and inhibits binding of TIGIT to PVR-L3. In some embodiments, an agent specifically binds TIGIT and inhibits or blocks the interaction between TIGIT and PVR-L3. In some embodiments, the agent is an antagonist of TIGIT. In some embodiments, an agent specifically binds TIGIT and inhibits TIGIT signaling. In some embodiments, an agent specifically binds TIGIT and is an antagonist of TIGIT-mediated signaling. In some embodiments, an agent specifically binds TIGIT and inhibits TIGIT activation. In some embodiments, an agent specifically binds TIGIT and inhibits phosphorylation of TIGIT. In some embodiments, an agent specifically binds TIGIT and decreases cell surface expression of TIGIT.

In some embodiments of each of the aforementioned aspects and embodiments, as well as other aspects and embodiments described herein, an agent described herein specifically binds TIGIT and induces, activates, promotes, increases, enhances, and/or prolongs an immune response. In some embodiments, the immune response is directed to a tumor or tumor cell. In some embodiments, the immune response is directed to a virus or a virally-infected cell. In some embodiments, the agent increases cell-mediated immunity. In some embodiments, the agent increases T-cell activity. In some embodiments, the agent increases cytolytic T-cell (CTL) activity. In some embodiments, the agent increases natural killer (NK) cell activity. In some embodiments, the agent increases IL-2 production and/or the number of IL-2-producing cells. In some embodiments, the agent increases IFN-gamma production and/or the number of IFN-gamma-producing cells. In some embodiments, the agent increases a Th1-type immune response. In some embodiments, the agent decreases IL-4 production and/or the number of IL-4-producing cells. In some embodiments, the agent decreases IL-10 and/or the number of IL-10-producing cells. In some embodiments, the agent decreases IL-6 production and/or the number of IL-6-producing cells. In some embodiments, the agent decreases IL-5 production and/or the number of IL-5-producing cells. In some embodiments, the agent decreases a Th2-type immune response. In some embodiments, the agent decreases the number of Treg cells. In some embodiments, the agent decreases Treg activity. In some embodiments, the agent inhibits and/or decreases the suppressive activity of Tregs. In some embodiments, the agent decreases the number of MDSCs. In some embodiments, the agent inhibits and/or decreases the suppressive activity of myeloid-derived suppressor cells (MDSCs).

In some embodiments of each of the aforementioned aspects and embodiments, as well as other aspects and embodiments described herein, an agent described herein specifically binds TIGIT and inhibits tumor growth. In some embodiments, the agent reduces tumor growth. In some embodiments, the agent reduces tumor growth to an undetectable size. In some embodiments, the agent induces long-term anti-tumor immunity.

In another aspect, the invention provides compositions comprising an agent described herein. Methods of using a composition comprising an agent described herein are also provided.

In another aspect, the invention provides pharmaceutical compositions comprising an agent described herein and a pharmaceutically acceptable carrier. Methods of treating cancer and/or inhibiting tumor growth in a subject (e.g., a human) comprising administering to the subject an effective amount of a composition comprising an agent described herein are also provided. Methods of treating a viral infection in a subject (e.g., a human) comprising administering to the subject an effective amount of a composition comprising an agent described herein are also provided.

In certain embodiments of each of the aforementioned aspects, as well as other aspects and/or embodiments described elsewhere herein, the agent is isolated. In certain embodiments, the agent is substantially pure.

In another aspect, the invention provides polynucleotides comprising a polynucleotide that encodes an agent described herein. In some embodiments, the polynucleotide is isolated. In some embodiments, the invention provides vectors that comprise the polynucleotides, as well as cells that comprise the vectors and/or the polynucleotides. In some embodiments, the invention also provides cells comprising or producing an agent described herein. In some embodiments, the cell is a monoclonal cell line.

In another aspect, the invention provides methods of modulating the immune response of a subject. In some embodiments, the method of modulating the immune response comprises a method of inducing, activating, promoting, increasing, enhancing, or prolonging an immune response in a subject. In some embodiments, a method of inducing, activating, promoting, increasing, enhancing, or prolonging an immune response in a subject, comprises administering a therapeutically effective amount of an antibody, bispecific agent, or polypeptide described herein. In some embodiments, a method of inducing, activating, promoting, increasing, enhancing, or prolonging an immune response in a subject, comprises administering a therapeutically effective amount of a heterodimeric bispecific agent or a homodimeric bispecific agent described herein. In some embodiments, a method of inducing, activating, promoting, increasing, enhancing, or prolonging an immune response in a subject, comprises administering a therapeutically effective amount of an antibody that specifically binds TIGIT described herein. In some embodiments, a method of inducing an immune response in a subject comprises administering an agent described herein. In some embodiments, a method of activating an immune response in a subject comprises administering an agent described herein. In some embodiments, a method of promoting an immune response in a subject comprises administering an agent described herein. In some embodiments, a method of increasing an immune response in a subject comprises administering an agent described herein. In some embodiments, a method of enhancing an immune response in a subject comprises administering an agent described herein. In some embodiments, a method of prolonging an immune response in a subject comprises administering an agent described herein. In some embodiments, the immune response is to an antigenic stimulation. In some embodiments, the antigenic stimulation is a tumor or a tumor cell. In some embodiments, the antigenic stimulation is a pathogen. In some embodiments, the antigenic stimulation is a virus. In some embodiments, the antigenic stimulation is a virally-infected cell. In some embodiments, the immune response is against a tumor or cancer.

In some embodiments, the invention provides methods of increasing the activity of immune cells. In some embodiments, a method of increasing the activity of immune cells comprises contacting the cells with an effective amount of an agent described herein. In some embodiments, the immune cells are T-cells, NK cells, monocytes, macrophages, myeloid-derived cells, antigen-presenting cells (APCs), and/or B-cells. In some embodiments, a method of increasing the activity of NK cells in a subject comprises administering to the subject a therapeutically effective amount of an agent described herein. In some embodiments, a method of increasing the activity of T-cells in a subject comprises administering to the subject a therapeutically effective amount of an agent described herein. In some embodiments, a method of increasing the activation of T-cells and/or NK cells in a subject comprises administering to the subject a therapeutically effective amount of an agent described herein. In some embodiments, a method of increasing the T-cell response in a subject comprises administering to the subject a therapeutically effective amount of an agent described herein. In some embodiments, a method of increasing the activity of CTLs in a subject comprises administering to the subject a therapeutically effective amount of an agent described herein. In some embodiments, a method of inhibiting the activity of Tregs in a subject comprises administering to the subject a therapeutically effective amount of an agent described herein. In some embodiments, a method of inhibiting the suppressive activity of Tregs in a subject comprises administering to the subject a therapeutically effective amount of an agent described herein. In some embodiments, a method of inhibiting the activity of MDSCs in a subject comprises administering to the subject a therapeutically effective amount of an agent described herein. In some embodiments, a method of inhibiting the suppressive activity of MDSCs in a subject comprises administering to the subject a therapeutically effective amount of an agent described herein.

In some embodiments, the invention provides methods of inducing, activating, promoting, increasing, enhancing, or prolonging an immune response in a subject, comprising administering to the subject a therapeutically effective amount of an agent that binds human TIGIT. In some embodiments, a method of inducing, activating, promoting, increasing, enhancing, or prolonging an immune response in a subject comprises administering to the subject a therapeutically effective amount of an agent that inhibits or reduces TIGIT activity. In some embodiments, a method of inducing, activating, promoting, increasing, enhancing, or prolonging an immune response in a subject comprises administering to the subject a therapeutically effective amount of an agent that inhibits or reduces TIGIT signaling. In some embodiments, the immune response is against a tumor cell, a tumor, or cancer. In some embodiments, the immune response is against a viral infection, a viral antigen, or a virally-infected cell.

In another aspect, the invention provides methods of inhibiting growth of tumor cells or a tumor comprising contacting the tumor or tumor cell with an effective amount of an agent described herein. In some embodiments, a method of inhibiting growth of a tumor comprises contacting a tumor or tumor cell with an effective amount of an agent that binds human TIGIT.

In another aspect, the invention provides methods of inhibiting growth of a tumor in a subject comprising administering to the subject a therapeutically effective amount of an agent described herein. In some embodiments, a method of inhibiting growth of a tumor in a subject comprises administering to the subject a therapeutically effective amount of an agent that binds human TIGIT. In some embodiments, a method of inhibiting growth of a tumor in a subject comprises administering to the subject a therapeutically effective amount of an antibody that binds human TIGIT. In some embodiments, a method of inhibiting growth of a tumor in a subject comprises administering to the subject a therapeutically effective amount of a bispecific agent that binds human TIGIT. In some embodiments, the tumor is selected from the group consisting of colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

In another aspect, the invention provides methods of treating cancer in a subject comprising administering to the subject a therapeutically effective amount of an agent described herein. In some embodiments, a method of treating cancer in a subject comprises administering to the subject a therapeutically effective amount of an agent that binds TIGIT. In some embodiments, a method of treating cancer in a subject comprises administering to the subject a therapeutically effective amount of an antibody that binds human TIGIT. In some embodiments, a method of treating cancer in a subject comprises administering to the subject a therapeutically effective amount of a bispecific agent that binds human TIGIT. In some embodiments, the cancer is selected from the group consisting of colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer.

In another aspect, the invention provides methods of stimulating and/or inducing long-term anti-tumor immunity in a subject comprising administering to the subject a therapeutically effective amount of an agent described herein.

In another aspect, the invention provides methods of stimulating a protective response in a subject comprising administering to the subject a therapeutically effective amount of an agent described herein in combination with an antigen of interest. In some embodiments, the antigen of interest is a tumor antigen. In some embodiments, the antigen of interest is a cancer cell biomarker. In some embodiments, the antigen of interest is a cancer stem cell marker.

In some embodiments of each of the aforementioned aspects and embodiments, as well as other aspects and embodiments described herein, the methods comprise administering to the subject an immune response stimulating agent. In some embodiments, the immune response stimulating agent is selected from the group consisting of GM-CSF, M-CSF, G-CSF, IL-3, IL-12, IL-1, IL-2, B7-1 (CD80), B7-2 (CD86), anti-CD3 antibodies, anti-CTLA-4 antibodies, anti-CD28 antibodies, anti-PD-L1 antibodies, and anti-PD1 antibodies.

In some embodiments of each of the aforementioned aspects and embodiments, as well as other aspects and embodiments described herein, a method further comprises administering at least one additional therapeutic agent. In some embodiments, the additional therapeutic agent is a chemotherapeutic agent. In some embodiments, the additional therapeutic agent is an antibody. In some embodiments, the additional therapeutic agent is an anti-PD-1 antibody, an anti-PD-L1 antibody, an anti-CTLA4 antibody, an anti-LAG-3 antibody, or an anti-TIM-3 antibody. In some embodiments, the additional therapeutic agent is an inhibitor of the Notch pathway, the Wnt pathway, or the RSPO/LGR pathway.

In some embodiments, the additional therapeutic agent is an immunotherapeutic agent. As used herein, the phrase "immunotherapeutic agent" is used in the broadest sense and refers to a substance that directly or indirectly affects or modulates the immune system. In some embodiments, an immunotherapeutic agent is an agent that directly or indirectly stimulates the immune system by inducing activation or increasing activity of any of the immune system's components. As the TIGIT-binding agents are considered immunotherapeutic agents, this additional immunotherapeutic agent may be considered a "second" immunotherapeutic agent. In some embodiments, the second immunotherapeutic agent is selected from the group consisting of: GM-CSF, M-CSF, G-CSF, IL-2, IL-3, IL-12, IL-15, B7-1 (CD80), B7-2 (CD86), 4-1BB ligand, GITRL, OX-40 ligand, anti-CD3 antibody, anti-CTLA-4 antibody, anti-CD28 antibody, anti-PD-1 antibody, anti-PD-L1 antibody, anti-4-1BB antibody, anti-GITR antibody, anti-OX-40 antibody, anti-LAG-3 antibody, and anti-TIM-3 antibody. In some embodiments, the second immunotherapeutic agent is a fusion protein comprising: GM-CSF, M-CSF, G-CSF, IL-2, IL-3, IL-12, IL-15, B7-1 (CD80), B7-2 (CD86), 4-1BB ligand, GITRL, OX-40 ligand, or a fragment thereof. In some embodiments, the second immunotherapeutic agent is a fusion protein comprising at least one copy of the extracellular domain of GITRL, OX40 ligand, or 4-1BB ligand.

In some embodiments of each of the aforementioned aspects and embodiments, as well as other aspects and embodiments described herein, the subject is human. In some embodiments, the subject has had a tumor or a cancer, at least partially, removed.

In some embodiments of each of the aforementioned aspects and embodiments, as well as other aspects and embodiments described herein, the tumor or the cancer expresses PD-L1. In some embodiments, a method further comprises a step of determining the level of PD-L1 expression in the tumor or cancer. In some embodiments, determining the level of PD-L1 expression is done prior to treatment or contact with an agent described herein. In some embodiments, if the tumor or cancer has an elevated expression level of PD-L1, an agent described herein is administered to the subject. In some embodiments, if the tumor or cancer has an elevated expression level of PD-L1, the tumor or cancer is contacted with an agent described herein.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

FIGS. 2A and 2B. Western blot analysis of protein phosphorylation after TIGIT-PVR interaction. Human Jurket T-cells were stably transduced with FLAG-tagged mouse TIGIT-GFP and E.G7-OVA cells were stably transduced with mouse PVR-GFP. (A) TIGIT phosphorylation. (B) SHP1 and Erk1/2 phosphorylation.

FIGS. 7A and 7B. Inhibition of tumor growth by anti-TIGIT antibodies. The colon tumor line CT26.WT was implanted subcutaneously into Balb/c mice (n=10 mice/ group). Mice were injected on days 10, 15, 18, 22, 25, and 29 with 0.25 mg/mouse of anti-TIGIT antibody 313R11, anti-TIGIT antibody 313R12, mouse IgG1 control antibody, and mouse IgG2 control antibody. Tumor growth was monitored and tumor volumes were measured with electronic calipers at the indicated time points. Data is shown as tumor volume (mm$^3$) over days post injection. (A) The figure shows the mean values±SEM for each group. (B) An additional study with anti-TIGIT antibody 313R12 and a control antibody.

Figure 8:
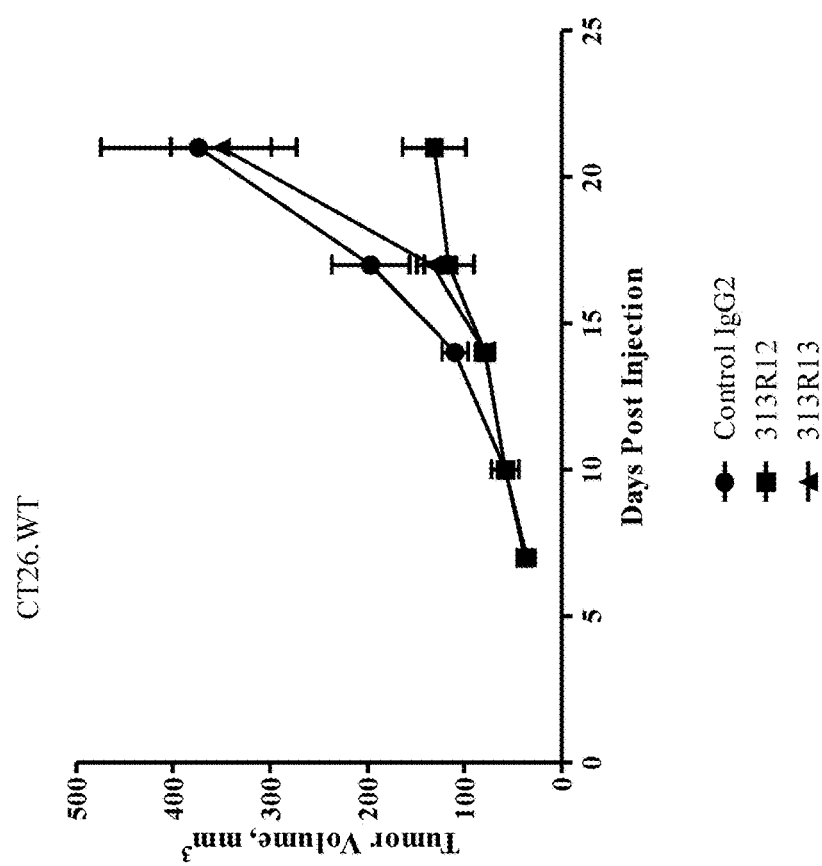

FIG. 8. Inhibition of tumor growth by anti-TIGIT antibodies. The colon tumor line CT26.WT was implanted subcutaneously into Balb/c mice (n=10 mice/group). Mice were injected on days 10, 14, 17, and 21 with 0.25 mg/mouse of anti-TIGIT antibody 313R12, anti-TIGIT antibody 313R13, and mouse IgG2 control antibody. Tumor growth was monitored and tumor volumes were measured with electronic calipers at the indicated time points. Data is shown as tumor volume (mm$^3$) over days post injection. The figure shows the mean values±SEM for each group.

FIG. 9A to 9D. ELISpot assays for IFN-gamma, IL-2, IL-4, and IL-10. Cells were harvested from the spleens of CT26.WT-tumor bearing mice treated with anti-TIGIT antibody 313R12 or an isotype-matched control antibody. Cells were incubated in the presence or absence of the AH-1 peptide and then analyzed using ELISpot kits. (A) Total optical density (TOD) of cells producing IFN-gamma is shown. (B) TOD of cells producing IL-2 is shown. (C) TOD of cells producing IL-4 is shown. (B) TOD of cells producing IL-10 is shown.

Figure 10:
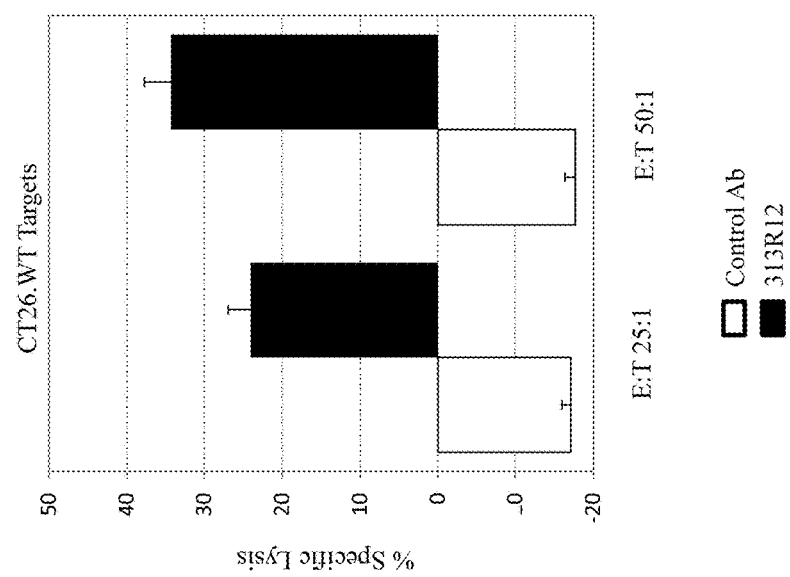

FIG. 10. Natural killer cell activity in splenocyte population from mice treated with anti-TIGIT antibody.

Figure 11:
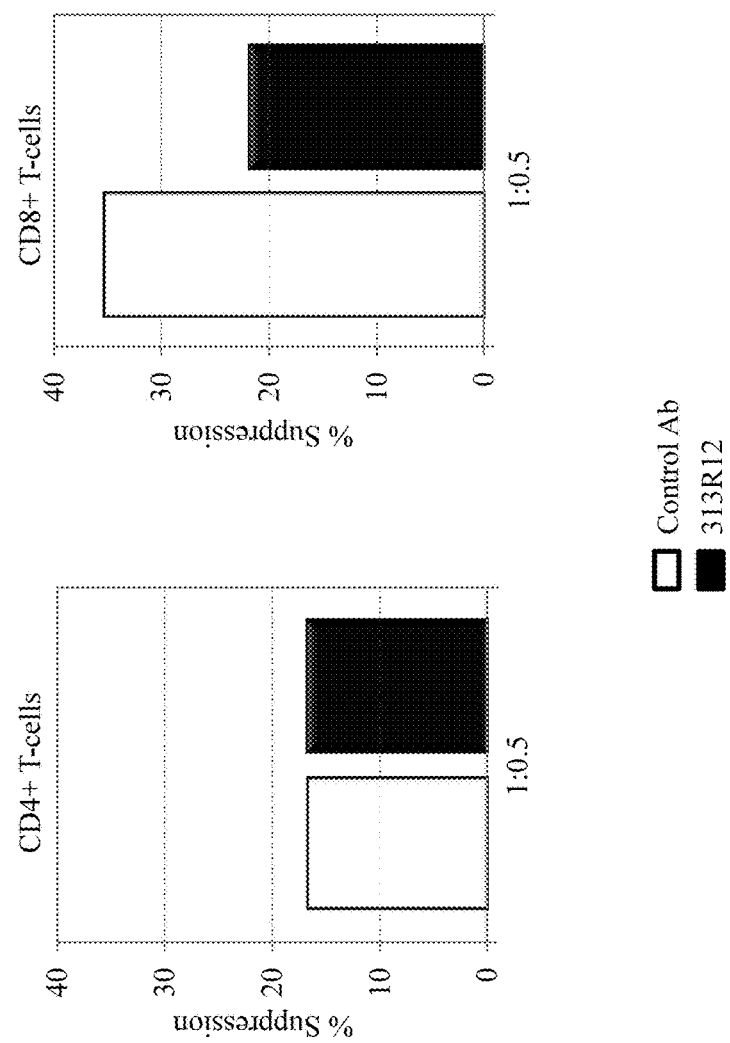

FIG. 11. Treg activity in splenocyte population from mice treated with anti-TIGIT antibody.

FIG. 12A to 12E. FACS analysis of splenocytes from mice treated with anti-TIGIT antibody. (A) Percentage of CD3+ cells of total live cells. (B) Percentage of CD4+ cells of total live cells. (C) Percentage of CD8+ cells of total live cells. (D) Percentage of CD4+ central memory T-cells of total CD4+ population. (E) Percentage of CD8+ central memory T-cells of total CD8+ population.

FIG. 13A to 13D. FACS analysis of TIGIT positive or negative Tregs in splenocyte population from mice treated with anti-TIGIT antibody. (A) Percentage of TIGIT-positive cells of total live cells. (B) Percentage of FoxP3+ cells of total CD4+ cells (identifying Tregs). (C) Percentage of TIGIT-positive cells of total Treg cells. (D) Percentage of TIGIT-negative cells of total Treg cells.

FIG. 14A to 14D. FACS analysis of MDSCs in splenocyte population from mice treated with anti-TIGIT antibody. (A) Percentage of CD11b+ cells of total live cells. (B) Percentage of MDSCs of total CD11b+ cells. (C) Percentage of G-MDSCs of total CD11b+ cells. (D) Percentage of M-MDSCs of total CD11b+ cells.

Figure 15:
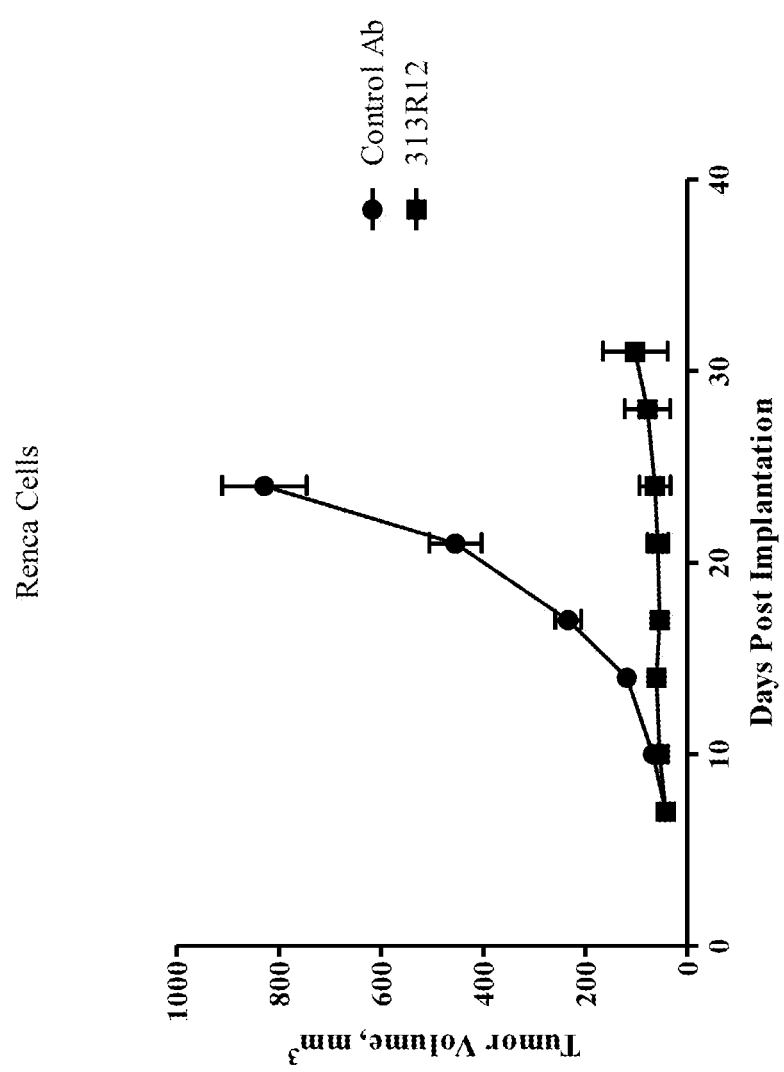

FIG. 15. Inhibition of tumor growth by anti-TIGIT antibodies. Renca cells (murine renal adenocarcinoma) was implanted subcutaneously into Balb/c mice (n=10 mice/group). Mice were injected on days 7, 10, 14, 17, 21, and 24 with 0.25 mg/mouse of anti-TIGIT antibody 313R12 and a mouse IgG2 control antibody. Tumor growth was monitored and tumor volumes were measured with electronic calipers at the indicated time points. Data is shown as tumor volume (mm$^3$) over days post injection. The figure shows the mean values±SEM for each group.

Figure 16:
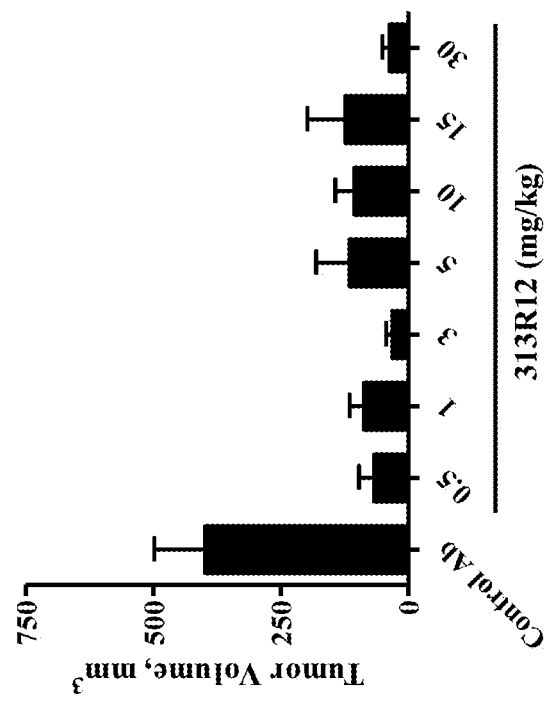

FIG. 16. Inhibition of tumor growth by anti-TIGIT antibody 313R12—a dose study. The murine colon tumor line CT26.WT was implanted subcutaneously into Balb/c mice (n=10 mice/group). Mice were treated with 0.5, 1, 3, 5, 10, 15, or 30 mg/kg of anti-TIGIT antibody 313R12 or were treated with a control antibody. Mice were dosed by intraperitoneal injection twice a week for a total of 6 doses. Tumor growth was monitored and tumor volumes were measured with electronic calipers.

FIG. 17A to 17F. In vivo tumor growth inhibition by anti-TIGIT antibody 313R12 and an anti-PD-L1 antibody. The murine colon tumor line CT26.WT was implanted subcutaneously (30,000 cells/mouse) in Balb/c mice. Mice were treated with 0.25 mg/mouse of anti-TIGIT antibody 313R12, an anti-PD-L1 antibody, a combination of 313R12 and anti-PD-L1 antibody, or a control antibody (n=10 per group). Mice were administered antibodies twice a week for 3 weeks. Tumor growth was monitored and tumor volumes were measured with electronic calipers at the indicated time points. (A) The tumor volumes of individual mice within group treated with control antibody. (B) The tumor volumes of individual mice within group treated with anti-TIGIT antibody 313R12. (C) The tumor volumes of individual mice within group treated with anti-PD-L1 antibody. (D) The tumor volumes of individual mice within group treated with anti-TIGIT antibody 313R12 and anti-PD-L1 antibody. (E) Average tumor growth of the four treatment groups. (F) Survival curve.

FIG. 18A to 18E. In vivo tumor growth inhibition by anti-TIGIT antibody 313R12 and anti-PD-1 antibody. The murine colon tumor line CT26.WT was implanted subcutaneously (30,000 cells/mouse) in Balb/c mice. Mice were treated with 0.25 mg/mouse of anti-TIGIT antibody 313R12, an anti-PD-1 antibody, a combination of 313R12 and anti-PD-1 antibody, or a control antibody (n=15 per group). Mice were administered antibodies twice a week for 3 weeks. Tumor growth was monitored and tumor volumes were measured with electronic calipers at the indicated time points. (A) The tumor volumes of individual mice within group treated with control antibody. (B) The tumor volumes of individual mice within group treated with anti-TIGIT antibody 313R12. (C) The tumor volumes of individual mice within group treated with anti-PD-1 antibody. (D) The tumor volumes of individual mice within group treated with anti-TIGIT antibody 313R12 and anti-PD-1 antibody. (E) Average tumor growth of the four treatment groups.

Figure 19A:
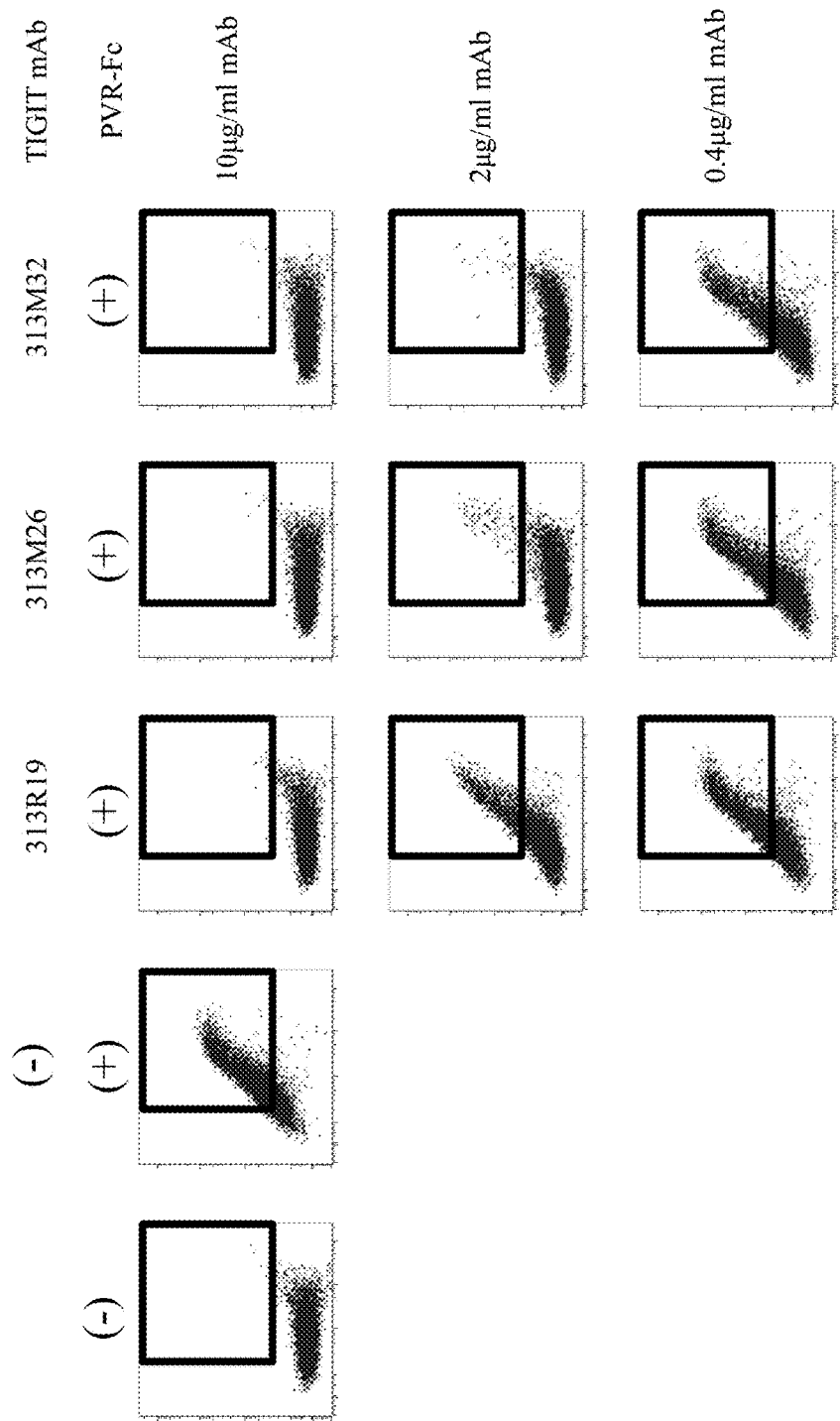
Figure 19B:
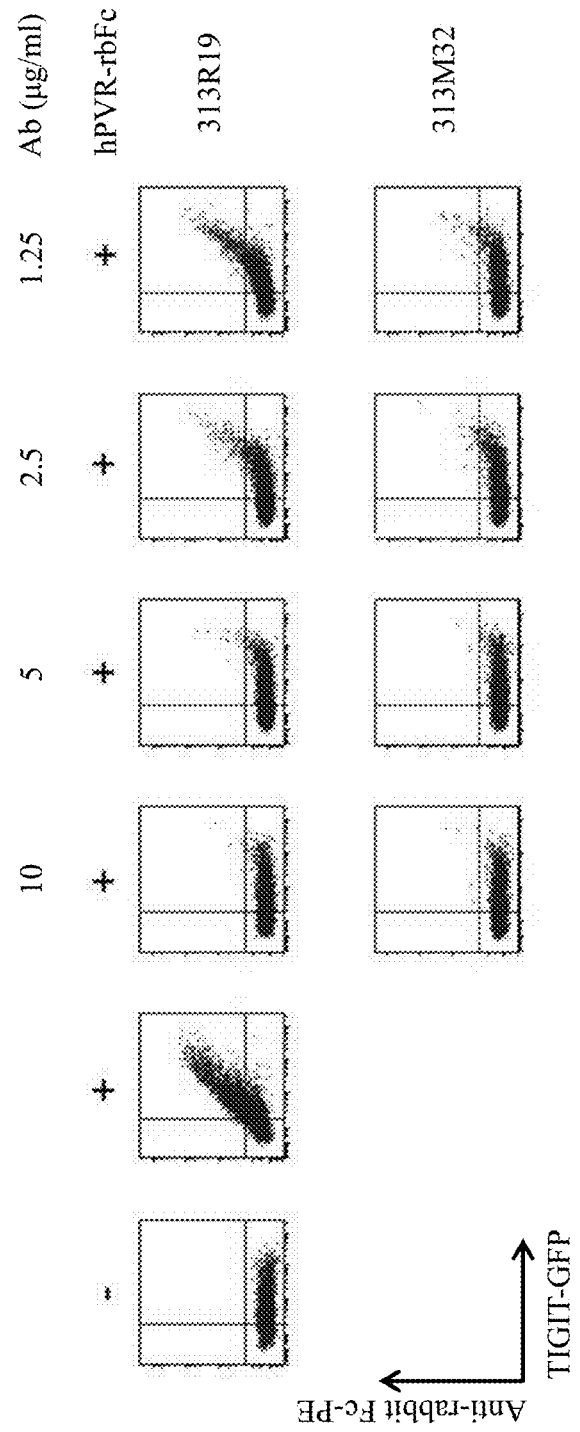

FIGS. 19A and 19B. FACS analysis of anti-TIGIT antibody blocking binding of human TIGIT to PVR. (A) HEK-293T cells were transiently transfected with a cDNA expression vector encoding human TIGIT ECD-CD4TM-GFP (green fluorescent protein) or human TIGIT ECD-CD4TM-GFP. Transfected cells were incubated with soluble human PVR-Fc fusion protein in the presence of antibodies generated to TIGIT (313R19, 313M26, or 313M32) at concentrations of 10, 2, or 0.4 µg/ml or no antibody and analyzed by flow cytometry. Specific binding is indicated by the presence of a diagonal signal within a FACS plot. Blocking of binding is demonstrated by the loss of specific binding within the dark black box over the FACS plot. (B) HEK-293T cells were transiently transfected with a cDNA expression vector encoding human TIGIT ECD-CD4TM-GFP (green fluorescent protein) or human TIGIT ECD-CD4TM-GFP. Transfected cells were incubated with soluble human PVR-rabbit Fc fusion protein in the presence of antibodies generated to TIGIT (313R19 or 313M32) at concentrations of 10, 5, 2.5, or 1.25 µg/ml or no antibody and analyzed by flow cytometry. Specific binding is indicated by the presence of a diagonal signal within a FACS plot. Blocking of binding is demonstrated by the loss of specific binding within the dark black box over the FACS plot.

Figure 20:
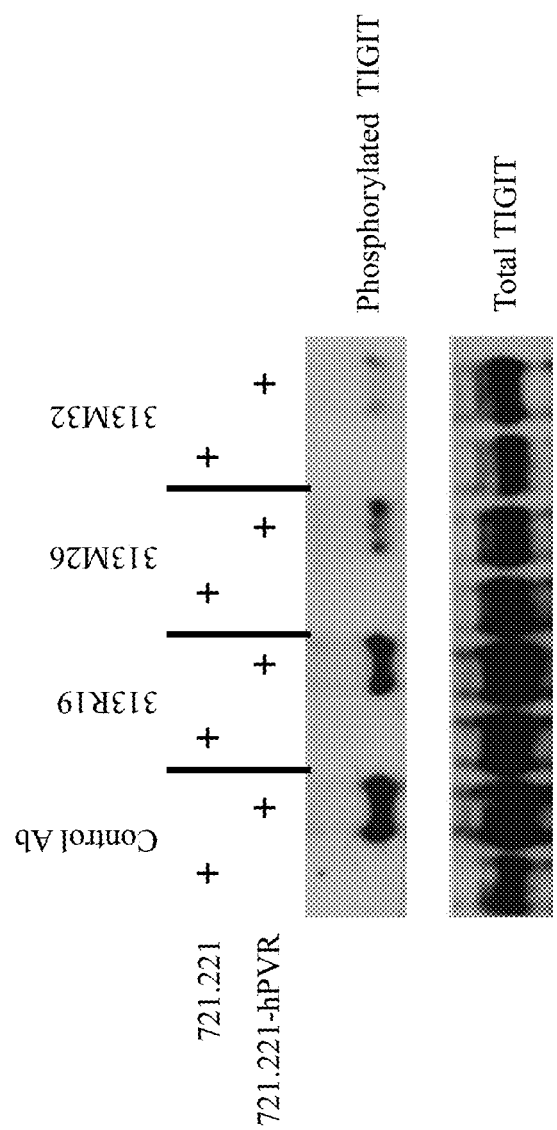

FIG. 20. Western blot analysis of TIGIT phosphorylation after TIGIT-PVR interaction in the absence or presence of anti-TIGIT antibodies 313R19, 313M26, and 313M32.

FIG. 21. A sequence alignment of human TIGIT (SEQ ID NO:4), cynomolgus monkey TIGIT (SEQ ID NO:77), and rhesus monkey TIGIT (SEQ ID NO:78).

Figure 22:
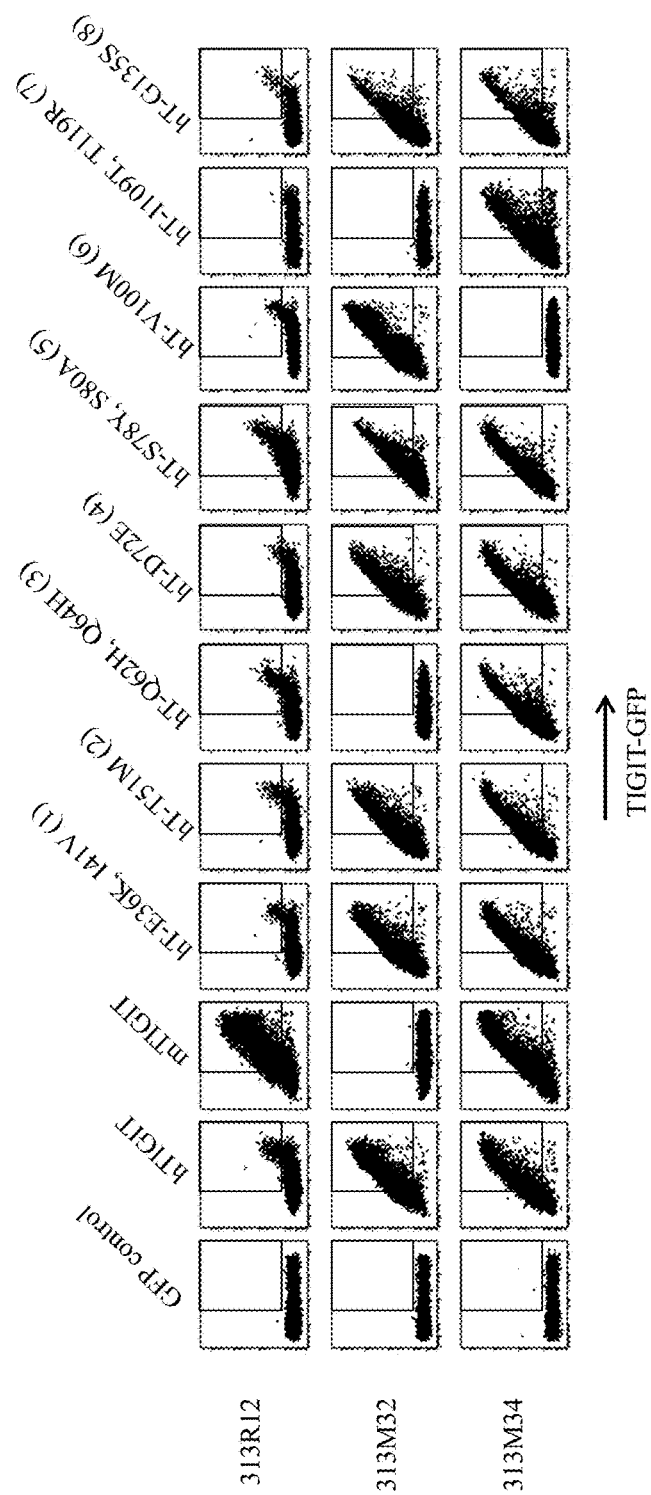

FIG. 22. Epitope mapping by FACS analysis of anti-TIGIT antibody binding to variant human TIGIT proteins containing specific amino acid substitutions. The hTIGIT variants are (1) E36K and I41V; (2) T51M, (3) Q62H and Q64H, (4) D72E, (5) S78Y and S80A, (6) V100M, (7) I109T and T119R, and (8) G135S.

Figure 23:
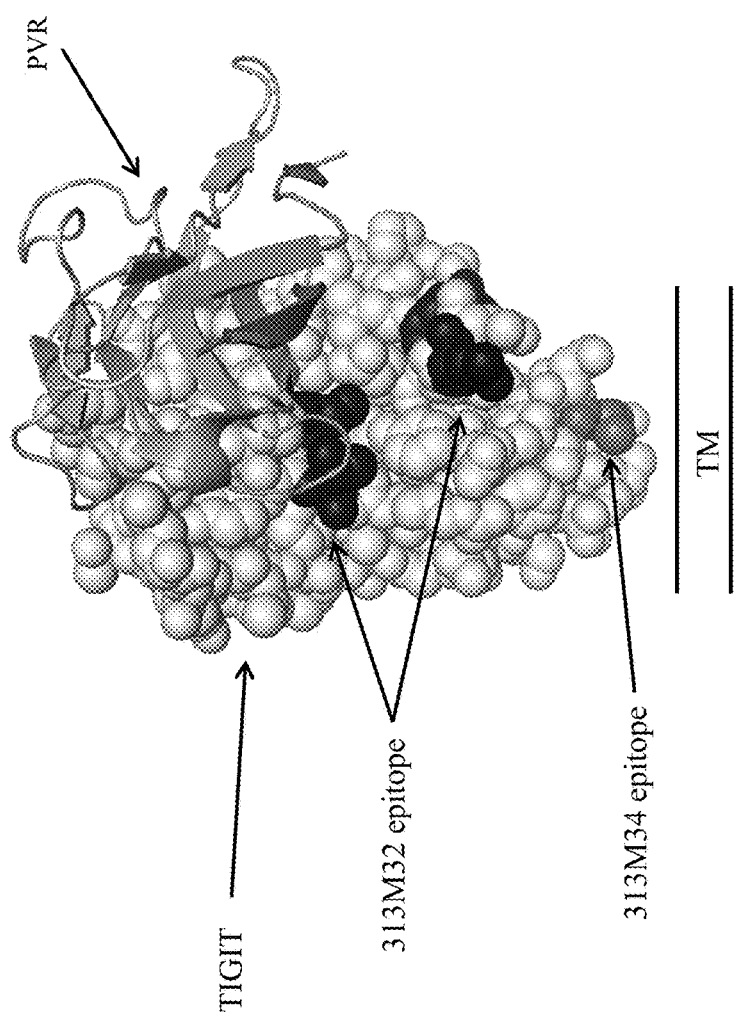

FIG. 23. A diagram representing PVR bound to TIGIT. The structure of human TIGIT is shown in sphere representation and the structure of PVR is provided in ribbon representation. Amino acids comprising at least part of the 313M32 epitope are shown as black spheres. Amino acid comprising at least part of the 313M34 epitope is shown as gray spheres.

Figures 24A, 24B:
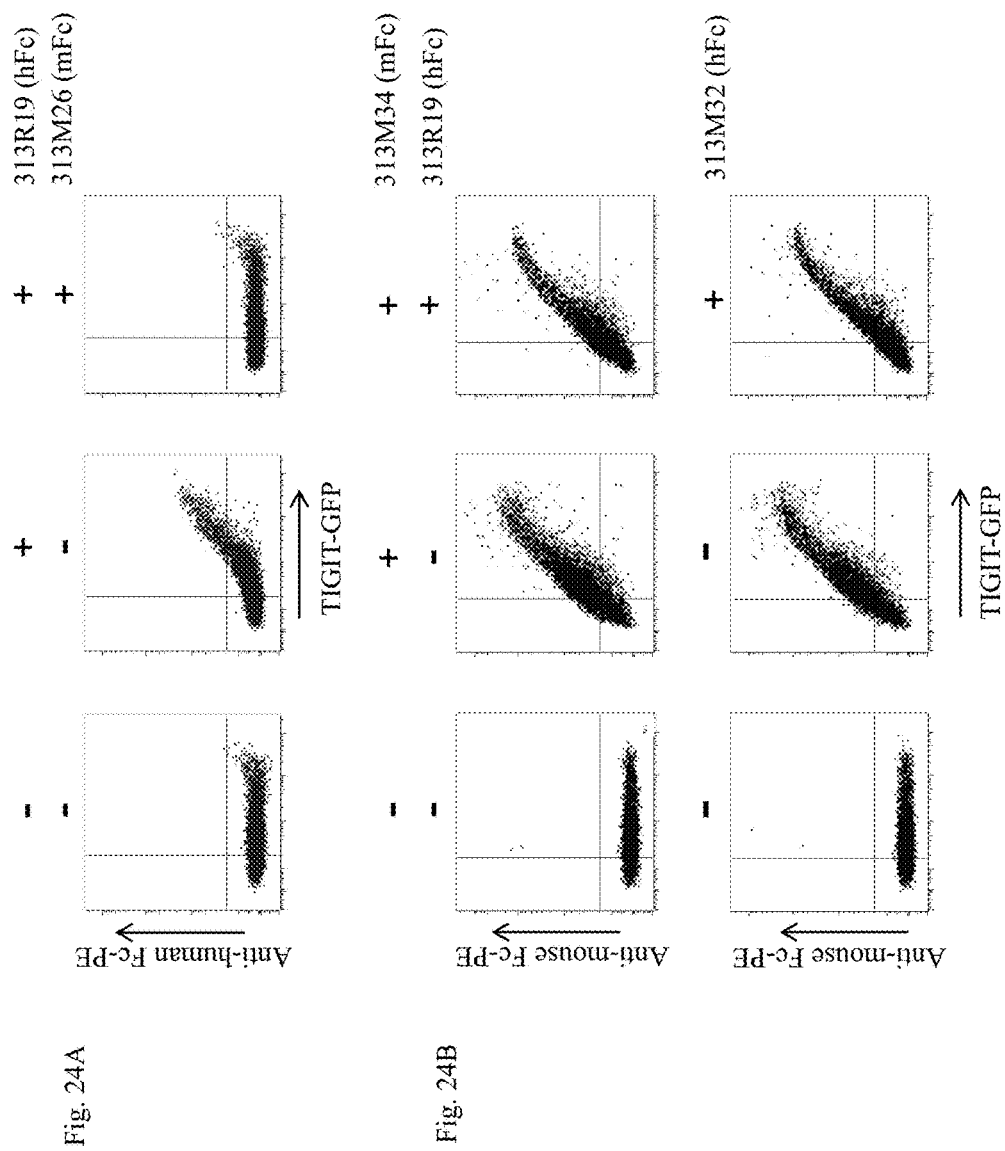

FIGS. 24A and 24B. Competitive binding studies between anti-TIGIT antibodies. (A) Competition study with 313R19 and 313M26. (B) Competition study with 313M34 and 313R19 or 313M34 and 313M32.

Figure 25:
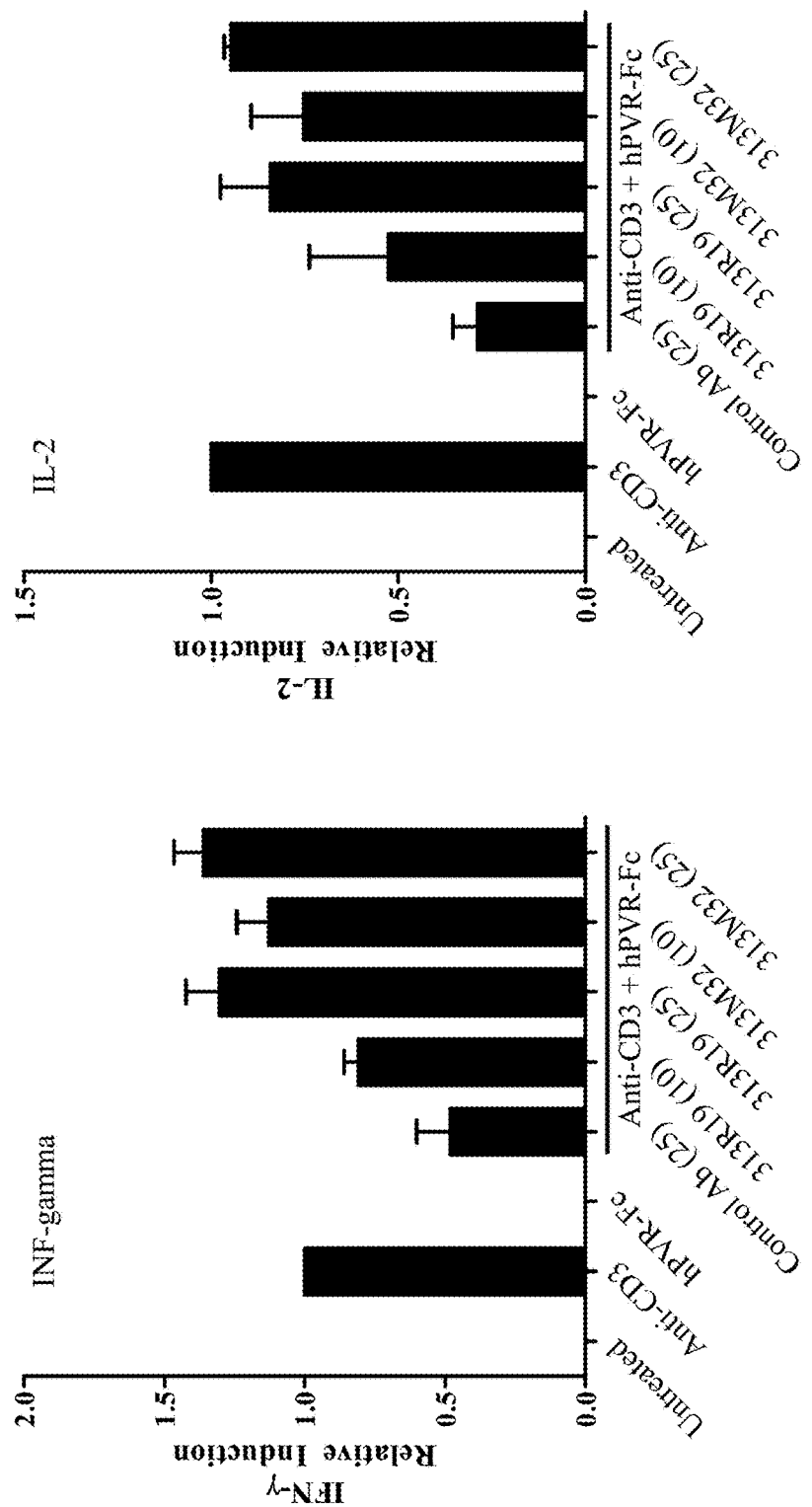

FIG. 25. Reversal of PVR-mediated inhibition of cytokine secretion by anti-TIGIT antibodies.

Figure 26:
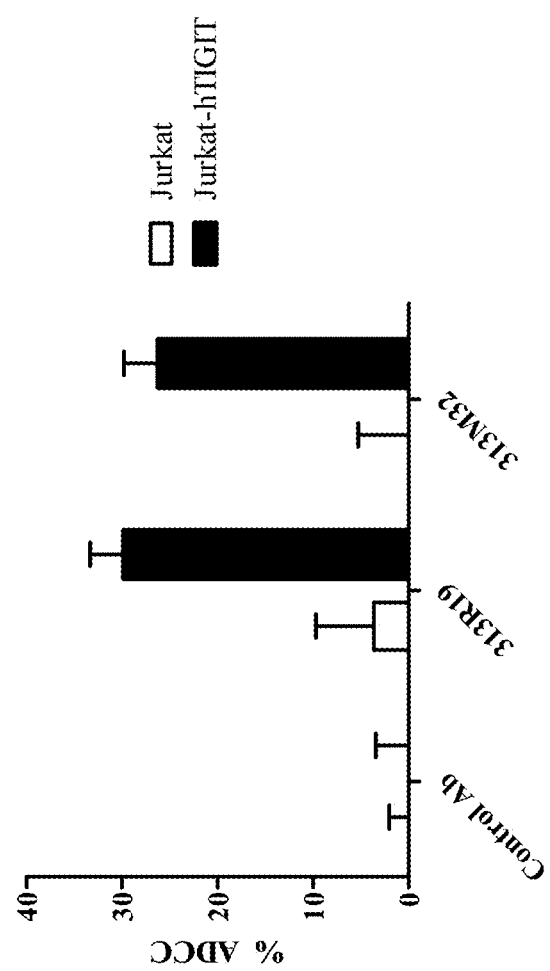

FIG. 26. Antibody-dependent cellular cytotoxicity assay.

Figure 27:
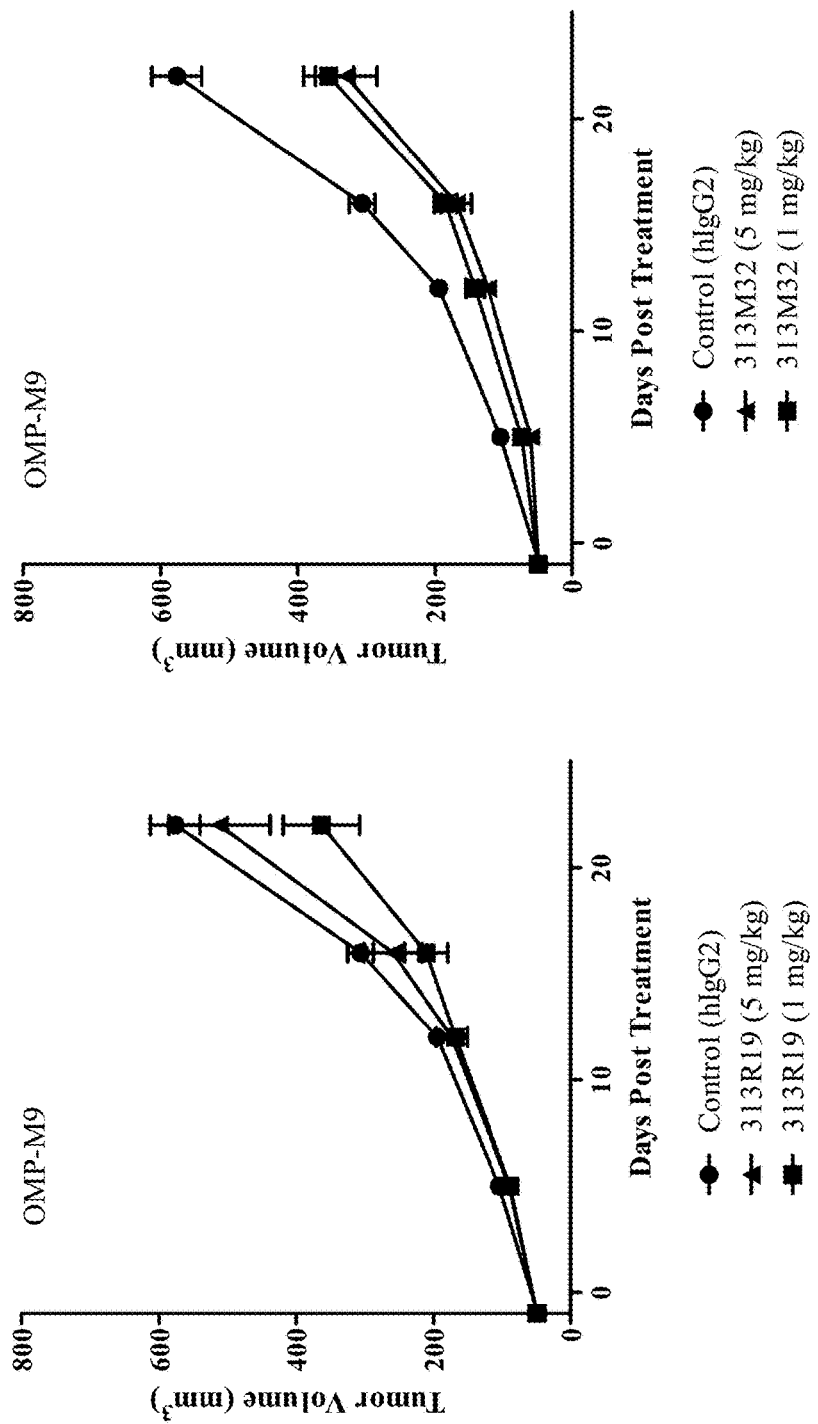

FIG. 27. Inhibition of tumor growth by anti-TIGIT antibodies 313R19 and 313M32 in a humanized mouse model. Humanized mice were injected subcutaneously with patient-derived melanoma tumor cells (OMP-M9, 75,000 cells/mouse). Tumors were allowed to grow 19 days until they had reached an average volume of approximately 50 mm$^3$. Tumor-bearing mice were randomized into groups (n=8 mice per group). Tumor-bearing mice were treated with either a control antibody, anti-TIGIT antibody 313R19, or anti-TIGIT antibody 313M32. Mice were dosed every 5 days at 1 or 5 mg/kg. Tumor growth was monitored and tumor volumes were measured with electronic calipers at the indicated time points.

DETAILED DESCRIPTION OF THE INVENTION

The present invention provides novel agents, including, but not limited to, polypeptides, antibodies, and heterodimeric molecules that modulate the immune response. The agents include polypeptides, antibodies, and heterodimeric molecules that specifically bind TIGIT and agents that modulate TIGIT activation and/or signaling. The agents include polypeptides, antibodies, and heterodimeric molecules that inhibit TIGIT activation and/or signaling, thereby enhancing an immune response. Related polypeptides and polynucleotides, compositions comprising the agents, and methods of making the agents are also provided. Methods of screening for agents that modulate the immune response are provided. Methods of using the novel agents, such as methods of inhibiting tumor growth and/or methods of treating cancer are provided. Methods of treating viral infections are also provided. Methods of using the novel agents, such as methods of activating an immune response, methods of stimulating an immune response, methods of promoting an immune response, methods of increasing an immune response, methods of activating natural killer (NK) cells and/or T-cells, methods of increasing the activity of NK cells and/or T-cells, methods of promoting the activity of NK cells and/or T-cells, methods of decreasing and/or inhibiting suppressor T-cells, and/or methods of decreasing and/or inhibiting myeloid-derived suppressor cells are further provided. In addition, the novel agents described herein may be used in methods of inhibiting an immune response, methods of suppressing an immune response, methods of decreasing activity of T-cells, and/or methods of treating autoimmune diseases.

I. Definitions

To facilitate an understanding of the present invention, a number of terms and phrases are defined below.

The terms "agonist" and "agonistic" as used herein refer to or describe an agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein.

The terms "antagonist" and "antagonistic" as used herein refer to or describe an agent that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein.

The terms "modulation" and "modulate" as used herein refer to a change or an alteration in a biological activity. Modulation includes, but is not limited to, stimulating an activity or inhibiting an activity. Modulation may be an increase or a decrease in activity, a change in binding characteristics, or any other change in the biological, functional, or immunological properties associated with the activity of a protein, a pathway, a system, or other biological targets of interest.

The term "antibody" as used herein refers to an immunoglobulin molecule that recognizes and specifically binds a target through at least one antigen-binding site. The target may be a protein, polypeptide, peptide, carbohydrate, polynucleotide, lipid, or a combination of any of the foregoing. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies, bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and generally refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain or the variable region of an antibody heavy chain, either alone or in combination. Generally, the variable region of a heavy chain or a light chain consists of four framework regions connected by three complementarity determining regions (CDRs), also known as "hypervariable regions". The CDRs in each chain are held together in close proximity by the framework regions and, with the CDRs from the other chain, contribute to the formation of the antigen-binding site(s) of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda Md.), and (2) an approach based on crystallographic studies of antigen-antibody complexes (Al Lazikani et al., 1997, *J. Mol. Biol.*, 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies that recognize different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The term "humanized antibody" as used herein refers to antibodies that are specific immunoglobulin chains, chimeric immunoglobulins, or fragments thereof that contain minimal non-human sequences. Typically, humanized antibodies are human immunoglobulins in which amino acid residues of the CDRs are replaced by amino acid residues from the CDRs of a non-human species (e.g., mouse, rat, rabbit, or hamster) that have the desired specificity, affinity, and/or binding capability. In some instances, the framework variable region amino acid residues of a human immunoglobulin may be replaced with the corresponding amino acid residues in an antibody from a non-human species. The humanized antibody can be further modified by the substitution of additional amino acid residues either in the framework variable region and/or within the replaced non-human amino acid residues to further refine and optimize antibody specificity, affinity, and/or binding capability. The humanized antibody may comprise variable domains containing all or substantially all of the CDRs that correspond to the non-human immunoglobulin, whereas all or substantially all of the framework variable regions are those of a human immunoglobulin sequence. In some embodiments, the variable domains comprise the framework regions of a human immunoglobulin sequence. In some embodiments, the variable domains comprise the framework regions of a human immunoglobulin consensus sequence. The humanized antibody can also comprise at least a portion of an immunoglobulin constant region or domain (Fc), typically that of a human immunoglobulin.

The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable regions of the light and heavy chains correspond to the variable regions of an antibody derived from one species of mammal (e.g., mouse, rat, rabbit, etc.) with the desired specificity, affinity, and/or binding capability, while the constant regions are homologous to the sequence in an antibody derived from another species. The constant regions are usually human to avoid eliciting an immune response in the antibody.

The terms "epitope" and "antigenic determinant" are used interchangeably herein and refer to that portion of an antigen or target capable of being recognized and specifically bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

The terms "selectively binds" or "specifically binds" mean that an agent interacts more frequently, more rapidly, with greater duration, with greater affinity, or with some combination of the above to the epitope, protein, or target molecule than with alternative substances, including related and unrelated proteins. In certain embodiments "specifically binds" means, for instance, that an agent binds a protein or target with a $K_D$ of about 0.1 mM or less, but more usually less than about 1 µM. In certain embodiments, "specifically binds" means that an agent binds a target with a $K_D$ of at least about 0.1 µM or less, at least about 0.01 µM or less, or at least about 1 nM or less. Because of the sequence identity between homologous proteins in different species, specific binding can include an agent that recognizes a protein or target in more than one species (e.g., mouse TIGIT and human TIGIT). Likewise, because of homology within certain regions of polypeptide sequences of different proteins, specific binding can include an agent that recognizes more than one protein or target. It is understood that, in certain embodiments, an agent that specifically binds a first target may or may not specifically bind a second target. As such, "specific binding" does not necessarily require (although it can include) exclusive binding, i.e. binding to a single target. Thus, an agent may, in certain embodiments, specifically bind more than one target. In certain embodiments, multiple targets may be bound by the same antigen-binding site on the agent. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or other members of the immunoglobulin superfamily, in certain embodiments, a "polypeptide" can occur as a single chain or as two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, the coding region of a nucleotide sequence.

A "conservative amino acid substitution" is one in which one amino acid residue is replaced with another amino acid residue having a similar side chain Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies of the invention do not abrogate the binding of the polypeptide or antibody containing the amino acid sequence, to the target binding site. Methods of identifying nucleotide and amino acid conservative substitutions which do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "immune response" as used herein includes responses from both the innate immune system and the adaptive immune system. It includes both cell-mediated and/or humoral immune responses. It includes, but is not limited to, both T-cell and B-cell responses, as well as responses from other cells of the immune system such as natural killer (NK) cells, monocytes, macrophages, etc.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (non-cancerous) or malignant (cancerous) including pre-cancerous lesions.

The term "metastasis" as used herein refers to the process by which a cancer spreads or transfers from the site of origin to other regions of the body with the development of a similar cancerous lesion at a new location. Generally, a "metastatic" or "metastasizing" cell is one that loses adhesive contacts with neighboring cells and migrates via the bloodstream or lymph from the primary site of disease to secondary sites throughout the body.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an appropriate host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into appropriate hosts (e.g., mice).

The term "subject" refers to any animal (e.g., a mammal), including, but not limited to, humans, non-human primates, canines, felines, rabbits, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier, or adjuvant" or "acceptable pharmaceutical carrier" refer to an excipient, carrier, or adjuvant that can be administered to a subject, together with at least one agent of the present disclosure, and which does not destroy the pharmacological activity thereof and is non-toxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of an agent described herein, an antibody, a polypeptide, a polynucleotide, a small organic molecule, or other drug effective to "treat" a disease or disorder in a subject such as, a mammal. In the case of cancer or a tumor, the therapeutically effective amount of an agent (e.g., polypeptide or antibody) has a therapeutic effect and as such can enhance or boost the immune response, enhance or boost the anti-tumor response, increase cytolytic activity of immune cells, increase killing of tumor cells, increase killing of tumor cells by immune cells, reduce the number of tumor cells; decrease tumorigenicity, tumorigenic frequency, or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods of the present invention if the patient shows one or more of the following: an increased immune response, an increased anti-tumor response, increased cytolytic activity of immune cells, increased killing of tumor cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Tigit Binding Agents

T-cell immunoreceptor with Ig and ITIM domains (TIGIT) is a type I transmembrane glycoprotein that contains an immunoglobulin variable (IgV) domain. TIGIT belongs to the poliovirus receptor (PVR) family and binds to the poliovirus receptor (PVR; CD155) with high affinity and to PVRL-2 (CD112) and PVRL-3 (CD113) with a lower affinity. TIGIT is expressed on T-cells, including regulatory T-cells and memory T-cells, as well as on NK cells and is upregulated following activation of naïve CD4+ T-cells. The full-length amino acid (aa) sequences for mouse TIGIT (UniProtKB No. P86176) and human TIGIT (UniProtKB No. Q495A1) are known in the art and are provided herein as SEQ ID NO:1 and SEQ ID NO:4, respectively. As used herein, reference to amino acid positions refer to the numbering of full-length amino acid sequences including the signal sequence.

The present invention provides agents that specifically bind TIGIT. These agents are referred to herein as "TIGIT-binding agents". In some embodiments, the TIGIT-binding agent is an antibody. In some embodiments, the TIGIT-binding agent is a polypeptide. In certain embodiments, the TIGIT-binding agent binds mouse TIGIT. In certain embodiments, the TIGIT-binding agent binds human TIGIT. In certain embodiments, the TIGIT-binding agent binds mouse TIGIT and human TIGIT. In some embodiments, the TIGIT-binding agent binds human TIGIT and does not bind mouse TIGIT.

In some embodiments, an agent binds TIGIT and interferes with the interaction of TIGIT with a second protein. In some embodiments, an agent binds TIGIT and interferes with the interaction of TIGIT with PVR. In some embodiments, an agent binds TIGIT and interferes with the interaction of TIGIT with PVRL-2. In some embodiments, an agent binds TIGIT and interferes with the interaction of TIGIT with PVRL-3. In some embodiments, an agent specifically binds TIGIT and the agent disrupts binding of TIGIT to PVR, and/or disrupts PVR activation of TIGIT signaling.

In certain embodiments, the TIGIT-binding agent is an antibody that specifically binds the extracellular domain of TIGIT, or a fragment thereof. In certain embodiments, the TIGIT-binding agent is an antibody that specifically binds the extracellular domain of mouse TIGIT, or a fragment thereof. In certain embodiments, the TIGIT-binding agent is an antibody that specifically binds the extracellular domain of human TIGIT, or a fragment thereof. In certain embodiments, the TIGIT-binding agent is an antibody that specifically binds the extracellular domain of mouse TIGIT and human TIGIT, or a fragment thereof. In some embodiments, the TIGIT-binding agent is an antibody that specifically binds the Ig-like domain of TIGIT. In some embodiments, the TIGIT-binding agent is an antibody that specifically binds the IgV domain of TIGIT. In some embodiments, the TIGIT-binding agent is an antibody that binds within amino acids 22-141 of human TIGIT and/or amino acids 29-148 of mouse TIGIT. In some embodiments, the TIGIT-binding agent is an antibody that binds within amino acids 22-141 of SEQ ID NO:4 and/or amino acids 29-148 of SEQ ID NO:1. In some embodiments, the agent binds within amino acids 22-124 of human TIGIT and/or amino acids 29-127 of mouse TIGIT. In some embodiments, the agent binds within amino acids 22-124 of SEQ ID NO:4 and/or amino acids 29-127 of SEQ ID NO:1. In certain embodiments, the TIGIT-binding agent binds within SEQ ID NO:3, or a fragment thereof. In certain embodiments, the TIGIT-binding agent binds within SEQ ID NO:6, or a fragment thereof. In some embodiments, the TIGIT-binding agent is an antibody that binds within amino acids 22-141 of human TIGIT. In some embodiments, the TIGIT-binding agent is an antibody that binds within amino acids 22-141 of SEQ ID NO:4. In some embodiments, the TIGIT-binding agent is an antibody that binds within amino acids 50-124 of human TIGIT. In some embodiments, the TIGIT-binding agent is an antibody that binds within amino acids 50-124 of SEQ ID NO:4. In certain embodiments, the TIGIT-binding agent binds within SEQ ID NO:6, or a fragment thereof.

In some embodiments, the TIGIT-binding agent is an antibody that binds an epitope comprising amino acids within SEQ ID NO:79. In some embodiments, the TIGIT-binding agent is an antibody that binds an epitope comprising amino acids within SEQ ID NO:80. In some embodiments, the TIGIT-binding agent is an antibody that binds an epitope comprising amino acids within SEQ ID NO:79 and SEQ ID NO:80. In some embodiments, the TIGIT-binding agent is an antibody that binds an epitope comprising amino acids Q62 and I109 of SEQ ID NO:4. In some embodiments, the TIGIT-binding agent is an antibody that binds an epitope comprising amino acids Q62 and T119 of SEQ ID NO:4. In some embodiments, the TIGIT-binding agent is an antibody that binds an epitope comprising amino acids Q64 and I109 of SEQ ID NO:4. In some embodiments, the TIGIT-binding agent is an antibody that binds an epitope comprising amino acids Q64 and T119 of SEQ ID NO:4. In some embodiments, the TIGIT-binding agent is an antibody that binds an epitope comprising amino acids Q62, Q64, and I109 of SEQ ID NO:4. In some embodiments, the TIGIT-binding agent is an antibody that binds an epitope comprising amino acids Q62, Q64, and T119 of SEQ ID NO:4. In some embodiments, the TIGIT-binding agent is an antibody that binds an epitope comprising amino acids Q62, I109, and T119 of SEQ ID NO:4. In some embodiments, the TIGIT-binding agent is an antibody that binds an epitope comprising amino acids Q64, I109, and T119 of SEQ ID NO:4. In some embodiments, the TIGIT-binding agent is an antibody that binds an epitope comprising amino acids Q62, Q64, I109, and T119 of SEQ ID NO:4. In some embodiments, the TIGIT-binding agent is an antibody that binds an epitope comprising at least one amino acid selected from the group consisting of: N58, E60, Q62, Q64, L65, F107, I109, H111, T117, T119, G120, and R121 of SEQ ID NO:4. In some embodiments, the epitope is a conformational epitope. In some embodiments, the TIGIT-binding agent is an antibody that binds an epitope which does not comprise amino acid V100 of SEQ ID NO:4.

In certain embodiments, the TIGIT-binding agent (e.g., an antibody) binds TIGIT with a dissociation constant ($K_D$) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a TIGIT-binding agent binds TIGIT with a $K_D$ of about 20 nM or less. In some embodiments, a TIGIT-binding agent binds TIGIT with a $K_D$ of about 10 nM or less. In some embodiments, a TIGIT-binding agent binds TIGIT with a $K_D$ of about 1 nM or less. In some embodiments, a TIGIT-binding agent binds TIGIT with a $K_D$ of about 0.5 nM or less. In some embodiments, a TIGIT-binding agent binds TIGIT with a $K_D$ of about 0.1 nM or less. In some embodiments, a TIGIT-binding agent binds TIGIT with a $K_D$ of about 50 pM or less. In some embodiments, a TIGIT-binding agent binds TIGIT with a $K_D$ of about 25 pM or less. In some embodiments, a TIGIT-binding agent binds TIGIT with a $K_D$ of about 10 pM or less. In some embodiments, a TIGIT-binding agent binds TIGIT with a $K_D$ of about 1 pM or less. In some embodiments, the TIGIT-binding agent binds both human TIGIT and mouse TIGIT with a $K_D$ of about 10 nM or less. In some embodiments, a TIGIT-binding agent binds both human TIGIT and mouse TIGIT with a $K_D$ of about 1 nM or less. In some embodiments, a TIGIT-binding agent binds both human TIGIT and mouse TIGIT with a $K_D$ of about 0.1 nM or less. In some embodiments, the dissociation constant of the binding agent (e.g., an antibody) to TIGIT is the dissociation constant determined using a TIGIT fusion protein comprising at least a portion of the extracellular domain of TIGIT protein immobilized on a Biacore chip. In some embodiments, the dissociation constant of the binding agent (e.g., an antibody) to TIGIT is the dissociation constant determined using the binding agent captured by an anti-human IgG antibody on a Biacore chip and a soluble TIGIT protein.

In some embodiments, a TIGIT-binding agent comprises a first antigen-binding site that specifically binds TIGIT and a second antigen-binding site that specifically binds a second target. In some embodiments, a TIGIT-binding agent is a bispecific agent that comprises a first antigen-binding site that specifically binds TIGIT and a second antigen-binding site that specifically binds a second target. In some embodiments, a TIGIT-binding agent binds both TIGIT and the second target with a $K_D$ of about 100 nM or less. In some embodiments, a TIGIT-binding agent binds both TIGIT and the second target with a $K_D$ of about 50 nM or less. In some embodiments, a TIGIT-binding agent binds both TIGIT and the second target with a $K_D$ of about 20 nM or less. In some embodiments, a TIGIT-binding agent binds both TIGIT and the second target with a $K_D$ of about 10 nM or less. In some embodiments, a TIGIT-binding agent binds both TIGIT and the second target with a $K_D$ of about 1 nM or less. In some embodiments, the affinity of one of the antigen-binding sites may be weaker than the affinity of the other antigen-binding site. For example, the $K_D$ of one antigen binding site may be about 1 nM and the $K_D$ of the second antigen-binding site may be about 10 nM. In some embodiments, the difference in affinity between the two antigen-binding sites may be about 2-fold or more, about 3-fold or more, about 5-fold or more, about 8-fold or more, about 10-fold or more, about 15-fold or more, about 20-fold or more, about 30-fold or more, about 50-fold or more, or about 100-fold or more. Modulation of the affinities of the two antigen-binding sites may affect the biological activity of the bispecific antibody. For example, decreasing the affinity of the antigen-binding site for TIGIT or the second target, may have a desirable effect, for example decreased toxicity of the binding agent and/or increased therapeutic index.

In certain embodiments, the TIGIT-binding agent (e.g., an antibody) binds TIGIT with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a TIGIT-binding agent binds to human TIGIT with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a TIGIT-binding agent binds mouse TIGIT and/or human TIGIT with an $EC_{50}$ of about 40 nM or less, about 20 nM or less, about 10 nM or less, about 1 nM or less or about 0.1 nM or less.

In certain embodiments, the TIGIT-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In certain embodiments, the antibody is an IgG1 antibody. In certain embodiments, the antibody is an IgG2 antibody. In some embodiments, the antibody is an IgG4 antibody. In certain embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some embodiments, the antibody is conjugated to a cytotoxic moiety. In some embodiments, the antibody is isolated. In some embodiments, the antibody is substantially pure.

In some embodiments, the TIGIT-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, full-length recombinant protein, or fusion protein) using multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, a TIGIT-binding agent is a monoclonal antibody. Monoclonal antibodies can be prepared using hybridoma methods known to one of skill in the art. In some embodiments, using the hybridoma method, a mouse, rat, rabbit, hamster, or other appropriate host animal, is immunized as described above to elicit the production of antibodies that specifically bind the immunizing antigen. In some embodiments, lymphocytes can be immunized in vitro. In some embodiments, the immunizing antigen can be a human protein or a fragment thereof. In some embodiments, the immunizing antigen can be a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species.

The polynucleotide(s) encoding a monoclonal antibody can be modified, for example, by using recombinant DNA technology to generate alternative antibodies. In some embodiments, the constant domains of the light chain and heavy chain of, for example, a mouse monoclonal antibody can be substituted for constant regions of, for example, a human antibody to generate a chimeric antibody, or for a non-immunoglobulin polypeptide to generate a fusion antibody. In some embodiments, the constant regions are truncated or removed to generate a desired antibody fragment of a monoclonal antibody. Site-directed or high-density mutagenesis of the variable region(s) can be used to optimize specificity, affinity, etc. of a monoclonal antibody.

In some embodiments, a TIGIT-binding agent is a humanized antibody. Typically, humanized antibodies are human immunoglobulins in which the amino acid residues of the CDRs are replaced by amino acid residues from CDRs of a non-human species (e.g., mouse, rat, rabbit, hamster, etc.) that have the desired specificity, affinity, and/or binding capability using methods known to one skilled in the art. In some embodiments, some of the framework variable region amino acid residues of a human immunoglobulin are replaced with corresponding amino acid residues in an antibody from a non-human species. In some embodiments, a humanized antibody can be further modified by the substitution of additional residues either in the framework variable region and/or within the replaced non-human residues to further refine and optimize antibody specificity, affinity, and/or capability. In general, a humanized antibody will comprise variable domain regions containing all, or substantially all, of the CDRs that correspond to the non-human immunoglobulin whereas all, or substantially all, of the framework regions are those of a human immunoglobulin sequence. In some embodiments, the framework regions are those of a human consensus immunoglobulin sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject.

In certain embodiments, a TIGIT-binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated. In some embodiments, the human antibody can be selected from a phage library, where that phage library expresses human antibodies. Alternatively, phage display technology can be used to produce human antibodies and antibody fragments in vitro, from immunoglobulin variable domain gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production.

In some embodiments, the TIGIT-binding agent is a bispecific antibody. Thus, this invention encompasses bispecific antibodies that specifically recognize TIGIT and at least one additional target. Bispecific antibodies are capable of specifically recognizing and binding at least two different antigens or epitopes. The different epitopes can either be within the same molecule (e.g., two epitopes on TIGIT) or on different molecules (e.g., one epitope on TIGIT and one epitope on a different protein). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., a tumor and/or tumor microenvironment). In some embodiments, a bispecific antibody has the ability to concentrate the actions of two agents to a common target (e.g., a tumor or a tumor cell). In some embodiments, a bispecific antibody has the ability to target the actions of two agents to more than one biological pathway or function. In some embodiments, a bispecific antibody has the ability to target two different cells and bring them closer together (e.g., an immune cell and a tumor cell).

In some embodiments, the bispecific antibody is a monoclonal antibody. In some embodiments, the bispecific antibody is a humanized antibody. In some embodiments, the bispecific antibody is a human antibody. In some embodiments, the bispecific antibody is an IgG1 antibody. In some embodiments, the bispecific antibody is an IgG2 antibody. In some embodiments, the bispecific antibody is an IgG4 antibody. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, the antibodies can specifically recognize and bind a first antigen target, (e.g., TIGIT) as well as a second antigen target, such as an effector molecule on an immune cell (e.g., CD2, CD3, CD28, CTLA4, PD-1, PD-L1, CD80, or CD86) or a Fc receptor (e.g., CD64, CD32, or CD16) so as to focus cellular defense mechanisms to the cell expressing and/or producing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy. In some cases, the "knobs" and "holes" terminology is replaced with the terms "protuberances" and "cavities". In some embodiments, the bispecific antibodies may comprise variant hinge regions incapable of forming disulfide linkages between the heavy chains. In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. For example, trispecific antibodies can be prepared. Thus, in certain embodiments the antibodies to TIGIT are multispecific.

In certain embodiments, the antibodies (or other polypeptides) described herein may be monospecific. In certain embodiments, each of the one or more antigen-binding sites that an antibody contains is capable of binding (or binds) a homologous epitope on TIGIT.

In certain embodiments, a TIGIT-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced by recombinant methods. In some embodiments, antibody fragments include Fv or single chain Fv (scFv) fragments. Fab, Fv, and scFv antibody fragments can be expressed in and secreted from *E. coli* or other host cells, allowing for the production of large amounts of these fragments. In some embodiments, antibody fragments are isolated from antibody phage libraries as discussed herein. For example, methods can be used for the construction of Fab expression libraries to allow rapid and effective identification of monoclonal Fab fragments with the desired specificity for TIGIT or derivatives, fragments, analogs or homologs thereof. In some embodiments, antibody fragments are linear antibody fragments. In certain embodiments, antibody fragments are monospecific or bispecific. In certain embodiments, the TIGIT-binding agent is a scFv. Various techniques can be used for the production of single-chain antibodies specific to TIGIT.

In some embodiments, especially in the case of antibody fragments, an antibody is modified in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells. It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., TIGIT). In this regard, the variable region may comprise or be derived from any type of mammal that can be induced to mount a humoral response and generate immunoglobulins against the desired antigen. As such, the variable region of the modified antibodies can be, for example, of human, murine, rat, rabbit, non-human primate (e.g. cynomolgus monkeys, macaques, etc.), or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding. In some embodiments, the mutation of a single amino acid in selected areas of the CH2 domain may be enough to substantially reduce Fc binding and increase cancer cell localization and/or tumor penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody. In some embodiments, the deletion or inactivation (through point mutations or other means) of a constant region domain may reduce Fc receptor binding of the circulating modified antibody thereby increasing cancer cell localization and/or tumor penetration. In other embodiments, the constant region modifications increase the serum half-life of the antibody. In other embodiments, the constant region modifications reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques.

In certain embodiments, a TIGIT-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor and/or complement factors. In certain embodiments, the antibody has no effector function(s).

The present invention further embraces variants and equivalents which are substantially homologous to the recombinant, monoclonal, chimeric, humanized, and human antibodies, or antibody fragments thereof, described herein. These variants can contain, for example, conservative substitution mutations, i.e. the substitution of one or more amino acids by similar amino acids.

The present invention provides methods for producing an antibody that binds TIGIT, including bispecific antibodies that specifically bind both TIGIT and a second target. In some embodiments, the method for producing an antibody that binds TIGIT comprises using hybridoma techniques. In some embodiments, a method for producing an antibody that binds human TIGIT is provided. In some embodiments, the method comprises using a polypeptide comprising the extracellular domain of mouse TIGIT or a fragment thereof as an antigen. In some embodiments, the method comprises using a polypeptide comprising the extracellular domain of human TIGIT or a fragment thereof as an antigen. In some embodiments, the method comprises using a polypeptide comprising amino acids 29-148 of mouse TIGIT as an antigen. In some embodiments, the method comprises using a polypeptide comprising amino acids 22-141 of human TIGIT as an antigen. In some embodiments, the method comprises using a polypeptide comprising amino acids 29-148 of SEQ ID NO:1 as an antigen. In some embodiments, the method comprises using a polypeptide comprising amino acids 22-141 of SEQ ID NO:4 as an antigen. In some embodiments, the method comprises using a polypeptide comprising SEQ ID NO:3 or a fragment thereof as an antigen. In some embodiments, the method comprises using a polypeptide comprising SEQ ID NO:6 or a fragment thereof as an antigen. In some embodiments, the method of generating an antibody that binds TIGIT comprises screening a phage library. In some embodiments, the method of generating an antibody that binds TIGIT comprises screening a human phage library. The present invention further provides methods of identifying an antibody that binds TIGIT. In some embodiments, the antibody is identified by FACS screening for binding to TIGIT or a fragment thereof. In some embodiments, the antibody is identified by screening using ELISA for binding to TIGIT, or a fragment thereof. In some embodiments, the antibody is identified by screening by FACS for blocking of binding of TIGIT to PVR.

In some embodiments, a method of generating an antibody to TIGIT comprises immunizing a mammal with a polypeptide comprising amino acids 29-148 of mouse TIGIT. In some embodiments, a method of generating an antibody to TIGIT comprises immunizing a mammal with a polypeptide comprising amino acids 22-141 of human TIGIT. In some embodiments, a method of generating an antibody to TIGIT comprises immunizing a mammal with a polypeptide comprising a fragment (e.g., a portion) of amino acids 29-148 of mouse TIGIT. In some embodiments, a method of generating an antibody to TIGIT comprises immunizing a mammal with a polypeptide comprising a fragment of amino acids 22-141 of human TIGIT. In some embodiments, the method further comprises isolating antibodies or antibody-producing cells from the mammal. In some embodiments, a method of generating a monoclonal antibody which binds TIGIT comprises: (a) immunizing a mammal with a polypeptide comprising a fragment of amino acids 29-148 of mouse TIGIT; (b) isolating antibody-producing cells from the immunized mammal; and (c) fusing the antibody-producing cells with cells of a myeloma cell line to form hybridoma cells. In some embodiments, a method of generating a monoclonal antibody which binds TIGIT comprises: (a) immunizing a mammal with a polypeptide comprising a fragment of amino acids 22-141 of human TIGIT; (b) isolating antibody-producing cells from the immunized mammal; and (c) fusing the antibody-producing cells with cells of a myeloma cell line to form hybridoma cells. In some embodiments, the method further comprises (d) selecting a hybridoma cell expressing an antibody that binds TIGIT. In certain embodiments, the mammal is a mouse. In some embodiments, the mammal is a rat. In some embodiments, the mammal is a rabbit. In some embodiments, the antibody is selected using a polypeptide comprising amino acids 29-148 or a fragment thereof of mouse TIGIT. In some embodiments, the antibody is selected using a polypeptide comprising amino acids 22-141 or a fragment thereof of human TIGIT. In some embodiments, the antibody binds both human TIGIT and mouse TIGIT. In some embodiments, the antibody does not bind mouse TIGIT. In some embodiments, the antibody does not bind cynomolgus monkey TIGIT. In some embodiments, the antibody does not bind rhesus monkey TIGIT. In some embodiments, the antibody does not bind rat TIGIT. In some embodiments, the antibody binds human TIGIT and does not bind mouse TIGIT. In some embodiments, the antibody binds human TIGIT and does not bind cynomolgus monkey TIGIT. In some embodiments, the antibody binds human TIGIT and does not bind rhesus monkey TIGIT. In some embodiments, the antibody binds human TIGIT and does not bind rat TIGIT.

In some embodiments, a method of producing an antibody that binds TIGIT comprises identifying an antibody using a membrane-bound heterodimeric molecule comprising a single antigen-binding site. In some non-limiting embodiments, the antibody is identified using methods and polypeptides described in International Publication WO 2011/100566.

In some embodiments, a method of producing an antibody that binds TIGIT comprises screening an antibody-expressing library. In some embodiments, the antibody-expressing library is a phage library. In some embodiments, the screening comprises panning. In some embodiments, the antibody-expressing library is a mammalian cell library. In some embodiments, the antibody-expressing library is screened using amino acids 29-148 of mouse TIGIT or a fragment thereof. In some embodiments, the antibody-expressing library is screened using amino acids 22-141 of human TIGIT or a fragment thereof. In some embodiments, the antibody identified in the screening binds both human TIGIT and mouse TIGIT. In some embodiments, the antibody identified in the screening is a TIGIT antagonist.

In some embodiments, the antibody generated by the methods described herein is a TIGIT antagonist. In some embodiments, the antibody generated by the methods described herein inhibits TIGIT signaling. In some embodiments, the antibody generated by the methods described herein inhibits TIGIT phosphorylation.

In certain embodiments, the antibodies described herein are isolated. In certain embodiments, the antibodies described herein are substantially pure.

The TIGIT-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well-known in the art (see, e.g., Ausubel et al., Editors, 1994-present, *Current Protocols in Molecular Biology*, John Wiley & Sons, Inc., New York, N.Y.).

In a non-limiting example, screening for specific binding of an antibody to human TIGIT may be determined using ELISA. An ELISA comprises preparing antigen (e.g., TIGIT or a fragment thereof), coating wells of a 96-well microtiter plate with antigen, adding the test antibodies conjugated to a detectable compound such as an enzymatic substrate (e.g. horseradish peroxidase or alkaline phosphatase) to the well, incubating for a period of time, and detecting the presence of an antibody bound to the antigen. In some embodiments, the test antibodies are not conjugated to a detectable compound, but instead a secondary antibody that recognizes the antibody (e.g., an anti-Fc antibody) and is conjugated to a detectable compound is added to the wells. In some embodiments, instead of coating the well with the antigen, the test antibodies can be coated to the wells, the antigen (e.g., TIGIT) is added to the wells, followed by a secondary antibody conjugated to a detectable compound. One of skill in the art would be knowledgeable as to the parameters that can be modified to increase the signal detected as well as other variations of ELISAs known in the art.

In another non-limiting example, the specific binding of an antibody to TIGIT may be determined using FACS. A FACS screening assay may comprise generating a cDNA construct that expresses an antigen as a full-length protein (TIGIT) or a fusion protein (e.g., TIGIT-CD4TM), transfecting the construct into cells, expressing the antigen on the surface of the cells, mixing the test antibodies with the transfected cells, and incubating for a period of time. The cells bound by the test antibodies may be identified using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding agent to an antigen (e.g., TIGIT) and the off-rate of an antibody-antigen interaction can be determined by competitive binding assays. One example of a competitive binding assay is a radioimmunoassay comprising the incubation of labeled antigen (e.g., $^3$H or $^{125}$I-TIGIT), or fragment or variant thereof, with the antibody of interest in the presence of increasing amounts of unlabeled antigen followed by the detection of the antibody bound to the labeled antigen. The affinity of the antibody for the antigen and the binding off-rates can be determined from the data by Scatchard plot analysis. In some embodiments, Biacore kinetic analysis is used to determine the binding on and off rates of antibodies or agents that bind an antigen (e.g., TIGIT). In some embodiments, Biacore kinetic analysis comprises analyzing the binding and dissociation of antibodies from chips with immobilized antigen (e.g., TIGIT) on their surface. In some embodiments, Biacore kinetic analysis comprises analyzing the binding and dissociation of antigen (e.g., TIGIT) from chips with immobilized antibody (e.g., anti-TIGIT antibody) on their surface.

In certain embodiments, the invention provides a TIGIT-binding agent (e.g., an antibody) that specifically binds TIGIT, wherein the TIGIT-binding agent comprises one, two, three, four, five, and/or six of the CDRs of antibody 313R11, 313R12, 313R14, or 313R19 (see Table 1). In some embodiments, the TIGIT-binding agent comprises one or more of the CDRs of 313R11, 313R12, 313R14, or 313R19, or humanized variants thereof; two or more of the CDRs of 313R11, 313R12, 313R14, or 313R19, or humanized variants thereof; three or more of the CDRs of 313R11, 313R12, 313R14, or 313R19, or humanized variants thereof; four or more of the CDRs of 313R11, 313R12, 313R14, or 313R19, or humanized variants thereof; five or more of the CDRs of 313R11, 313R12, 313R14, or 313R19, or humanized variants thereof; or all six of the CDRs of 313R11, 313R12, 313R14, or 313R19, or humanized variants thereof.

TABLE 1

|  | 313R11, 313R12 | 313R14, 313R19 |
| --- | --- | --- |
| HC CDR1 | GSSLSSSYMS (SEQ ID NO: 7) | GFSLSSSYMS (SEQ ID NO: 13) |
| HC CDR2 | IIGSNGNTYYANWAKG (SEQ ID NO: 8) | IIGSNGNTYYANWAKG (SEQ ID NO: 8) |
| HC CDR3 | GGYRTSGMDP (SEQ ID NO: 9) | GGYRTSGMDP (SEQ ID NO: 9) |
| LC CDR1 | QASQSISSYLNW (SEQ ID NO: 10) | QASQSNIYSDLAW (SEQ ID NO: 14) or QASQNIYSDLAW (SEQ ID NO: 81) |
| LC CDR2 | DALKLAS (SEQ ID NO: 11) | RASTLAS (SEQ ID NO: 15) |
| LC CDR3 | QQEHSVGNVDN (SEQ ID NO: 12) | QQEHLVAWIYN (SEQ ID NO: 16) |

In certain embodiments, the invention provides a TIGIT-binding agent (e.g., an antibody) that specifically binds TIGIT, wherein the TIGIT-binding agent comprises a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9). In some embodiments, the TIGIT-binding agent further comprises a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16). In some embodiments, the TIGIT-binding agent comprises a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16). In some embodiments, the TIGIT-binding agent comprises: (a) a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9) and (b) a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16). In some embodiments, the TIGIT-binding agent comprises: (a) a heavy chain CDR1 comprising GSSLSSSYMS (SEQ ID NO:7), a heavy chain CDR2 comprising IIGSNGNTYYANWAKG (SEQ ID NO:8), and a heavy chain CDR3 comprising GGYRTSGMDP (SEQ ID NO:9) and (b) a light chain CDR1 comprising QASQSISSYLNW (SEQ ID NO:10), a light chain CDR2 comprising DALKLAS (SEQ ID NO:11), and a light chain CDR3 comprising QQEHSVGNVDN (SEQ ID NO:12). In some embodiments, the TIGIT-binding agent comprises: (a) a heavy chain CDR1 comprising GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9) and (b) a light chain CDR1 comprising QASQSNIYSDLAW (SEQ ID NO:14), a light chain CDR2 comprising RASTLAS (SEQ ID NO:15), and a light chain CDR3 comprising QQEHLVAWIYN (SEQ ID NO:16). In some embodiments, the TIGIT-binding agent comprises: (a) a heavy chain CDR1 comprising GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9) and (b) a light chain CDR1 comprising QASQNIYSDLAW (SEQ ID NO:81), a light chain CDR2 comprising RASTLAS (SEQ ID NO:15), and a light chain CDR3 comprising QQEHLVAWIYN (SEQ ID NO:16).

In certain embodiments, the invention provides a TIGIT-binding agent (e.g., an antibody) that specifically binds human TIGIT, wherein the TIGIT-binding agent comprises: (a) a heavy chain CDR1 comprising GSSLSSSYMS (SEQ ID NO:7), GFSLSSSYMS (SEQ ID NO:13), or a variant thereof comprising 1, 2, 3, or 4 amino acid substitutions; (b) a heavy chain CDR2 comprising IIGSNGNTYYANWAKG (SEQ ID NO:8), or a variant thereof comprising 1, 2, 3, or 4 amino acid substitutions; (c) a heavy chain CDR3 comprising GGYRTSGMDP (SEQ ID NO:9), or a variant thereof comprising 1, 2, 3, or 4 amino acid substitutions; (d) a light chain CDR1 comprising QASQSISSYLNW (SEQ ID NO:10), QASQSNIYSDLAW (SEQ ID NO:14), QASQNI- YSDLAW (SEQ ID NO:81), or a variant thereof comprising 1, 2, 3, or 4 amino acid substitutions; (e) a light chain CDR2 comprising DALKLAS (SEQ ID NO:11), RASTLAS (SEQ ID NO:15), or a variant thereof comprising 1, 2, 3, or 4 amino acid substitutions; and (f) a light chain CDR3 comprising QQEHSVGNVDN (SEQ ID NO:12), QQEHLVAWIYN (SEQ ID NO:16), or a variant thereof comprising 1, 2, 3, or 4 amino acid substitutions. In certain embodiments, the amino acid substitutions are conservative substitutions. In some embodiments, the substitutions are made as part of a humanization process. In some embodiments, the substitutions are made as part of a germline humanization process.

In certain embodiments, the invention provides a TIGIT-binding agent (e.g., an antibody) that specifically binds TIGIT, wherein the TIGIT-binding agent comprises a heavy chain variable region having at least about 80% sequence identity to SEQ ID NO:17, SEQ ID NO:19, or SEQ ID NO:32 and/or a light chain variable region having at least 80% sequence identity to SEQ ID NO:18 or SEQ ID NO:20. In certain embodiments, the TIGIT-binding agent comprises a heavy chain variable region having at least about 85%, at least about 90%, at least about 95%, at least about 97%, or at least about 99% sequence identity to SEQ ID NO:17. In certain embodiments, the TIGIT-binding agent comprises a heavy chain variable region having at least about 85%, at least about 90%, at least about 95%, at least about 97%, or at least about 99% sequence identity to SEQ ID NO:19. In certain embodiments, the TIGIT-binding agent comprises a heavy chain variable region having at least about 85%, at least about 90%, at least about 95%, at least about 97%, or at least about 99% sequence identity to SEQ ID NO:32. In certain embodiments, the TIGIT-binding agent comprises a light chain variable region having at least about 85%, at least about 90%, at least about 95%, at least about 97%, or at least about 99% sequence identity to SEQ ID NO:18. In certain embodiments, the TIGIT-binding agent comprises a light chain variable region having at least about 85%, at least about 90%, at least about 95%, at least about 97%, or at least about 99% sequence identity to SEQ ID NO:20. In certain embodiments, the TIGIT-binding agent comprises a heavy chain variable region having at least about 95% sequence identity to SEQ ID NO:17, SEQ ID NO:19, or SEQ ID NO:32 and/or a light chain variable region having at least about 95% sequence identity to SEQ ID NO:18 or SEQ ID NO:20. In certain embodiments, the TIGIT-binding agent comprises a heavy chain variable region comprising SEQ ID NO:17, SEQ ID NO:19, or SEQ ID NO:32 and/or a light chain variable region comprising SEQ ID NO:18 or SEQ ID NO:20. In certain embodiments, the TIGIT-binding agent comprises a heavy chain variable region comprising SEQ ID NO:17, SEQ ID NO:19, or SEQ ID NO:32 and a light chain variable region comprising SEQ ID NO:18 or SEQ ID NO:20. In certain embodiments, the TIGIT-binding agent comprises a heavy chain variable region consisting essentially of SEQ ID NO:17, SEQ ID NO:19, or SEQ ID NO:32 and a light chain variable region consisting essentially of SEQ ID NO:18 or SEQ ID NO:20. In certain embodiments, the TIGIT-binding agent comprises a heavy chain variable region consisting of SEQ ID NO:17, SEQ ID NO:19, or SEQ ID NO:32 and a light chain variable region consisting of SEQ ID NO:18 or SEQ ID NO:20.

In certain embodiments, the TIGIT-binding agent comprises a heavy chain variable region comprising SEQ ID NO:17 and a light chain variable region comprising SEQ ID NO:18. In certain embodiments, the TIGIT-binding agent comprises of a heavy chain variable region consisting essentially of SEQ ID NO:17 and a light chain variable region consisting essentially of SEQ ID NO:18. In certain embodiments, the TIGIT-binding agent comprises a heavy chain variable region consisting of SEQ ID NO:17 and a light chain variable region consisting of SEQ ID NO:18.

In certain embodiments, the TIGIT-binding agent comprises a heavy chain variable region comprising SEQ ID NO:19 and a light chain variable region comprising SEQ ID NO:20. In certain embodiments, the TIGIT-binding agent comprises a heavy chain variable region consisting essentially of SEQ ID NO:19 and a light chain variable region consisting essentially of SEQ ID NO:20. In certain embodiments, the TIGIT-binding agent comprises a heavy chain variable region consisting of SEQ ID NO:19 and a light chain variable region consisting of SEQ ID NO:20.

In certain embodiments, the TIGIT-binding agent comprises a heavy chain variable region comprising SEQ ID NO:32 and a light chain variable region comprising SEQ ID NO:20. In certain embodiments, the TIGIT-binding agent comprises a heavy chain variable region consisting essentially of SEQ ID NO:32 and a light chain variable region consisting essentially of SEQ ID NO:20. In certain embodiments, the TIGIT-binding agent comprises a heavy chain variable region consisting of SEQ ID NO:32 and a light chain variable region consisting of SEQ ID NO:20.

In certain embodiments, the invention provides a TIGIT-binding agent (e.g., an antibody) that specifically binds TIGIT, wherein the TIGIT-binding agent comprises: (a) a heavy chain having at least 90% sequence identity to SEQ ID NO:26, SEQ ID NO:27, SEQ ID NO:29, SEQ ID NO:34, or SEQ ID NO:56; and/or (b) a light chain having at least 90% sequence identity to SEQ ID NO:28 or SEQ ID NO:30. In some embodiments, the TIGIT-binding agent comprises: (a) a heavy chain having at least 95% sequence identity to SEQ ID NO:26, SEQ ID NO:27, SEQ ID NO:29, SEQ ID NO:34, or SEQ ID NO:56; and/or (b) a light chain having at least 95% sequence identity to SEQ ID NO:28 or SEQ ID NO:30. In some embodiments, the TIGIT-binding agent comprises a heavy chain comprising SEQ ID NO:26 and/or a light chain comprising SEQ ID NO:28. In some embodiments, the TIGIT-binding agent comprises a heavy chain comprising SEQ ID NO:27 and/or a light chain comprising SEQ ID NO:28. In some embodiments, the TIGIT-binding agent comprises a heavy chain comprising SEQ ID NO:29 and/or a light chain comprising SEQ ID NO:30. In some embodiments, the TIGIT-binding agent comprises a heavy chain comprising SEQ ID NO:34 and/or a light chain comprising SEQ ID NO:30. In some embodiments, the TIGIT-binding agent comprises a heavy chain comprising SEQ ID NO:56 and/or a light chain comprising SEQ ID NO:30. In some embodiments, the TIGIT-binding agent comprises a heavy chain consisting essentially of SEQ ID NO:26 or SEQ ID NO:27, and a light chain consisting essentially of SEQ ID NO:28. In some embodiments, the TIGIT-binding agent comprises a heavy chain consisting essentially of SEQ ID NO:29, SEQ ID NO:34, or SEQ ID NO:56 and a light chain consisting essentially of SEQ ID NO:30. In some embodiments, the TIGIT-binding agent comprises a heavy chain consisting of SEQ ID NO:26 and a light chain consisting of SEQ ID NO:28. In some embodiments, the TIGIT-binding agent comprises a heavy chain consisting of SEQ ID NO:27 and a light chain consisting of SEQ ID NO:28. In some embodiments, the TIGIT-binding agent comprises a heavy chain consisting of SEQ ID NO:29 and a light chain consisting of SEQ ID NO:30. In some embodiments, the TIGIT-binding agent comprises a heavy chain consisting of SEQ ID NO:34 and a light chain consisting of SEQ ID NO:30. In some embodiments, the TIGIT-binding agent comprises a heavy chain consisting of SEQ ID NO:56 and a light chain consisting of SEQ ID NO:30.

In certain embodiments, a TIGIT-binding agent comprises the heavy chain variable region and light chain variable region of the 313R11 antibody. In some embodiments, the TIGIT-binding agent comprises the variable regions of the 313R11 antibody wherein the heavy chain variable region and/or the light chain variable region from the 313R11 antibody have been affinity-matured. In certain embodiments, a TIGIT-binding agent comprises the heavy chain and light chain of the 313R11 antibody (with or without the leader sequence). In certain embodiments, a TIGIT-binding agent is the 313R11 antibody. In certain embodiments, a TIGIT-binding agent comprises the heavy chain variable region and/or the light chain variable region of the 313R11 antibody wherein the heavy chain variable region and/or the light chain variable region have been humanized. In certain embodiments, a TIGIT-binding agent comprises the heavy chain variable region and/or the light chain variable region of the 313R11 antibody in a humanized form. In certain embodiments, a TIGIT-binding agent comprises the heavy chain variable region of the 313R11 antibody as part of an IgG1, IgG2, or IgG4 heavy chain.

In certain embodiments, a TIGIT-binding agent comprises, consists essentially of, or consists of, the antibody 313R11. In certain embodiments, a TIGIT-binding agent comprises, consists essentially of, or consists of, a variant of the antibody 313R11.

In certain embodiments, a TIGIT-binding agent comprises the heavy chain variable region and light chain variable region of the 313R12 antibody. In some embodiments, the TIGIT-binding agent comprises the variable regions of the 313R12 antibody wherein the heavy chain variable region and/or the light chain variable region from the 313R12 antibody have been affinity-matured. In certain embodiments, a TIGIT-binding agent comprises the heavy chain and light chain of the 313R12 antibody (with or without the leader sequence). In certain embodiments, a TIGIT-binding agent is the 313R12 antibody. In certain embodiments, a TIGIT-binding agent comprises the heavy chain variable region and/or the light chain variable region of the 313R12 antibody wherein the heavy chain variable region and/or the light chain variable region have been humanized. In certain embodiments, a TIGIT-binding agent comprises the heavy chain variable region and/or the light chain variable region of the 313R12 antibody in a humanized form. In certain embodiments, a TIGIT-binding agent comprises the heavy chain variable region of the 313R12 antibody as part of an IgG1, IgG2, or IgG4 heavy chain.

In certain embodiments, a TIGIT-binding agent comprises, consists essentially of, or consists of, the antibody 313R12. In certain embodiments, a TIGIT-binding agent comprises, consists essentially of, or consists of, a variant of the antibody 313R12.

In certain embodiments, a TIGIT-binding agent comprises the heavy chain variable region and light chain variable region of the 313R14 antibody. In some embodiments, the TIGIT-binding agent comprises the variable regions of the 313R14 antibody wherein the heavy chain variable region and/or the light chain variable region from the 313R14 antibody have been affinity-matured. In certain embodiments, a TIGIT-binding agent comprises the heavy chain and light chain of the 313R14 antibody (with or without the leader sequence). In certain embodiments, a TIGIT-binding agent is the 313R14 antibody. In certain embodiments, a TIGIT-binding agent comprises the heavy chain variable region and/or the light chain variable region of the 313R14 antibody wherein the heavy chain variable region and/or the light chain variable region have been humanized. In certain embodiments, a TIGIT-binding agent comprises the heavy chain variable region and/or the light chain variable region of the 313R14 antibody in a humanized form. In certain embodiments, a TIGIT-binding agent comprises the heavy chain variable region of the 313R14 antibody as part of an IgG1, IgG2, or IgG4 heavy chain.

In certain embodiments, a TIGIT-binding agent comprises, consists essentially of, or consists of, the antibody 313R14. In certain embodiments, a TIGIT-binding agent comprises, consists essentially of, or consists of, a variant of the antibody 313R14.

In certain embodiments, a TIGIT-binding agent comprises the heavy chain variable region and light chain variable region of the 313R19 antibody. In some embodiments, the TIGIT-binding agent comprises the variable regions of the 313R19 antibody wherein the heavy chain variable region and/or the light chain variable region from the 313R19 antibody have been affinity-matured. In certain embodiments, a TIGIT-binding agent comprises the heavy chain and light chain of the 313R19 antibody (with or without the leader sequence). In certain embodiments, a TIGIT-binding agent is the 313R19 antibody. In certain embodiments, a TIGIT-binding agent comprises the heavy chain variable region and/or the light chain variable region of the 313R19 antibody wherein the heavy chain variable region and/or the light chain variable region have been humanized. In certain embodiments, a TIGIT-binding agent comprises the heavy chain variable region and/or the light chain variable region of the 313R19 antibody in a humanized form. In certain embodiments, a TIGIT-binding agent comprises the heavy chain variable region of the 313R19 antibody as part of an IgG1, IgG2, or IgG4 heavy chain.

In certain embodiments, a TIGIT-binding agent comprises, consists essentially of, or consists of, the antibody 313R19. In certain embodiments, a TIGIT-binding agent comprises, consists essentially of, or consists of, a variant of the antibody 313R19.

In some embodiments, the TIGIT-binding agent comprises a heavy chain variable region encoded by the plasmid deposited with American Type Culture Collection (ATCC), 10801 University Boulevard, Manassas, Va., USA, under the conditions of the Budapest Treaty on May 27, 2015, and designated PTA-122180. In some embodiments, the TIGIT-binding agent comprises a light chain variable region encoded by the plasmid deposited with ATCC, 10801 University Boulevard, Manassas, Va., USA, under the conditions of the Budapest Treaty on May 27, 2015, and designated PTA-122181. In some embodiments, the TIGIT-binding agent comprises a heavy chain variable region encoded by the plasmid deposited with ATCC and designated PTA-122180 and a light chain variable region encoded by the plasmid deposited with ATCC and designated PTA-122181. In some embodiments, the TIGIT-binding agent comprises a heavy chain comprising the heavy chain variable region encoded by the plasmid deposited with ATCC and designated PTA-122180. In some embodiments, the TIGIT-binding agent comprises a light chain comprising the light chain variable region encoded by the plasmid deposited with ATCC and designated PTA-122181. In some embodiments, the TIGIT-binding agent comprises a heavy chain comprising the heavy chain variable region encoded by the plasmid deposited with ATCC and designated PTA-122180 and a light chain comprising the light chain variable region encoded by the plasmid deposited with ATCC and designated PTA-122181.

In certain embodiments, the invention provides a TIGIT-binding agent (e.g., an antibody) that specifically binds TIGIT, wherein the TIGIT-binding agent comprises one, two, three, four, five, and/or six of the CDRs of antibody 313M26 or 313M32 (see Table 2). In some embodiments, the TIGIT-binding agent comprises one or more of the CDRs of 313M26 or 313M32; two or more of the CDRs of 313M26 or 313M32; three or more of the CDRs of 313M26 or 313M32; four or more of the CDRs of 313M26 or 313M32; five or more of the CDRs of 313M26 or 313M32; or all six of the CDRs of 313M26 or 313M32.

TABLE 2

|  | 313M26 and 313M32 |
| --- | --- |
| HC CDR1 | TSDYAWN (SEQ ID NO: 57) |
| HC CDR2 | YISYSGSTSYNPSLRS (SEQ ID NO: 58) |
| HC CDR3 | ARRQVGLGFAY (SEQ ID NO: 59) |
| LC CDR1 | KASQDVSTAVA (SEQ ID NO: 60) |
| LC CDR2 | SASYRYT (SEQ ID NO: 61) |
| LC CDR3 | QQHYSTP (SEQ ID NO: 62) |

In certain embodiments, the invention provides a TIGIT-binding agent (e.g., an antibody) that specifically binds TIGIT, wherein the TIGIT-binding agent comprises a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59). In some embodiments, the TIGIT-binding agent further comprises a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62). In some embodiments, the TIGIT-binding agent comprises a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62). In some embodiments, the TIGIT-binding agent comprises: (a) a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59); and (b) a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

In certain embodiments, the invention provides a TIGIT-binding agent (e.g., an antibody) that specifically binds human TIGIT, wherein the TIGIT-binding agent comprises: (a) a heavy chain CDR1 comprising TSDYAWN (SEQ ID NO:57) or a variant thereof comprising 1, 2, 3, or 4 amino acid substitutions; (b) a heavy chain CDR2 comprising YISYSGSTSYNPSLRS (SEQ ID NO:58) or a variant thereof comprising 1, 2, 3, or 4 amino acid substitutions; (c) a heavy chain CDR3 comprising ARRQVGLGFAY (SEQ ID NO:59) or a variant thereof comprising 1, 2, 3, or 4 amino acid substitutions; (d) a light chain CDR1 comprising KASQDVSTAVA (SEQ ID NO:60) or a variant thereof comprising 1, 2, 3, or 4 amino acid substitutions; (e) a light chain CDR2 comprising SASYRYT (SEQ ID NO:61) or a variant thereof comprising 1, 2, 3, or 4 amino acid substitutions; and (f) a light chain CDR3 comprising QQHYSTP (SEQ ID NO:62) or a variant thereof comprising 1, 2, 3, or 4 amino acid substitutions. In certain embodiments, the amino acid substitutions are conservative substitutions. In some embodiments, the substitutions are made as part of a humanization process. In some embodiments, the substitutions are made as part of a germline humanization process. In some embodiments, the substitutions are made as part of a binding optimization process.

In certain embodiments, the invention provides a TIGIT-binding agent (e.g., an antibody) that specifically binds TIGIT, wherein the TIGIT-binding agent comprises a heavy chain variable region having at least about 80% sequence identity to SEQ ID NO:63 or SEQ ID NO:67 and/or a light chain variable region having at least 80% sequence identity to SEQ ID NO:64 or SEQ ID NO:68. In certain embodiments, the TIGIT-binding agent comprises a heavy chain variable region having at least about 85%, at least about 90%, at least about 95%, at least about 97%, or at least about 99% sequence identity to SEQ ID NO:63. In certain embodiments, the TIGIT-binding agent comprises a heavy chain variable region having at least about 85%, at least about 90%, at least about 95%, at least about 97%, or at least about 99% sequence identity to SEQ ID NO:67. In certain embodiments, the TIGIT-binding agent comprises a light chain variable region having at least about 85%, at least about 90%, at least about 95%, at least about 97%, or at least about 99% sequence identity to SEQ ID NO:64. In certain embodiments, the TIGIT-binding agent comprises a light chain variable region having at least about 85%, at least about 90%, at least about 95%, at least about 97%, or at least about 99% sequence identity to SEQ ID NO:68. In certain embodiments, the TIGIT-binding agent comprises a heavy chain variable region having at least about 95% sequence identity to SEQ ID NO:63 or SEQ ID NO:67 and/or a light chain variable region having at least about 95% sequence identity to SEQ ID NO:64 or SEQ ID NO:68. In certain embodiments, the TIGIT-binding agent comprises a heavy chain variable region comprising SEQ ID NO:63 or SEQ ID NO:67 and/or a light chain variable region comprising SEQ ID NO:64 or SEQ ID NO:68. In certain embodiments, the TIGIT-binding agent comprises a heavy chain variable region comprising SEQ ID NO:63 or SEQ ID NO:67 and a light chain variable region comprising SEQ ID NO:64 or SEQ ID NO:68. In certain embodiments, the TIGIT-binding agent comprises a heavy chain variable region consisting essentially of SEQ ID NO:63 or SEQ ID NO:67 and a light chain variable region consisting essentially of SEQ ID NO:64 or SEQ ID NO:68. In certain embodiments, the TIGIT-binding agent comprises a heavy chain variable region consisting of SEQ ID NO:63 or SEQ ID NO:67 and a light chain variable region consisting of SEQ ID NO:64 or SEQ ID NO:68.

In certain embodiments, the TIGIT-binding agent comprises a heavy chain variable region comprising SEQ ID NO:63 and a light chain variable region comprising SEQ ID NO:64. In certain embodiments, the TIGIT-binding agent comprises a heavy chain variable region consisting essentially of SEQ ID NO:63 and a light chain variable region consisting essentially of SEQ ID NO:64. In certain embodiments, the TIGIT-binding agent comprises a heavy chain variable region consisting of SEQ ID NO:63 and a light chain variable region consisting of SEQ ID NO:64.

In certain embodiments, the TIGIT-binding agent comprises a heavy chain variable region comprising SEQ ID NO:67 and a light chain variable region comprising SEQ ID NO:68. In certain embodiments, the TIGIT-binding agent comprises a heavy chain variable region consisting essentially of SEQ ID NO:67 and a light chain variable region consisting essentially of SEQ ID NO:68. In certain embodiments, the TIGIT-binding agent comprises a heavy chain variable region consisting of SEQ ID NO:67 and a light chain variable region consisting of SEQ ID NO:68.

In certain embodiments, the invention provides a TIGIT-binding agent (e.g., an antibody) that specifically binds TIGIT, wherein the TIGIT-binding agent comprises: a heavy chain having at least 90% sequence identity to SEQ ID NO:70 and/or a light chain having at least 90% sequence identity to SEQ ID NO:72. In some embodiments, the TIGIT-binding agent comprises: a heavy chain having at least 95% sequence identity to SEQ ID NO:70 and/or a light chain having at least 95% sequence identity to SEQ ID NO:72. In some embodiments, the TIGIT-binding agent comprises a heavy chain comprising SEQ ID NO:70 and/or a light chain comprising SEQ ID NO:72. In some embodiments, the TIGIT-binding agent comprises a heavy chain consisting essentially of SEQ ID NO:70 and a light chain consisting essentially of SEQ ID NO:72. In some embodiments, the TIGIT-binding agent comprises a heavy chain consisting of SEQ ID NO:70 and a light chain consisting of SEQ ID NO:72.

In certain embodiments, the invention provides a TIGIT-binding agent (e.g., an antibody) that specifically binds TIGIT, wherein the TIGIT-binding agent comprises: a heavy chain having at least 90% sequence identity to SEQ ID NO:82 and/or a light chain having at least 90% sequence identity to SEQ ID NO:72. In some embodiments, the TIGIT-binding agent comprises: a heavy chain having at least 95% sequence identity to SEQ ID NO:82 and/or a light chain having at least 95% sequence identity to SEQ ID NO:72. In some embodiments, the TIGIT-binding agent comprises a heavy chain comprising SEQ ID NO:82 and/or a light chain comprising SEQ ID NO:72. In some embodiments, the TIGIT-binding agent comprises a heavy chain consisting essentially of SEQ ID NO:82 and a light chain consisting essentially of SEQ ID NO:72. In some embodiments, the TIGIT-binding agent comprises a heavy chain consisting of SEQ ID NO:82 and a light chain consisting of SEQ ID NO:72.

In certain embodiments, a TIGIT-binding agent comprises the heavy chain variable region and light chain variable region of the 313M26 antibody. In some embodiments, the TIGIT-binding agent comprises the variable regions of the 313M26 antibody wherein the heavy chain variable region and/or the light chain variable region from the 313M26 antibody have been affinity-matured. In certain embodiments, a TIGIT-binding agent comprises the heavy chain and light chain of the 313M26 antibody (with or without the leader sequence). In certain embodiments, a TIGIT-binding agent is the 313M26 antibody. In certain embodiments, a TIGIT-binding agent comprises the heavy chain variable region and/or the light chain variable region of the 313M26 antibody wherein the heavy chain variable region and/or the light chain variable region have been humanized. In certain embodiments, a TIGIT-binding agent comprises the heavy chain variable region and/or the light chain variable region of the 313M26 antibody in a humanized form. In certain embodiments, a TIGIT-binding agent comprises the heavy chain variable region of the 313M26 antibody as part of an IgG1, IgG2, or IgG4 heavy chain.

In certain embodiments, a TIGIT-binding agent comprises, consists essentially of, or consists of, the antibody 313M26. In certain embodiments, a TIGIT-binding agent comprises, consists essentially of, or consists of, a variant of the antibody 313M26.

In certain embodiments, a TIGIT-binding agent comprises the heavy chain variable region and light chain variable region of the 313M32 antibody. In some embodiments, the TIGIT-binding agent comprises the variable regions of the 313M32 antibody wherein the heavy chain variable region and/or the light chain variable region from the 313M32 antibody have been affinity-matured. In certain embodiments, a TIGIT-binding agent comprises the heavy chain and light chain of the 313M32 antibody (with or without the leader sequence). In certain embodiments, a TIGIT-binding agent is the 313M32 antibody. In certain embodiments, a TIGIT-binding agent comprises the heavy chain variable region of the 313M32 antibody as part of an IgG1, IgG2, or IgG4 heavy chain. In certain embodiments, a TIGIT-binding agent comprises the heavy chain variable region of the 313M32 antibody as part of a human IgG1 heavy chain. In certain embodiments, a TIGIT-binding agent comprises the heavy chain variable region of the 313M32 antibody as part of a human IgG2 heavy chain. In certain embodiments, a TIGIT-binding agent comprises the heavy chain variable region of the 313M32 antibody as part of a human IgG4 heavy chain. In certain embodiments, a TIGIT-binding agent which comprises the heavy chain variable region of the 313M32 antibody as part of a human IgG4 heavy chain is referred to as the 313M33 antibody.

In certain embodiments, a TIGIT-binding agent comprises, consists essentially of, or consists of, the antibody 313M32. In certain embodiments, a TIGIT-binding agent comprises, consists essentially of, or consists of, a variant of the antibody 313M32.

In some embodiments, the TIGIT-binding agent comprises a heavy chain variable region encoded by the plasmid deposited with American Type Culture Collection (ATCC), 10801 University Boulevard, Manassas, Va., USA, under the conditions of the Budapest Treaty on Aug. 11, 2015, and designated PTA-122346. In some embodiments, the TIGIT-binding agent comprises a light chain variable region encoded by the plasmid deposited with ATCC, 10801 University Boulevard, Manassas, Va., USA, under the conditions of the Budapest Treaty on Aug. 11, 2015, and designated PTA-122347. In some embodiments, the TIGIT-binding agent comprises a heavy chain variable region encoded by the plasmid deposited with ATCC and designated PTA-122346 and a light chain variable region encoded by the plasmid deposited with ATCC and designated PTA-122347. In some embodiments, the TIGIT-binding agent comprises a heavy chain comprising a variable region encoded by the plasmid deposited with ATCC and designated PTA-122346. In some embodiments, the TIGIT-binding agent comprises a light chain encoded by the plasmid deposited with ATCC and designated PTA-122347. In some embodiments, the TIGIT-binding agent comprises a heavy chain comprising a variable region encoded by the plasmid deposited with ATCC and designated PTA-122346 and a light chain encoded by the plasmid deposited with ATCC and designated PTA-122347.

This invention also encompasses homodimeric agents/molecules and heterodimeric agents/molecules. In some embodiments, the homodimeric agents are polypeptides. In some embodiments, the heterodimeric molecules are polypeptides. Generally the homodimeric molecule comprises two identical polypeptides. Generally the heterodimeric molecule comprises at least two different polypeptides. In some embodiments, the heterodimeric molecule is capable of binding at least two targets, e.g., a bispecific agent. The targets may be, for example, two different proteins on a single cell or two different proteins on two separate cells. The term "arm" may be used herein to describe the structure of a homodimeric agent, a heterodimeric agent, and/or a bispecific agent. In some embodiments, each arm comprises at least one polypeptide. Generally, each arm of a heterodimeric molecule has a different function, for example, binding two different targets. In some embodiments, one arm may comprise an antigen-binding site from an antibody. In some embodiments, one arm may comprise a binding portion of a receptor. In some embodiments, one arm may comprise a ligand. In some embodiments, one arm may comprise a binding region of a ligand. In some embodiments, a homodimeric agent comprises two identical arms. In some embodiments, a heterodimeric agent comprises two different arms. In some embodiments, a bispecific agent comprises two different arms.

In some embodiments, the invention provides a TIGIT-binding agent that is a homodimeric molecule. In some embodiments, the homodimeric molecule comprises two identical polypeptides. In some embodiments, the invention provides a TIGIT-binding agent that is a heterodimeric molecule. In some embodiments, the heterodimeric molecule comprises at least two different polypeptides. In some embodiments, the invention provides a TIGIT-binding agent that is a heterodimeric agent. In some embodiments, the invention provides a TIGIT-binding agent that is a bispecific agent. In certain embodiments, the TIGIT-binding agent is a bispecific antibody.

In some embodiments, a heterodimeric agent (e.g., a bispecific agent) comprises a TIGIT-binding agent described herein. In certain embodiments, a heterodimeric agent comprises an immune response stimulating agent or functional fragment thereof. In some embodiments, a heterodimeric molecule comprises at least two functions (i) binding to TIGIT and (ii) binding to a second target. In some embodiments, a heterodimeric agent comprises at least two functions, (i) binding to TIGIT and (ii) a "non-binding" function. In certain embodiments, a heterodimeric molecule comprises a second immunotherapeutic agent or functional fragment thereof. In some embodiments, one arm of the heterodimeric molecule comprises a TIGIT-binding agent described herein and one arm of the heterodimeric molecule comprises a second immunotherapeutic agent. In some embodiments, one arm of the heterodimeric agent comprises a TIGIT-binding agent described herein and one arm of the heterodimeric agent comprises an immune response stimulating agent. As used herein, the phrase "immune response stimulating agent" is used in the broadest sense and refers to a substance that directly or indirectly stimulates the immune system by inducing activation or increasing activity of any of the immune system's components. For example, immune response stimulating agents may include cytokines, as well as various antigens including tumor antigens, and antigens derived from pathogens. In some embodiments, the second immunotherapeutic agent (e.g., an immune response stimulating agent) includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), a cytokine (e.g., gamma-interferon), an antibody that blocks immunosuppressive functions (e.g., an anti-CTLA4 antibody, anti-CD28 antibody, anti-PD-1 antibody, anti-PD-L1 antibody), atoll-like receptor (e.g., TLR4, TLR7, TLR9), or a member of the B7 family (e.g., CD80, CD86). In some embodiments, the immunotherapeutic agent includes, but is not limited to, an agonist antibody (e.g., an anti-GITR antibody, an anti-OX40 antibody) or an agonist ligand (e.g., GITRL or OX40L).

In some embodiments, the TIGIT-binding agent is a heterodimeric molecule (e.g., a bispecific agent) that comprises a first CH3 domain and a second CH3 domain, each of which is modified to promote formation of heteromultimers. In some embodiments, the first and second CH3 domains are modified using a knobs-into-holes technique. In some embodiments, the first and second CH3 domains comprise changes in amino acids that result in altered electrostatic interactions. In some embodiments, the first and second CH3 domains comprise changes in amino acids that result in altered hydrophobic/hydrophilic interactions.

In some embodiments, the TIGIT-binding agent is a bispecific agent that comprises heavy chain constant regions selected from the group consisting of: (a) a first human IgG1 constant region, wherein the amino acids corresponding to positions 253 and 292 of IgG1 (SEQ ID NO:41) are replaced with glutamate or aspartate, and a second human IgG1 constant region, wherein the amino acids corresponding to positions 240 and 282 of IgG1 (SEQ ID NO:41) are replaced with lysine; (b) a first human IgG2 constant region, wherein the amino acids corresponding to positions 249 and 288 of IgG2 (SEQ ID NO:42) are replaced with glutamate or aspartate, and a second human IgG2 constant region wherein the amino acids corresponding to positions 236 and 278 of IgG2 (SEQ ID NO:42) are replaced with lysine; (c) a first human IgG3 constant region, wherein the amino acids corresponding to positions 300 and 339 of IgG3 (SEQ ID NO:43) are replaced with glutamate or aspartate, and a second human IgG3 constant region wherein the amino acids corresponding to positions 287 and 329 of IgG3 (SEQ ID NO:43) are replaced with lysine; and (d) a first human IgG4 constant region, wherein the amino acids corresponding to positions 250 and 289 of IgG4 (SEQ ID NO:44) are replaced with glutamate or aspartate, and a second IgG4 constant region wherein the amino acids corresponding to positions 237 and 279 of IgG4 (SEQ ID NO:44) are replaced with lysine.

In some embodiments, the TIGIT-binding agent is a bispecific agent which comprises a first human IgG1 constant region with amino acid substitutions at positions corresponding to positions 253 and 292 of IgG1 (SEQ ID NO:41), wherein the amino acids at positions corresponding to positions 253 and 292 of IgG1 (SEQ ID NO:41) are replaced with glutamate or aspartate, and a second human IgG1 constant region with amino acid substitutions at positions corresponding to positions 240 and 282 of IgG1 (SEQ ID NO:41), wherein the amino acids at positions corresponding to positions 240 and 282 of IgG1 (SEQ ID NO:41) are replaced with lysine. In some embodiments, the TIGIT-binding agent is a bispecific antibody which comprises a first human IgG2 constant region with amino acid substitutions at positions corresponding to positions 249 and 288 of IgG2 (SEQ ID NO:42), wherein the amino acids at positions corresponding to positions 249 and 288 of IgG2 (SEQ ID NO:42) are replaced with glutamate or aspartate, and a second human IgG2 constant region with amino acid substitutions at positions corresponding to positions 236 and 278 of IgG2 (SEQ ID NO:42), wherein the amino acids at positions corresponding to positions 236 and 278 of IgG2 (SEQ ID NO:42) are replaced with lysine. In some embodiments, the TIGIT-binding agent is a bispecific antibody which comprises a first human IgG3 constant region with amino acid substitutions at positions corresponding to positions 300 and 339 of IgG3 (SEQ ID NO:43), wherein the amino acids at positions corresponding to positions 300 and 339 of IgG3 (SEQ ID NO:43) are replaced with glutamate or aspartate, and a second human IgG3 constant region with amino acid substitutions at positions corresponding to positions 287 and 329 of IgG3 (SEQ ID NO:43), wherein the amino acids at positions corresponding to positions 287 and 329 of IgG3 (SEQ ID NO:43) are replaced with lysine. In some embodiments, the TIGIT-binding agent is a bispecific antibody which comprises a first human IgG4 constant region with amino acid substitutions at positions corresponding to positions 250 and 289 of IgG4 (SEQ ID NO:44), wherein the amino acids at positions corresponding to positions 250 and 289 of IgG4 (SEQ ID NO:44) are replaced with glutamate or aspartate, and a second human IgG4 constant region with amino acid substitutions at positions corresponding to positions 237 and 279 of IgG4 (SEQ ID NO:44), wherein the amino acids at positions corresponding to positions 237 and 279 of IgG4 (SEQ ID NO:44) are replaced with lysine.

In some embodiments, the TIGIT-binding agent is a bispecific agent which comprises a first human IgG1 constant region with amino acid substitutions at positions corresponding to positions 253 and 292 of IgG1 (SEQ ID NO:41), wherein the amino acids are replaced with glutamate, and a second human IgG1 constant region with amino acid substitutions at positions corresponding to positions 240 and 282 of IgG1 (SEQ ID NO:41), wherein the amino acids are replaced with lysine. In some embodiments, the TIGIT-binding agent is a bispecific antibody which comprises a first human IgG1 constant region with amino acid substitutions at positions corresponding to positions 253 and 292 of IgG1 (SEQ ID NO:41), wherein the amino acids are replaced with aspartate, and a second human IgG1 constant region with amino acid substitutions at positions corresponding to positions 240 and 282 of IgG1 (SEQ ID NO:41), wherein the amino acids are replaced with lysine.

In some embodiments, the TIGIT-binding agent is a bispecific agent which comprises a first human IgG2 constant region with amino acid substitutions at positions corresponding to positions 249 and 288 of IgG2 (SEQ ID NO:42), wherein the amino acids are replaced with glutamate, and a second human IgG2 constant region with amino acid substitutions at positions corresponding to positions 236 and 278 of IgG2 (SEQ ID NO:42), wherein the amino acids are replaced with lysine. In some embodiments, the TIGIT-binding agent is a bispecific antibody which comprises a first human IgG2 constant region with amino acid substitutions at positions corresponding to positions 249 and 288 of IgG2 (SEQ ID NO:42), wherein the amino acids are replaced with aspartate, and a second human IgG2 constant region with amino acid substitutions at positions corresponding to positions 236 and 278 of IgG2 (SEQ ID NO:42), wherein the amino acids are replaced with lysine.

In some embodiments, the TIGIT-binding agent is a bispecific agent which comprises a heavy chain constant region of SEQ ID NO:45. In some embodiments, the TIGIT-binding agent is a bispecific antibody which comprises a heavy chain constant region of SEQ ID NO:46. In some embodiments, the TIGIT-binding agent is a bispecific antibody which comprises a heavy chain constant region of SEQ ID NO:47. In some embodiments, the TIGIT-binding agent is a bispecific antibody which comprises a heavy chain constant region of SEQ ID NO:48. In some embodiments, the TIGIT-binding agent is a bispecific antibody which comprises a first heavy chain constant region of SEQ ID NO:45 and a second heavy chain constant region of SEQ ID NO:46. In some embodiments, the TIGIT-binding agent is a bispecific antibody which comprises a first heavy chain constant region of SEQ ID NO:47 and a second heavy chain constant region of SEQ ID NO:48.

In some embodiments, the TIGIT-binding agent is a bispecific agent which comprises a heavy chain constant region of SEQ ID NO:49. In some embodiments, the TIGIT-binding agent is a bispecific antibody which comprises a heavy chain constant region of SEQ ID NO:50. In some embodiments, the TIGIT-binding agent is a bispecific antibody which comprises a heavy chain constant region of SEQ ID NO:51. In some embodiments, the TIGIT-binding agent is a bispecific antibody which comprises a heavy chain constant region of SEQ ID NO:52. In some embodiments, the TIGIT-binding agent is a bispecific antibody which comprises a first heavy chain constant region of SEQ ID NO:49 and a second heavy chain constant region of SEQ ID NO:50. In some embodiments, the TIGIT-binding agent is a bispecific antibody which comprises a first heavy chain constant region of SEQ ID NO:51 and a second heavy chain constant region of SEQ ID NO:52.

In some embodiments, the TIGIT-binding agent is a bispecific antibody comprising a first antigen-binding site that specifically binds human TIGIT. In some embodiments, the TIGIT-binding agent is a bispecific antibody comprising a first antigen-binding site that specifically binds human TIGIT and a second antigen-binding site that binds a second target. In some embodiments, the TIGIT-binding agent is a bispecific antibody comprising: a first antigen-binding site that specifically binds human TIGIT, wherein the first antigen-binding site comprises a heavy chain CDR1 comprising GSSLSSSYMS (SEQ ID NO:7) or GFSLSSSYMS (SEQ ID NO:13), a heavy chain CDR2 comprising IIGSNGNTYY-ANWAKG (SEQ ID NO:8), and a heavy chain CDR3 comprising GGYRTSGMDP (SEQ ID NO:9). In some embodiments, the TIGIT-binding agent is a bispecific antibody comprising: a first antigen-binding site that specifically binds human TIGIT, wherein the first antigen-binding site comprises a heavy chain CDR1 comprising GSSLSSSYMS (SEQ ID NO:7), a heavy chain CDR2 comprising IIG-SNGNTYYANWAKG (SEQ ID NO:8), and a heavy chain CDR3 comprising GGYRTSGMDP (SEQ ID NO:9). In some embodiments, the TIGIT-binding agent is a bispecific antibody comprising: a first antigen-binding site that specifically binds human TIGIT, wherein the first antigen-binding site comprises a heavy chain CDR1 comprising GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9). In some embodiments, the TIGIT-binding agent is a bispecific antibody comprising: a first antigen-binding site that specifically binds human TIGIT, wherein the first antigen-binding site comprises (a) a heavy chain CDR1 comprising GSSLSSSYMS (SEQ ID NO:7) or GFSLSSSYMS (SEQ ID NO:13), a heavy chain CDR2 comprising IIG-SNGNTYYANWAKG (SEQ ID NO:8), and a heavy chain CDR3 comprising GGYRTSGMDP (SEQ ID NO:9), and (b) a second antigen-binding site, wherein the first antigen-binding site and the second antigen-binding site comprise a common (i.e., identical) light chain. In some embodiments, the TIGIT-binding agent is a bispecific antibody comprising:

a first antigen-binding site that specifically binds human TIGIT, wherein the first antigen-binding site comprises (a) a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTS-GMDP (SEQ ID NO:9), a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16) and (b) a second antigen-binding site. In some embodiments, the bispecific antibody comprises a first antigen-binding site comprising a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16).

In some embodiments, the TIGIT-binding agent is a bispecific antibody comprising a first heavy chain variable region having at least about 80% sequence identity to SEQ ID NO:17, SEQ ID NO:19, or SEQ ID NO:32. In certain embodiments, the TIGIT-binding agent is a bispecific antibody comprising a first heavy chain variable region having at least about 85%, at least about 90%, at least about 95%, at least about 97%, or at least about 99% sequence identity to SEQ ID NO:17, SEQ ID NO:19, or SEQ ID NO:32. In some embodiments, the bispecific antibody comprises a light chain variable region at least about 80% sequence identity to SEQ ID NO:18 or SEQ ID NO:20. In some embodiments, the bispecific antibody comprises a light chain variable region at least about 85%, at least about 90%, at least about 95%, at least about 97%, or at least about 99% sequence identity to SEQ ID NO:18 or SEQ ID NO:20. In some embodiments, the TIGIT-binding agent is a bispecific antibody comprising a first heavy chain variable region comprising SEQ ID NO:17. In some embodiments, the TIGIT-binding agent is a bispecific antibody comprising a first heavy chain variable region comprising SEQ ID NO:19. In some embodiments, the TIGIT-binding agent is a bispecific antibody comprising a first heavy chain variable region comprising SEQ ID NO:32. In some embodiments, the TIGIT-binding agent is a bispecific antibody comprising a first light chain variable region comprising SEQ ID NO:18. In some embodiments, the TIGIT-binding agent is a bispecific antibody comprising a first light chain variable region comprising SEQ ID NO:20.

In some embodiments, the TIGIT-binding agent is a bispecific antibody comprising a first heavy chain variable region comprising SEQ ID NO:17 and a first heavy chain constant region comprising SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments, the TIGIT-binding agent is a bispecific antibody comprising a first heavy chain variable region comprising SEQ ID NO:19 and a first heavy chain constant region comprising SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments, the TIGIT-binding agent is a bispecific antibody comprising a first heavy chain variable region comprising SEQ ID NO:32 and a first heavy chain constant region comprising SEQ ID NO:45, SEQ ID NO:46, SEQ ID NO:47, SEQ ID NO:48, SEQ ID NO:49, SEQ ID NO:50, SEQ ID NO:51, or SEQ ID NO:52.

In some embodiments, the TIGIT-binding agent is a bispecific antibody comprising a first antigen-binding site that specifically binds human TIGIT. In some embodiments, the TIGIT-binding agent is a bispecific antibody comprising a first antigen-binding site that specifically binds human TIGIT and a second antigen-binding site that binds a second target. In some embodiments, the TIGIT-binding agent is a bispecific antibody comprising: a first antigen-binding site that specifically binds human TIGIT, wherein the first antigen-binding site comprises a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59). In some embodiments, the TIGIT-binding agent is a bispecific antibody comprising: a first antigen-binding site that specifically binds human TIGIT, wherein the first antigen-binding site comprises (a) a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59); and (b) a second antigen-binding site, wherein the first antigen-binding site and the second antigen-binding site comprise a common (i.e., identical) light chain. In some embodiments, the TIGIT-binding agent is a bispecific antibody comprising: a first antigen-binding site that specifically binds human TIGIT, wherein the first antigen-binding site comprises (a) a heavy chain CDR1 comprising TSDYAWN (SEQ ID NO:57), a heavy chain CDR2 comprising YISYS-GSTSYNPSLRS (SEQ ID NO:58), and a heavy chain CDR3 comprising ARRQVGLGFAY (SEQ ID NO:59), a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62); and (b) a second antigen-binding site. In some embodiments, the bispecific antibody comprises a first antigen-binding site comprising a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

In some embodiments, the TIGIT-binding agent is a bispecific antibody comprising a first heavy chain variable region having at least about 80% sequence identity to SEQ ID NO:63 or SEQ ID NO:67. In certain embodiments, the TIGIT-binding agent is a bispecific antibody comprising a first heavy chain variable region having at least about 85%, at least about 90%, at least about 95%, at least about 97%, or at least about 99% sequence identity to SEQ ID NO:63 or SEQ ID NO:67. In some embodiments, the bispecific antibody comprises a light chain variable region at least about 80% sequence identity to SEQ ID NO:64 or SEQ ID NO:68. In some embodiments, the bispecific antibody comprises a light chain variable region at least about 85%, at least about 90%, at least about 95%, at least about 97%, or at least about 99% sequence identity to SEQ ID NO:64 or SEQ ID NO:68. In some embodiments, the TIGIT-binding agent is a bispecific antibody comprising a first heavy chain variable region comprising SEQ ID NO:63. In some embodiments, the TIGIT-binding agent is a bispecific antibody comprising a first heavy chain variable region comprising SEQ ID NO:67. In some embodiments, the TIGIT-binding agent is a bispecific antibody comprising a first light chain variable region comprising SEQ ID NO:64. In some embodiments, the TIGIT-binding agent is a bispecific antibody comprising a first light chain variable region comprising SEQ ID NO:68.

In some embodiments, the TIGIT-binding agent is a bispecific antibody comprising a first heavy chain variable region comprising SEQ ID NO:63 and a first heavy chain constant region comprising SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments, the TIGIT-binding agent is a bispecific antibody comprising a first heavy chain variable region comprising SEQ ID NO:67 and a first heavy chain constant region comprising SEQ ID NO:45, SEQ ID NO:46, SEQ ID NO:47, SEQ ID NO:48, SEQ ID NO:49, SEQ ID NO:50, SEQ ID NO:51, or SEQ ID NO:52.

In certain embodiments, the TIGIT-binding agent is a bispecific antibody that specifically binds human TIGIT and a second target. In some embodiments, the second target is a tumor antigen. In some embodiments, the bispecific antibody comprises a TIGIT-binding agent described herein and a second polypeptide comprising an antibody that specifically binds a tumor antigen. A bispecific antibody with a binding specificity for a tumor antigen can be used to direct the TIGIT-binding agent to a tumor. This may be useful to induce and/or enhance an immune response near or within the tumor microenvironment. In some embodiments, a bispecific antibody may be used to induce or enhance the activity of tumor infiltrating immune cells. In some embodiments, a bispecific antibody may be used to induce or enhance the activity of tumor infiltrating lymphocytes (TILs). In some embodiments, a bispecific antibody may be used to inhibit or decrease the activity of Treg cells. In some embodiments, a bispecific antibody may be used to inhibit or decrease the activity of MSDCs.

In some embodiments, the TIGIT-binding agent is a bispecific antibody, wherein the first target is TIGIT and the second target is on an immune response cell. In some embodiments, the second target is on a T-cell, a NK cell, a B-cell, a macrophage, a dendritic cell, or a myeloid cell. In some embodiments, the second target is PD-1, PD-L1, CTLA4, TIM-3, LAG-3, GITR, OX-40, GITRL, or OX-40L. In some embodiments, the second target is CD28 or 4-1BB.

In some embodiments, a bispecific antibody comprises a first arm comprising a TIGIT-binding agent described herein and a second arm comprising an antibody that specifically binds PD-1. In some embodiments, a bispecific antibody comprises a first arm comprising a TIGIT-binding agent described herein and a second arm comprising an antibody that specifically binds PD-L1. In some embodiments, a bispecific antibody comprises a first arm comprising a TIGIT-binding agent described herein and a second arm comprising an antibody that specifically binds GITR. In some embodiments, a bispecific antibody comprises a first arm comprising a TIGIT-binding agent described herein and a second arm comprising an antibody that specifically binds OX-40. In some embodiments, a bispecific antibody comprises a first arm comprising a TIGIT-binding antibody described herein and a second arm comprising an antibody that specifically binds CD40. In some embodiments, a bispecific antibody comprises a first arm comprising a TIGIT-binding agent described herein and a second arm comprising an antibody that specifically binds CTLA4. In some embodiments, a bispecific antibody comprises a first arm comprising a TIGIT-binding antibody described herein and a second arm comprising an antibody that specifically binds CD28. In some embodiments, a bispecific antibody comprises a first arm comprising a TIGIT-binding agent described herein and a second arm comprising an antibody that specifically binds GITRL. In some embodiments, a bispecific antibody comprises a first arm comprising a TIGIT-binding agent described herein and a second arm comprising an antibody that specifically binds OX-40L.

In some embodiments, the TIGIT-binding agent is a bispecific antibody that comprises a heavy chain variable region from the anti-TIGIT antibody 313R11. In some embodiments, the TIGIT-binding agent is a bispecific antibody that comprises a heavy chain variable region from the anti-TIGIT antibody 313R12. In some embodiments, the TIGIT-binding agent is a bispecific antibody that comprises a heavy chain variable region from the anti-TIGIT antibody 313R14. In some embodiments, the TIGIT-binding agent is a bispecific antibody that comprises a heavy chain variable region from the anti-TIGIT antibody 313R19 or 313R20. In some embodiments, the TIGIT-binding agent is a bispecific antibody that comprises a light chain variable region from the anti-TIGIT antibody 313R11 or 313R12. In some embodiments, the TIGIT-binding agent is a bispecific antibody that comprises a light chain variable region from the anti-TIGIT antibody 313R14, 313R19, or 313R20.

In some embodiments, the TIGIT-binding agent is a bispecific antibody that comprises a heavy chain variable region from the anti-TIGIT antibody 313M26. In some embodiments, the TIGIT-binding agent is a bispecific antibody that comprises a light chain variable region from the anti-TIGIT antibody 313M26.

In some embodiments, the TIGIT-binding agent is a bispecific antibody that comprises a heavy chain variable region from the anti-TIGIT antibody 313M32. In some embodiments, the TIGIT-binding agent is a bispecific antibody that comprises a light chain variable region from the anti-TIGIT antibody 313M32.

In some embodiments, a bispecific agent comprises a first arm comprising a TIGIT-binding agent described herein and a second arm comprising a polypeptide comprising GITRL that specifically binds GITR. In some embodiments, the second arm comprises a polypeptide comprising at least one copy of the extracellular domain of GITRL. In some embodiments, a bispecific agent comprises a first arm comprising a TIGIT-binding agent described herein and a second arm comprising a polypeptide comprising OX-40L that specifically binds OX-40. In some embodiments, the second arm comprises a polypeptide comprising at least one copy of the extracellular domain of OX-40L. In some embodiments, a bispecific agent comprises a first arm comprising a TIGIT-binding agent described herein and a second arm comprising a polypeptide comprising CD40L that specifically binds CD40. In some embodiments, the second arm comprises a polypeptide comprising at least one copy of the extracellular domain of CD40L. In some embodiments, a bispecific agent comprises a first arm comprising a TIGIT-binding agent described herein and a second arm comprising a polypeptide comprising 4-1BB ligand that specifically binds 4-1BB. In some embodiments, the second arm comprises a polypeptide comprising at least one copy of the extracellular domain of 4-1BB ligand.

In some embodiments, the TIGIT-binding agent is a bispecific agent that binds TIGIT with a $K_D$ of about 50 nM or less, about 25 nM or less, about 10 nM or less, about 1 nM or less, or about 0.1 nM or less. In some embodiments, the TIGIT-binding agent is a bispecific agent that binds a second target with a $K_D$ of about 50 nM or less, about 25 nM or less, about 10 nM or less, about 1 nM or less, or about 0.1 nM or less. In some embodiments, the TIGIT-binding agent comprises is a bispecific agent that binds TIGIT with a $K_D$ of about 50 nM or less and binds a second target with a $K_D$ of about 50 nM or less. In some embodiments, the TIGIT-binding agent is a bispecific agent that binds TIGIT with a $K_D$ of about 25 nM or less and binds a second target with a $K_D$ of about 25 nM or less. In some embodiments, the TIGIT-binding agent is a bispecific agent that binds TIGIT with a $K_D$ of about 10 nM or less and binds a second target with a $K_D$ of about 10 nM or less. In some embodiments, the TIGIT-binding agent is a bispecific agent that binds TIGIT with a $K_D$ of about 1 nM or less and binds a second target with a $K_D$ of about 1 nM or less.

In some embodiments, the TIGIT-binding agent is a bispecific agent which comprises one antigen-binding site with a binding affinity that is weaker than the binding affinity of the second antigen-binding site. For example, in some embodiments, the bispecific agent may bind TIGIT with a $K_D$ ranging from about 0.1 nM to 1 nM and may bind a second target with a $K_D$ ranging from about 1 nM to 10 nM. Or the bispecific agent may bind TIGIT with a $K_D$ ranging from about 1 nM to 10 nM and may bind a second target with a $K_D$ ranging from about 0.1 nM to 1 nM. In some embodiments, the bispecific agent may bind TIGIT with a $K_D$ ranging from about 0.1 nM to 1 nM and may bind a second target with a $K_D$ ranging from about 1 nM to 10 nM. Or the bispecific agent may bind TIGIT with a $K_D$ ranging from about 1 nM to 10 nM and may bind a second target with a $K_D$ ranging from about 0.1 nM to 1 nM. In some embodiments, the difference in affinity between the two antigen-binding sites may be about 2-fold or more, about 3-fold or more, about 5-fold or more, about 8-fold or more, about 10-fold or more, about 15-fold or more, about 30-fold or more, about 50-fold or more, or about 100-fold or more. In some embodiments, at least one amino acid residue in at least one CDR of the antigen-binding site for TIGIT is substituted with a different amino acid so that the affinity of the TIGIT-binding site is altered. In some embodiments, the affinity of the TIGIT-binding site is increased. In some embodiments, the affinity of the TIGIT-binding site is decreased. In some embodiments, at least one amino acid residue in at least one CDR of the antigen-binding site for the second target is substituted with a different amino acid so that the affinity of the second antigen-binding site is altered. In some embodiments, the affinity of the second antigen-binding site is increased. In some embodiments, the affinity of the second antigen-binding site is decreased. In some embodiments, the affinities of both the TIGIT and the second antigen-binding sites are altered.

The invention provides polypeptides, including, but not limited to, antibodies that specifically bind TIGIT. In some embodiments, a polypeptide binds human TIGIT. In some embodiments, a polypeptide binds mouse TIGIT. In some embodiments, a polypeptide binds mouse TIGIT and human TIGIT. In some embodiments, a polypeptide binds human TIGIT and does not bind mouse TIGIT. In some embodiments, a polypeptide binds human TIGIT and does not bind rat TIGIT. In some embodiments, a polypeptide binds human TIGIT and does not bind rabbit TIGIT. In some embodiments, a polypeptide binds human TIGIT and does not bind marmoset TIGIT. In some embodiments, a polypeptide binds human TIGIT and does not bind dog TIGIT. In some embodiments, a polypeptide binds human TIGIT and does not bind pig TIGIT. In some embodiments, a polypeptide binds human TIGIT and does not bind cynomolgus monkey TIGIT. In some embodiments, a polypeptide binds human TIGIT and does not bind rhesus monkey TIGIT.

In certain embodiments, a polypeptide comprises one, two, three, four, five, and/or six of the CDRs of antibody 313R11, 313R12, 313R14, or 313R19 (see Table 1 herein). Antibody 313R20 comprises the same CDRs and heavy and light chain variable domains as antibody 313R19, but 313R20 comprises an IgG4 format. In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds TIGIT, wherein the polypeptide comprises an amino acid sequence having at least about 80% sequence identity to SEQ ID NO:17, SEQ ID NO:19, or SEQ ID NO:32, and/or an amino acid sequence having at least about 80% sequence identity to SEQ ID NO:18 or SEQ ID NO:20. In certain embodiments, the polypeptide comprises an amino acid sequence having at least about 85%, at least about 90%, at least about 95%, at least about 97%, or at least about 99% sequence identity to SEQ ID NO:17, SEQ ID NO:19 or SEQ ID NO:32. In certain embodiments, the polypeptide comprises an amino acid sequence having at least about 85%, at least about 90%, at least about 95%, at least about 97%, or at least about 99% sequence identity to SEQ ID NO:18 or SEQ ID NO:20. In certain embodiments, the polypeptide comprises an amino acid sequence having at least about 95% sequence identity to SEQ ID NO:17, SEQ ID NO:19, or SEQ ID NO:32, and/or an amino acid sequence having at least about 95% sequence identity to SEQ ID NO:18 or SEQ ID NO:20. In certain embodiments, the polypeptide comprises an amino acid sequence comprising SEQ ID NO:17 and/or an amino acid sequence comprising SEQ ID NO:18. In certain embodiments, the polypeptide comprises an amino acid sequence comprising SEQ ID NO:19 and/or an amino acid sequence comprising SEQ ID NO:20. In certain embodiments, the polypeptide comprises an amino acid sequence comprising SEQ ID NO:32 and/or an amino acid sequence comprising SEQ ID NO:20.

In some embodiments, a polypeptide comprises an amino acid sequence comprising SEQ ID NO:17, SEQ ID NO:18, SEQ ID NO:19, SEQ ID NO:20, and/or SEQ ID NO:32. As defined herein, a polypeptide can occur as a single chain or as two or more associated chains. In certain embodiments, a polypeptide comprises an amino acid sequence comprising SEQ ID NO:17 and an amino acid sequence comprising SEQ ID NO:18. In certain embodiments, a polypeptide comprises an amino acid sequence comprising SEQ ID NO:19 and an amino acid sequence comprising SEQ ID NO:20. In certain embodiments, a polypeptide comprises an amino acid sequence comprising SEQ ID NO:32 and an amino acid sequence comprising SEQ ID NO:20. In certain embodiments, the polypeptide comprises an amino acid sequence consisting essentially of SEQ ID NO:17 and an amino acid sequence consisting essentially of SEQ ID NO:18. In certain embodiments, the polypeptide comprises an amino acid sequence consisting essentially of SEQ ID NO:19 and an amino acid sequence consisting essentially of SEQ ID NO:20. In certain embodiments, the polypeptide comprises an amino acid sequence consisting essentially of SEQ ID NO:32 and an amino acid sequence consisting essentially of SEQ ID NO:20. In certain embodiments, the polypeptide comprises an amino acid sequence consisting of SEQ ID NO:17 and an amino acid sequence consisting of SEQ ID NO:18. In certain embodiments, the polypeptide comprises an amino acid sequence consisting of SEQ ID NO:19 and an amino acid sequence consisting of SEQ ID NO:20. In certain embodiments, the polypeptide comprises an amino acid sequence consisting of SEQ ID NO:32 and an amino acid sequence consisting of SEQ ID NO:20.

In some embodiments, the polypeptide comprises an amino acid sequence comprising SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:33, SEQ ID NO:34, SEQ ID NO:55, and/or SEQ ID NO:56. In certain embodiments, the polypeptide comprises an amino acid sequence comprising SEQ ID NO:21 and an amino acid sequence comprising SEQ ID NO:23. In certain embodiments, the polypeptide comprises an amino acid sequence comprising SEQ ID NO:22 and an amino acid sequence comprising SEQ ID NO:23. In certain embodiments, the polypeptide comprises an amino acid sequence comprising SEQ ID NO:24 and an amino acid sequence comprising SEQ ID NO:25. In certain embodiments, the polypeptide comprises an amino acid sequence comprising SEQ ID NO:33 and an amino acid sequence comprising SEQ ID NO:25. In certain embodiments, the polypeptide comprises an amino acid sequence comprising SEQ ID NO:55 and an amino acid sequence comprising SEQ ID NO:25. In certain embodiments, the polypeptide comprises an amino acid sequence comprising SEQ ID NO:26 and an amino acid sequence comprising SEQ ID NO:28. In certain embodiments, the polypeptide comprises an amino acid sequence comprising SEQ ID NO:27 and an amino acid sequence comprising SEQ ID NO:28. In certain embodiments, the polypeptide comprises an amino acid sequence comprising SEQ ID NO:29 and an amino acid sequence comprising SEQ ID NO:30. In certain embodiments, the polypeptide comprises an amino acid sequence comprising SEQ ID NO:34 and an amino acid sequence comprising SEQ ID NO:30. In certain embodiments, the polypeptide comprises an amino acid sequence comprising SEQ ID NO:56 and an amino acid sequence comprising SEQ ID NO:30.

In some embodiments, a TIGIT-binding agent comprises a polypeptide comprising a sequence selected from the group consisting of: SEQ ID NO:17, SEQ ID NO:18, SEQ ID NO:19, SEQ ID NO:20, SEQ ID NO:26, SEQ ID NO:27, SEQ ID NO:28, SEQ ID NO:29, SEQ ID NO:30, SEQ ID NO:32, SEQ ID NO:34, and SEQ ID NO:56.

In certain embodiments, a polypeptide comprises an amino acid sequence consisting of SEQ ID NO:21 and an amino acid sequence consisting of SEQ ID NO:23. In certain embodiments, a polypeptide comprises an amino acid sequence consisting of SEQ ID NO:22 and an amino acid sequence consisting of SEQ ID NO:23. In certain embodiments, a polypeptide comprises an amino acid sequence consisting of SEQ ID NO:24 and an amino acid sequence consisting of SEQ ID NO:25. In certain embodiments, a polypeptide comprises an amino acid sequence consisting of SEQ ID NO:33 and an amino acid sequence consisting of SEQ ID NO:25. In certain embodiments, a polypeptide comprises an amino acid sequence consisting of SEQ ID NO:55 and an amino acid sequence consisting of SEQ ID NO:25. In certain embodiments, a polypeptide comprises an amino acid sequence consisting of SEQ ID NO:26 and an amino acid sequence consisting of SEQ ID NO:28. In certain embodiments, a polypeptide comprises an amino acid sequence consisting of SEQ ID NO:27 and an amino acid sequence consisting of SEQ ID NO:28. In certain embodiments, a polypeptide comprises an amino acid sequence consisting of SEQ ID NO:29 and an amino acid sequence consisting of SEQ ID NO:30. In certain embodiments, a polypeptide comprises an amino acid sequence consisting of SEQ ID NO:34 and an amino acid sequence consisting of SEQ ID NO:30. In certain embodiments, a polypeptide comprises an amino acid sequence consisting of SEQ ID NO:56 and an amino acid sequence consisting of SEQ ID NO:30.

In certain embodiments, a polypeptide comprises one, two, three, four, five, and/or six of the CDRs of antibody 313M26 or 313M32 (see Table 2 herein). In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds TIGIT, wherein the polypeptide comprises an amino acid sequence having at least about 80% sequence identity to SEQ ID NO:63 or SEQ ID NO:67, and/or an amino acid sequence having at least about 80% sequence identity to SEQ ID NO:64 or SEQ ID NO:68. In certain embodiments, the polypeptide comprises an amino acid sequence having at least about 85%, at least about 90%, at least about 95%, at least about 97%, or at least about 99% sequence identity to SEQ ID NO:63 or SEQ ID NO:67. In certain embodiments, the polypeptide comprises an amino acid sequence having at least about 85%, at least about 90%, at least about 95%, at least about 97%, or at least about 99% sequence identity to SEQ ID NO:64 or SEQ ID NO:68. In certain embodiments, the polypeptide comprises an amino acid sequence having at least about 95% sequence identity to SEQ ID NO:63 or SEQ ID NO:167 and/or an amino acid sequence having at least about 95% sequence identity to SEQ ID NO:64 or SEQ ID NO:68. In certain embodiments, the polypeptide comprises an amino acid sequence comprising SEQ ID NO:63 and/or an amino acid sequence comprising SEQ ID NO:64. In certain embodiments, the polypeptide comprises an amino acid sequence comprising SEQ ID NO:67 and/or an amino acid sequence comprising SEQ ID NO:68.

In some embodiments, a polypeptide comprises an amino acid sequence selected from the group consisting of: SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:82, and/or SEQ ID NO:83. As defined herein, a polypeptide can occur as a single chain or as two or more associated chains. In certain embodiments, a polypeptide comprises an amino acid sequence comprising SEQ ID NO:63 and an amino acid sequence comprising SEQ ID NO:64. In certain embodiments, a polypeptide comprises an amino acid sequence comprising SEQ ID NO:67 and an amino acid sequence comprising SEQ ID NO:68. In certain embodiments, a polypeptide comprises an amino acid sequence comprising SEQ ID NO:69 and an amino acid sequence comprising SEQ ID NO:71. In certain embodiments, the polypeptide comprises an amino acid sequence comprising SEQ ID NO:70 and an amino acid sequence comprising SEQ ID NO:72. In certain embodiments, the polypeptide comprises an amino acid sequence comprising SEQ ID NO:82 and an amino acid sequence comprising SEQ ID NO:72.

In certain embodiments, a polypeptide comprises an amino acid sequence consisting of SEQ ID NO:63 and an amino acid sequence consisting of SEQ ID NO:64. In certain embodiments, a polypeptide comprises an amino acid sequence consisting of SEQ ID NO:67 and an amino acid sequence consisting of SEQ ID NO:68. In certain embodiments, a polypeptide comprises an amino acid sequence consisting of SEQ ID NO:69 and an amino acid sequence consisting of SEQ ID NO:71. In certain embodiments, a polypeptide comprises an amino acid sequence consisting of SEQ ID NO:70 and an amino acid sequence consisting of SEQ ID NO:72. In certain embodiments, a polypeptide comprises an amino acid sequence consisting of SEQ ID NO:82 and an amino acid sequence consisting of SEQ ID NO:72.

Many proteins, including antibodies, contain a signal sequence that directs the transport of the proteins to various locations. Generally, signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or may be used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to a "native" or "parental" signal sequence. In some embodiments, the signal sequence of the polypeptide comprises amino acid substitutions and/or deletions that allow one cleavage site to be dominant, thereby resulting in a substantially homogeneous polypeptide with one N-terminus. In some embodiments, a signal sequence of the polypeptide affects the expression level of the polypeptide, e.g., increased expression or decreased expression.

In certain embodiments, an antibody competes for specific binding to TIGIT with a TIGIT-binding agent described herein. In some embodiments, an antibody competes for specific binding to TIGIT with a TIGIT-binding agent comprising: (a) a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9) and (b) a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16).

In certain embodiments, an antibody competes for specific binding to TIGIT with a TIGIT-binding agent comprising (a) a heavy chain variable region comprising SEQ ID NO:17, SEQ ID NO:19, or SEQ ID NO:32 and (b) a light chain variable region comprising SEQ ID NO:18 or SEQ ID NO:20. In certain embodiments, an antibody competes for specific binding to TIGIT with a TIGIT-binding agent comprising a heavy chain variable region comprising SEQ ID NO:17 and a light chain variable region comprising SEQ ID NO:18. In certain embodiments, an antibody competes for specific binding to TIGIT with a TIGIT-binding agent comprising a heavy chain variable region comprising SEQ ID NO:19 and a light chain variable region comprising SEQ ID NO:20. In certain embodiments, an antibody competes for specific binding to TIGIT with a TIGIT-binding agent comprising a heavy chain variable region comprising SEQ ID NO:32 and a light chain variable region comprising SEQ ID NO:20.

In certain embodiments, an antibody competes for specific binding to TIGIT with a TIGIT-binding agent comprising a heavy chain comprising SEQ ID NO:26, SEQ ID NO:27, SEQ ID NO:29, SEQ ID NO:34, or SEQ ID NO:56 and a light chain comprising SEQ ID NO:28 or SEQ ID NO:30. In certain embodiments, an antibody competes for specific binding to TIGIT with a TIGIT-binding agent comprising a heavy chain comprising SEQ ID NO:26 and a light chain comprising SEQ ID NO:28. In certain embodiments, an antibody competes for specific binding to TIGIT with a TIGIT-binding agent comprising a heavy chain comprising SEQ ID NO:27 and a light chain comprising SEQ ID NO:28. In certain embodiments, an antibody competes for specific binding to TIGIT with a TIGIT-binding agent comprising a heavy chain comprising SEQ ID NO:29 and a light chain comprising SEQ ID NO:30. In certain embodiments, an antibody competes for specific binding to TIGIT with a TIGIT-binding agent comprising a heavy chain comprising SEQ ID NO:34 and a light chain comprising SEQ ID NO:30. In some embodiments, an antibody competes for specific binding to TIGIT with a TIGIT-binding agent comprising a heavy chain comprising SEQ ID NO:56 and a light chain comprising SEQ ID NO:30.

In certain embodiments, an antibody competes with antibody 313R11 for specific binding to TIGIT. In certain embodiments, an antibody competes with antibody 313R12 for specific binding to TIGIT. In certain embodiments, an antibody competes with antibody 313R14 for specific binding to human TIGIT. In certain embodiments, an antibody competes with antibody 313R19 for specific binding to human TIGIT. In certain embodiments, an antibody competes with antibody 313R20 for specific binding to human TIGIT.

In some embodiments, an antibody competes with a reference antibody for specific binding to TIGIT, wherein the reference antibody is antibody 313R11. In some embodiments, an antibody competes with a reference antibody for specific binding to TIGIT, wherein the reference antibody is antibody 313R12. In some embodiments, an antibody competes with a reference antibody for specific binding to TIGIT, wherein the reference antibody is antibody 313R14. In some embodiments, an antibody competes with a reference antibody for specific binding to TIGIT, wherein the reference antibody is antibody 313R19. In some embodiments, an antibody competes with a reference antibody for specific binding to TIGIT, wherein the reference antibody is antibody 313R20.

In certain embodiments, an antibody binds the same epitope, or essentially the same epitope, on TIGIT as a TIGIT-binding agent of the invention. In certain embodiments, an antibody binds the same epitope, or essentially the same epitope, on TIGIT as antibody 313R11. In certain embodiments, an antibody binds the same epitope, or essentially the same epitope, on TIGIT as antibody 313R12. In certain embodiments, an antibody binds the same epitope, or essentially the same epitope, on TIGIT as antibody 313R14.

In certain embodiments, an antibody binds the same epitope, or essentially the same epitope, on TIGIT as antibody 313R19. In certain embodiments, an antibody binds the same epitope, or essentially the same epitope, on TIGIT as antibody 313R20.

In another embodiment, an antibody binds an epitope on TIGIT that overlaps with the epitope on TIGIT bound by a TIGIT-binding agent of the invention. In some embodiments, the antibody binds an epitope on TIGIT that overlaps with the epitope on TIGIT bound by antibody 313R11. In another embodiment, the antibody binds an epitope on TIGIT that overlaps with the epitope on TIGIT bound by antibody 313R12. In some embodiments, the antibody binds an epitope on TIGIT that overlaps with the epitope on TIGIT bound by antibody 313R14. In certain embodiments, the antibody binds an epitope on TIGIT that overlaps with the epitope on TIGIT bound by antibody 313R19. In certain embodiments, the antibody binds an epitope on TIGIT that overlaps with the epitope on TIGIT bound by antibody 313R20.

In certain embodiments, an antibody competes for specific binding to TIGIT with a TIGIT-binding agent described herein. In some embodiments, an antibody competes for specific binding to TIGIT with a TIGIT-binding agent comprising: (a) a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59) and (b) a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

In certain embodiments, an antibody competes for specific binding to TIGIT with a TIGIT-binding agent comprising (a) a heavy chain variable region comprising SEQ ID NO:63 or SEQ ID NO:67 and (b) a light chain variable region comprising SEQ ID NO:64 or SEQ ID NO:68. In certain embodiments, an antibody competes for specific binding to TIGIT with a TIGIT-binding agent comprising a heavy chain variable region comprising SEQ ID NO:63 and a light chain variable region comprising SEQ ID NO:64. In certain embodiments, an antibody competes for specific binding to TIGIT with a TIGIT-binding agent comprising a heavy chain variable region comprising SEQ ID NO:167 and a light chain variable region comprising SEQ ID NO:68. In certain embodiments, an antibody competes for specific binding to TIGIT with a TIGIT-binding agent comprising a heavy chain comprising SEQ ID NO:70 and a light chain comprising SEQ ID NO:72. In certain embodiments, an antibody competes for specific binding to TIGIT with a TIGIT-binding agent comprising a heavy chain comprising SEQ ID NO:82 and a light chain comprising SEQ ID NO:72.

In certain embodiments, an antibody competes with antibody 313M26 for specific binding to TIGIT. In certain embodiments, an antibody competes with antibody 313M32 for specific binding to TIGIT. In certain embodiments, an antibody competes with antibody 313M32 for specific binding to human TIGIT. In some embodiments, an antibody competes with a reference antibody for specific binding to TIGIT, wherein the reference antibody is antibody 313M26. In some embodiments, an antibody competes with a reference antibody for specific binding to TIGIT, wherein the reference antibody is antibody 313M32. In some embodiments, an antibody competes with a reference antibody for specific binding to TIGIT, wherein the reference antibody is antibody 313M33. In some embodiments, an antibody competes with a reference antibody for specific binding to human TIGIT, wherein the reference antibody is antibody 313M32. In some embodiments, an antibody competes with a reference antibody for specific binding to human TIGIT, wherein the reference antibody is antibody 313M33.

In certain embodiments, an antibody binds the same epitope, or essentially the same epitope, on TIGIT as a TIGIT-binding agent described herein. In certain embodiments, an antibody binds the same epitope, or essentially the same epitope, on TIGIT as antibody 313M26. In certain embodiments, an antibody binds the same epitope, or essentially the same epitope, on TIGIT as antibody 313M32. In certain embodiments, an antibody binds the same epitope, or essentially the same epitope, on TIGIT as antibody 313M33. In certain embodiments, an antibody binds the same epitope, or essentially the same epitope, on human TIGIT as antibody 313M32. In certain embodiments, an antibody binds the same epitope, or essentially the same epitope, on human TIGIT as antibody 313M33.

In another embodiment, an antibody binds an epitope on TIGIT that overlaps with the epitope on TIGIT bound by a TIGIT-binding agent described herein. In some embodiments, the antibody binds an epitope on TIGIT that overlaps with the epitope on TIGIT bound by antibody 313M26. In another embodiment, the antibody binds an epitope on TIGIT that overlaps with the epitope on TIGIT bound by antibody 313M32. In another embodiment, the antibody binds an epitope on TIGIT that overlaps with the epitope on TIGIT bound by antibody 313M33. In another embodiment, the antibody binds an epitope on TIGIT that overlaps with the epitope on human TIGIT bound by antibody 313M32. In another embodiment, the antibody binds an epitope on TIGIT that overlaps with the epitope on human TIGIT bound by antibody 313M33.

In some embodiments, an antibody competes for binding to an epitope comprising amino acids within SEQ ID NO:79 with a TIGIT-binding agent described herein. In some embodiments, an antibody competes for binding to an epitope comprising amino acids within SEQ ID NO:80 with a TIGIT-binding agent described herein. In some embodiments, an antibody competes for binding to an epitope comprising amino acids within SEQ ID NO:79 and SEQ ID NO:80 with a TIGIT-binding agent described herein. In some embodiments, an antibody competes for binding to an epitope comprising amino acids Q62 and I109 of SEQ ID NO:4 with a TIGIT-binding agent described herein. In some embodiments, an antibody competes for binding to an epitope comprising amino acids Q62 and T119 of SEQ ID NO:4 with a TIGIT-binding agent described herein. In some embodiments, an antibody competes for binding with an epitope comprising amino acids Q64 and I109 of SEQ ID NO:4 with a TIGIT-binding agent described herein. In some embodiments, an antibody competes for binding to an epitope comprising amino acids Q64 and T119 of SEQ ID NO:4 with a TIGIT-binding agent described herein. In some embodiments, an antibody competes for binding to an epitope comprising amino acids Q62, Q64, and I109 of SEQ ID NO:4 with a TIGIT-binding agent described herein. In some embodiments, an antibody competes for binding to an epitope comprising amino acids Q62, Q64, and T119 of SEQ ID NO:4 with a TIGIT-binding agent described herein. In some embodiments, an antibody competes for binding to an epitope comprising amino acids Q62, I109, and T119 of SEQ ID NO:4 with a TIGIT-binding agent described herein. In some embodiments, an antibody competes for binding to an epitope comprising amino acids Q64, I109, and T119 of SEQ ID NO:4 with a TIGIT-binding agent described herein. In some embodiments, an antibody competes for binding to an epitope comprising amino acids Q62, Q64, I109, and T119 of SEQ ID NO:4 with a TIGIT-binding agent described herein. In some embodiments, an antibody competes for binding to an epitope comprising at least one amino acid selected from the group consisting of: N58, E60, Q62, Q64, L65, F107, I109, H111, T117, T119, G120, and R121 of SEQ ID NO:4 with a TIGIT-binding agent described herein.

In certain embodiments, the TIGIT-binding agent (e.g., an antibody) described herein binds TIGIT and modulates TIGIT activity. In some embodiments, the TIGIT-binding agent is a TIGIT antagonist and decreases TIGIT activity. In certain embodiments, the TIGIT-binding agent inhibits TIGIT activity by at least about 10%, at least about 20%, at least about 30%, at least about 50%, at least about 75%, at least about 90%, or about 100%. In certain embodiments, a TIGIT-binding agent that inhibits TIGIT activity is antibody 313R11, antibody 313R12, antibody 313R14, antibody 313R19, or antibody 313R20. In certain embodiments, a TIGIT-binding agent that inhibits human TIGIT activity is a humanized version of antibody 313R11, antibody 313R12, antibody 313R14, antibody 313R19, or antibody 313R20. In certain embodiments, a TIGIT-binding agent that inhibits TIGIT activity is antibody 313M26 or antibody 313M32. In certain embodiments, a TIGIT-binding agent that inhibits human TIGIT activity is a humanized version of antibody 313M26 (e.g., antibody 313M32). In certain embodiments, a TIGIT-binding agent that inhibits TIGIT activity is antibody 313M32.

In some embodiments, the TIGIT-binding agents described herein bind TIGIT and inhibit or reduce TIGIT signaling. In certain embodiments, the TIGIT-binding agent (e.g., an antibody) inhibits TIGIT signaling by at least about 10%, at least about 20%, at least about 30%, at least about 50%, at least about 75%, at least about 90%, or about 100%. In some embodiments, the TIGIT-binding agent inhibits mouse TIGIT signaling. In some embodiments, the TIGIT-binding agent inhibits human TIGIT signaling. In some embodiments, the TIGIT-binding agent inhibits mouse and human TIGIT signaling. In certain embodiments, a TIGIT-binding agent that inhibits TIGIT signaling is antibody 313R11, antibody 313R12, antibody 313R14, antibody 313R19, or antibody 313R20. In certain embodiments, a TIGIT-binding agent that inhibits TIGIT signaling is antibody 313M26 or antibody 313M32. In certain embodiments, a TIGIT-binding agent that inhibits TIGIT signaling is antibody 313M32.

TIGIT is phosphorylated at its cytoplasmic tail after interaction with its counter-receptor PVR. The phosphorylation of TIGIT is the beginning of a cascade that includes downstream events affecting other known signaling pathways. Therefore, evaluating TIGIT phosphorylation can give information about TIGIT activity and TIGIT signaling.

Phosphorylation assays are known to those of skill in the art and are commonly used to monitor protein activation and/or pathway activation. The assays may be used to monitor the effect of various treatments on activation of a target protein and/or a target pathway. For example, an in vitro phosphorylation assay can be used to evaluate the effect of a TIGIT antagonist on the PVR-induced activation of TIGIT.

In certain embodiments, the TIGIT-binding agent (e.g., antibody) inhibits binding of TIGIT to a receptor. In certain embodiments, the TIGIT-binding agent inhibits binding of TIGIT to PVR. In some embodiments, the TIGIT-binding agent inhibits binding of TIGIT to PVR-L2, PVR-L3, and/or PVR-L4. In certain embodiments, the inhibition of binding of a TIGIT-binding agent to PVR is at least about 10%, at least about 25%, at least about 50%, at least about 75%, at least about 90%, or at least about 95%. In certain embodiments, the inhibition of binding of a TIGIT-binding agent to PVR-L2, PVR-L3, and/or PVR-L4 is at least about 10%, at least about 25%, at least about 50%, at least about 75%, at least about 90%, or at least about 95%. In certain embodiments, a TIGIT-binding agent that inhibits binding of TIGIT to PVR is antibody 313R11, antibody 313R12, antibody 313R14, antibody 313R19, or antibody 313R20. In certain embodiments, a TIGIT-binding agent that inhibits binding of TIGIT to PVR-L2, PVR-L3, and/or PVR-L4 is antibody 313R11, antibody 313R12, antibody 313R14, antibody 313R19, or antibody 313R20. In certain embodiments, a TIGIT-binding agent that inhibits binding of TIGIT to PVR is antibody 313M26 or antibody 313M32. In certain embodiments, a TIGIT-binding agent that inhibits binding of TIGIT to PVR is antibody 313M32. In certain embodiments, a TIGIT-binding agent that inhibits binding of TIGIT to PVR-L2, PVR-L3, and/or PVR-L4 is antibody 313M26 or antibody 313M32. In certain embodiments, a TIGIT-binding agent that inhibits binding of TIGIT to PVR-L2, PVR-L3, and/or PVR-L4 is antibody 313M32.

In certain embodiments, the TIGIT-binding agent (e.g., antibody) blocks binding of TIGIT to a receptor. In certain embodiments, the TIGIT-binding agent blocks binding of TIGIT to PVR. In certain embodiments, the blocking of binding of a TIGIT-binding agent to PVR is at least about 10%, at least about 25%, at least about 50%, at least about 75%, at least about 90%, or at least about 95%. In some embodiments, the TIGIT-binding agent blocks binding of TIGIT to PVR-L2, PVR-L3, and/or PVR-L4. In certain embodiments, the blocking of binding of a TIGIT-binding agent to PVR-L2, PVR-L3, and/or PVR-L4 is at least about 10%, at least about 25%, at least about 50%, at least about 75%, at least about 90%, or at least about 95%. In certain embodiments, a TIGIT-binding agent that blocks binding of TIGIT to PVR is antibody 313R11, antibody 313R12, antibody 313R14, antibody 313R19, or antibody 313R20. In certain embodiments, a TIGIT-binding agent that blocks binding of TIGIT to PVR-L2, PVR-L3, and/or PVR-L4 is antibody 313R11, antibody 313R12, antibody 313R14, antibody 313R19, or antibody 313R20. In certain embodiments, a TIGIT-binding agent that blocks binding of TIGIT to PVR is antibody 313M26 or antibody 313M32. In certain embodiments, a TIGIT-binding agent that blocks binding of TIGIT to PVR is antibody 313M32. In certain embodiments, a TIGIT-binding agent that blocks binding of TIGIT to PVR-L2, PVR-L3, and/or PVR-L4 is antibody 313M26 or antibody 313M32. In certain embodiments, a TIGIT-binding agent that blocks binding of TIGIT to PVR-L2, PVR-L3, and/or PVR-L4 is antibody 313M32.

Binding assays are known to those of skill in the art and are described herein. Binding assays may be used to monitor the effect of a test agent on the interaction between a target protein and the protein's binding partner (e.g., receptor or ligand). For example, an in vitro binding assay can be used to evaluate if a TIGIT antagonist blocks the interaction of TIGIT to PVR.

In certain embodiments, the TIGIT-binding agents described herein have one or more of the following effects: inhibit proliferation of tumor cells, inhibit tumor growth, reduce the tumorigenicity of a tumor, reduce the tumorigenicity of a tumor by reducing the frequency of cancer stem cells in the tumor, trigger cell death of tumor cells, enhance or boost the immune response, enhance or boost the anti-tumor response, increase cytolytic activity of immune cells, increase killing of tumor cells, increase killing of tumor cells by immune cells, induce cells in a tumor to differentiate, differentiate tumorigenic cells to a non-tumorigenic state, induce expression of differentiation markers in the tumor cells, prevent metastasis of tumor cells, decrease survival of tumor cells, increase cell contact-dependent growth inhibition, increase tumor cell apoptosis, reduce epithelial mesenchymal transition (EMT), or decrease survival of tumor cells. In some embodiments, the agents have one or more of the following effects: inhibit viral infection, inhibit chronic viral infection, reduce viral load, trigger cell death of virus-infected cells, or reduce the number or percentage of virus-infected cells.

In certain embodiments, the TIGIT-binding agents described herein inhibit tumor growth. In certain embodiments, the TIGIT-binding agents inhibit tumor growth in vivo (e.g., in a mouse model, and/or in a human having cancer). In certain embodiments, tumor growth is inhibited at least about two-fold, about three-fold, about five-fold, about ten-fold, about 50-fold, about 100-fold, or about 1000-fold as compared to a untreated tumor.

In certain embodiments, the TIGIT-binding agents described herein reduce the tumorigenicity of a tumor. In certain embodiments, the TIGIT-binding agents reduce the tumorigenicity of a tumor in an animal model, such as a mouse model. In some embodiments, the mouse model is a mouse xenograft model. In some embodiments, a TIGIT-binding agent does not bind mouse TIGIT and is not effective in a mouse model. In some embodiments, a surrogate TIGIT-binding agent that binds mouse TIGIT is used in a mouse model. In certain embodiments, the TIGIT-binding agents reduce the tumorigenicity of a tumor comprising cancer stem cells in an animal model, such as a mouse model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236; U.S. Patent Publication No. 2008/0064049; and U.S. Patent Publication No. 2008/0178305.

In certain embodiments, the agents (e.g., polypeptides and/or antibodies) described herein bind TIGIT and modulate an immune response. In some embodiments, a TIGIT-binding agent described herein activates and/or increases an immune response. In some embodiments, a TIGIT-binding agent increases, promotes, or enhances cell-mediated immunity. In some embodiments, a TIGIT-binding agent increases, promotes, or enhances innate cell-mediated immunity. In some embodiments, a TIGIT-binding agent increases, promotes, or enhances adaptive cell-mediated immunity. In some embodiments, a TIGIT-binding agent increases, promotes, or enhances T-cell activity. In some embodiments, a TIGIT-binding agent increases, promotes, or enhances cytolytic T-cell (CTL) activity. In some embodiments, a TIGIT-binding agent increases, promotes, or enhances NK cell activity. In some embodiments, a TIGIT-binding agent increases, promotes, or enhances lymphokine-activated killer cell (LAK) activity. In some embodiments, a TIGIT-binding agent increases, promotes, or enhances tumor-infiltrating lymphocyte (TIF) activity. In some embodiments, a TIGIT-binding agent inhibits or decreases Treg cell activity. In some embodiments, a TIGIT-binding agent inhibits or decreases MDSC activity. In some embodiments, a TIGIT-binding agent increases, promotes, or enhances tumor cell killing. In some embodiments, a TIGIT-binding agent increases, promotes, or enhances the inhibition of tumor growth.

In certain embodiments, an agent described herein is an antagonist of human TIGIT. In some embodiments, the agent is an antagonist of TIGIT and activates and/or increases an immune response. In some embodiments, the agent is an antagonist of TIGIT and activates and/or increases activity of NK cells. In certain embodiments, the agent increases the activity by at least about 10%, at least about 20%, at least about 30%, at least about 50%, at least about 75%, at least about 90%, or about 100%. In some embodiments, the agent is an antagonist of TIGIT and activates and/or increases activity of T-cells (e.g., T-cell cytolytic activity). In certain embodiments, the agent increases the activity by at least about 10%, at least about 20%, at least about 30%, at least about 50%, at least about 75%, at least about 90%, or about 100%. In some embodiments, the agent is an antagonist of TIGIT and induces and/or enhances a Th1-type immune response. In general, a Th1-type immune response includes production of interferon-gamma (IFN-γ), IL-2, and tumor necrosis factor-beta (TNF-β). In comparison, a Th2-type immune response generally includes production of IL-4, IL-5, IL-6, IL-9, IL-10, and IL-13. In some embodiments, the agent is an antagonist of TIGIT and induces and/or increases cytokine or lymphokine production. In some embodiments, the induction and/or increase in cytokine or lymphokines production may be an indirect effect.

In certain embodiments, a TIGIT-binding agent described herein increases activation of NK cells. In certain embodiments, a TIGIT-binding agent increases activation of T-cells. In certain embodiments, the activation of NK cells and/or T-cells by a TIGIT-binding agent results in an increase in the level of activation of NK cells and/or T-cells of at least about 10%, at least about 25%, at least about 50%, at least about 75%, at least about 90%, or at least about 95%. In certain embodiments, a TIGIT-binding agent that increases activation of NK cells is antibody 313R11, antibody 313R12, antibody 313R14, antibody 313R19, or antibody 313R20. In certain embodiments, a TIGIT-binding agent that increases activation of NK cells is antibody 313M26 or antibody 313M32. In certain embodiments, a TIGIT-binding agent that increases activation of NK cells is antibody 313M32.

In certain embodiments, the TIGIT-binding agent (e.g., antibody) is an antagonist of regulatory T-cell (Treg) activity. In certain embodiments, a TIGIT-binding agent described herein inhibits or decreases the activity of Tregs. In certain embodiments, the inhibition of activity of Tregs by a TIGIT-binding agent results in an inhibition of suppressive activity of a Treg cell of at least about 10%, at least about 25%, at least about 50%, at least about 75%, at least about 90%, at least about 95%, or about 100%. In certain embodiments, a TIGIT-binding agent that inhibits Treg activity is antibody 313R11, antibody 313R12, antibody 313R14, antibody 313R19, or antibody 313R20. In certain embodiments, a TIGIT-binding agent that inhibits Treg activity is antibody 313M26 or antibody 313M32. In certain embodiments, a TIGIT-binding agent that inhibits Treg activity is antibody 313M32.

In certain embodiments, the TIGIT-binding agent (e.g., antibody) is an antagonist of myeloid-derived suppressor cells (MDSCs). In certain embodiments, the TIGIT-binding agent inhibits MDSC activity. In certain embodiments, the TIGIT-binding agent inhibits MDSC activity by at least about 10%, at least about 20%, at least about 30%, at least about 50%, at least about 75%, at least about 90%, or about 100%. In certain embodiments, a TIGIT-binding agent that inhibits MDSC activity is antibody 313R11, antibody 313R12, antibody 313R14, antibody 313R19, or antibody 313R20. In certain embodiments, a TIGIT-binding agent that inhibits MDSC activity is antibody 313M26 or antibody 313M32. In certain embodiments, a TIGIT-binding agent that inhibits MDSC activity is antibody 313M32.

In certain embodiments, the TIGIT-binding agent (e.g., antibody) increases natural killer (NK) cell activity. In certain embodiments, the TIGIT-binding agent increases NK cell activity by at least about 10%, at least about 20%, at least about 30%, at least about 50%, at least about 75%, at least about 90%, or about 100%. In certain embodiments, a TIGIT-binding agent that increases NK cell activity is antibody 313R11, antibody 313R12, antibody 313R14, antibody 313R19, or antibody 313R20. In certain embodiments, a TIGIT-binding agent that increases NK cell activity is antibody 313M26 or antibody 313M32. In certain embodiments, a TIGIT-binding agent that increases NK cell activity is antibody 313M32.

In certain embodiments, the TIGIT-binding agent (e.g., antibody) increases tumor-infiltrating lymphocyte (TIL) activity. In certain embodiments, the TIGIT-binding agent increases TIL activity by at least about 10%, at least about 20%, at least about 30%, at least about 50%, at least about 75%, at least about 90%, or about 100%. In certain embodiments, a TIGIT-binding agent that increases TIL cell activity is antibody 313R11, antibody 313R12, antibody 313R14, antibody 313R19, or antibody 313R20. In certain embodiments, a TIGIT-binding agent that increases TIL cell activity is antibody 313M26 or antibody 313M32. In certain embodiments, a TIGIT-binding agent that increases TIL cell activity is antibody 313M32.

In certain embodiments, the TIGIT-binding agent (e.g., antibody) increases or enhances lymphokines-activated killer cell (LAK) activity. In certain embodiments, the TIGIT-binding agent increases LAK activity by at least about 10%, at least about 20%, at least about 30%, at least about 50%, at least about 75%, at least about 90%, or about 100%. In certain embodiments, a TIGIT-binding agent that increases LAK cell activity is antibody 313R11, antibody 313R12, antibody 313R14, antibody 313R19, or antibody 313R20. In certain embodiments, a TIGIT-binding agent that increases LAK cell activity is antibody 313M26 or antibody 313M32. In certain embodiments, a TIGIT-binding agent that increases LAK cell activity is antibody 313M32.

In vivo and in vitro assays for determining whether a TIGIT-binding agent (or candidate binding agent) modulates an immune response are known in the art or are being developed. In some embodiments, a functional assay that detects T-cell activation may be used. In some embodiments, a functional assay that detects T-cell proliferation may be used. In some embodiments, a functional assay that detects NK activity may be used. In some embodiments, a functional assay that detects CTL activity may be used. In some embodiments, a functional assay that detects Treg activity may be used. In some embodiments, a functional assay that detects MDSC activity may be used. In some embodiments, a functional assay that detects production of cytokines or lymphokines or cells producing cytokines or lymphokines may be used. In some embodiments, an ELISpot assay is used to measure antigen-specific T-cell frequency. In some embodiments, an ELISpot assay is used to measure cytokine release/production and/or used to measure the number of cytokine producing cells. In some embodiments, cytokine assays are used to identify a Th1-type response. In some embodiments, cytokine assays are used to identify a Th2-type response. In some embodiments, cytokine assays are used to identify a Th17-type response. In some embodiments, FACS analysis is used to measure activation markers on immune cells, including but not limited to, T-cells, B-cells, NK cells, macrophages, and/or myeloid cells.

In certain embodiments, the TIGIT-binding agents described herein have a circulating half-life in mice, rats, cynomolgus monkeys, or humans of at least about 2 hours, at least about 5 hours, at least about 10 hours, at least about 24 hours, at least about 3 days, at least about 1 week, or at least about 2 weeks. In certain embodiments, the TIGIT-binding agent is an IgG (e.g., IgG1, IgG2, or IgG4) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0. Known methods of increasing the circulating half-life of antibody fragments lacking the Fc region include such techniques as PEGylation.

In some embodiments described herein, the TIGIT-binding agents are polypeptides. In some embodiments, the polypeptides are recombinant polypeptides, natural polypeptides, or synthetic polypeptides comprising an antibody, or fragment thereof, that bind TIGIT. It will be recognized in the art that some amino acid sequences of the invention can be varied without significant effect of the structure or function of the protein. Thus, the invention further includes variations of the polypeptides which show substantial activity or which include regions of an antibody, or fragment thereof, that binds TIGIT. In some embodiments, amino acid sequence variations of TIGIT-binding polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in Remington: *The Science and Practice of Pharmacy*, $22^{st}$ Edition, 2012, Pharmaceutical Press, London.

In certain embodiments, the polypeptides described herein are isolated. In certain embodiments, the polypeptides described herein are substantially pure.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human TIGIT. For example, recombinant expression vectors can be replicable DNA constructs which have synthetic or cDNA-derived DNA fragments encoding a polypeptide chain of a TIGIT-binding agent, such as an anti-TIGIT antibody, or fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, in situations where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

The TIGIT-binding agents (e.g., polypeptides or antibodies) of the present invention can be expressed from one or more vectors. For example, in some embodiments, one heavy chain polypeptide is expressed by one vector, a second heavy chain polypeptide is expressed by a second vector and a light chain polypeptide is expressed by a third vector. In some embodiments, a first heavy chain polypeptide and a light chain polypeptide is expressed by one vector and a second heavy chain polypeptide is expressed by a second vector. In some embodiments, two heavy chain polypeptides are expressed by one vector and a light chain polypeptide is expressed by a second vector. In some embodiments, three polypeptides are expressed from one vector. Thus, in some embodiments, a first heavy chain polypeptide, a second heavy chain polypeptide, and a light chain polypeptide are expressed by a single vector.

Suitable host cells for expression of a TIGIT-binding polypeptide or antibody (or a TIGIT protein to use as an antigen) include prokaryotes, yeast cells, insect cells, or higher eukaryotic cells under the control of appropriate promoters. Prokaryotes include gram-negative or gram-positive organisms, for example E. coli or Bacillus. Higher eukaryotic cells include established cell lines of mammalian origin as described below. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present invention provides cells comprising the TIGIT-binding agents described herein. In some embodiments, the cells produce the TIGIT-binding agents described herein. In certain embodiments, the cells produce an antibody. In some embodiments, the cells produce an antibody that binds mouse TIGIT. In some embodiments, the cells produce an antibody that binds human TIGIT. In some embodiments, the cells produce an antibody that binds mouse TIGIT and human TIGIT. In certain embodiments, the cells produce antibody 313R11. In certain embodiments, the cells produce antibody 313R12. In certain embodiments, the cells produce antibody 313R14. In certain embodiments, the cells produce antibody 313R19. In certain embodiments, the cells produce antibody 313R20. In certain embodiments, the cells produce antibody 313M26. In certain embodiments, the cells produce antibody 313M32. In certain embodiments, the cells produce antibody 313M33. In some embodiments, the cells produce a bispecific antibody that binds TIGIT. In some embodiments, the cells produce a bispecific antibody that binds TIGIT and a second target. In some embodiments, the cell is a hybridoma cell. In some embodiments, the cell is a mammalian cell. In some embodiments, the cell is a prokaryotic cell. In some embodiments, the cell is an eukaryotic cell.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a recombinant protein (e.g., a TIGIT-binding agent). Some or all of the foregoing purification steps, in various combinations, can be employed to provide a homogeneous recombinant protein.

In some embodiments, heterodimeric proteins such as bispecific antibodies are purified according the any of the methods described herein. In some embodiments, anti-TIGIT bispecific antibodies are isolated and/or purified using at least one chromatography step. In some embodiments, the at least one chromatography step comprises affinity chromatography. In some embodiments, the at least one chromatography step further comprises anion exchange chromatography. In some embodiments, the isolated and/or purified antibody product comprises at least 90% heterodimeric antibody. In some embodiments, the isolated and/or purified antibody product comprises at least 95%, 96%, 97%, 98% or 99% heterodimeric antibody. In some embodiments, the isolated and/or purified antibody product comprises about 100% heterodimeric antibody.

In some embodiments, a polypeptide produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

In certain embodiments, the TIGIT-binding agent is a polypeptide that is not an antibody or does not comprise an immunoglobulin Fc region. A variety of methods for identifying and producing non-antibody polypeptides that bind with high affinity to a protein target are known in the art. In certain embodiments, phage or mammalian display technology may be used to produce and/or identify a TIGIT-binding polypeptide. In certain embodiments, the polypeptide comprises a protein scaffold of a type selected from the group consisting of protein A, protein G, a lipocalin, a fibronectin domain, an ankyrin consensus repeat domain, and thioredoxin. A variety of methods for identifying and producing non-antibody polypeptides that bind with high affinity to a protein target are known in the art. In certain embodiments, phage display technology may be used to produce and/or identify a binding polypeptide. In certain embodiments, mammalian cell display technology may be used to produce and/or identify a binding polypeptide.

It can further be desirable to modify a polypeptide in order to increase (or decrease) its serum half-life. This can be achieved, for example, by incorporation of a salvage receptor binding epitope into the polypeptide by mutation of the appropriate region in the polypeptide or by incorporating the epitope into a peptide tag that is then fused to the polypeptide at either end or in the middle (e.g., by DNA or peptide synthesis).

Heteroconjugate molecules are also within the scope of the present invention. Heteroconjugate molecules are composed of two covalently joined polypeptides. Such molecules have, for example, been proposed to target immune cells to unwanted cells, such as tumor cells. It is also contemplated that the heteroconjugate molecules can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In certain embodiments, the TIGIT-binding agents can be used in any one of a number of conjugated (i.e. an immunoconjugate or radioconjugate) or non-conjugated forms. In certain embodiments, the agents can be used in a non-conjugated form to harness the subject's natural defense mechanisms including complement-dependent cytotoxicity (CDC) and antibody dependent cellular cytotoxicity (ADCC) to eliminate malignant or cancer cells.

In some embodiments, the TIGIT-binding agent is conjugated to a cytotoxic agent. In some embodiments, the TIGIT-binding agent is an antibody is conjugated to a cytotoxic agent as an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, daunorubicin, pyrrolobenzodiazepines (PBDs), or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as calicheamicins, maytansinoids, trichothenes, and CC1065, and the derivatives of these toxins that have toxin activity, can also be used. Conjugates of an antibody and cytotoxic agent may be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode an agent described herein. The term "polynucleotides that encode a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide (e.g., a nucleotide sequence) encoding a polypeptide comprising an amino acid sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:55, and SEQ ID NO:56.

In certain embodiments, a polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding an amino acid sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:55, and SEQ ID NO:56. Also provided is a polynucleotide that comprises a polynucleotide that hybridizes to a polynucleotide encoding an amino acid sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:55, and SEQ ID NO:56. In certain embodiments, the hybridization is under conditions of high stringency. Conditions of high stringency are known to those of skill in the art and may include but are not limited to, (1) employ low ionic strength and high temperature for washing, for example 15 mM sodium chloride/1.5 mM sodium citrate (1×SSC) with 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes in 0.2×SSC containing 50% formamide at 55° C., followed by a high-stringency wash consisting of 0.1×SSC containing EDTA at 55° C.

In certain embodiments, the polynucleotide comprises a polynucleotide encoding a polypeptide comprising an amino acid sequence selected from the group consisting of: SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:82, and SEQ ID NO:83.

In certain embodiments, a polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding an amino acid sequence selected from the group consisting of: SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:82, and SEQ ID NO:83. Also provided is a polynucleotide that comprises a polynucleotide that hybridizes to a polynucleotide encoding an amino acid sequence selected from the group consisting of: SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:82, and SEQ ID NO:83.

In some embodiments, the polynucleotide comprises a polynucleotide sequence selected from the group consisting of: SEQ ID NO:65, SEQ ID NO:66, SEQ ID NO:73, SEQ ID NO:74, SEQ ID NO:75, SEQ ID NO:76, and SEQ ID NO:84. In certain embodiments, a polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a nucleotide sequence selected from the group consisting of: SEQ ID NO:65, SEQ ID NO:66, SEQ ID NO:73, SEQ ID NO:74, SEQ ID NO:75, SEQ ID NO:76, and SEQ ID NO:84. Also provided is a polynucleotide that comprises a polynucleotide that hybridizes to a polynucleotide sequence selected from the group consisting of: SEQ ID NO:65, SEQ ID NO:66, SEQ ID NO:73, SEQ ID NO:74, SEQ ID NO:75, SEQ ID NO:76, and SEQ ID NO:84. In certain embodiments, the hybridization techniques are conducted under conditions of high stringency as described above.

In certain embodiments, a polynucleotide comprises the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide. The polynucleotides can also encode for a pro-protein which is the mature protein plus additional 5' amino acid residues. A mature protein having a pro-sequence is a pro-protein and is an inactive form of the protein. Once the pro-sequence is cleaved an active mature protein remains.

In certain embodiments, a polynucleotide comprises the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:40) which can be used in conjunction with other affinity tags.

The present invention further relates to variants of the polynucleotides described herein, wherein the variant encodes, for example, fragments, analogs, and/or derivatives.

In certain embodiments, the present invention provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a TIGIT-binding agent described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heterodimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The TIGIT-binding agents of the invention are useful in a variety of applications including, but not limited to, therapeutic treatment methods, such as treatment of cancer. In some embodiments, the therapeutic treatment methods comprise immunotherapy for cancer. In certain embodiments, a TIGIT-binding agent is useful for activating, promoting, increasing, and/or enhancing an immune response, inhibiting tumor growth, reducing tumor volume, increasing tumor cell apoptosis, and/or reducing the tumorigenicity of a tumor. In some embodiments, a TIGIT-binding agent of the invention is also useful for immunotherapy against pathogens, such as viruses. In certain embodiments, a TIGIT-binding agent is useful for activating, promoting, increasing, and/or enhancing an immune response, inhibiting viral infection, reducing viral infection, increasing virally-infected cell apoptosis, and/or increasing killing of virus-infected cells. The methods of use may be in vitro, ex vivo, or in vivo methods.

The present invention provides methods for activating an immune response in a subject using a TIGIT-binding agent described herein. In some embodiments, the invention provides methods for promoting an immune response in a subject using a TIGIT-binding agent described herein. In some embodiments, the invention provides methods for increasing an immune response in a subject using a TIGIT-binding agent described herein. In some embodiments, the invention provides methods for enhancing an immune response in a subject using a TIGIT-binding agent described herein. In some embodiments, the activating, promoting, increasing, and/or enhancing of an immune response comprises increasing cell-mediated immunity. In some embodiments, the activating, promoting, increasing, and/or enhancing of an immune response comprises increasing T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CTL activity and increasing NK cell activity. In some embodiments, the activating, promoting, increasing, and/or enhancing of an immune response comprises inhibiting or decreasing the suppressive activity of Tregs. In some embodiments, the activating, promoting, increasing, and/or enhancing of an immune response comprises inhibiting or decreasing the suppressive activity of MDSCs. In some embodiments, the immune response is a result of antigenic stimulation. In some embodiments, the antigenic stimulation is a tumor cell. In some embodiments, the antigenic stimulation is cancer. In some embodiments, the antigenic stimulation is a pathogen. In some embodiments, the antigenic stimulation is a virus. In some embodiments, the antigenic stimulation is a virally-infected cell. In some embodiments of any of the methods described herein, the TIGIT-binding agent is an anti-TIGIT antibody. In some embodiments of any of the methods described herein, the TIGIT-binding agent is antibody 313M32.

In some embodiments, a method of increasing an immune response in a subject comprises administering to the subject a therapeutically effective amount of a TIGIT-binding agent described herein, wherein the agent is an antibody that specifically binds the extracellular domain of TIGIT. In some embodiments, a method of increasing an immune response in a subject comprises administering to the subject a therapeutically effective amount of a TIGIT-binding agent described herein, wherein the agent is an antibody that specifically binds the extracellular domain of human TIGIT. In some embodiments, the method of increasing an immune response in a subject comprises administering to the subject a therapeutically effective amount of antibody 313M32.

In some embodiments, the invention provides use of a TIGIT-binding agent described herein in the manufacture or preparation of a medicament for activating, promoting, increasing, and/or enhancing an immune response. In some embodiments, the invention provides use of a TIGIT-binding agent described herein in the manufacture or preparation of a medicament for increasing cell-mediated immunity. In some embodiments, the invention provides use of a TIGIT-binding agent described herein in the manufacture or preparation of a medicament for increasing T-cell activity. In some embodiments, the invention provides use of a TIGIT-binding agent described herein in the manufacture or preparation of a medicament for increasing CTL activity. In some embodiments, the invention provides use of a TIGIT-binding agent described herein in the manufacture or preparation of a medicament for increasing NK activity. In some embodiments, the invention provides use of a TIGIT-binding agent described herein in the manufacture or preparation of a medicament for inhibiting or decreasing the suppressive activity of Tregs. In some embodiments, the invention provides use of a TIGIT-binding agent described herein in the manufacture or preparation of a medicament for inhibiting or decreasing the suppressive activity of MDSCs.

The invention also provides methods of inhibiting and/or reducing TIGIT signaling in a cell comprising contacting the cell with an effective amount of a TIGIT-binding agent described herein. In some embodiments, the method of inhibiting and/or reducing TIGIT signaling in a cell comprises contacting the cell with an effective amount of antibody 313M32. In some embodiments, the invention provides use of a TIGIT-binding agent described herein in the manufacture or preparation of a medicament for inhibiting and/or reducing TIGIT signaling in a cell. In certain embodiments, the cell is a T-cell. In some embodiments, the cell is an activated T-cell. In some embodiments, the cell is a NK cell. In some embodiments, the cell is a Treg. In some embodiments, the cell is a MDSC. In certain embodiments, the method is an in vivo method wherein the step of contacting the cell with the agent comprises administering a therapeutically effective amount of the TIGIT-binding agent to the subject. In some embodiments, the method is an in vitro or ex vivo method.

The present invention also provides methods for inhibiting growth of a tumor using a TIGIT-binding agent described herein. In some embodiments, the method of inhibiting growth of a tumor comprises using antibody 313M32. In certain embodiments, the method of inhibiting growth of a tumor comprises contacting a cell mixture with a TIGIT-binding agent in vitro. For example, an immortalized cell line or a cancer cell line mixed with immune cells (e.g., T-cells or NK cells) is cultured in medium to which is added a test agent that binds TIGIT. In some embodiments, tumor cells are isolated from a patient sample such as, for example, a tissue biopsy, pleural effusion, or blood sample, mixed with immune cells (e.g., T-cells and/or NK cells), and cultured in medium to which is added a test agent that binds TIGIT. In some embodiments, the invention provides use of a TIGIT-binding agent described herein in the manufacture or preparation of a medicament for inhibiting growth of a tumor or a tumor cell. In some embodiments, a TIGIT-binding agent increases, promotes, and/or enhances the activity of the immune cells. In some embodiments, a TIGIT-binding agent inhibits tumor cell growth.

In some embodiments, the method of inhibiting growth of a tumor comprises contacting the tumor or tumor cells with a TIGIT-binding agent described herein in vivo. In certain embodiments, contacting a tumor or tumor cell with a TIGIT-binding agent is undertaken in an animal model. For example, a test agent may be administered to mice which have tumors. In some embodiments, a TIGIT-binding agent increases, promotes, and/or enhances the activity of immune cells in the mice. In some embodiments, a TIGIT-binding agent inhibits tumor growth. In some embodiments, a TIGIT-binding agent causes a tumor to regress. In some embodiments, a TIGIT-binding agent is administered at the same time or shortly after introduction of tumor cells into the animal to prevent tumor growth ("preventative model"). In some embodiments, a TIGIT-binding agent is administered as a therapeutic after tumors have grown to a specified size or have become "established" ("therapeutic model").

In certain embodiments, the method of inhibiting growth of a tumor comprises administering to a subject a therapeutically effective amount of a TIGIT-binding agent described herein. In certain embodiments, the subject is a human. In certain embodiments, the subject has a tumor or the subject had a tumor which was at least partially removed. In some embodiments, the method of inhibiting growth of a tumor comprises administering to a subject a therapeutically effective amount of antibody 313M32.

In addition, the invention provides a method of inhibiting growth of a tumor in a subject, comprising administering to the subject a therapeutically effective amount of a TIGIT-binding agent described herein. In some embodiments, the invention provides use of a TIGIT-binding agent described herein in the manufacture or preparation of a medicament for inhibiting growth of a tumor or tumor cell. In certain embodiments, the tumor comprises cancer stem cells. In certain embodiments, the frequency of cancer stem cells in the tumor is reduced by administration of the agent. In some embodiments, a method of reducing the frequency of cancer stem cells in a tumor in a subject, comprising administering to the subject a therapeutically effective amount of a TIGIT-binding agent is provided.

In addition, the invention provides a method of reducing the tumorigenicity of a tumor in a subject, comprising administering to the subject a therapeutically effective amount of a TIGIT-binding agent described herein. In certain embodiments, the tumor comprises cancer stem cells. In some embodiments, the tumorigenicity of a tumor is reduced by reducing the frequency of cancer stem cells in the tumor. In some embodiments, the methods comprise using the TIGIT-binding agents described herein. In certain embodiments, the frequency of cancer stem cells in the tumor is reduced by administration of a TIGIT-binding agent described herein. In some embodiments, a method of reducing the tumorigenicity of a tumor in a subject comprises administering to the subject a therapeutically effective amount of antibody 313M32.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a lung tumor. In certain embodiments, the tumor is a pancreatic tumor. In certain embodiments, the tumor is a melanoma tumor.

The present invention provides for methods of treating cancer comprising administering to a subject a therapeutically effective amount of a TIGIT-binding agent described herein (e.g., a subject in need of treatment). In some embodiments, the invention provides use of a TIGIT-binding agent described herein in the manufacture or preparation of a medicament for the treatment of cancer. In some embodiments, a TIGIT-binding agent binds human TIGIT and inhibits or reduces growth of the cancer. In certain embodiments, the subject is a human. In certain embodiments, the subject has a cancerous tumor. In certain embodiments, the subject has had a tumor at least partially removed. In some embodiments, a method for treating cancer in a subject comprises administering to the subject a therapeutically effective amount of antibody 313M32.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma.

In some embodiments, the cancer is a hematologic cancer. In some embodiments, the hematologic cancer is a leukemia. In other embodiments, the hematologic cancer is a lymphoma. In some embodiment, the cancer is selected from the group consisting of: acute myelogenous leukemia (AML), Hodgkin lymphoma, multiple myeloma, T-cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T-cell lymphoma (CTCL).

In some embodiments of the methods described herein, a method further comprises a step of determining the level of PD-L1 expression in the tumor or cancer. In some embodiments, the determining of the level of PD-L1 expression is done prior to treatment with a TIGIT-binding agent described herein. In some embodiments, if a tumor or cancer has an elevated expression level of PD-L1, a TIGIT-binding agent is administered to the subject. In some embodiments, a method comprises (i) obtaining a sample of a subject's cancer or tumor; (ii) measuring the expression level of PD-L1 in the sample; and (iii) administering an effective amount of a TIGIT-binding agent to the subject if the tumor or cancer has an elevated expression level of PD-L1. In some embodiments, the sample is a biopsy sample. In some embodiments, the sample comprises tumor cells, tumor infiltrating immune cells, stromal cells, and any combination thereof. In some embodiments, the sample is a formalin-fixed paraffin embedded (FFPE) sample. In some embodiments, the sample is archival, fresh, or frozen tissue. In some embodiments, the expression level of PD-L1 in the sample is compared to a pre-determined expression level of PD-L1. In some embodiments, the pre-determined expression level of PD-L1 expression is an expression level of PD-L1 in a reference tumor sample, a reference normal tissue sample, a series of reference tumor samples, or a series of reference normal tissue samples. In some embodiments, the expression level of PD-L1 is determined using an immunohistochemistry (IHC) assay. In some embodiments, the expression level of PD-L1 is determined using an assay which comprises an H-score evaluation. In some embodiments, the expression level of PD-L1 is determined using an antibody that specifically binds PD-L1. In some embodiments, PD-L1 is detected on tumor cells. In some embodiments, PD-L1 is detected on tumor infiltrating immune cells.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments, the combination of an agent described herein and at least one additional therapeutic agent results in additive or synergistic results. In some embodiments, the combination therapy results in an increase in the therapeutic index of the agent. In some embodiments, the combination therapy results in an increase in the therapeutic index of the additional therapeutic agent(s). In some embodiments, the combination therapy results in a decrease in the toxicity and/or side effects of the agent. In some embodiments, the combination therapy results in a decrease in the toxicity and/or side effects of the additional therapeutic agent(s).

In certain embodiments, in addition to administering a TIGIT-binding agent described herein, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that may be administered in combination with the agents described herein include chemotherapeutic agents. Thus, in some embodiments, the method or treatment involves the administration of an agent of the present invention in combination with a chemotherapeutic agent or in combination with a cocktail of chemotherapeutic agents. Treatment with an agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4$^{th}$ *Edition*, 2008, M. C. Perry, Editor, Lippincott, Williams & Wilkins, Philadelphia, Pa.

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In certain embodiments, the additional therapeutic agent is albumin-bound paclitaxel (ABRAXANE).

In some embodiments, an additional therapeutic agent comprises an agent such as a small molecule. For example, treatment can involve the combined administration of an agent of the present invention with a small molecule that acts as an inhibitor against tumor-associated antigens including, but not limited to, EGFR, HER2 (ErbB2), and/or VEGF. In some embodiments, an agent of the present invention is administered in combination with a protein kinase inhibitor selected from the group consisting of: gefitinib (IRESSA), erlotinib (TARCEVA), sunitinib (SUTENT), lapatinib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In certain embodiments, the additional therapeutic agent is an agent that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the RSPO/LGR pathway. In some embodiments, the additional therapeutic agent is an inhibitor of the mTOR/AKR pathway.

In some embodiments, an additional therapeutic agent comprises a biological molecule, such as an antibody. For example, treatment can involve the combined administration of an agent of the present invention with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In certain embodiments, in addition to administering a TIGIT-binding agent described herein, the method or treatment further comprises administering at least one additional immunotherapeutic agent. In some embodiments, the additional immunotherapeutic agent is an immune response stimulating agent. In some embodiments, the immunotherapeutic agent (e.g., immune response stimulating agent) includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), an antibody that blocks immunosuppressive functions (e.g., an anti-CTLA4 antibody, anti-CD28 antibody, anti-CD3 antibody, anti-PD-1 antibody, anti-PD-L1 antibody), an antibody that enhances immune cell functions (e.g., an anti-GITR antibody or an anti-OX-40 antibody), a toll-like receptor (e.g., TLR4, TLR7, TLR9), a soluble ligand (e.g., GITRL or OX-40L), or a member of the B7 family (e.g., CD80, CD86). An additional immunotherapeutic agent (e.g., an immune response stimulating agent) can be administered prior to, concurrently with, and/or subsequently to, administration of the TIGIT-binding agent. Pharmaceutical compositions comprising a TIGIT-binding agent and an additional immunotherapeutic agent (e.g., an immune response stimulating agent(s)) are also provided. In some embodiments, the immunotherapeutic agent comprises 1, 2, 3, or more immunotherapeutic agents. In some embodiments, the immune response stimulating agent comprises 1, 2, 3, or more immune response stimulating agents.

In some embodiments, the additional therapeutic agent is an antibody that is an immune checkpoint inhibitor. In some embodiments, the immune checkpoint inhibitor is an anti-PD-1 antibody, an anti-PD-L1 antibody, an anti-CTLA4 antibody, an anti-CD28 antibody, an anti-LAG3 antibody, an anti-TIM3 antibody, an anti-GITR antibody, or an anti-OX-40 antibody. In some embodiments, the immune checkpoint inhibitor is an anti-4-1BB antibody. In some embodiments, the additional therapeutic agent is an anti-PD-1 antibody selected from the groups consisting of: nivolumab (OPDIVO), pembrolizumab (KEYTRUDA), or pidilzumab. In some embodiments, the additional therapeutic agent is an anti-PD-1 antibody selected from the groups consisting of: MEDI0680, REGN2810, BGB-A317, and PDR001. In some embodiments, the additional therapeutic agent is an anti-PD-L1 antibody selected from the group consisting of: BMS935559 (MDX-1105), atexolizumab (MPDL3280A), durvalumab (MEDI4736), or avelumab (MSB0010718C). In some embodiments, the additional therapeutic agent is an anti-CTLA-4 antibody selected from the group consisting of: ipilimumab (YERVOY) or tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566.

Furthermore, treatment with a TIGIT-binding agent described herein can include combination treatment with other biologic molecules, such as one or more cytokines (e.g., lymphokines, interleukins, interferons, tumor necrosis factors, and/or growth factors) or can be accompanied by surgical removal of tumors, removal of cancer cells, or any other therapy deemed necessary by a treating physician.

In some embodiments, the TIGIT-binding agent can be administered in combination with a biologic molecule selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, PlGF, gamma-IFN, IL-1, IL-2, IL-3, IL-4, IL-5, IL-6, IL-7, IL-12, IL-15, and IL-18. In some embodiments, the TIGIT-binding agent can be administered in combination with a biologic molecule selected from the group consisting of: macrophage colony stimulating factor (M-CSF) and stem cell factor (SCF), In some embodiments, treatment with a TIGIT-binding agent described herein can be accompanied by surgical removal of tumors, removal of cancer cells, or any other surgical therapy deemed necessary by a treating physician.

In certain embodiments, treatment involves the administration of a TIGIT-binding agent of the present invention in combination with radiation therapy. Treatment with an agent can occur prior to, concurrently with, or subsequent to administration of radiation therapy. Dosing schedules for such radiation therapy can be determined by the skilled medical practitioner.

In certain embodiments, treatment involves the administration of a TIGIT-binding agent of the present invention in combination with anti-viral therapy. Treatment with an agent can occur prior to, concurrently with, or subsequent to administration of antiviral therapy. The anti-viral drug used in combination therapy will depend upon the virus the subject is infected with.

Combined administration can include co-administration, either in a single pharmaceutical formulation or using separate formulations, or consecutive administration in either order but generally within a time period such that all active agents can exert their biological activities simultaneously.

It will be appreciated that the combination of a TIGIT-binding agent described herein and at least one additional therapeutic agent may be administered in any order or concurrently. In some embodiments, the agent will be administered to patients that have previously undergone treatment with a second therapeutic agent. In certain other embodiments, the TIGIT-binding agent and a second therapeutic agent will be administered substantially simultaneously or concurrently. For example, a subject may be given an agent while undergoing a course of treatment with a second therapeutic agent (e.g., chemotherapy). In certain embodiments, a TIGIT-binding agent will be administered within 1 year of the treatment with a second therapeutic agent. In certain alternative embodiments, a TIGIT-binding agent will be administered within 10, 8, 6, 4, or 2 months of any treatment with a second therapeutic agent. In certain other embodiments, a TIGIT-binding agent will be administered within 4, 3, 2, or 1 weeks of any treatment with a second therapeutic agent. In some embodiments, an agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a TIGIT-binding agent of the present invention depends on the type of disease to be treated, the severity and course of the disease, the responsiveness of the disease, whether the agent is administered for therapeutic or preventative purposes, previous therapy, the patient's clinical history, and so on, all at the discretion of the treating physician. The TIGIT-binding agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates. In certain embodiments, dosage is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the agent is from about 0.1 mg to about 20 mg/kg of body weight. In some embodiments, the dosage of the agent is about 0.5 mg/kg of body weight. In some embodiments, the dosage of the agent is about 1 mg/kg of body weight. In some embodiments, the dosage of the agent is about 1.5 mg/kg of body weight. In some embodiments, the dosage of the agent is about 2 mg/kg of body weight. In some embodiments, the dosage of the agent is about 2.5 mg/kg of body weight. In some embodiments, the dosage of the agent is about 5 mg/kg of body weight. In some embodiments, the dosage of the agent is about 7.5 mg/kg of body weight. In some embodiments, the dosage of the agent is about 10 mg/kg of body weight. In some embodiments, the dosage of the agent is about 12.5 mg/kg of body weight. In some embodiments, the dosage of the agent is about 15 mg/kg of body weight. In certain embodiments, the dosage can be given once or more daily, weekly, monthly, or yearly. In certain embodiments, the agent is given once every week, once every two weeks, once every three weeks, or once every four weeks.

In some embodiments, a TIGIT-binding agent may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

In some embodiments, the dosing schedule may be limited to a specific number of administrations or "cycles". In some embodiments, the agent is administered for 3, 4, 5, 6, 7, 8, or more cycles. For example, the agent is administered every 2 weeks for 6 cycles, the agent is administered every 3 weeks for 6 cycles, the agent is administered every 2 weeks for 4 cycles, the agent is administered every 3 weeks for 4 cycles, etc. Dosing schedules can be decided upon and subsequently modified by those skilled in the art.

The present invention provides methods of administering to a subject the TIGIT-binding agents described herein comprising using an intermittent dosing strategy for administering one or more agents, which may reduce side effects and/or toxicities associated with administration of an agent, chemotherapeutic agent, etc. In some embodiments, a method for treating cancer in a human subject comprises administering to the subject a therapeutically effective dose of an agent in combination with a therapeutically effective dose of a chemotherapeutic agent, wherein one or both of the agents are administered according to an intermittent dosing strategy. In some embodiments, the intermittent dosing strategy comprises administering an initial dose of an agent to the subject, and administering subsequent doses of the agent about once every 2 weeks. In some embodiments, the intermittent dosing strategy comprises administering an initial dose of an agent to the subject, and administering subsequent doses of the agent about once every 3 weeks. In some embodiments, the intermittent dosing strategy comprises administering an initial dose of an agent to the subject, and administering subsequent doses of the agent about once every 4 weeks. In some embodiments, the agent is administered using an intermittent dosing strategy and the chemotherapeutic agent is administered weekly.

The present invention provides compositions comprising the TIGIT-binding agents described herein. The present invention also provides pharmaceutical compositions comprising the TIGIT-binding agents described herein and a pharmaceutically acceptable vehicle. In some embodiments, the pharmaceutical compositions find use in immunotherapy. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified antibody or agent of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{st}$ Edition, 2012, Pharmaceutical Press, London.).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The TIGIT-binding agents described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy, 22ⁿᵈ Edition*, 2012, Pharmaceutical Press, London.

In certain embodiments, pharmaceutical formulations include an agent of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the TIGIT-binding agents described herein can be produced. Suitable examples of sustained-release preparations include semi-permeable matrices of solid hydrophobic polymers containing an agent, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

V. Selected Embodiments

In embodiment 1, an isolated antibody that specifically binds the extracellular domain of TIGIT, which comprises: (a) a heavy chain CDR1 comprising GSSLSSSYMS (SEQ ID NO:7) or GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ ID NO:9), and/or (b) a light chain CDR1 comprising QASQSISSYLNW (SEQ ID NO:10), QASQSNIYSDLAW (SEQ ID NO:14), or QASQNIYSDLAW (SEQ ID NO:81), a light chain CDR2 comprising DALKLAS (SEQ ID NO:11) or RASTLAS (SEQ ID NO:15), and a light chain CDR3 comprising QQEHSVGNVDN (SEQ ID NO:12) or QQEHLVAWIYN (SEQ ID NO:16).

In embodiment 2, the antibody of embodiment 1 comprises: (a) a heavy chain CDR1 comprising GSSLSSSYMS (SEQ ID NO:7), a heavy chain CDR2 comprising IIGSNGNTYYANWAKG (SEQ ID NO:8), and a heavy chain CDR3 comprising GGYRTSGMDP (SEQ ID NO:9), and/or (b) a light chain CDR1 comprising QASQSISSYLNW (SEQ ID NO:10), a light chain CDR2 comprising DALKLAS (SEQ ID NO:11), and a light chain CDR3 comprising QQEHSVGNVDN (SEQ ID NO:12).

In embodiment 3, the antibody of embodiment 1 comprises: (a) a heavy chain CDR1 comprising GFSLSSSYMS (SEQ ID NO:13), a heavy chain CDR2 comprising IIGSNGNTYYANWAKG (SQ ID NO:8), and a heavy chain CDR3 comprising GGYRTSGMDP (SEQ ID NO:9); and/or (b) a light chain CDR1 comprising QASQNIYSDLAW (SEQ ID NO:81), a light chain CDR2 comprising RASTLAS (SEQ ID NO:15), and a light chain CDR3 comprising QQEHLVAWIYN (SEQ ID NO:16).

In embodiment 4, an isolated antibody that specifically binds TIGIT, which comprises: (a) a heavy chain variable region having at least 90% sequence identity to SEQ ID NO:17, SEQ ID NO:19, or SEQ ID NO:32; and/or (b) a light chain variable region having at least 90% sequence identity to SEQ ID NO:18 or SEQ ID NO:20.

In embodiment 5, the antibody of any one of embodiments 1-4 comprises: (a) a heavy chain variable region having at least 95% sequence identity to SEQ ID NO:17, SEQ ID NO:19, or SEQ ID NO:32; and/or (b) a light chain variable region having at least 95% sequence identity to SEQ ID NO:18 or SEQ ID NO:20.

In embodiment 6, the antibody of embodiment 5 comprises: (a) a heavy chain variable region comprising SEQ ID NO:17; and (b) a light chain variable region comprising SEQ ID NO:18.

In embodiment 7, the antibody of embodiment 5 comprises: (a) a heavy chain variable region comprising SEQ ID NO:19; and (b) a light chain variable region comprising SEQ ID NO:20.

In embodiment 8, the antibody of embodiment 5 comprises: (a) a heavy chain variable region comprising SEQ ID NO:32; and (b) a light chain variable region comprising SEQ ID NO:20.

In embodiment 9, the antibody of any one of embodiments 1-8 is a monoclonal antibody.

In embodiment 10, the antibody of any one of embodiments 1-9 is a humanized antibody.

In embodiment 11, the antibody of any one of embodiments 1-9 is a human antibody.

In embodiment 12, the antibody of any one of embodiments 1-10 is a recombinant antibody or a chimeric antibody.

In embodiment 13, the antibody of any one of embodiments 1-12 is a bispecific antibody.

In embodiment 14, the antibody of any one of embodiments 1-13 is an antibody fragment comprising an antigen binding site.

In embodiment 15, the antibody of any one of embodiments 1-13 is an IgG antibody.

In embodiment 16, the antibody of embodiment 15 is an IgG1 antibody, an IgG2 antibody, or an IgG4 antibody.

In embodiment 17, an antibody comprises (a) a heavy chain amino acid sequence selected from the group consisting of: SEQ ID NO:26, SEQ ID NO:27, SEQ ID NO:29, SEQ ID NO:34, and SEQ ID NO:56; and (b) a light chain amino acid sequence selected from the group consisting of: SEQ ID NO:28 and SEQ ID NO:30.

In embodiment 18, the antibody of embodiment 17 comprises a heavy chain amino acid sequence of SEQ ID NO:26 and a light chain amino acid sequence of SEQ ID NO:28.

In embodiment 19, the antibody of embodiment 17 comprises a heavy chain amino acid sequence of SEQ ID NO:27 and a light chain amino acid sequence of SEQ ID NO:28.

In embodiment 20, the antibody of embodiment 17 comprises a heavy chain amino acid sequence of SEQ ID NO:29 and a light chain amino acid sequence of SEQ ID NO:30.

In embodiment 21, the antibody of embodiment 17 comprises a heavy chain amino acid sequence of SEQ ID NO:34 and a light chain amino acid sequence of SEQ ID NO:30.

In embodiment 22, the antibody of embodiment 17 comprises a heavy chain amino acid sequence of SEQ ID NO:56 and a light chain amino acid sequence of SEQ ID NO:30.

In embodiment 23, an antibody comprises the heavy chain variable region and the light chain variable region from an antibody selected from the group consisting of: 313R11, 313R12, 313R14, 313R19, and 313R20.

In embodiment 24, an antibody is selected from the group consisting of: 313R11, 313R12, 313R14, 313R19, and 313R20.

In embodiment 25, an antibody comprises the heavy chain variable region encoded by the plasmid deposited with ATCC as PTA-122180.

In embodiment 26, an antibody comprises the light chain variable region encoded by the plasmid deposited with ATCC as PTA-122181.

In embodiment 27, an antibody comprises a polypeptide comprising the heavy chain variable region encoded by the plasmid deposited with ATCC as PTA-121180.

In embodiment 28, an antibody comprises a polypeptide comprising the light chain variable region encoded by the plasmid deposited with ATCC as PTA-122181.

In embodiment 29, an antibody comprises the heavy chain variable region encoded by the plasmid deposited with ATCC as PTA-122180 and the light chain variable region encoded by the plasmid deposited with ATCC as PTA-122181.

In embodiment 30, an antibody comprises a polypeptide encoded by the plasmid deposited with ATCC as PTA-122180 and the plasmid deposited with ATCC as PTA-122181.

In embodiment 31, an isolated antibody competes with the antibody of any one of embodiments 1-30 for specific binding to TIGIT.

In embodiment 32, an isolated antibody that binds the same epitope on TIGIT as the antibody of any one of embodiments 1-30.

In embodiment 33, an isolated antibody that binds an epitope on TIGIT that overlaps with the epitope on TIGIT bound by the antibody of any one of embodiments 1-30.

In embodiment 34, the antibody of any one of embodiments 1-33 which inhibits binding of TIGIT to poliovirus receptor (PVR).

In embodiment 35, the antibody of any one of embodiments 1-33 which inhibits or blocks the interaction between TIGIT and PVR.

In embodiment 36, the antibody of any one of embodiments 1-33 which inhibits TIGIT signaling.

In embodiment 37, the antibody of any one of embodiments 1-33 which is an antagonist of TIGIT-mediated signaling.

In embodiment 38, the antibody of any one of embodiments 1-33 which inhibits TIGIT activation.

In embodiment 39, the antibody of any one of embodiments 1-33 which inhibits phosphorylation of TIGIT.

In embodiment 40, the antibody of any one of embodiments 1-33 which decreases cell surface expression of TIGIT.

In embodiment 41, the antibody of any one of embodiments 1-33 which induces and/or enhances an immune response.

In embodiment 42, the antibody of embodiment 41, wherein the immune response is directed to a tumor or tumor cell.

In embodiment 43, the antibody of embodiment 41, wherein the immune response is directed to a virus or a virally-infected cell.

In embodiment 44, the antibody of any one of embodiments 1-33 which increases cell-mediated immunity.

In embodiment 45, the antibody of any one of embodiments 1-33 which increases T-cell activity.

In embodiment 46, the antibody of any one of embodiments 1-33 which increases cytolytic T-cell (CTL) activity.

In embodiment 47, the antibody of any one of embodiments 1-33 which increases natural killer (NK) cell activity.

In embodiment 48, the antibody of any one of embodiments 1-33 which increases IL-2 production and/or the number of IL-2-producing cells.

In embodiment 49, the antibody of any one of embodiments 1-33, which increases IFN-gamma production and/or the number of IFN-gamma-producing cells.

In embodiment 50, the antibody of any one of embodiments 1-33 which increases a Th1-type immune response.

In embodiment 51, the antibody of any one of embodiments 1-33 which decreases IL-4 production and/or the number of IL-4-producing cells.

In embodiment 52, the antibody of any one of embodiments 1-33 which decreases IL-10 and/or the number of IL-10-producing cells.

In embodiment 53, the antibody of any one of embodiments 1-33 which decreases a Th2-type immune response.

In embodiment 54, the antibody of any one of embodiments 1-33 which inhibits and/or decreases the suppressive activity of regulatory T-cells (Tregs).

In embodiment 55, the antibody of any one of embodiments 1-33 which inhibits and/or decreases the suppressive activity of myeloid-derived suppressor cells (MDSCs).

In embodiment 56, the antibody of any one of embodiments 1-55 which inhibits tumor growth.

In embodiment 57, a heterodimeric agent comprises the antibody of any one of embodiments 1-33.

In embodiment 58, a bispecific agent comprises a) a first arm that specifically binds TIGIT, and b) a second arm, wherein the first arm comprises an antibody of any one of embodiments 1-33.

In embodiment 59, the bispecific agent of embodiment 58, wherein the second arm comprises an antigen-binding site from an antibody.

In embodiment 60, the bispecific agent of embodiment 58, wherein the second arm specifically binds PD-1, PD-L1, CTLA4, TIM-3, LAG-3, OX-40, or GITR.

In embodiment 61, the bispecific agent of embodiment 58, wherein the second arm specifically binds a tumor antigen.

In embodiment 62, the bispecific agent of embodiment 58, wherein the second arm comprises an immune response stimulating agent.

In embodiment 63, the bispecific agent of embodiment 62, wherein the immune response stimulating agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA4 antibody, anti-PD-1 antibody, anti-PD-L1 antibody, anti-GITR antibody, anti-OX-40 antibody, anti-LAG-3 antibody, and anti-TIM-3 antibody.

In embodiment 64, the bispecific agent of any one of embodiments 58-63, wherein the first arm comprises a first CH3 domain and the second arm comprises a second CH3 domain, each of which is modified to promote formation of heterodimers.

In embodiment 65, the bispecific agent of embodiment 64, wherein the first and second CH3 domains are modified based upon electrostatic effects.

In embodiment 66, the bispecific agent of any one of embodiments 58-63, wherein the first arm comprises a first human IgG1 constant region with amino acid substitutions at positions corresponding to positions 253 and 292 of SEQ ID NO:41, wherein the amino acids are replaced with glutamate or aspartate, and the second arm comprises a second human IgG1 constant region with amino acid substitutions at positions corresponding to positions 240 and 282 of SEQ ID NO:41, wherein the amino acids are replaced with lysine.

In embodiment 67, the bispecific agent of any one of embodiments 58-63, wherein the first arm comprises a first human IgG1 constant region with amino acid substitutions at positions corresponding to positions 240 and 282 of SEQ ID NO:41, wherein the amino acids are replaced with lysine, and the second arm comprises a second human IgG1 constant region with amino acid substitutions at positions corresponding to positions 253 and 292 of SEQ ID NO:41, wherein the amino acids are replaced with glutamate or aspartate.

In embodiment 68, the bispecific agent of any one of embodiments 58-63, wherein the first arm comprises a first human IgG2 constant region with amino acid substitutions at positions corresponding to positions 249 and 288 of SEQ ID NO:42, wherein the amino acids are replaced with glutamate or aspartate, and the second arm comprises a second human IgG2 constant region with amino acid substitutions at positions corresponding to positions 236 and 278 of SEQ ID NO:42, wherein the amino acids are replaced with lysine.

In embodiment 69, the bispecific agent of any one of embodiments 58-63, wherein the first arm comprises a first human IgG2 constant region with amino acid substitutions at positions corresponding to positions 236 and 278 of SEQ ID NO:42, wherein the amino acids are replaced with lysine, and the second arm comprises a second human IgG2 constant region with amino acid substitutions at positions corresponding to positions 249 and 288 of SEQ ID NO:42, wherein the amino acids are replaced with glutamate or aspartate.

In embodiment 70, the bispecific agent of embodiment 64, wherein the first and second CH3 domains are modified using a knobs-into-holes technique.

In embodiment 71, the bispecific agent of any one of embodiments 58-70 which inhibits binding of TIGIT to PVR.

In embodiment 72, the bispecific agent of any one of embodiments 58-70 which inhibits or blocks the interaction between TIGIT and PVR.

In embodiment 73, the bispecific agent of any one of embodiments 58-70 which inhibits TIGIT signaling.

In embodiment 74, the bispecific agent of any one of embodiments 58-70 which is an antagonist of TIGIT-mediated signaling.

In embodiment 75, the bispecific agent of any one of embodiments 58-70 which inhibits TIGIT activation.

In embodiment 76, the bispecific agent of any one of embodiments 58-70 which inhibits phosphorylation of TIGIT.

In embodiment 77, the bispecific agent of any one of embodiments 58-70 which decreases cell surface expression of TIGIT.

In embodiment 78, the bispecific agent of any one of embodiments 58-70 which induces and/or enhances an immune response.

In embodiment 79, the bispecific agent of embodiment 78, wherein the immune response is directed to a tumor or tumor cell.

In embodiment 80, the bispecific agent of embodiment 78, wherein the immune response is directed to a virus or a virally-infected cell.

In embodiment 81, the bispecific agent of any one of embodiments 58-70 which increases cell-mediated immunity.

In embodiment 82, the bispecific agent of any one of embodiments 58-70 which increases T-cell activity.

In embodiment 83, the bispecific agent of any one of embodiments 58-70 which increases CTL activity.

In embodiment 84, the bispecific agent of any one of embodiments 58-70 which increases NK cell activity.

In embodiment 85, the bispecific agent of any one of embodiments 58-70 which increases IL-2 production and/or the number of IL-2-producing cells.

In embodiment 86, the bispecific agent of any one of embodiments 58-70 which increases IFN-gamma production and/or the number of IFN-gamma-producing cells.

In embodiment 87, the bispecific agent of any one of embodiments 58-70 which increases a Th1-type immune response.

In embodiment 88, the bispecific agent of any one of embodiments 58-70 which decreases IL-4 production and/or the number of IL-4-producing cells.

In embodiment 89, the bispecific agent of any one of embodiments 58-70 which decreases IL-10 and/or the number of IL-10-producing cells.

In embodiment 90, the bispecific agent of any one of embodiments 58-70 which decreases a Th2-type immune response.

In embodiment 91, the bispecific agent of any one of embodiments 58-70 which inhibits and/or decreases the suppressive activity of Tregs.

In embodiment 92, the bispecific agent of any one of embodiments 58-70 which inhibits and/or decreases the suppressive activity of MDSCs.

In embodiment 93, the bispecific agent of any one of embodiments 58-92 which inhibits tumor growth.

In embodiment 94, a polypeptide comprises a sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:55, and SEQ ID NO:56.

In embodiment 95, a cell comprises or produces the antibody, bispecific agent, or polypeptide of any one of embodiments 1-94.

In embodiment 96, a composition comprises the antibody, bispecific agent, or polypeptide of any one of embodiments 1-94.

In embodiment 97, a pharmaceutical composition comprises the antibody, bispecific agent, or polypeptide of any one of embodiments 1-94 and a pharmaceutically acceptable carrier.

In embodiment 98, an isolated polynucleotide molecule comprises a polynucleotide that encodes an antibody, bispecific agent, or polypeptide of any one of embodiments 1-94.

In embodiment 99, a vector comprises the polynucleotide of embodiment 98.

In embodiment 100, an isolated cell comprises the polynucleotide of embodiment 98 or the vector of embodiment 99.

In embodiment 101, a method of inducing, activating, promoting, increasing, enhancing, or prolonging an immune response in a subject, comprising administering a therapeutically effective amount of the antibody, bispecific agent, or polypeptide of any one of embodiments 1-94.

In embodiment 102, a method of inducing, activating, promoting, increasing, enhancing, or prolonging an immune response in a subject, comprising administering a therapeutically effective amount of the antibody of any one of embodiments 1-33.

In embodiment 103, the method of embodiment 101 or embodiment 102, wherein the immune response is against a tumor or cancer.

In embodiment 104, a method of inhibiting growth of tumor cells, wherein the method comprises contacting the tumor cells with an effective amount of an antibody, bispecific agent, or polypeptide of any one of embodiments 1-94.

In embodiment 105, a method of inhibiting growth of a tumor in a subject, wherein the method comprises administering to the subject a therapeutically effective amount of an antibody, bispecific agent, or polypeptide of any one of embodiments 1-94.

In embodiment 106, a method of inhibiting growth of a tumor in a subject, wherein the method comprises administering to the subject a therapeutically effective amount of an antibody of any one of embodiments 1-33.

In embodiment 107, the method of any one of embodiments 103-106, wherein the tumor or tumor cell is selected from the group consisting of colorectal tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

In embodiment 108, a method of treating cancer in a subject, wherein the method comprises administering to the subject a therapeutically effective amount of an antibody, bispecific agent, or polypeptide of any one of embodiments 1-94.

In embodiment 109, a method of treating cancer in a subject, wherein the method comprises administering to the subject a therapeutically effective amount of an antibody of any one of embodiments 1-33.

In embodiment 110, the method of embodiment 108 or embodiment 109, wherein the cancer is selected from the group consisting of colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer.

In embodiment 111, the method of any one of embodiments 101-110 which further comprises administering at least one additional therapeutic agent.

In embodiment 112, the method of embodiment 111, wherein the additional therapeutic agent is a chemotherapeutic agent.

In embodiment 113, the method of embodiment 111, wherein the additional therapeutic agent is an antibody.

In embodiment 114, the method of embodiment 111, wherein the additional therapeutic agent is an anti-PD-1 antibody, an anti-PD-L1 antibody, an anti-CTLA4 antibody, an anti-LAG-3 antibody, or an anti-TIM-3 antibody.

In embodiment 115, the method of embodiment 111, wherein the additional therapeutic agent is an immune response stimulating agent.

In embodiment 116, the method of embodiment 115, wherein the immune response stimulating agent is selected from the group consisting of: GM-CSF, M-CSF, G-CSF, IL-2, IL-3, IL-12, IL-15, B7-1 (CD80), B7-2 (CD86), 4-1BB ligand, GITRL, OX-40 ligand, anti-CD3 antibody, anti-CTLA4 antibody, anti-PD-1 antibody, anti-PD-L1 antibody, anti-GITR antibody, anti-OX-40 antibody, anti-LAG-3 antibody, and anti-TIM-3 antibody.

In embodiment 117, the method of embodiment 111, wherein the additional therapeutic agent is an inhibitor of the Notch pathway, the Wnt pathway, or the RSPO/LGR pathway.

In embodiment 118, the method of any one of embodiments 101-103 or 105-117, wherein the subject is human.

In embodiment 119, the method of any one of embodiments 101-103 or 105-118, wherein the subject has had a tumor or a cancer removed.

In embodiment 120, the method of any one of embodiments 101-119, wherein the tumor or the cancer expresses PD-L1.

In embodiment 121, the method of any one of embodiments 101-120, further comprising a step of determining the level of PD-L1 expression in the tumor or cancer.

In embodiment 122, the method of embodiment 121, wherein determining the level of PD-L1 expression is done prior to treatment or contact with the antibody.

In embodiment 123, the method of embodiment 121 or embodiment 122, wherein if the tumor or cancer has an elevated expression level of PD-L1, the antibody, bispecific agent, or polypeptide is: (a) administered to the subject; or (b) contacted with the tumor or tumor cell.

In embodiment 124, a plasmid deposited with ATCC and assigned designation number PTA-122180.

In embodiment 125, a plasmid deposited with ATCC and assigned designation number PTA-122181.

In embodiment 126, an isolated antibody that specifically binds the extracellular domain of human TIGIT, which comprises: (a) a heavy chain CDR1 comprising TSDYAWN (SEQ ID NO:57), a heavy chain CDR2 comprising YISYS-GSTSYNPSLRS (SEQ ID NO:58), and a heavy chain CDR3 comprising ARRQVGLGFAY (SEQ ID NO:59), and/or (b) a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

In embodiment 127, an isolated antibody that specifically binds human TIGIT, which comprises: (a) a heavy chain variable region having at least 90% sequence identity to SEQ ID NO:63 or SEQ ID NO:67; and/or (b) a light chain variable region having at least 90% sequence identity to SEQ ID NO:64 or SEQ ID NO:68.

In embodiment 128, the antibody of embodiment 126 or embodiment 127, which comprises: (a) a heavy chain variable region having at least 95% sequence identity to SEQ ID NO:63 or SEQ ID NO:67; and/or (b) a light chain variable region having at least 95% sequence identity to SEQ ID NO:64 or SEQ ID NO:68.

In embodiment 129, the antibody of embodiment 128, which comprises a heavy chain variable region comprising SEQ ID NO:63 and a light chain variable region comprising SEQ ID NO:64.

In embodiment 130, the antibody of embodiment 128, which comprises a heavy chain variable region comprising SEQ ID NO:67 and a light chain variable region comprising SEQ ID NO:68

In embodiment 131, the antibody of any one of embodiments 126-130 which is a monoclonal antibody.

In embodiment 132, the antibody of any one of embodiments 126-128, 130, or 131 which is a humanized antibody.

In embodiment 133, the antibody of embodiment 126 which is a human antibody.

In embodiment 134, the antibody of any one of embodiments 126-133 which is a recombinant antibody or a chimeric antibody.

In embodiment 135, the antibody of any one of embodiments 126-134 which is a bispecific antibody.

In embodiment 136, the antibody of any one of embodiments 126-135 which is an antibody fragment comprising an antigen binding site.

In embodiment 137, the antibody of any one of embodiments 126-136 which is an IgG antibody.

In embodiment 138, the antibody of embodiment 137 which is an IgG1 antibody, an IgG2 antibody, or an IgG4 antibody.

In embodiment 139, an antibody comprising a heavy chain amino acid sequence of SEQ ID NO:70 and a light chain amino acid sequence of SEQ ID NO:72.

In embodiment 140, an antibody comprising the same heavy chain variable region and the light chain variable region amino acid sequences as antibody 313M32.

In embodiment 141, an antibody comprising the heavy chain variable region encoded by the plasmid deposited with ATCC as PTA-122346.

In embodiment 142, an antibody comprising the light chain variable region encoded by the plasmid deposited with ATCC as PTA-122347.

In embodiment 143, an antibody comprising the light chain encoded by the plasmid deposited with ATCC as PTA-122347.

In embodiment 144, an antibody comprising the heavy chain variable region encoded by the plasmid deposited with ATCC as PTA-122346 and the light chain variable region encoded by the plasmid deposited with ATCC as PTA-122347.

In embodiment 145, an antibody comprising the heavy chain variable region encoded by the plasmid deposited with ATCC as PTA-122346 and the light chain encoded by the plasmid deposited with ATCC as PTA-122347.

In embodiment 146, the antibody of any one of embodiments 126-145 which does not bind: (a) mouse TIGIT; (b) rat TIGIT; (c) cynomolgus monkey TIGIT; and/or (d) rhesus monkey TIGIT.

In embodiment 147, an isolated antibody that competes with the antibody of any one of embodiments 126-146 for specific binding to TIGIT.

In embodiment 148, an isolated antibody that binds the same epitope on TIGIT as the antibody of any one of embodiments 126-146.

In embodiment 149, an isolated antibody that binds an epitope on TIGIT that overlaps with the epitope on TIGIT bound by the antibody of any one of embodiments 126-146.

In embodiment 150, an isolated antibody that specifically binds human TIGIT, wherein the antibody binds an epitope comprising: (a) amino acids within SEQ ID NO:79; (b) amino acids within SEQ ID NO:80; (c) amino acids within SEQ ID NO:79 and SEQ ID NO:80; (d) amino acids Q62 and I109 of SEQ ID NO:4; (e) amino acids Q62 and T119 of SEQ ID NO:4; (f) amino acids Q64 and I109 of SEQ ID NO:4; (g) amino acids Q64 and T119 of SEQ ID NO:4; (h) amino acids Q62, Q64, and I109 of SEQ ID NO:4; (i) amino acids Q62, Q64, and T119 of SEQ ID NO:4; (j) amino acids Q62, I109, and T119 of SEQ ID NO:4; (k) amino acids Q64, I109, and T119 of SEQ ID NO:4; or (1) amino acids Q62, Q64, I109, and T119 of SEQ ID NO:4.

In embodiment 151, the antibody of embodiment 150, wherein the antibody binds an epitope comprising amino acids within SEQ ID NO:79 and SEQ ID NO:80.

In embodiment 152, the antibody of embodiment 150, wherein the antibody binds an epitope comprising at least one of amino acids N58, E60, Q62, Q64, L65, F107, I109, H111, T117, T119, and G120 of SEQ ID NO:4.

In embodiment 153, the antibody of any one of embodiments 150-152, wherein the epitope is a conformational epitope.

In embodiment 154, the antibody of any one of embodiments 126-153 which inhibits binding of TIGIT to poliovirus receptor (PVR).

In embodiment 155, the antibody of any one of embodiments 126-153 which inhibits or blocks the interaction between TIGIT and PVR.

In embodiment 156, the antibody of any one of embodiments 126-153 which inhibits TIGIT signaling.

In embodiment 157, the antibody of any one of embodiments 126-153 which is an antagonist of TIGIT-mediated signaling.

In embodiment 158, the antibody of any one of embodiments 126-153 which inhibits TIGIT activation.

In embodiment 159, the antibody of any one of embodiments 126-153 which inhibits phosphorylation of TIGIT.

In embodiment 160, the antibody of any one of embodiments 126-153 which decreases cell surface expression of TIGIT.

In embodiment 161, the antibody of any one of embodiments 126-153 which induces and/or enhances an immune response.

In embodiment 162, the antibody of embodiment 161, wherein the immune response is directed to a tumor or tumor cell.

In embodiment 163, the antibody of any one of embodiments 126-153 which increases cell-mediated immunity.

In embodiment 164, the antibody of any one of embodiments 126-153 which increases T-cell activity.

In embodiment 165, the antibody of any one of embodiments 126-153 which increases cytolytic T-cell (CTL) activity.

In embodiment 166, the antibody of any one of embodiments 126-153 which increases natural killer (NK) cell activity.

In embodiment 167, the antibody of any one of embodiments 126-153 which increases IL-2 production and/or the number of IL-2-producing cells.

In embodiment 168, the antibody of any one of embodiments 126-153 which increases IFN-gamma production and/or the number of IFN-gamma-producing cells.

In embodiment 169, the antibody of any one of embodiments 126-153 which increases a Th1-type immune response.

In embodiment 170, the antibody of any one of embodiments 126-153 which decreases IL-4 production and/or the number of IL-4-producing cells.

In embodiment 171, the antibody of any one of embodiments 126-153 which decreases IL-10 production and/or the number of IL-10-producing cells.

In embodiment 172, the antibody of any one of embodiments 126-153 which decreases a Th2-type immune response.

In embodiment 173, the antibody of any one of embodiments 126-153 which inhibits and/or decreases the suppressive activity of regulatory T-cells (Tregs).

In embodiment 174, the antibody of any one of embodiments 126-153, which inhibits and/or decreases the suppressive activity of myeloid-derived suppressor cells (MDSCs).

In embodiment 175, the antibody of any one of embodiments 126-174 which inhibits tumor growth.

In embodiment 176, a heterodimeric agent which comprises the antibody of any one of embodiments 126-146.

In embodiment 177, a bispecific agent comprising: a) a first arm that specifically binds TIGIT, and b) a second arm, wherein the first arm comprises an antibody of any one of embodiments 126-146.

In embodiment 178, the bispecific agent of embodiment 177, wherein the second arm comprises an antigen-binding site from an antibody.

In embodiment 179, the bispecific agent of claim 177, wherein the second arm specifically binds PD-1, PD-L1, CTLA-4, TIM-3, LAG-3, OX-40, or GITR.

In embodiment 180, the bispecific agent of claim 177, wherein the second arm specifically binds a tumor antigen.

In embodiment 181, the bispecific agent of embodiment 177, wherein the second arm comprises an immunotherapeutic agent.

In embodiment 182, the bispecific agent of embodiment 181, wherein the immunotherapeutic agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA4 antibody, anti-PD-1 antibody, anti-PD-L1 antibody, anti-GITR antibody, anti-OX-40 antibody, anti-4-1BB antibody, anti-LAG-3 antibody, and anti-TIM-3 antibody.

In embodiment 183, the bispecific agent of any one of embodiments 177-182, wherein the first arm comprises a first CH3 domain and the second arm comprises a second CH3 domain, each of which is modified to promote formation of heterodimers.

In embodiment 184, the bispecific agent of embodiment 183, wherein the first and second CH3 domains are modified based upon electrostatic effects.

In embodiment 185, the bispecific agent of any one of embodiments 177-182, wherein the first arm comprises a first human IgG1 constant region with amino acid substitutions at positions corresponding to positions 253 and 292 of SEQ ID NO:41, wherein the amino acids are replaced with glutamate or aspartate, and the second arm comprises a second human IgG1 constant region with amino acid substitutions at positions corresponding to positions 240 and 282 of SEQ ID NO:41, wherein the amino acids are replaced with lysine.

In embodiment 186, the bispecific agent of any one of embodiments 177-182, wherein the first arm comprises a first human IgG1 constant region with amino acid substitutions at positions corresponding to positions 240 and 282 of SEQ ID NO:41, wherein the amino acids are replaced with lysine, and the second arm comprises a second human IgG1 constant region with amino acid substitutions at positions corresponding to positions 253 and 292 of SEQ ID NO:41, wherein the amino acids are replaced with glutamate or aspartate.

In embodiment 187, the bispecific agent of embodiment 183, wherein the first and second CH3 domains are modified using a knobs-into-holes technique.

In embodiment 188, the bispecific agent of any one of embodiments 177-187 which inhibits binding of TIGIT to PVR.

In embodiment 189, the bispecific agent of any one of embodiments 177-187 which inhibits or blocks the interaction between TIGIT and PVR.

In embodiment 190, the bispecific agent of any one of embodiments 177-187 which inhibits TIGIT signaling.

In embodiment 191, the bispecific agent of any one of embodiments 177-187 which is an antagonist of TIGIT-mediated signaling.

In embodiment 192, the bispecific agent of any one of embodiments 177-187 which inhibits TIGIT activation.

In embodiment 193, the bispecific agent of any one of embodiments 177-187 which inhibits phosphorylation of TIGIT.

In embodiment 194, the bispecific agent of any one of embodiments 177-187 which decreases cell surface expression of TIGIT.

In embodiment 195, the bispecific agent of any one of embodiments 177-187 which induces and/or enhances an immune response.

In embodiment 196, the bispecific agent of embodiment 195, wherein the immune response is directed to a tumor or tumor cell.

In embodiment 197, the bispecific agent of any one of embodiments 177-187 which increases cell-mediated immunity.

In embodiment 198, the bispecific agent of any one of embodiments 177-187 which increases T-cell activity.

In embodiment 199, the bispecific agent of any one of embodiments 177-187 which increases CU activity.

In embodiment 200, the bispecific agent of any one of embodiments 177-187 which increases NK cell activity.

In embodiment 201, the bispecific agent of any one of embodiments 177-187 which increases IL-2 production and/or the number of IL-2-producing cells.

In embodiment 202, the bispecific agent of any one of embodiments 177-187 which increases IFN-gamma production and/or the number of IFN-gamma-producing cells.

In embodiment 203, the bispecific agent of any one of embodiments 177-187 which increases a Th1-type immune response.

In embodiment 204, the bispecific agent of any one of embodiments 177-187 which decreases IL-4 production and/or the number of IL-4-producing cells.

In embodiment 205, the bispecific agent of any one of embodiments 177-187 which decreases IL-10 production and/or the number of IL-10-producing cells.

In embodiment 206, the bispecific agent of any one of embodiments 177-187 which decreases a Th2-type immune response.

In embodiment 207, the bispecific agent of any one of embodiments 177-187 which inhibits and/or decreases the suppressive activity of Tregs.

In embodiment 208, the bispecific agent of any one of embodiments 177-187 which inhibits and/or decreases the suppressive activity of MDSCs.

In embodiment 209, the bispecific agent of any one of embodiments 177-208 which inhibits tumor growth.

In embodiment 210, a polypeptide comprising a sequence selected from the group consisting of: SEQ ID NO:63, SEQ ID NO:64, SEQ ID NO:67, SEQ ID NO:68, SEQ ID NO:69, SEQ ID NO:70, SEQ ID NO:71, SEQ ID NO:72, SEQ ID NO:82, and SEQ ID NO:83.

In embodiment 211, a cell comprising or producing the antibody, bispecific agent, or polypeptide of any one of embodiments 126-210.

In embodiment 212, a composition comprising the antibody, bispecific agent, or polypeptide of any one of embodiments 126-210.

In embodiment 213, a pharmaceutical composition comprising the antibody, bispecific agent, or polypeptide of any one of embodiments 126-210 and a pharmaceutically acceptable carrier.

In embodiment 214, an isolated polynucleotide molecule comprising a polynucleotide that encodes an antibody, bispecific agent, or polypeptide of any one of embodiments 126-210.

In embodiment 215, an isolated polynucleotide comprising a polynucleotide sequence selected from the group consisting of: SEQ ID NO:65, SEQ ID NO:66, SEQ ID NO:73, SEQ ID NO:74, SEQ ID NO:75, SEQ ID NO:76, and SEQ ID NO:84.

In embodiment 216, a vector comprising the polynucleotide of embodiment 214 or embodiment 215.

In embodiment 217, an isolated cell comprising the polynucleotide of embodiment 214 or embodiment 215.

In embodiment 218, an isolated cell comprising the vector of embodiment 216.

In embodiment 219, a method of inducing, activating, promoting, increasing, enhancing, or prolonging an immune response in a subject, comprising administering a therapeutically effective amount of the antibody, bispecific agent, or polypeptide of any one of embodiments 126-210.

In embodiment 220, a method of inducing, activating, promoting, increasing, enhancing, or prolonging an immune response in a subject, comprising administering a therapeutically effective amount of the antibody of any one of embodiments 126-153.

In embodiment 221, the method of embodiment 219 or embodiment 220, wherein the immune response is against a tumor or cancer.

In embodiment 222, a method of inhibiting growth of tumor cells, wherein the method comprises contacting the tumor cells with an effective amount of an antibody, bispecific agent, or polypeptide of any one of embodiments 126-210.

In embodiment 223, a method of inhibiting growth of a tumor in a subject, wherein the method comprises administering to the subject a therapeutically effective amount of an antibody, bispecific agent, or polypeptide of any one of embodiments 126-210.

In embodiment 224, a method of inhibiting growth of a tumor in a subject, wherein the method comprises administering to the subject a therapeutically effective amount of an antibody of any one of embodiments 126-153.

In embodiment 225, the method of any one of embodiments 221-224, wherein the tumor or tumor cell is selected from the group consisting of colorectal tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, and head and neck tumor.

In embodiment 226, a method of treating cancer in a subject, wherein the method comprises administering to the subject a therapeutically effective amount of an antibody, bispecific agent, or polypeptide of any one of embodiments 126-210.

In embodiment 227, a method of treating cancer in a subject, wherein the method comprises administering to the subject a therapeutically effective amount of an antibody of any one of embodiments 126-153.

In embodiment 228, the method of embodiment 226 or embodiment 227, wherein the cancer is selected from the group consisting of colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer.

In embodiment 229, the method of any one of embodiments 219-228 which further comprises administering at least one additional therapeutic agent.

In embodiment 230, the method of embodiment 229, wherein the additional therapeutic agent is a chemotherapeutic agent.

In embodiment 231, the method of embodiment 229, wherein the additional therapeutic agent is an antibody.

In embodiment 232, the method of embodiment 229, wherein the additional therapeutic agent is an immunotherapeutic agent.

In embodiment 233, the method of embodiment 232, wherein the immunotherapeutic agent is selected from the group consisting of: GM-CSF, M-CSF, G-CSF, IL-2, IL-3, IL-12, IL-15, B7-1 (CD80), B7-2 (CD86), 4-1BB ligand, GITRL, OX-40 ligand, anti-CD3 antibody, anti-CTLA-4 antibody, anti-PD-1 antibody, anti-PD-L1 antibody, anti-GITR antibody, anti-OX-40 antibody, anti-4-1BB antibody, anti-LAG-3 antibody, and anti-TIM-3 antibody.

In embodiment 234, the method of embodiment 229, wherein the additional therapeutic agent is an inhibitor of the Notch pathway, the Wnt pathway, or the RSPO/LGR pathway.

In embodiment 235, the method of any one of embodiments 219-221 or 223-234, wherein the subject has had a tumor or a cancer removed.

In embodiment 236, the method of any one of embodiments 221-235, wherein the tumor or the cancer expresses PD-L1.

In embodiment 237, the method of any one of embodiments 221-236, further comprising a step of determining the level of PD-L1 expression in the tumor or cancer.

In embodiment 238, the method of embodiment 237, wherein determining the level of PD-L1 expression is done prior to treatment or contact with the antibody.

In embodiment 239, the method of embodiment 236 or embodiment 237, wherein if the tumor or cancer has an elevated expression level of PD-L1, the antibody, bispecific agent, or polypeptide is: (a) administered to the subject; or (b) contacted with the tumor or tumor cell.

In embodiment 240, a plasmid deposited with ATCC and assigned designation number PTA-122346.

In embodiment 241, a plasmid deposited with ATCC and assigned designation number PTA-122347.

In embodiment 242, an antibody comprising a heavy chain amino acid sequence of SEQ ID NO:82 and a light chain amino acid sequence of SEQ ID NO:72.

VI. Screening

The present invention provides screening methods to identify TIGIT-binding agents that modulate the immune response. In some embodiments, the present invention provides methods for screening candidate agents, including but not limited to, polypeptides, antibodies, peptides, peptidomimetics, small molecules, compounds, or other drugs, which modulate the immune response.

In some embodiments, a method of screening for a candidate TIGIT-binding agent that modulates the immune response comprises determining if the agent has an effect on immune cells. In some embodiments, a method of screening for a candidate TIGIT-binding agent that modulates the immune response comprises determining if the agent is capable of increasing the activity of immune cells. In some embodiments, a method of screening for a candidate TIGIT-binding agent that modulates the immune response comprises determining if the agent is capable of increasing the activity of cytolytic cells, such as CTLs and/or NK cells. In some embodiments, a method of screening for a candidate TIGIT-binding agent that modulates the immune response comprises determining if the agent is capable of decreasing the activity of immune suppressor cells, such as Tregs or MDSCs.

VII. Kits Comprising Agents Described Herein

The present invention provides kits that comprise the TIGIT-binding agents described herein and that can be used to perform the methods described herein. In certain embodiments, a kit comprises at least one purified TIGIT-binding agent in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed TIGIT-binding agents of the present invention can be readily incorporated into one of the established kit formats which are well known in the art.

Further provided are kits that comprise a TIGIT-binding agent as well as at least one additional therapeutic agent. In certain embodiments, the second (or more) therapeutic agent is a chemotherapeutic agent. In certain embodiments, the second (or more) therapeutic agent is an antibody.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Generation of Anti-TIGIT Antibodies

Figure 1A:
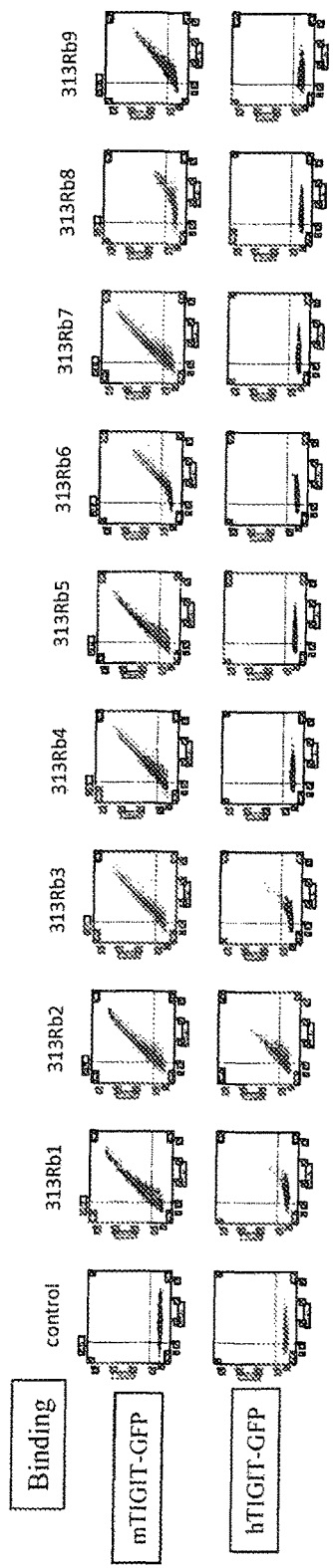
FIGS. 1A and 1B. FACS analysis of rabbit antibodies generated to mouse TIGIT. (A) HEK-293T cells were transiently transfected with a cDNA expression vector encoding mouse TIGIT ECD-CD4TM-GFP (green fluorescent protein) or human TIGIT ECD-CD4TM-GFP. Transfected cells were incubated with rabbit antibodies and analyzed by flow cytometry. Specific binding is indicated by the presence of the diagonal signal within each FACS plot. (B) HEK-293T cells were transiently transfected with a cDNA expression vector encoding mouse TIGIT-CD4TM-GFP. Transfected cells were incubated with soluble mouse PVR-Fc fusion protein in the presence of rabbit antibodies generated to mouse TIGIT or no antibody and analyzed by flow cytometry. Specific binding is indicated by the presence of the diagonal signal within each FACS plot. Blocking of binding is demonstrated by the loss of specific binding and is indicated by a circle over the FACS plot.
Figure 1B:
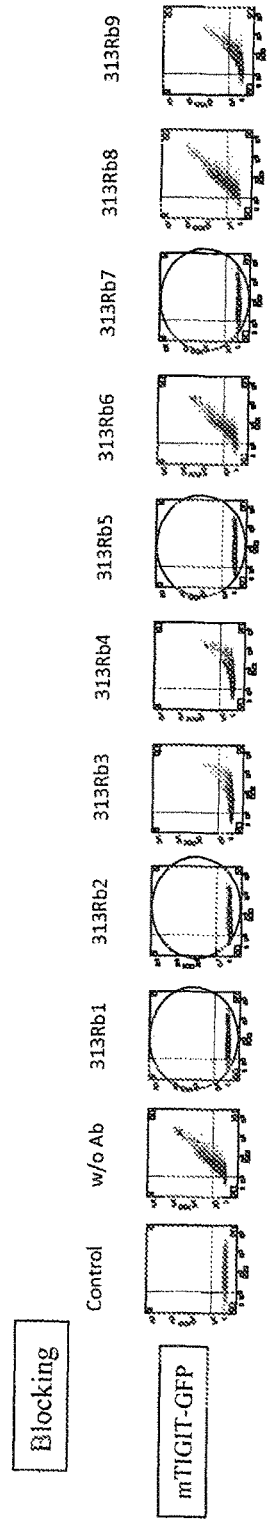

Anti-TIGIT antibodies were generated using the extracellular domain of mouse TIGIT to immunize rabbits. Supernatants were screened by flow cytometry for antibody binding to mouse TIGIT and human TIGIT and 9 antibody clones were chosen for further characterization (FIG. 1). The supernatants from these antibodies were screened for their ability to specifically block the interaction of mouse TIGIT with its counter-receptor, mouse PVR. Four antibodies were shown to block the TIGIT/PVR interaction. Importantly, two of these antibodies were able to bind human TIGIT (313Rb1 and 313Rb2).

The heavy chain and light chain variable regions of 313Rb1 were cloned into a mouse IgG1 format to generate chimeric antibody 313R11 and into a mouse IgG2a format to generate chimeric antibody 313R12. The sequences of the CDRs of 313R11 and 313R12 are (i) heavy chain CDR1 GSSLSSSYMS (SEQ ID NO:7), (ii) heavy chain CDR2 IIGSNGNTYYANWAKG (SEQ ID NO:8), (iii) heavy chain CDR3 GGYRTSGMDP (SEQ ID NO:9), (iv) light chain CDR1 QASQSISSYLNW (SEQ ID NO:10), (v) light chain CDR2 DALKLAS (SEQ ID NO:11), and (vi) light chain CDR3 QQEHSVGNVDN (SEQ ID NO:12). The sequence of the heavy chain variable region of 313R11 and 313R12 is SEQ ID NO:17 and the sequence of the light chain variable region of 313R11 and 313R12 is SEQ ID NO:18. The sequence of the heavy chain of 313R11 is SEQ ID NO:21 or SEQ ID NO:26 (without signal sequence). The sequence of the heavy chain of 313R12 is SEQ ID NO:22 or SEQ ID NO:27 (without signal sequence). The sequence of the light chain of 313R11 and 313R12 is SEQ ID NO:23 or SEQ ID NO:28 (without signal sequence).

The heavy chain and light chain variable regions of 313Rb2 were cloned into a human IgG1 format to generate antibody 313R14. The CDRs were modified to increase affinity for human TIGIT and the framework regions were optimized and/or humanized generating several variants, including 313R19. The sequences of the CDRs of 313R14 and 313R19 are (i) heavy chain CDR1 GFSLSSSYMS (SEQ ID NO:13), (ii) heavy chain CDR2 IIGSNGNTYYANWAKG (SEQ ID NO:8), (iii) heavy chain CDR3 GGYRTSGMDP (SEQ ID NO:9), (iv) light chain CDR1 QASQSNIYSDLAW (SEQ ID NO:14) or QASQNIYSDLAW (SEQ ID NO:81), (v) light chain CDR2 RASTLAS (SEQ ID NO:15), and (vi) light chain CDR3 QQEHLVAWIYN (SEQ ID NO:16). The sequence of the heavy chain variable region of 313R14 is SEQ ID NO:19 and the sequence of the light chain variable region of 313R14 is SEQ ID NO:20. The sequence of the heavy chain variable region of 313R19 is SEQ ID NO:32 and the sequence of the light chain variable region of 313R19 is SEQ ID NO:20. The sequence of the heavy chain of 313R14 is SEQ ID NO:24 or SEQ ID NO:29 (without signal sequence). The sequence of the heavy chain of 313R19 is SEQ ID NO:33 or SEQ ID NO:34 (without signal sequence). The sequence of the light chain of 313R14 and 313R19 is SEQ ID NO:25 or SEQ ID NO:30 (without signal sequence).

A plasmid encoding a polypeptide comprising the heavy chain variable region of the 313R19 antibody was deposited with American Type Culture Collection (ATCC), 10801 University Boulevard, Manassas, Va., USA, under the conditions of the Budapest Treaty on May 27, 2015, and designated PTA-122180. A plasmid encoding a polypeptide comprising the light chain variable region of the 313R19 antibody was deposited with ATCC, 10801 University Boulevard, Manassas, Va., USA, under the conditions of the Budapest Treaty on May 27, 2015, and designated PTA-122181.

Example 2

TIGIT Signaling and TIGIT Phosphorylation

As described herein, TIGIT is phosphorylated at its cytoplasmic tail after interaction with its counter-receptor PVR. The phosphorylation of TIGIT is the beginning of a cascade that includes downstream events affecting other known signaling pathways. Therefore, evaluating TIGIT phosphorylation as well as the phosphorylation status of downstream proteins can give information about TIGIT function and the effect of a TIGIT antagonist.

The Jurkat CD4+ human T cell line lacks human or murine TIGIT expression as determined by real-time PCR and by FACS (data not shown). To generate a TIGIT-expressing cell line, Jurkat cells were infected with a lentivirus construct expressing murine TIGIT (mTIGIT) tagged with FLAG and green fluorescent protein (GFP). The E.G7-OVA murine lymphoma cell line lacks expression of human or murine PVR as determined by real-time PCR and/or by FACS. E.G7-OVA cells synthesize and secrete ovalbumin (OVA) constitutively and C57BL/6 mice immunized with E.G7-OVA cells give rise to H-2 $K^b$ restricted cytotoxic lymphocytes specific for the OVA 258-276 peptide. To generate a PVR-expressing cell line, E.G7-OVA cells were infected with a lentivirus construct expressing murine PVR (mPVR) and GFP. GFP-positive cells from each infected cell line were sorted into 96-well plates using a FACSAria II instrument (BD Biosciences) and isolated single cells were expanded into clones. GFP positivity and mTIGIT or mPVR expression were confirmed in the single cell-derived clones by FACS analysis and real-time PCR (data not shown).

To evaluate TIGIT phosphorylation in response to PVR, cell lines were incubated in serum-free media for 2 hours at 37° C. Jurkat-mTIGIT cells were mixed with parental E.G7-OVA cells or E.G7-OVA-mPVR cells at a cell ratio of 5:1 and incubated for 5 minutes at 37° C. in the presence of a tyrosine phosphastase inhibitor (10 mM sodium orthovanadate, New England Biolabs). Cell lysates were prepared and immunoprecipitated with anti-FLAG-coated magnetic beads which captured the FLAG-tagged mTIGIT proteins. Immunoprecipitates were evaluated by Western blot analysis. The presence of phosphorylated TIGIT was evaluated using an anti-phosphotyrosine antibody (Cell Signaling Technology). The presence of total TIGIT was evaluated by using an anti-FLAG antibody (Cell Signaling Technology).

TIGIT was observed to be heavily phosphorylated in the T-cells in response to mPVR-expressing tumor cells as compared to cells not expressing PVR (FIG. 2A).

To evaluate other signaling pathways potentially affected by TIGIT, cell lines were incubated in serum-free media for 2 hours at 37° C. Jurkat-mTIGIT cells were combined with parental E.G7-OVA cells or E.G7-OVA-mPVR cells at a cell 5:1 ratio and incubated at 37° C. for 0, 5, 15, 45, or 60 minutes. Cell lysates were prepared and were evaluated by Western Blot analysis. Levels of phosphorylated SHP1 (SH2-containing tyrosine phosphatase 1) and Erk1/2 were determined using an anti-phospho SHP1 (Tyr564) antibody and an anti-phospho Erk1/2 (Thr202/Tyr204) antibody, respectively (both from Cell Signaling Technology). The level of total Erk1/2 was evaluated using an anti-Erk1/2 antibody (Cell Signaling Technology). SHP1 is an important negative regulator of cytokine-mediated signal transduction pathways, including the JAK/STAT pathway, while Erk1/2 are protein kinases that participate in the Ras-Raf-MEK-ERK signal transduction cascade.

As shown in FIG. 2B, SHP1 and Erk1/2 were specifically activated when TIGIT-expressing T-cells were incubated with mPVR-expressing tumor cells. The activation as indicated by phosphorylation was observed as early as the 5 minute time point and appeared to begin to decrease by 45 minutes for Erk1/2 and by 60 minutes for SHP1. SHP1 and Erk1/2 were not activated in response to mPVR in the parental Jurkat T-cells not expressing mTIGIT (data not shown).

To study if TIGIT antagonists would inhibit TIGIT activity, a TIGIT phosphorylation assay was conducted in the presence of anti-TIGIT antibodies. As described above, Jurkat-mTIGIT cells were mixed with parental E.G7-OVA cells or E.G7-OVA-mPVR cells at a cell ratio of 5:1 and incubated for 5 minutes at 37° C. in the presence of 10 mM sodium orthovanadate and 20 µg/ml control antibody (polyclonal murine IgG; Sigma), anti-TIGIT antibody 313R11, anti-TIGIT antibody 313R12, or anti-TIGIT antibody 313Rb1. Cell lysates were prepared and immunoprecipitated with anti-FLAG-coated magnetic beads which captured the FLAG-tagged mTIGIT proteins. Immunoprecipitates were evaluated by Western blot analysis. The presence of phosphorylated TIGIT was evaluated using an anti-phosphotyrosine antibody. The presence of total TIGIT was evaluated by using an anti-FLAG antibody.

Figure 3:
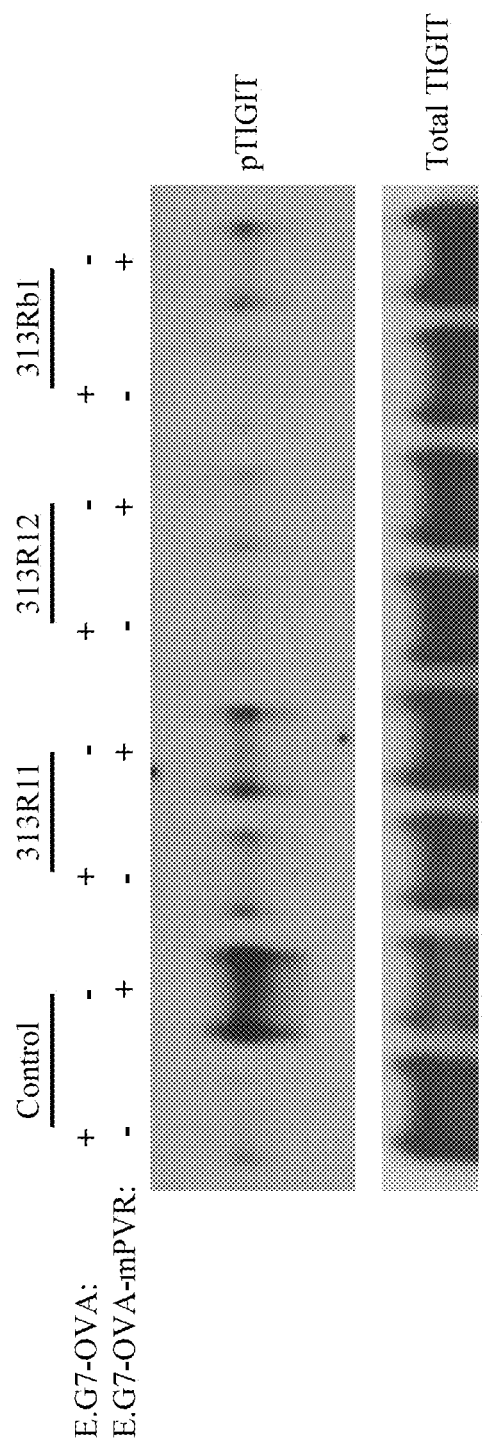
FIG. 3. Western blot analysis of TIGIT phosphorylation after TIGIT-PVR interaction in the absence or presence of anti-TIGIT antibodies.

As previously shown, mTIGIT was heavily phosphorylated when mTIGIT-expressing Jurkat T-cells were combined with mPVR-expressing tumor cells. The phosphorylation of mTIGIT in response to interaction with mPVR was reduced and/or abrogated when cells were incubated in the presence of the anti-TIGIT antibodies. The decrease in TIGIT phosphorylation was most striking with anti-TIGIT antibody 313R12 (FIG. 3).

Additional experiments to study if TIGIT antagonists would inhibit TIGIT signaling were undertaken. Similar to studies described herein, Jurkat-mTIGIT cells were mixed with parental E.G7-OVA cells or E.G7-OVA-mPVR cells at a cell ratio of 5:1 and incubated for 15 minutes at 37° C. in the presence of increasing concentrations (0-40 µg/ml) of anti-TIGIT antibody 313R11, anti-TIGIT antibody 313R12, or anti-TIGIT antibody 313Rb1. Cell lysates were prepared and evaluated by Western Blot analysis. Phosphorylated SHP1 (SH2-containing tyrosine phosphatase 1) and phosphorylated Erk1/2 were determined using an anti-phospho SHP1 (Tyr562) antibody and an anti-phospho Erk1/2 (Thr202/Tyr204) antibody, respectively. The level of total SHP1 was evaluated using an anti-SHP1 antibody. The level of total Erk1/2 was evaluated using an anti-Erk1/2 antibody.

Figure 4:
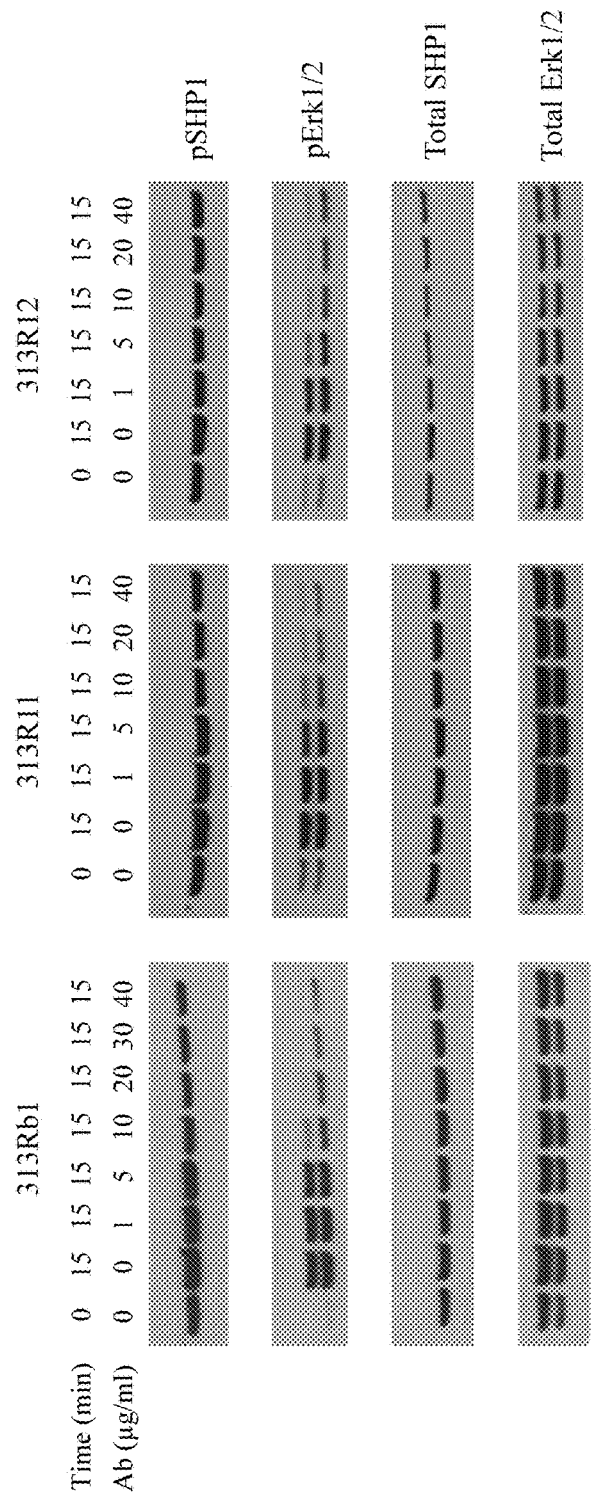
FIG. 4. Western blot analysis of SHP1 and Erk1/2 phosphorylation after TIGIT-PVR interaction in the absence or presence of anti-TIGIT antibodies.

Phosphorylation of Erk1/2 in response to the mTIGIT-mPVR interaction was clearly inhibited by the anti-TIGIT antibodies in a dose-dependent manner (FIG. 4). Phosphorylation of SHP1 in response to the mTIGIT-mPVR interaction was inhibited by anti-TIGIT antibody 313Rb1 and 313#11 in a dose-dependent manner. In the experiment shown, antibody 313R12 appeared to have only a weak effect on phosphorylation of SHP1.

These results strongly suggest that the anti-TIGIT antibodies inhibit TIGIT function and affect downstream signaling pathways.

Example 3

TIGIT Inhibition of Cytokine Production

The T-cell hybridoma B3Z86/90.14 (B3Z) stably expresses an OVA-specific H-2K$^b$ T-cell receptor (TCR). B3Z cells were infected with a lentivirus construct expressing murine TIGIT (mTIGIT) and a single cell-derived mTIGIT clone (B3Z-mTIGIT) was generated. The E.G7-OVA murine lymphoma cell line stably expresses OVA and can activate the OVA-specific TCR on B3Z cells, resulting in IL-2 secretion. To determine the effect of mTIGIT/mPVR interactions on antigen-specific IL-2 secretion, parental B3Z cells or B3Z-mTIGIT cells were incubated with parental E.G7-OVA or E.G7-OVA-mPVR cells (described above, see Example 2) at a ratio of 2:1 in 12-well plates. After 24 hours IL-2 concentrations were measured in cell-free culture supernatants by ELISA (R&D Systems). The data are expressed as the ratio of IL-2 secretion by the parental B3Z or the B3Z-mTIGIT T-cells in response to mPVR-expressing tumor cells compared to IL-2 secretion in response to mPVR-negative tumor cells.

Figure 5B:
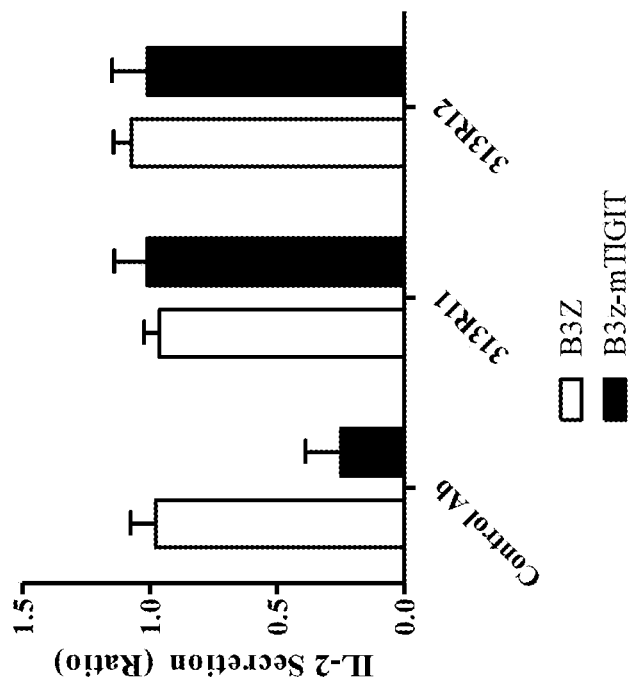
FIGS. 5A and 5B. TIGIT inhibition of cytokine production. (A) IL-2 secretion in B3Z T-cells and B3Z T-cells expressing TIGIT. (B) IL-2 secretion in B3Z T-cells and B3Z T-cells expressing TIGIT after pre-treatment with anti-TIGIT antibodies.
Figure 5A:
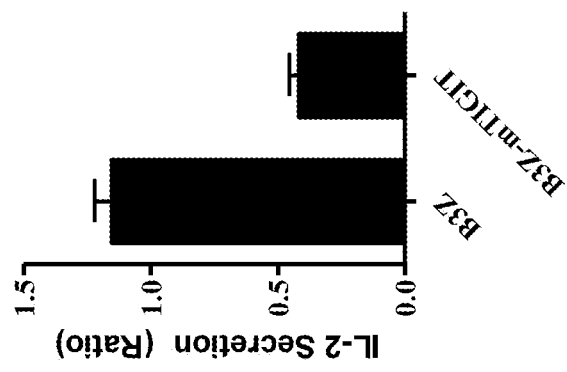

For parental B3Z T-cells, IL-2 secretion was similar regardless of the expression of mPVR on the OVA-presenting tumor cells (i.e., a ratio of approximately 1.0). In contrast, IL-2 secretion from B3Z-mTIGIT T-cells was lower in the presence of mPVR-expressing tumor cells than in the presence of mPVR-negative tumor cells (i.e., a ratio of <1.0) (FIG. 5A). When B3Z-mTIGIT T-cells were pre-treated with 20 µg/ml anti-TIGIT antibody 313R11 or 313R12 prior to co-culture with E.G7-OVA cells, IL-2 production was no longer inhibited (FIG. 5B).

These results suggest that activation of mTIGIT by mPVR inhibits T-cell activation in response to antigen as evidenced by the decrease in IL-2 production. Furthermore, the blockade of TIGIT with a TIGIT antagonist inhibits the activation of TIGIT and appears to reduce the TIGIT-associated inhibition of T-cell activity as seen by the strong production of IL-2. These data support the theory that inhibition of TIGIT can "release the brake on" T-cell suppression and enhance immune responses.

Example 4

TIGIT Inhibition of NK Cell Cytotoxicity

The NK-92 human natural killer (NK) cell line was infected with a lentivirus construct expressing mTIGIT tagged with FLAG and GFP and a clonal cell line (NK-92-mTIGIT) was derived as described above. The 721.221 human B-cell line was infected with a lentivirus construct expressing mPVR and GFP and a clonal cell line was generated (721.221-mPVR). Parental 721.221 cells were confirmed to lack expression of human or murine PVR by FACS and real-time PCR (data not shown). The ability of parental NK-92 cells or NK-92-mTIGIT cells to lyse parental 721.221 or 721.221-mPVR tumor cells was tested in a standard 4-hour calcein release assay. NK-92 or NK-92-mTIGIT cells were plated into 96-well V-bottom plates. Target 721.221 or 721-221-mPVR cells were labeled with 1004 calcein AM (Life Technologies) for 1 hour at 37° C. and then combined with the NK-92 cells at an effector:target ratio of 25:1 or 12:1. Following a 4-hour incubation at 37° C., cell-free supernatants were harvested and calcein release was quantified on a fluorometer at an excitation of 485 nm and an emission of 535 nm. In a follow-up experiment, the NK-92 cells and the NK-92-mTIGIT were incubated in the presence of 20 µg/ml anti-TIGIT antibody 313R11, antibody 313R12, or a control antibody for X minutes. The cells were then used in a calcein release assay as described above.

The percentage of specific cell lysis is determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS. Data is presented as the ratio of the cytotoxicity of NK-92 cells (parental or NK-92-mTIGIT) against 721.221-mPVR target cells to the cytotoxicity of NK-92 cells (parental or NK-92-mTIGIT) against parental (mPVR-negative) 721.221 target cells.

Figure 6B:
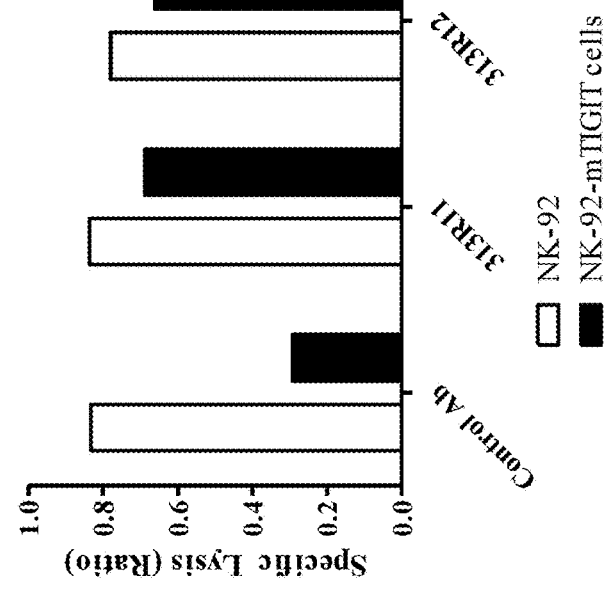
FIGS. 6A and 6B. TIGIT inhibition of natural killer cell activity. (A) Cytotoxicity of parental NK-92 cells and NK-92 cells expressing TIGIT. (B) Cytotoxicity of parental NK-92 cells and NK-92 cells expressing TIGIT after pre-treatment with anti-TIGIT antibodies.
Figure 6A:
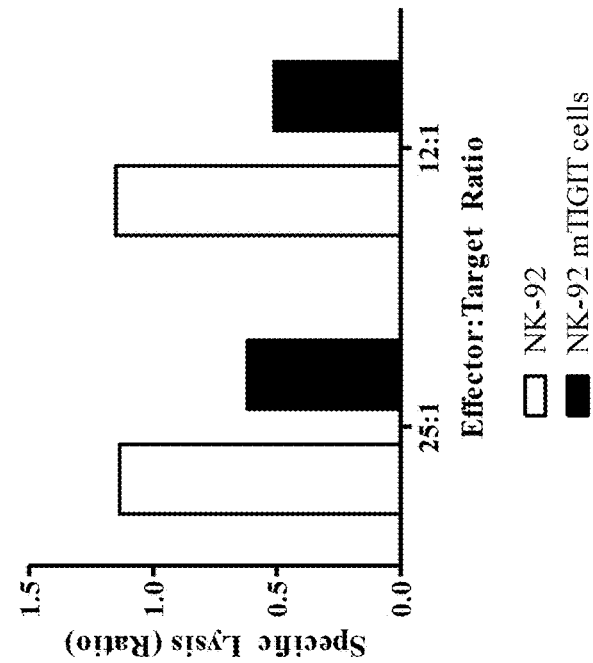

As shown in FIG. 6A, for parental NK-92 cells, cytotoxicity against mPVR-positive and mPVR-negative 721.221 target cells was similar (i.e., a ratio of approximately 1.0). In contrast, for NK-92-mTIGIT cells cytotoxicity against 721.221-mPVR cells was decreased compared to cytotoxicity against the mPVR-negative parental 721.221 cell line (i.e., a ratio of <1.0). There was no difference in results when effector:target ratio was 25:1 or 12:1. When NK-92 or NK-92-mTIGIT cells were treated with anti-TIGIT antibody 313R11 or antibody 313R12 prior to use in cytotoxicity assays, the inhibition of cell-mediated cytotoxicity was reduced and/or abrogated (FIG. 6B).

These results suggest that activation of mTIGIT by mPVR inhibits NK cell-mediated cytotoxicity. Importantly, the results demonstrate that a TIGIT antagonist can interfere with the PVR-TIGIT interaction and lead to a restoration of or "releasing the brake on" the cytotoxic capabilities of the NK cells.

Example 5

In Vivo Tumor Growth Inhibition by Anti-TIGIT Antibody

The murine colon tumor line CT26.WT was implanted subcutaneously (30,000 cells/mouse) in the rear flanks of 6-8 week old Balb/c mice. Tumors were allowed to grow for 10 days until they reached a volume of approximately 50 mm$^3$. Mice were treated with 0.25 mg/mouse of anti-TIGIT antibody 313R11 (mIgG1 antibody), anti-TIGIT antibody 313R12 (mIgG2a antibody), a mIgG1 control antibody, or a mIgG2a control antibody (n=10 per group for control antibodies and 20 per group for test antibodies). Mice were dosed by intraperitoneal injection twice a week for three weeks. Tumor growth was monitored and tumor volumes were measured with electronic calipers at Days 10, 15, 18, 22, 25, and 29.

As shown in FIG. 7A, anti-TIGIT antibody 313R12 inhibited tumor growth by almost 75% as compared to an isotype-matched control antibody. Tumors in nine mice had regressed to undetectable levels by Day 29. Anti-TIGIT antibody 313R11 inhibited tumor growth by only about 15% as compared to an isotype-matched control antibody. Antibody 313R11 and 313R12 differ only by their IgG isotypes, as 313R12 is an IgG2a antibody and 313R11 is an IgG1 antibody. These results suggest that the isotype of the antibody may have a significant effect on the therapeutic efficacy of the anti-TIGIT antibodies. Mouse IgG2 antibodies (equivalent to human IgG1 antibodies) are known to have increased ADCC activity as compared to mouse IgG1 antibodies (equivalent of human IgG2) and this biological characteristic may play a part in the strong anti-tumor effect of antibody 313R12.

The experiment was repeated with anti-TIGIT antibody 313R12 and a control mIgG2a antibody. As described above, CT26.WT cells were implanted subcutaneously (30,000 cells/mouse) in the rear flanks of 6-8 week old Balb/c mice. Tumors were allowed to grow for 7 days until they reached a volume of approximately 55 mm$^3$. Mice were treated with 0.25 mg/mouse of anti-TIGIT antibody 313R12 or a mIgG2a control antibody (n=10 per group). Mice were dosed by intraperitoneal injection twice a week for 3 weeks. Tumor growth was monitored and tumor volumes were measured with electronic calipers at Days 7, 14, 17, 21, 25, 28, and 31.

As observed in the previous study, anti-TIGIT antibody 313R12 inhibited growth of the CT26.WT tumors, with inhibition of tumor growth seen in all ten mice (FIG. 7B). Furthermore, tumors in 9 of the 10 mice treated with antibody 313R12 regressed from the original tumor size with 8 tumors regressing to undetectable levels after 2 weeks of treatment. In this study, there were three tumors that regressed in the IgG2 antibody control group, but it is known that tumor regression may occur in untreated, immunocompetent mice, especially if the starting number of tumor cells is low. However, the complete growth inhibition and/or tumor regression in the antibody 313R12-treated group demonstrated that treatment with an anti-TIGIT antibody had a significant therapeutic effect and that this may be attributed to the modulation and/or enhancement of the subject's immune response.

Successful immunotherapy against cancer will include generating long-term anti-tumor immunity. To study whether long-term immunity had been established, mice from studies described herein which had CT26.WT tumors that regressed to undetectable levels after anti-TIGIT antibody treatment were challenged with fresh CT26.WT tumor cells. Eleven mice with complete tumor regression were injected with an increased number of CT26.WT cells (60,000 cells/mouse) on Day 132 (102 days after the last dose of anti-TIGIT antibody 313R12). As a control, 10 naïve mice were injected with CT26.WT cells with the same number of CT26.WT cells. Mice were not treated, tumor growth was monitored, and tumor volumes were measured with electronic calipers.

In the control group all 10 mice developed large tumors by Day 23 and were euthanized. In contrast, no tumors grew in 10 of the mice that had previously rejected the CT26.WT tumors. The remaining mouse developed a small tumor growth 14 days after injection, but the tumor had completely regressed at day 21. These 11 mice were then re-challenged for a second time with 150,000 CT26.WT cells (5 times the number of cells of initial dose). Again as a control, 10 naïve mice were injected with CT26.WT cells with the same number of CT26.WT cells (150,000 cells/mouse). As in the earlier experiment, all 10 mice in the control group developed large tumors and were euthanized at Day 22. No tumors grew in 6 of the mice and 2 additional mice developed small tumors that completely regressed by Day 22. The other 3 mice had small tumors that appeared to be regressing or stabilized. These results are summarized in Table 3 and presented as the percentage of tumor-free mice in each group.

TABLE 3

|  | Initial Challenge 30,000 cells | 1st Re-challenge 60,000 cells | 2nd Re-challenge 150,000 cells |
| --- | --- | --- | --- |
| Control Mice | 10% (1/10) | 0% (0/10) | 0% (0/10) |
| Mice treated with 313R12 Antibody[1] | 55% (11/20) | 100% (11/11) | 72% (8/11) |

[1]Mice treated with 313R12 antibody only after initial tumor challenge

These results indicate that treatment with an anti-TIGIT antibody can generate a strong and effective anti-tumor response. Importantly, the anti-tumor response appeared to result in long-term immunity and protection against the tumor cells.

Example 6

Effector Activity of Anti-TIGIT IgG2 Antibody

It has been shown that glycosylation of the IgG-Fc region is essential for optimal expression of biological activities mediated through FcγRI, FcγII, FcγRIII and the C1q component of complement (i.e., ADCC and CDC). For example, the glycosylation site of a mouse IgG2a antibody heavy chain is at asparagine 314 of SEQ ID NO:22. Substitution of the asparagine with an alanine residue results in deglycosylation of the antibody and reduced ADCC activity. A deglycosylated variant of the anti-TIGIT antibody 313R12 antibody was generated that comprised an alanine residue at position 314, and named 313R13.

The activity of anti-TIGIT antibody 313R13 was compared to anti-TIGIT antibody 313R12 to study the effect of deglycosylation on anti-tumor activity. CT26.WT cells were implanted (30,000 cells/mouse) in the rear flanks of 6-8 week old Balb/c mice. Tumors were allowed to grow for 10 days until they reached a volume of approximately 50 mm³. Mice were treated with 0.25 mg/mouse of anti-TIGIT antibody 313R12, anti-TIGIT antibody 313R13, or a mIgG2a control antibody (n=10 per group for control antibody and 20 per group for test antibodies). Mice were dosed by intraperitoneal injection twice a week for three weeks. Tumor growth was monitored and tumor volumes were measured with electronic calipers at Days 7, 10, 14, 17, and 21.

As shown in FIG. 8, anti-TIGIT antibody 313R12 showed significant tumor growth inhibition as compared to the isotype-matched control. In contrast, deglycosylated anti-TIGIT antibody 313R13 showed no significant anti-tumor activity.

As it is believed that the deglycosylated antibody would have limited or no ADCC activity, these results suggest that ADCC may play a significant part in the strong anti-tumor activity of anti-TIGIT antibody 313R12.

Example 7

ELISpot Assays for IFN-Gamma, IL-2, IL-4, and IL-10

ELISpot is a highly sensitive immunoassay for the detection of cytokine-secreting cells. Briefly, an ELISpot assay employs a capture antibody specific for a desired cytokine, pre-coated onto the wells of a microplate. Stimulated cells are dispersed into the wells and the immobilized antibody in the immediate vicinity of any cytokine-secreting cell binds the secreted cytokine. Standard wash steps and incubation with appropriate detection reagents follow. For example, a combination of a biotinylated detection antibody followed by streptavidin conjugated to alkaline-phosphatase and a colored substrate solution is commonly used. A colored precipitate forms at the sites of cytokine localization and appears as a spot, with each individual spot representing an individual cytokine-secreting cell. The spots may be counted with an automated reader system or manually using a microscope. In some embodiments, an image of each well is captured using an automated reader system, and total spots, spot area, or total optical density (TOD) is used for quantification.

IFN-gamma secreting cells were detected using a mouse IFN-gamma ELISpot kit (MabTech). Cells were isolated from the spleens of CT26.WT tumor-bearing mice treated with anti-TIGIT antibody 313R12 (n=6) or an isotype-matched control antibody (n=6) (see Example 5). Splenocytes (5×10⁵/well) from each mouse in each treatment group were dispensed into a 96-well plate coated with an antibody specific for mouse IFN-gamma. The cells were cultured in the presence or the absence of tumor specific CD8+ T-cell peptide AH-1 and incubated for 48 hours. The AH-1 peptide (SPSYVYHQF; SEQ ID NO:31) is a H2-L$^d$-restricted epitope of the gp70 envelope protein of an ecotropic murine leukemia provirus endogenous to the CT26.WT cell line. Cells secreting IFN-gamma were detected following the manufacturer's instructions. Images were captured using a Bioreader 6000-F-z instrument (BioSys) and spot number, spot area, and total optical density were determined. Results are shown as total optical density and data are expressed as mean±S.E.M.

Figure 9:
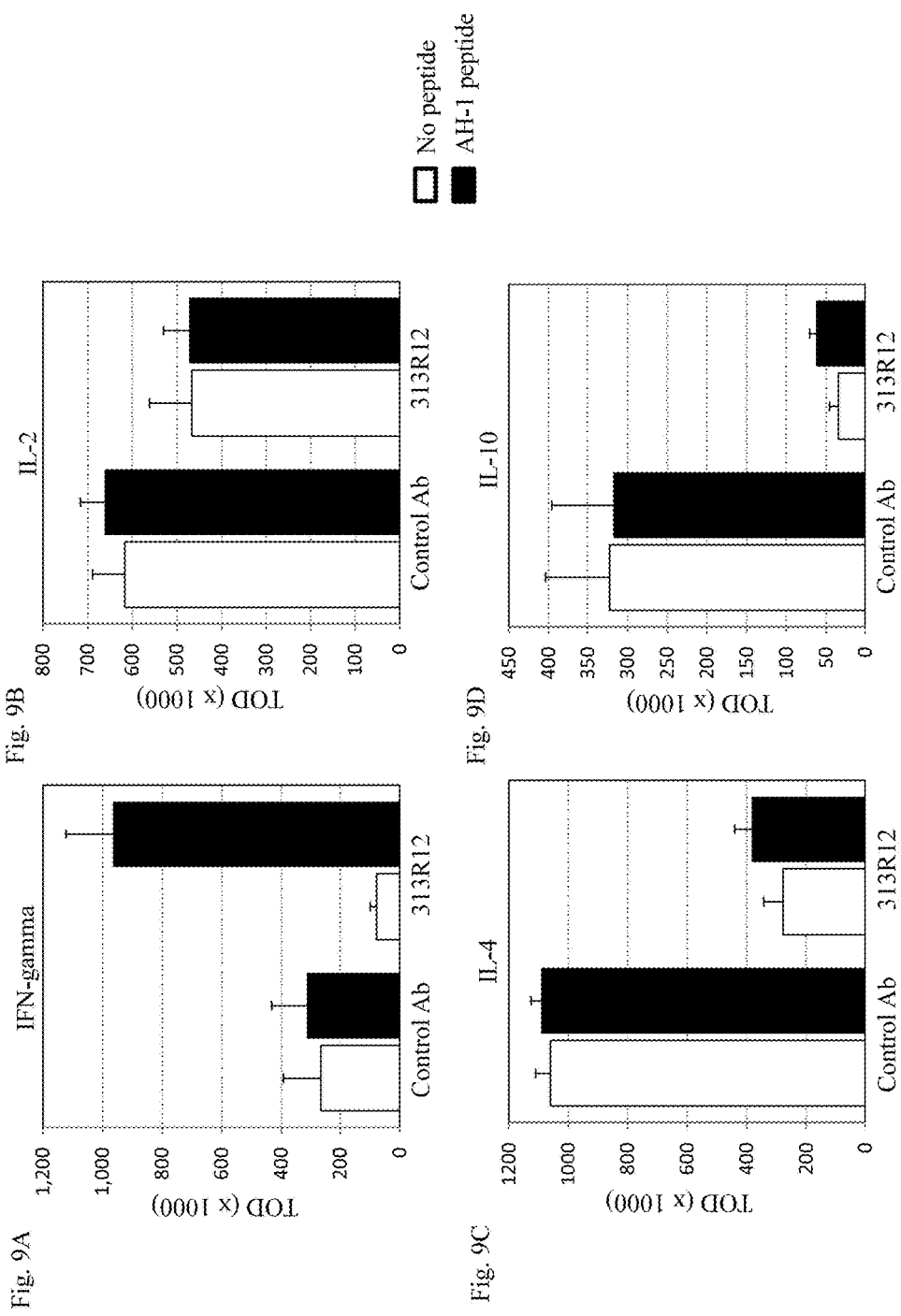

As shown in FIG. 9A, IFN-gamma secreting cells were significantly increased in mice treated with anti-TIGIT antibody 313R12 as compared to mice treated with control antibody. Importantly, IFN-gamma secreting cells were increased only in the presence of the AH-1 peptide. These results indicate that the anti-TIGIT antibody 313R12 activated tumor-specific CD8+ T-cells. The activation may be direct or indirect, i.e., an inhibition of suppressor cells.

IL-2 secreting cells were detected using a mouse IL-2 ELISpot kit (MabTech). Cells were isolated from the spleens of tumor-bearing mice treated with anti-TIGIT antibody 313R12 (n=6) or an isotype matched control antibody (n=6). Splenocytes ($5\times10^5$/well) from each mouse in each treatment group were dispensed into a 96-well plate coated with an antibody specific for mouse IL-2. The cells were incubated for 48 hours. Cells secreting IL-2 were detected following the manufacturer's instructions. Images were captured using a Bioreader 6000-F-z instrument (BioSys) and spot number, spot area, and total optical density were determined. Results are shown as total optical density and data are expressed as mean±S.E.M.

As shown in FIG. 9B, IL-2 secreting cells were slightly decreased in mice treated with anti-TIGIT antibody 313R12 as compared to mice treated with a control antibody. IL-2 secreting cells were decreased to an equivalent level in the presence or the absence of the AH-1 peptide.

IL-4 secreting cells were detected using a mouse IL-4 ELISPOT kit (MabTech). Cells were isolated from the spleens of tumor-bearing mice treated with anti-TIGIT antibody 313R12 (n=6) or an isotype matched control antibody (n=6). Splenocytes ($5\times10^5$/well) from each mouse within each treatment group were dispensed into a 96-well plate coated with an antibody specific for mouse IL-4. The cells were incubated for 48 hours. Cells secreting IL-4 were detected following the manufacturer's instructions. Images were captured using a Bioreader 6000-F-z instrument (BioSys) and spot number, spot area, and total optical density were determined. Results are shown as total optical density and data are expressed as mean±S.E.M.

As shown in FIG. 9C, IL-4 secreting cells were significantly decreased in mice treated with anti-TIGIT antibody 313R12 as compared to mice treated with a control antibody.

IL-10 secreting cells were detected using a mouse IL-10 ELISPOT kit (MabTech). Cells were isolated from the spleens of tumor-bearing mice treated with anti-TIGIT antibody 313R12 (n=6) or an isotype matched control antibody (n=6). Splenocytes ($5\times10^5$/well) from each mouse within each treatment group were dispensed into a 96-well plate coated with an antibody specific for mouse IL-10. The cells were incubated for 48 hours. Cells secreting IL-10 were detected following the manufacturer's instructions. Images were captured using a Bioreader 6000-F-z instrument (BioSys) and spot number, spot area, and total optical density were determined. Results are shown as total optical density and data are expressed as mean±S.E.M.

As shown in FIG. 9D, IL-10 secreting cells were significantly decreased in mice treated with anti-TIGIT antibody 313R12 as compared to mice treated with a control antibody.

IFN-gamma is generally produced by NK cells, Th1 CD4+ T-cells, CD8+ T-cells, antigen presenting cells, and B-cells. Studies have suggested a role for IFN-gamma in tumor immunity and that it may be a regulator of anti-tumor activity mediated by other cytokines, in particular IL-12 and IL-2. Thus, treatment with an anti-TIGIT antibody that results in an increase in IFN-gamma should enhance anti-tumor immunity.

IL-4 is produced by CD4+ Th2 cells and induces differentiation of naïve CD4+ T-cells to Th2 cells. In addition, IL-4 inhibits generation of Th1 cells, inhibits production of Th1 cytokines such as TNF-alpha and IL-12, and inhibits macrophage activation. IL-10 is generally produced by Tregs and helper T-cells. IL-10 was originally recognized as a Th2 cytokine that modulates growth and/or differentiation of innate immune cells and that suppresses the activation and effector functions of T-cells, particularly cytotoxic T-cells. More recently, IL-10 has been shown to have some immune stimulatory effects and thus is viewed as having pleiotropic functions. The significant decrease in IL-4 and IL-10-producing cells from mice treated with an anti-TIGIT antibody in the present study suggests that targeting TIGIT can result in inhibition of Th2 responses and may inhibit Tregs and/or Treg function.

Example 8

Cell Cytotoxicity Assays

For T-cell cytotoxicity assays, cells were harvested from the spleens of the CT26.WT tumor-bearing mice described above (Example 5). Cells were plated in 96-well V-bottom plates in RPMI 1640 culture medium (Gibco/Life Technologies, Grand Island, N.Y.) supplemented with 10% (v/v) fetal bovine serum (FBS), 2 mM L-glutamine, 100 U/ml penicillin, and 100 µg/ml streptomycin (Gibco). CT26.WT target cells were labeled with 10 µM calcein AM (Life Technologies) for 1 hour at 37° C. and then combined with the splenocytes at an effector:target (E:T) ratio of 50:1. Following a 4 hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

As shown in FIG. 10, CD8+ cytotoxic T-cells from CT26.WT tumor-bearing mice demonstrated an increased ability to kill CT26.WT target cells when the mice had been treated with anti-TIGIT antibody 313R12 as compared to cells from mice treated with control antibody.

These results suggest that an anti-TIGIT antibody can increase antigen-specific cytotoxic T-cell activity and therefore enhance anti-tumor immune responses. This increased cytotoxic T-cell activity may be due to a direct or indirect effect of the anti-TIGIT antibody, i.e., inhibiting the effect of suppressor cells.

Example 9

T Regulatory Cell (Treg) Assay

T regulatory cells (Tregs) play an essential role in the maintenance of homeostasis and prevention of autoimmune responses. Tregs are a small subset of T-cells, most which are CD4+ cells and express CD25 (an IL-2 receptor alpha chain) and other Treg cell-related molecular markers. Foxp3, a transcription factor, has been recognized to be a factor for Treg cell development and function. Foxp3 has been considered a specific marker for defining and identifying Treg cells and for separating Tregs from other T-cell subpopulations. However, the specificity of Foxp3 for Tregs has been challenged in human cells. In addition to CD4+ Treg cells, CD8+ Treg cells represent another cell subpopulation and Foxp3 may not be so crucial for their development and function when compared to CD4+ Treg cells.

The functionality of Tregs in mice treated with an anti-TIGIT antibody was evaluated by determining the effect Tregs had on proliferation of naïve CD4+ or CD8+ T-cells. Naïve T-cells were purified from the spleens of untreated mice using a mouse CD3+ T-cell enrichment column (R&D Systems). These purified T-cells were labeled with 5 µM violet tracking dye (VTD; Life Technologies). $2 \times 10^5$ VTD-labeled T-cells were incubated with anti-CD3 and anti-CD28 antibody-coated beads to stimulate cell proliferation. Tregs were isolated from the spleens of CT26.WT tumor-bearing mice (see Example 5) treated with anti-TIGIT antibody 313R12 (n=6) or an isotype-matched control antibody (n=5) using a mouse Treg isolation kit (Miltenyi Biotec). To determine the impact of Tregs on T-cell proliferation, the stimulated VTD-labeled T-cells (effectors) were co-cultured with isolated splenic Tregs from the mice treated with anti-TIGIT antibody 313R12 and the mice treated with the control antibody (effector:Treg ratio of 1:0.5). On day 4, cells were washed, and incubated with anti-mouse CD4 or anti-mouse CD8 antibodies. Cells were evaluated by FACS analysis using a FACSCanto II instrument and FACSDiva software v6.1.3 (BD Biosciences). VTD signals are reduced by half as the labeled cells divide, therefore the analysis gate was set between the maximum signal obtained with no Treg cells in the assay and the minimum signal obtained with no anti-CD3/CD28 stimulation. The percentage of cells within this region (reduced VTD expression) on CD4+ T-cells and CD8+ T-cells was used to calculate CD4+ and CD8+ T-cell proliferation. Percent suppression was calculated as [maximum signal−(sample signal/maximum signal)]×100.

As shown in FIG. 11, treatment with anti-TIGIT antibody 313R12 did not have any observable effect on the suppressive function of spleen-derived Tregs on CD4+ T-cell proliferation. In contrast, treatment with anti-TIGIT antibody 313R12 reduced the suppressive function of spleen-derived Tregs on the CD8+ T-cell proliferation by approximately 30%.

These results suggest that treatment with an anti-TIGIT antibody can lead to reduced Treg function and/or suppression, i.e., "taking the brake off" the immune response. A reduction of Treg function or Treg suppression could enhance total anti-tumor immune responses.

Example 10

Characterization of Immune Cells from CT26.WT Tumor-Bearing Mice Treated with Anti-TIGIT Antibody 313R12

To better characterize the immune cells in CT26.WT tumor-bearing mice treated with anti-TIGIT antibody 313R12 splenocytes isolated from individual mice were analyzed by FACS. CT26.WT cells (20,000 cells/mouse) were injected subcutaneously into the rear flanks of 6-8 week old Balb/c mice. Tumors were allowed to grow for 10 days until they reached approximately 50 mm³. Mice were treated with 0.25 mg/mouse of anti-TIGIT antibody 313R12 or an isotype-matched control antibody (n=10-20 per group). Mice were dosed by intraperitoneal injection twice a week. Tumor growth was monitored and tumor volumes were measured with electronic calipers. Six mice from each treatment group were used for analysis. At day 32 post-cell injection (1 day after the last antibody dose) splenocytes were isolated. Splenocytes ($1 \times 10^6$) were incubated for 10 minutes with a recombinant Fc protein to block non-specific binding, and then incubated with fluorochrome-conjugated antibodies in 100 µl FACS staining buffer (HBSS plus 2% heat inactivated calf serum) for 20 min on ice. Unbound antibodies were removed by washing and dead cells were labeled with a fixable viability dye. Cells were fixed in 2% paraformaldehyde for 20 min at room temperature and analyzed using a FACSCanto II instrument and FACSDiva Software v6.1.3 (BD Biosciences).

Total T-cells were identified using an anti-mouse CD3e antibody, CD4+ T-cells using an anti-mouse CD4 antibody, and CD8+ T-cells using an anti-mouse CD8 antibody. Central memory cells were identified using an anti-mouse/human CD44 antibody and effector memory cells were identified using an anti-human CD62L antibody. FACS staining was done as described above using anti-mouse CD8b antibody (clone 53-5.8, BioLegend), anti-mouse CD4 antibody (clone GK1.5, BioLegend), anti-mouse CD62L antibody (clone MEL-14, BioLegend), and anti-mouse CD44 antibody (clone 1M7, BioLegend). Cells were analyzed for $CD44^{high}CD62L^{high}$ expression, indicating central memory cells, and $CD44^{high}CD62L^{low}$ expression, indicating effector memory cells (gated on CD8+ T-cells).

Figure 12D:
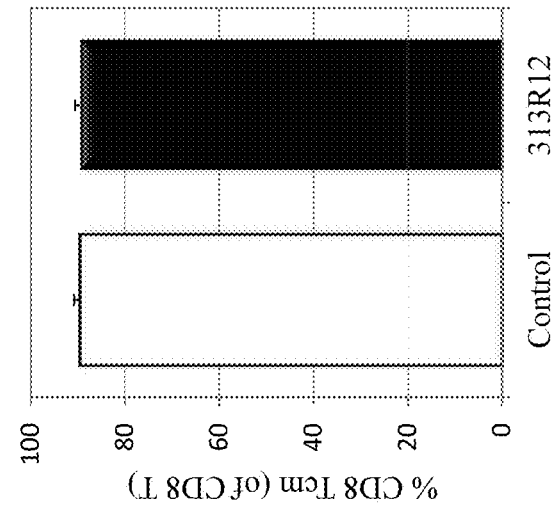
Figure 12E:
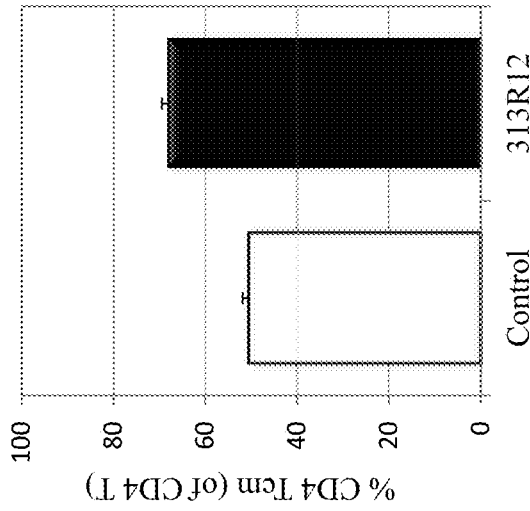

FACS analysis indicated that CT26.WT tumor-bearing mice treated with anti-TIGIT antibody 313R12 had an increased T-cell population of total live splenocytes as compared to the T-cell population from mice treated with a control antibody (FIG. 12A). The percentage of CD4+ T-cells (of total live cells) as well as the percentage of CD8+ T-cells (of total live cells) was increased in the mice treated with antibody 313R12 as compared to mice treated with control (FIG. 12B and FIG. 12C). In addition, the percentage of central memory cells within the CD4+ T-cell population was increased (FIG. 12D). However, the percentage of central memory cells within the CD8+ T-cell population was not increased (FIG. 12E).

These data indicated that treatment with an anti-TIGIT antibody increased the percentage of both CD4+ and CD8+ T-cell populations. The results are consistent with an enhanced immune response.

To assess the effect of the anti-TIGIT antibody on target expression, TIGIT expression on Tregs was analyzed by flow cytometry. As described herein, Tregs are suppressor cells and CD4+ Tregs are known to express transcription factor Foxp3. As described above, splenocytes from CT26.WT tumor-bearing mice treated with anti-TIGIT antibody 313R12 or control antibody were isolated. Splenocytes ($1 \times 10^6$) were incubated for 10 minutes with a recombinant Fc protein to block non-specific binding and then incubated with anti-TIGIT antibody 313R12 and an anti-mouse CD4 antibody in 100 µl FACS staining buffer (HBSS plus 2% heat inactivated calf serum) for 20 min on ice. After washing with FACS staining buffer, cells were labeled with a fixable cell viability dye, fixed, and permeabilized overnight. Following permeabilization, the cells were washed twice with 1× permeabilization buffer. Cells were stained using an anti-mouse Foxp3 antibody for 30 minutes on ice, washed, and fixed with 2% formaldehyde for 20 min at room temperature. Flow cytometry was performed using a FACSCanto II instrument and data analyses were done using FACSDiva Software v6.1.3 (BD Biosciences).

As shown in FIG. 13A, the percentage of total splenocytes expressing TIGIT was reduced in CT26.WT tumor-bearing mice treated with anti-TIGIT antibody 313R12 as compared to splenocytes from tumor-bearing mice treated with control antibody. The percentage of Foxp3+CD4+ cells (indicating Tregs) of total CD4+ cells was approximately 22-23% for both groups of mice and did not appear to be affected by treatment with the anti-TIGIT antibody (FIG. 13B). However, the percentage of TIGIT-positive Tregs (of total Tregs) was drastically reduced in the splenocyte population from CT26.WT tumor-bearing mice treated with anti-TIGIT antibody 313R12 as compared to tumor-bearing mice treated with control antibody (FIG. 13C). Conversely, the percentage of TIGIT-negative Tregs were slightly increased in the splenocyte population from CT26.WT tumor-bearing mice treated with anti-TIGIT antibody 313R12 as compared to tumor-bearing mice treated with control antibody (FIG. 13D).

These results suggest that anti-TIGIT antibody 313R12 depleted TIGIT-positive cells, particularly Tregs. However, the reduction in TIGIT-positive cells as assessed by FACS may be due to an internalization of TIGIT proteins and/or down-regulation of TIGIT cell surface expression and not an actual depletion of cells.

Myeloid-derived suppressor cells (MDSCs) are a heterogeneous family of myeloid cells and have been shown to be potent suppressors of both adaptive and innate immunity. MDSCs suppress the proliferation and activation of CD4+ T-cells and CD8+ T-cells and facilitate the generation of Tregs. MDSCs are believed to facilitate cancer progression by inhibiting anti-tumor immune responses, promoting angiogenesis, and creating a pre-metastatic environment. MDSCs are characterized by the cell surface expression of the myeloid lineage differentiation antigens Gr1 and CD11b. Gr1 is primarily limited to expression on cells of a granulocytic lineage and CD11b is a cell surface integrin that is found on the surface of macrophages, granulocyte, NK cells, and T-cells. In mice, MDSCs can be divided into two subpopulations, granulocytic MDSCs (G-MDSC) and monocytic MDSCs (M-MDSC), partially based on these markers. G-MDSCs typically have multi-lobed nuclei and a CD11b+Gr1$^{high}$ phenotype, whereas M-MDSCs have a monocytic morphology and a CD11b+Gr1$^{low}$ phenotype. Both populations of MDSCs have been shown to suppress T-cell responses by multiple mechanisms including increased production of arginase, inducible nitric oxide synthase (iNOS), nitric oxide, and reactive oxygen species. Thus, MDSCs contribute to an immunosuppressive tumor microenvironment and may limit the effects of anti-tumor immune responses.

Myeloid cells, particularly MDSCs from CT26.WT tumor-bearing mice treated with anti-TIGIT antibody 313R12 or control antibody were analyzed by FACS. Splenocytes (1×10$^6$) were incubated for 10 minutes with a recombinant Fc protein to block non-specific binding, and then incubated with fluorochrome-conjugated antibodies in 100 µl FACS staining buffer (HBSS plus 2% heat inactivated calf serum) for 20 min on ice. The cells were subsequently incubated with an anti-mouse CD11b antibody and an anti-mouse Gr1 antibody. Unbound antibodies were removed by washing and cells were labeled with a fixable viability dye. Cells were fixed in 2% paraformaldehyde for 20 min at room temperature and analyzed using a FACSCanto II instrument and FACSDiva Software v6.1.3 (BD Biosciences).

As shown in FIG. 14A, the percentage of CD11b+ myeloid cells (of total live cells) from the spleens of CT26.WT tumor-bearing mice treated with anti-TIGIT antibody 313R12 was reduced approximately 25% as compared to CD11b+ myeloid cells from tumor-bearing mice treated with control antibody. The percentage of CD11b+Gr1+ MDSCs (of total CD11b+ myeloid cells) in the spleens of tumor-bearing mice treated with anti-TIGIT antibody 313R12 was reduced approximately 45% as compared to CD11b+Gr1+ MDSCs from tumor-bearing mice treated with control antibody (FIG. 14B). Within the MDSC population, the percentage of G-MDSCs (as identified as CD11b+ Gr1$^{high}$) from the spleens of CT26.WT tumor-bearing mice treated with anti-TIGIT antibody 313R12 was reduced approximately 66%, but the percentage of M-MDSCs (as identified as CD11b+Gr1$^{low}$) from the spleens of CT26.WT tumor-bearing mice treated with anti-TIGIT antibody 313R12 was increased approximately 30% (FIGS. 14C and 14D, respectively).

These results suggest that treatment with an anti-TIGIT antibody may enhance anti-tumor responses by reducing the suppressive activity of specific immune cells, i.e., MDSCs.

Example 11

In Vivo Tumor Growth Inhibition by Anti-TIGIT Antibody

Renca is a Balb/c-derived renal adenocarcinoma cell line obtained from ATCC. Renca cells (5×10$^5$ cells/mouse) were implanted subcutaneously in the rear flanks of 6-8 week old Balb/c mice. Tumors were allowed to grow for 7 days until they reached a volume of approximately 43 mm$^3$. Mice were treated with 0.25 mg/mouse of anti-TIGIT antibody 313R12 (mIgG2a antibody) or a mIgG2a control antibody (n=10 per group). Mice were dosed by intraperitoneal injection twice a week for 3 weeks. Tumor growth was monitored and tumor volumes were measured with electronic calipers at Days 7, 10, 14, 17, 21, and 24.

As shown in FIG. 15, anti-TIGIT antibody 313R12 strongly inhibited tumor growth as compared to the isotype-matched control antibody. All control mice were euthanized by Day 28 due to tumor size. In contrast, at Day 28 the tumors from 8 of 10 mice treated with antibody 313R12 had regressed and 5 of those mice had no detectable tumors. Five of the original ten mice were maintained and no tumors were detectable out to at least 100 days post injection.

These results show that the anti-tumor activity of anti-TIGIT antibody 313R12 was effective in several different tumor types.

Example 12

In Vivo Tumor Growth Inhibition by Anti-TIGIT Antibody—Dose Study

Since the anti-TIGIT antibody had been shown to be effective in inhibiting tumor growth, a dose range study was conducted. The murine colon tumor line CT26.WT was implanted subcutaneously (30,000 cells/mouse) in Balb/c mice and tumors were allowed to grow to an average size of approximately 35 mm$^3$. Mice were treated with 30, 15, 10, 5, 3, 1, or 0.5 mg/kg of anti-TIGIT antibody 313R12 or with a control antibody (n=10 per group). Mice were dosed by intraperitoneal injection once a week for a total of 3 doses. Tumor growth was monitored and tumor volumes were measured with electronic calipers at the indicated time points.

FIG. 16 shows the average tumor volume of each treatment group. Treatment with anti-TIGIT antibody 313R12 strongly inhibited growth of CT26.WT tumors at each dose including at the lowest level of 0.5 mg/kg. As shown in Table 4, at Day 20 tumors had regressed in at least 40% of the mice at every dose level. In every treated group there were individual mice where the tumor had regressed to an undetectable level. A dose response curve was not seen in this experiment, which may have been due to the size of the tumors at the beginning of treatment.

TABLE 4

| Dose in mg/kg | No. of Mice with Regressed Tumors | No of Mice with Undetectable Tumors |
|---|---|---|
| Control Ab | 1/10 | 0/10 |
| 0.5 | 8/10 | 3/10 |
| 1 | 6/10 | 1/10 |
| 3 | 8/10 | 4/10 |
| 5 | 7/10 | 3/10 |
| 10 | 5/10 | 3/10 |
| 15 | 4/10 | 2/10 |
| 30 | 7/10 | 4/10 |

These results demonstrate the potency of the anti-TIGIT antibody 313R12 as an immunotherapeutic agent. In general, these results are surprising in regard to the small amount of anti-TIGIT antibody needed to see a significant anti-tumor effect.

Example 13

In Vivo Tumor Growth Inhibition by Anti-TIGIT Antibody and Anti-PD-L1 Antibody

The murine colon tumor line CT26.WT was implanted subcutaneously (30,000 cells/mouse) in Balb/c mice and on the first day of treatment (Day 10 post-implantation) the tumors were an average size of approximately 105 mm$^3$. Mice were treated with 0.25 mg/mouse of anti-TIGIT antibody 313R12, an anti-PD-L1 antibody, a combination of 313R12 and anti-PD-L1 antibody, or a control antibody (n=10-20 per group). Mice were administered antibodies twice a week for 3 weeks. Tumor growth was monitored and tumor volumes were measured with electronic calipers.

Figures 17A, 17B, 17C, 17D:
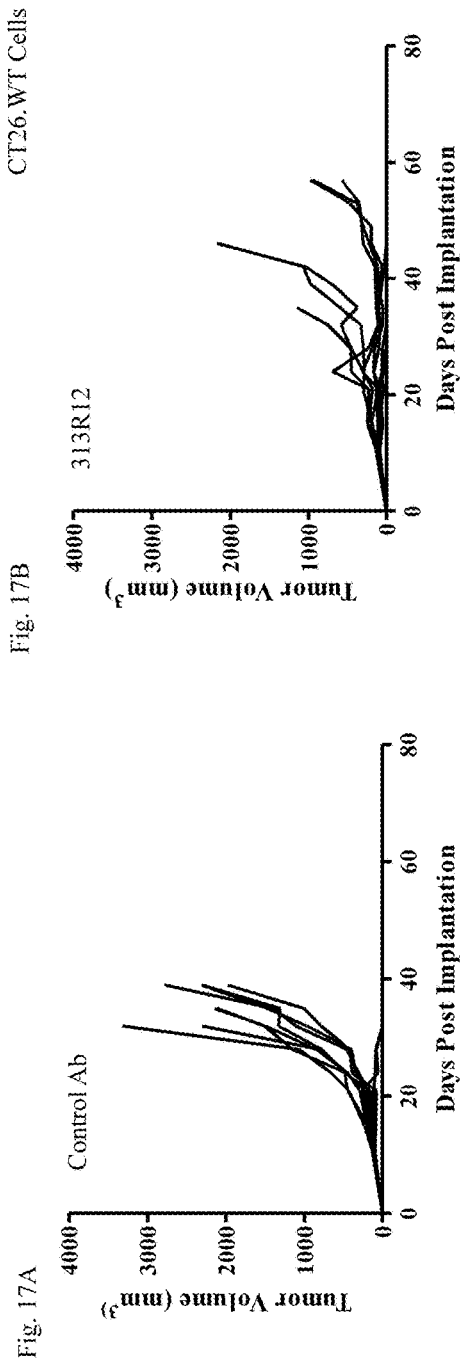
Figure 17F:
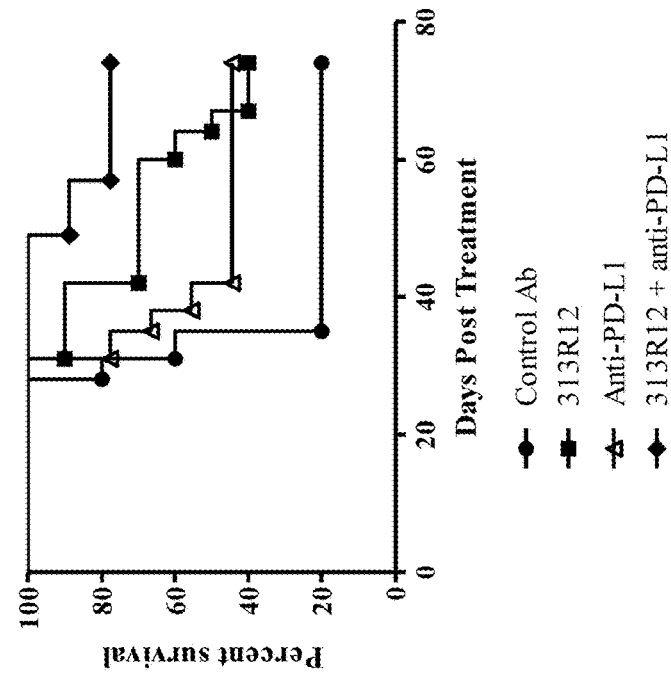
Figure 17E:
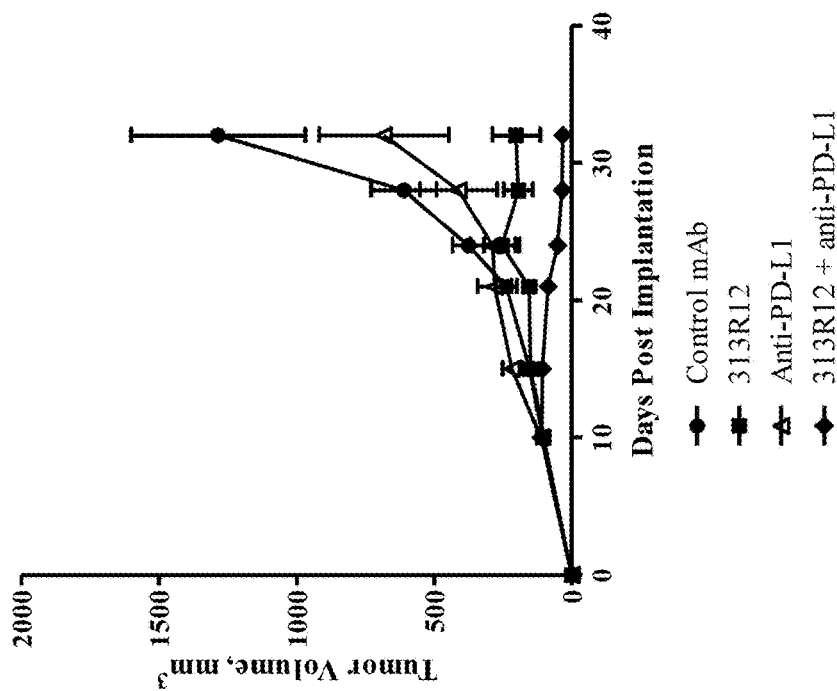

As is shown in FIG. 17B, treatment with anti-TIGIT antibody 313R12 strongly inhibited growth of the CT26.WT tumors in a high percentage of the mice. It should be noted that treatment with anti-TIGIT antibody 313R12 is not only able to inhibit growth of tumors in the majority of mice, but is able to induce regression of individual tumors, often to undetectable levels. Treatment with the anti-PD-L1 antibody was much less successful at inhibiting tumor growth as a single agent (FIG. 17C). Treatment with the combination of anti-TIGIT antibody 313R12 and an anti-PD-L1 antibody inhibited tumor growth to a greater extent than either agent alone (FIG. 17D). Average tumor volume is shown in FIG. 17E and percent survival of the mice from each group is shown in FIG. 17F.

One method of evaluating the presence and/or functionally of an anti-tumor memory cell population is to re-challenge previously treated mice with fresh tumor cells. Mice (from the studies described above) previously treated with anti-TIGIT antibody 313R12, anti-mPD-L1 antibody, or a combination of 313R12 and anti-mPD-L1 antibody were used for a re-challenge study. Mice whose tumors had regressed completely and were undetectable at least 128 days after the first tumor injection were re-challenged with CT26.WT tumor cells (30,000 cells). The mice subjected to tumor re-challenge had received a last treatment dose 100 days prior to re-challenge. Naïve Balb/c mice (n=10) were injected with CT26.WT tumor cells (30,000 cells) as a control group. Tumor growth was monitored and tumor volumes were measured with electronic calipers at the indicated time points. Data are expressed as mean±S.E.M.

The average tumor volume of CT26.WT tumors in naive mice grew steadily up to Day 28 with an average tumor volume of approximately 1750 mm$^3$. From the previous experiment there were only two mice with completely regressed tumors that had been previously treated with the anti-PD-L1 antibody, but these two mice demonstrated complete immunity to the tumor re-challenge. There were 4 mice with completely regressed tumors that had been previously treated with anti-TIGIT antibody and tumors grew in none of these mice after re-challenge and demonstrated complete immunity to the tumor re-challenge. In addition, there were 7 mice with completely regressed tumors that had been previously treated with the combination of 313R12 and an anti-PD-L1 antibody and these mice demonstrated complete immunity to the tumor challenge.

The mice treated with anti-TIGIT antibody, either as a single agent or in combination with an anti-PD-L1 antibody, appeared to be strongly protected from re-challenge with the CT26.WT tumor cells. These results suggest the existence of immunogenic memory after treatment with an anti-TIGIT antibody, either as a single agent or in combination with a checkpoint inhibitor.

Example 14

In Vivo Tumor Growth Inhibition by an Anti-TIGIT Antibody and Anti-PD-1 Antibody The murine colon tumor line CT26.WT was implanted subcutaneously (30,000 cells/mouse) in Balb/c mice and on the first day of treatment (Day 7 post-implantation) the tumors were an average size of approximately 62 mm$^3$. Mice (n=15) were treated with 12.5 mg of anti-TIGIT antibody 313R12, an anti-PD-1 antibody, a combination of 313R12 and anti-PD-1 antibody, or a control antibody (n=15 per group). Mice were administered the antibodies by intraperitoneal injection twice a week for 3 weeks. Tumor growth was monitored and tumor volumes were measured with electronic calipers.

Figure 18E:
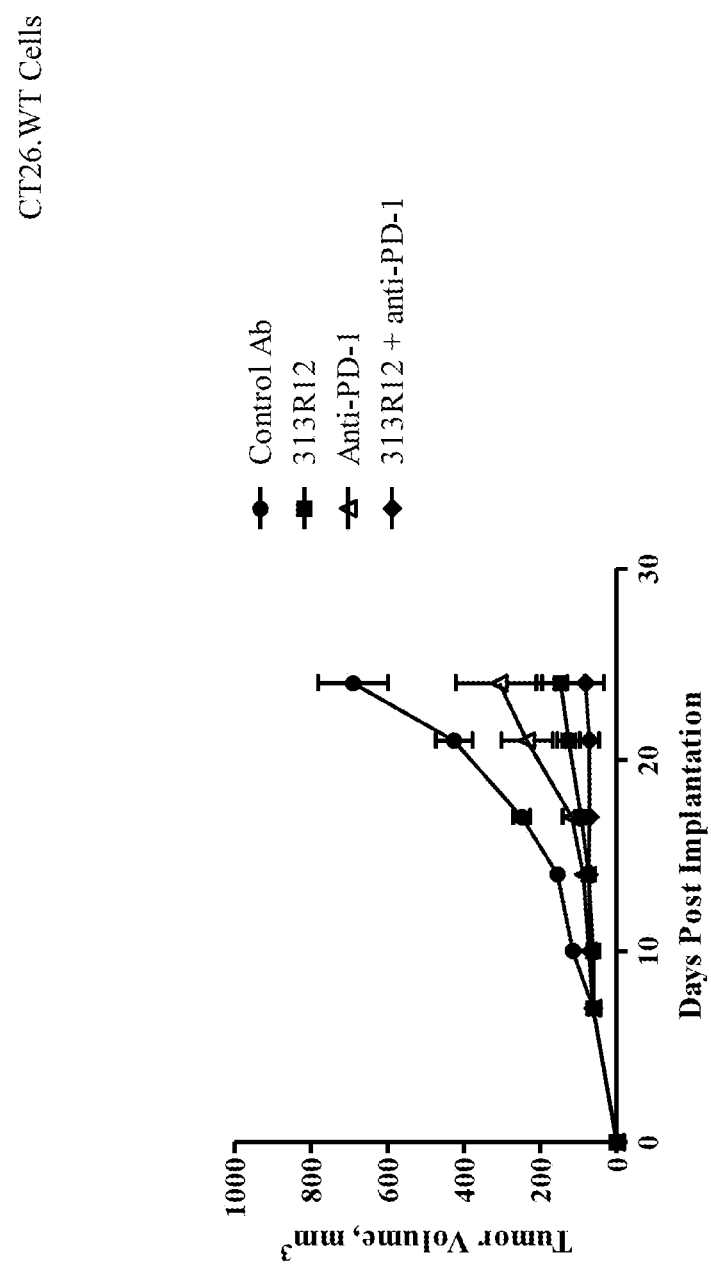

As is shown in FIG. 18B, treatment with anti-TIGIT antibody 313R12 strongly inhibited tumor growth. As seen in earlier examples, treatment with 313R12 is not only able to inhibit growth of the tumors, but is able to induce regression of some tumors. Treatment with the combination of anti-TIGIT antibody 313R12 and an anti-PD-1 antibody inhibited tumor growth to a greater extent than either agent alone (FIG. 18D). Average tumor volume in the four groups at Day 24 is shown in FIG. 18E.

Mice previously treated with anti-TIGIT antibody 313R12, anti-mPD-1 antibody, or a combination of 313R12 and anti-mPD-L1 antibody were used for a re-challenge study. Mice whose tumors had regressed completely and were undetectable at least 100 days after the first tumor injection were re-challenged with CT26.WT tumor cells (60,000 cells). Naïve Balb/c mice (n=10) were injected with CT26.WT tumor cells (60,000 cells) as a control group. Tumor growth was monitored and tumor volumes were measured with electronic calipers at the indicated time points. Data are expressed as mean±S.E.M.

The average tumor volume of CT26.WT tumors in naive mice grew steadily with an average tumor volume at Day 21 of approximately 1250 mm$^3$. From the previous experiment there were 13 mice with completely regressed tumors that had been previously treated with the combination of 313R12 and an anti-PD-1 antibody and these mice demonstrated complete immunity to the tumor challenge.

These results further support the idea that the anti-TIGIT antibody 313R12 is a very potent immunotherapeutic agent, even when administered as a single agent. In addition, the efficacy of an anti-TIGIT antibody may be further enhanced by combining it with other immunotherapeutic agents.

Example 15

Generation of Anti-TIGIT Monoclonal Antibodies

Antibodies were generated against recombinant human TIGIT amino acids 22-141 (R&D Systems) and/or recombinant human TIGIT amino acids 22-138 (Sino Biological Inc.). Mice (n=3) were immunized with TIGIT using standard techniques. Sera from individual mice were screened against human TIGIT approximately 70 days after initial immunization using FACS analysis. The animal with the highest antibody titer was selected for a final antigen boost after which spleen cells were isolated for hybridoma production. SP2/0 cells were used as fusion partners for the mouse spleen cells. Hybridoma cells were plated at 1 cell per well in 96 well plates, and the supernatants were screened against human TIGIT by FACS analysis.

For FACS screening of anti-TIGIT antibodies a chimeric fusion protein enabling cell surface expression of the extracellular domain of human TIGIT was constructed (FLAG-hTIGIT-CD4TM-GFP) and transfected into HEK-293T cells. After 48 hours, transfected cells were suspended in ice cold PBS containing 2% FBS and heparin and incubated on ice in the presence of 50 µl of hybridoma supernatants for 30 minutes. A second incubation with 100 µl PE-conjugated anti-human Fc secondary antibody was performed to detect cells bound by antibody. Cells were incubated with an anti-FLAG antibody (Sigma-Aldrich) as a positive control and an anti-PE antibody as a negative control. The cells were analyzed on a FACSCalibur instrument (BD Biosciences) and the data was processed using FlowJo software.

Several hybridomas were identified that bound human TIGIT and antibody 313M26 was selected. The amino acid sequences of the heavy chain variable region and the light chain variable region of 313M26 are SEQ ID NO:63 and SEQ ID NO:64, respectively. The nucleotide sequences of the heavy chain variable region and the light chain variable region of 313M26 are SEQ ID NO:65 and SEQ ID NO:66, respectively.

The 313M26 antibody was humanized using standard techniques known to those of skill in the art. The humanized version of 313M26 is referred to herein as 313M32 and is an IgG1 antibody. The humanized heavy chain variable region of 313M32 was reformatted onto a IgG4 backbone, and in combination with the 313M32 light chain is referred to as 313M33. The amino acid sequences of the heavy chain variable region and the light chain variable region of 313M32 (and 313M33) are SEQ ID NO:67 and SEQ ID NO:68, respectively. The nucleotide sequences of the heavy chain variable region and the light chain variable region of 313M32 are SEQ ID NO:73 and SEQ ID NO:74, respectively. The heavy chain and light chain CDRs of 313M26/313M32 are listed in Table 2 herein (SEQ ID NOs:57-62).

The amino acid sequence of the heavy chain of 313M32 with the predicted signal sequence is SEQ ID NO:69 and without a signal sequence is SEQ ID NO:70; the amino acid sequence of the light chain of 313M32 with the predicted signal sequence is SEQ ID NO:71 and without a signal sequence is SEQ ID NO:72. The nucleotide sequences of the heavy chain and light chain of 313M32 are SEQ ID NO:75 and SEQ ID NO:76, respectively. The amino acid sequence of the heavy chain of 313M33 with the predicted signal sequence is SEQ ID NO:83 and without a signal sequence is SEQ ID NO:82; the amino acid sequence of the light chain of 313M33 with the predicted signal sequence is SEQ ID NO:71 and without a signal sequence is SEQ ID NO:72. The nucleotide sequences of the heavy chain and light chain of 313M33 are SEQ ID NO:84 and SEQ ID NO:76, respectively.

A plasmid encoding the variable region of the heavy chain of the 313M32 antibody was deposited with American Type Culture Collection (ATCC), 10801 University Boulevard, Manassas, Va., USA, under the conditions of the Budapest Treaty on Aug. 11, 2015, and designated PTA-122346. A plasmid encoding the light chain of the 313M32 antibody was deposited with ATCC, 10801 University Boulevard, Manassas, Va., USA, under the conditions of the Budapest Treaty on Aug. 11, 2015, and designated PTA-122347.

The humanized anti-TIGIT antibody 313M32 was screened for binding to TIGIT proteins from several different species. It was determined that 313M32 strongly binds human TIGIT and does not bind TIGIT from any other species that were tested, including mouse, rat, guinea pig, rabbit, marmoset, pig, dog, rhesus monkey, and cynomolgus monkey. This is in contrast to another anti-TIGIT antibody generated at OncoMed Pharmaceuticals, 313R19, which bound to TIGIT from all of these species except guinea pig. Antibody 313R19 is a humanized version of a rabbit anti-TIGIT antibody (313R12) that was originally identified as binding to both mouse and human TIGIT. Table 5 summarizes the anti-TIGIT antibodies and binding to mouse, human, cynomolgus monkey, and rhesus monkey TIGIT.

TABLE 5

| Antibody | Origin | Backbone | Type | Bind mTIGIT | Bind hTIGIT | Bind cynoTIGIT | Bind rhTIGIT |
| --- | --- | --- | --- | --- | --- | --- | --- |
| 313R12 | Rabbit | mIgG2a |  | Yes | Yes | No | No |
| 313R19 | 313R12 | hIgG1 | Humanized | Yes | Yes | Yes | Yes |
| 313M26 | Mouse | mIgG2a |  | No | Yes | ND | ND |
| 313M32 | 313M26 | hIgG1 | Humanized | No | Yes | No | No |

Example 16

FACS Analysis of Anti-TIGIT Antibody Blocking Binding of Human TIGIT to PVR

A cell surface human TIGIT protein was generated by ligating amino acids 22-141 of human TIGIT to the transmembrane domain of CD4 and a C-terminal GFP protein tag using standard recombinant DNA techniques (hTIGIT-CD4TM-GFP). PVR-Fc constructs were generated using standard recombinant DNA techniques. Specifically, the extracellular domain of human PVR was ligated in-frame to a rabbit Fc region and the recombinant hPVR-rbFc protein was expressed in CHO cells. The fusion proteins were purified from cell culture medium using protein A chromatography.

HEK-293T cells were transiently transfected with the hTIGIT-CD4TM-GFP construct. After 16 hours, transfected cells were suspended in ice cold HBSS containing 2% FBS and heparin and incubated on ice with 0.5 µg/ml hPVR-rbFc fusion protein in the presence of anti-TIGIT antibodies 313R19, 313M26, or 313M32 for 60 minutes. Antibody 313R19 is a humanized version of a rabbit anti-TIGIT antibody. 313R19 binds mouse and human TIGIT. The antibodies were tested at concentrations of 10, 2, and 0.4 ug/ml. Cells were incubated without antibody or without hPVR-rbFc as controls. A second incubation with 100 µl PE-conjugated anti-rabbit Fc secondary antibody was performed to detect cells bound by the hPVR-rbFc fusion protein. The cells were analyzed on a FACSCanto instrument (BD Biosciences) and the data was processed using FlowJo software.

As shown in FIG. 19A, in the absence of any anti-TIGIT antibody, hPVR-rbFc bound strongly to hTIGIT expressed on the surface of the HEK-293T cells. All three anti-TIGIT antibodies blocked binding of hPVR-rbFc to hTIGIT at the highest concentration of 10 µg/ml. However, at the lower concentrations of 2 µg/ml and 0.4 µg/ml antibody, the 313R19 antibody did not block binding of hPVR-rbFc to TIGIT. In contrast, anti-hTIGIT antibody 313M32 strongly blocked binding of hPVR-rbFc to hTIGIT at 2 µg/ml and the level of blockade was higher than the parental mouse antibody 313M26. These results suggested that the affinity of the humanized 313M32 antibody for hTIGIT was higher than parental antibody 313M26 and antibody 313R19. An additional experiment using antibody 313R19 and antibody 313M32 at concentrations of 10, 5, 2.5, and 1.25 µg/ml was performed (FIG. 19B). The results from these two studies suggest that the affinity of antibody 313M32 for hTIGIT is approximately 5-fold higher than antibody 313R19. Additionally, preliminary Biacore results showed that the affinity of 313R19 was 2 nM and the affinity of 313M32 was 0.4 nM.

Example 17

TIGIT Signaling and TIGIT Phosphorylation

TIGIT is phosphorylated at its cytoplasmic tail after interaction with its counter-receptor PVR. The phosphorylation of TIGIT is the beginning of a cascade that includes downstream events affecting other known signaling pathways. Therefore, evaluating TIGIT phosphorylation can give information about TIGIT function and the effect of a TIGIT antagonist.

The Jurkat CD4+ human T cell line lacks human TIGIT expression as determined by real-time PCR and by FACS (data not shown). To generate a TIGIT-expressing cell line, Jurkat cells were infected with a lentivirus construct expressing human TIGIT (hTIGIT) tagged with FLAG and green fluorescent protein (GFP). GFP-positive cells were sorted into 96-well plates using a FACSAria II cell sorter (BD Biosciences), single cells were expanded into clones, and a clonal cell line was selected (Jurkat-hTIGIT).

The 721.221 human B cell lymphoma line lacks PVR expression as determined by real-time PCR and by FACS (data not shown). To generate a PVR-expressing cell line, 721.221 cells were infected with a lentivirus construct expressing human PVR (hPVR) and GFP. GFP-positive cells were sorted into 96-well plates using a FACSAria II cell sorter (BD Biosciences), single cells were expanded into clones, and a clonal cell line was selected (721.221-hPVR).

To evaluate TIGIT phosphorylation in response to PVR, Jurkat-hTIGIT cells were incubated in serum-free media for 2 hours at 37° C. The cells were then pre-treated with 20 µg/ml of anti-TIGIT antibodies 313R19, 313M26, or 313M32, or a control antibody for 20 minutes at room temperature. Jurkat-hTIGIT cells were mixed with parental 721.221 cells or 721.221-mPVR cells at a cell ratio of 5:1 and incubated for 5 minutes at 37° C. in the presence of a tyrosine phosphastase inhibitor (10 mM sodium orthovanadate, New England Biolabs). Cell lysates were prepared and immunoprecipitated with anti-FLAG-coated magnetic beads which captured the FLAG-tagged hTIGIT proteins. Immunoprecipitates were resolved on 4-12% Bis-Tris gels (Novex/Life Technologies) and transferred to nitrocellulose membranes using an iBlot 2 apparatus (Life Technologies). The membranes were incubated with an anti-tyrosine antibody conjugated to horseradish peroxidase and phosphorylated TIGIT (pTIGIT) was visualized using standard detection reagents. The presence of total TIGIT was evaluated by using an anti-FLAG antibody (Cell Signaling Technology).

hTIGIT was observed to be highly phosphorylated in the Jurkat cells in response to hPVR-expressing tumor cells. This phosphorylation was inhibited in the presence of anti-TIGIT antibodies, especially the 313M32 antibody (FIG. 20).

Example 18

Epitope Mapping

Epitope Mapping of Anti-hTIGIT Antibodies

To identify the binding epitope of antibody 313M32, an analysis was performed with a series of variants of human TIGIT with specific amino acid substitutions. The variants were based upon the differences between human TIGIT and cynomolgus TIGIT amino acid sequences, SEQ ID NO:4 and SEQ ID NO:77, respectively. The amino acid sequence of rhesus monkey TIGIT (SEQ ID NO:78) is identical to cynomolgus TIGIT (FIG. 21). The amino acid variants introduce amino acid residues present in cynomolgus monkey TIGIT into corresponding positions in human TIGIT. The hTIGIT variants generated have substitutions at (1) E36K and I41V; (2) T51M, (3) Q62H and Q64H, (4) D72E, (5) S78Y and S80A, (6) V100M, (7) I109T and T119R, and (8) G135S. Each variant hTIGIT was generated using the hTIGIT (aa 22-141)-CD4TM-GFP construct described in Example 15.

The TIGIT variants were evaluated by FACS with anti-hTIGIT antibodies. HEK-293T cells were transiently transfected with hTIGIT-CD4TM-GFP, mTIGIT-CD4TM-GFP, or one of the variant hTIGIT-CD4TM-GFP constructs. After 16 hours, transfected cells were suspended in ice cold HBSS containing 2% FBS and incubated on ice with 1 µg/ml anti-hTIGIT antibodies 313R12, 313M32, or 313M34 for 30 minutes. 313M34 is an anti-hTIGIT antibody that was generated based upon the amino acid sequences of the 10A7 antibody described in U.S. Publication 2009/0258013. The 10A7 antibody is an anti-mouse TIGIT antibody that binds both mouse TIGIT and human TIGIT. A second incubation with 50 µl PE-conjugated anti-Fc secondary antibody was performed to detect cells bound by the antibodies. The cells were analyzed on a FACSCanto instrument (BD Biosciences) and the data was processed using FlowJo software.

As shown in FIG. 22, antibody 313M32 did not bind to TIGIT variant 3 with substitutions at amino acid residues 62 and 64 and TIGIT variant 7 with substitutions at amino acid residues 109 and 119. The antibody retained its strong binding to hTIGIT and TIGIT variants 1, 2, 4, 5, 6, and 8. Amino acid residues 62, 64, 109, and 119 are highlighted in black on a representation of the crystal structure of TIGIT bound to PVR (FIG. 23). The structure of human TIGIT is shown in sphere representation and the structure of PVR is provided in ribbon representation. The positions of the amino acids reveal that antibody 313M32 binds hTIGIT in an area that should block and/or interfere with PVR binding. It is noteworthy that antibody 313R12 also lost binding to TIGIT variant 7 with substitutions at amino acid residues 109 and 119 suggesting that 313R12 binds an epitope overlapping with the epitope bound by 313M32. Interestingly, binding of antibody 313M34 to TIGIT was not impacted by the amino acid substitutions of TIGIT variant 3 or variant 7 but was impacted by the amino acid substitution at residue 100 of TIGIT variant 6. This result shows that antibody 313M34 does not bind the same epitope as antibody 313M32. The relative positions of the critical binding residues for antibodies 313M32 and 313M34 on TIGIT are indicated on the representation of FIG. 23.

To confirm that antibody 313M26 (parental murine anti-hTIGIT antibody of 313M32) and 313R19 (humanized rabbit anti-hTIGIT antibody generated from 313R12) bind a common epitope, competition studies were performed. Since the Fc portions of the 313M26 and 313R19 antibodies are different, i.e., murine Fc and human Fc, respectively, the binding of one antibody (313R19) in the presence or absence of the second antibody (313M26) can be determined. Briefly, HEK-293T cells were transiently transfected with an expression vector encoding human TIGIT-CD4TM-GFP. Cells were incubated for 1 hr with 0.5 µg of antibody 313M19 and an excess of antibody 313M26 (from 50 to 0.78 µg/ml, 2-fold dilutions). Cells were washed and incubated with a fluorescent-labeled secondary antibody specific for human Fc and analyzed by flow cytometry.

As shown in FIG. 24A, antibody 313M26 competed with 313R19 for binding to hTIGIT and an excess of 313M26 effectively blocked 313R19 binding to hTIGIT. These data indicate that 313M26/313M32 and 313R12/313R19 bind to overlapping epitopes and are consistent with the epitope analysis presented in FIG. 23. In parallel experiments, the ability of 313R19 or 313M32 to compete with 313M34 for binding to TIGIT was examined. As shown in FIG. 24B, neither 313R19 nor 313M32 antibodies were observed to compete with 313M34 for binding to hTIGIT. These results indicate that 313R19 and 313M32 bind to an epitope distinct from the epitope bound by 313M34. These results are also consistent with the epitope analysis presented in FIG. 23.

Example 19

Cytokine Production

Engagement of TIGIT with PVR (CD155) expressed on tumor cells or antigen-presenting cells has been shown to downregulate T-cell effector functions and inhibit anti-tumor immune responses (see e.g., Joller et al., 2014, *Immunity*, 40:569-581). The ability of anti-TIGIT antibodies 313R19 and 313M32 to block PVR-mediated inhibition of T-cell cytokine secretion was investigated. Activated human T-cell blasts were generated by 10 day culture of primary human T-cells with phytohemagglutinin (PHA, 2 µg/ml) and IL-2 (4 ng/ml). The blasts were rested in PHA/IL-2-free media for 24 hours, resuspended at 5×10$^5$ cells/ml, and treated with a control antibody (polyclonal human IgG, 25 µg/ml), anti-TIGIT antibody 313R19 or 313M32 at 10 or 25 µg/mL for 15 minutes at room temperature. Cells were then plated into wells that had been coated overnight at 4° C. with anti-CD3 antibody (Ebioscience), human PVR-Fc, or anti-CD3 antibody and hPVR-Fc (each at 10 µg/m). Cell-free culture supernatants were harvested after 48 hours and IFN-γ and IL-2 cytokines were determined by ELISA (R&D Systems). Results are expressed relative to cytokine production by cells activated with anti-CD3 alone wherein the anti-CD3 cytokine level is set at 1.0.

As seen in FIG. 25, hPVR-Fc does not induce production of either IFN-gamma or IL-2 in the activated cells. However, hPVR-Fc strongly inhibits cytokine production that is induced by anti-CD3 engagement. This inhibition is reversed by anti-TIGIT antibodies 313R19 and 313M32 and at the higher dose of 25 ug/ml the production of IFN-gamma or IL-2 is actually greater than amount generated by anti-CD3. Activated T-cells express both TIGIT and CD226, and both can interact with PVR, but the TIGIT/PVR interaction is inhibitory and the CD226/PVR interaction is activating. Without wishing to be bound by theory, it is suggested that when the activated T-cells are in contact with PVR, the TIGIT/PVR interaction "wins," because TIGIT binds PVR more strongly than CD226. In addition, there appears to be higher levels of TIGIT on activated T-cells than CD226, so the overall interaction is inhibitory. For example, in FIG. 25 compare anti-CD3 alone to anti-CD3 plus PVR. When TIGIT is blocked with 313R19 or 313M32 the TIGIT-mediated inhibition is reversed, but theoretically the CD226/PVR interaction still occurs, and that interaction is activating. Therefore, as seen in FIG. 25, when TIGIT is blocked and T-cells are stimulated with anti-CD3 plus PVR, the IFN-gamma levels are actually higher than when you stimulate with anti-CD3 alone.

These results demonstrate that blockade of human TIGIT with an anti-TIGIT antibody can disrupt TIGIT/PVR interactions and restore cytokine production that is beneficial to an anti-tumor response.

Example 20

Antibody-Dependent Cell-Mediated Cytotoxicity Assay

Antibody-dependent cell-mediated cytotoxicity (ADCC) refers to the killing of an antibody-coated target cell by a cytotoxic effector cell through a non-phagocytic process, usually characterized by the release of cytotoxic granules or by the expression of cell death-inducing molecules. Effector cells that mediate ADCC include natural killer (NK) cells, monocytes, macrophages, neutrophils, eosinophils and dendritic cells. The ability of anti-TIGIT antibodies 313R19 and 313M32 to mediate NK cell NK cell ADCC was investigated. ADCC was tested in a standard 4 hour calcein release assay using primary human NK cells as effectors and parental Jurkat cells or Jurkat-hTIGIT cells as targets. Human NK cells were isolated directly from fresh peripheral blood buffy coats (Stanford Blood Center, Palo Alto, Calif.) by 30 minute incubation with RosetteSep cocktail (Stem Cell Technologies) prior to Ficoll-Hypaque (Sigma) density gradient centrifugation. Target parental Jurkat or Jurkat-hTIGIT cells were labeled with 10 µM calcein AM (Life Technologies) for 1 hour at 37° C. and then treated with a control polyclonal IgG antibody, anti-TIGIT antibody 313R19, or anti-TIGIT antibody 313M32 (all at 10 µg/mL) for 15 minutes at room temperature. Following the incubation, Jurkat or Jurkat-hTIGIT cells were combined with the NK cells at an effector:target ratio of 20:1 in 96-well V-bottom plates. Following a 4 hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental release, spontaneous release, and maximum calcein release, respectively. Spontaneous release is the fluorescence emitted by target cells incubated in media alone (i.e., in the absence of effector cells), while maximum release is determined by lysing target cells with an equal volume of 10% SDS. For both the Jurkat and the Jurkat-hTIGIT cell lines, the percentage of ADCC is determined as the percentage of specific lysis in the presence of experimental antibody (313R19 or 313M32) minus the percentage of specific lysis in the presence of the control antibody.

As shown in FIG. 26, the percentage of ADCC was significantly increased in the presence of anti-TIGIT antibodies 313R19 and 313M32 when the target cells expressed TIGIT. The ability of anti-TIGIT antibodies to induce ADCC would suggest that anti-TIGIT antibodies may have multiple mechanisms for enhancing the immune response to tumor cells.

Example 21

In Vivo Tumor Growth Inhibition in Humanized Mice by an Anti-TIGIT Antibody

A humanized mouse model was used to study the efficacy of treatment with an anti-TIGIT antibody on a human tumor. The humanized mice were obtained from Jackson Laboratories. These mice are created by injecting human hematopoietic stem cells (CD34+ cells) into irradiated NSG mice. After 15 weeks, the presence of mature human lymphocytes is confirmed by flow cytometry. Each mouse was injected subcutaneously with patient-derived melanoma tumor cells (OMP-M9, 75,000 cells/mouse). Tumors were allowed to grow 19 days until they had reached an average volume of approximately 50 mm$^3$. Tumor-bearing mice were randomized into groups (n=8 mice per group). Tumor-bearing mice were treated with either a control antibody, anti-TIGIT antibody 313R19, or anti-TIGIT antibody 313M32. Mice were dosed every 5 days at 1 mg/kg or 5 mg/kg. Tumor growth was monitored and tumor volumes were measured with electronic calipers at the indicated time points.

As shown in FIG. 27, tumor growth was inhibited in the mice treated with antibody 313R19 and antibody 313M32 as compared to control. These results show that targeting TIGIT was effective at augmenting an anti-tumor immune response of human lymphocytes and contributing to inhibiting human tumor growth in vivo. In this experiment, the combination of anti-TIGIT antibody 313R19 or 313M32 and an anti-hPD-1 antibody did not inhibit tumor growth to any greater extent than the anti-TIGIT antibodies as single agents (data not shown).

Antibodies 313M32 and 313R19 were found to inhibit tumor growth in the context of human lymphocytes and to have similar in vivo potencies. These results demonstrated that humanized mouse models bearing patient-derived xenografts can be used to study the anti-TIGIT antibody 313M32 (which only binds human TIGIT) in parallel with preclinical studies carried out with the anti-TIGIT antibodies 313R12 and 313R19 and murine tumor models.

Example 22

Pharmacokinetics of Anti-TIGIT Antibodies

As described herein, anti-TIGIT antibody 313R12 binds preferentially to mouse TIGIT and is the mouse surrogate molecule utilized in most of the preclinical efficacy studies. The PK of anti-TIGIT antibody 313R12 was determined in C57BL-6J mice at doses of 0.1, 1 and 10 mg/kg. Blood samples were taken over 21 days. 313R12 exhibited non-linear 2-compartmental PK characteristics at the dose levels studied. It is believed that such concentration-dependent clearance is a typical feature of monoclonal antibodies for which target-mediated clearance may be a significant component of the overall elimination mechanism when the target is abundant and readily accessible by the drug. At 10 mg/kg the concentration-time profile of 313R12 approximated linearity over 21 days, suggesting saturation of accessible target molecules. Estimation of terminal half-life is not applicable for non-linear PK data.

The PK of anti-TIGIT antibody 313R19 was determined in Balb/c mice. A single dose of 10 mg/kg was given to each mouse either IV or IP. Blood samples were taken over 21 days. 313R19 exhibited linear 2-compartmental PK characteristics with a typical IgG clearance. The terminal half-life in mice at 10 mg/kg was estimated to be 7.6 days.

The PK of anti-TIGIT antibody 313R19 was also determined in cynomolgus monkeys. Doses of 10, 30, and 100 mg/kg were given to each animal, twice a week for 4 doses. Each dose group was 4 male animals and termination of study was after the fourth dose with no recovery period. 313R19 in cynomolgus monkeys exhibited linear 2-compartmental PK characteristics with a typical IgG clearance. The terminal half-life in cynomolgus monkeys was estimated to be 15.3 days.

The pharmacokinetics of anti-TIGIT antibody 313M32 was determined in Balb/c mice. A single dose of 1 or 10 mg/kg was given to each mouse IV or 10 mg/kg IP. Blood samples were taken over 21 days. 313M32 in mice exhibited linear 2-compartmental PK characteristics, which was consistent with the fact that 313M32 had no detectable binding to mouse TIGIT. The clearance was slow and preliminarily demonstrated typical IgG PK behavior. The terminal half-life in mice was estimated to be 11.7 days.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

Following are the sequences disclosed in the application:

```
Mouse TIGIT amino acid sequence
                                                                    (SEQ ID NO: 1)
MHGWLLLVWVQGLIQAAFLATAIGATAGTIDTKRNISAEEGGSVILQCHFSSDTAEVTQVDWKQQDQLLAIYSVDLGWHVASVFSD RVVPGPSLGLTFQSLTMNDTGEYFCTYHTYPGGIYKGRIFLKVQESSDDRNGLAQFQTAPLGGTMAAVLGLICLMVTGVTVLARKD KSIRMHSIESGLGRTEAEPQEWNLRSLSSPGSPVQTQTAPAGPCGEQAEDDYADPQEYFNVLSYRSLESFIAVSKTG
```

-continued

Mouse TIGIT amino acid sequence without predicted signal sequence
(SEQ ID NO: 2)
TIDTKRNISAEEGGSVILQCHFSSDTAEVTQVDWKQQDQLLAIYSVDLGWHVASVFSDRVVPGPSLGLTFQSLTMNDTGEYFCTYH TYPGGIYKGRIFLKVQESSDDRNGLAQFQTAPLGGTMAAVLGLICLMVTGVTVLARKDKSIRMHSIESGLGRTEAEPQEWNLRSLS

SPGSPVQTQTAPAGPCGEQAEDDYADPQEYFNVLSYRSLESFIAVSKTG

Mouse TIGIT extracellular domain amino acid sequence
(SEQ ID NO: 3)
TIDTKRNISAEEGGSVILQCHFSSDTAEVTQVDWKQQDQLLAIYSVDLGWHVASVFSDRVVPGPSLGLTFQSLTMNDTGEYFCTYH

TYPGGIYKGRIFLKVQESSDDRNGLAQFQTAPLG

Human TIGIT amino acid sequence
(SEQ ID NO: 4)
MRWCLLLIWAQGLRQAPLASGMMTGTIETTGNISAEKGGSIILQCHLSSTTAQVTQVNWEQQDQLLAICNADLGWHISPSFKDRVA PGPGLGLTLQSLTVNDTGEYFCIYHTYPDGTYTGRIFLEVLESSVAEHGARFQIPLLGAMAATLVVICTAVIVVVALTRKKKALRI

HSVEGDLRRKSAGQEEWSPSAPSPPGSCVQAEAAPAGLCGEQRGEDCAELHDYFNVLSYRSLGNCSFFTETG

Human TIGIT amino acid sequence without predicted signal sequence
(SEQ ID NO: 5)
MMTGTIETTGNISAEKGGSIILQCHLSSTTAQVTQVNWEQQDQLLAICNADLGWHISPSFKDRVAPGPGLGLTLQSLTVNDTGEYF CIYHTYPDGTYTGRIFLEVLESSVAEHGARFQIPLLGAMAATLVVICTAVIVVVALTRKKKALRIHSVEGDLRRKSAGQEEWSPSA

PSPPGSCVQAEAAPAGLCGEQRGEDCAELHDYFNVLSYRSLGNCSFFTETG

Human TIGIT extracellular domain amino acid sequence
(SEQ ID NO: 6)
MMTGTIETTGNISAEKGGSIILQCHLSSTTAQVTQVNWEQQDQLLAICNADLGWHISPSFKDRVAPGPGLGLTLQSLTVNDTGEYF

CIYHTYPDGTYTGRIFLEVLESSVAEHGARFQIP

313R11/313R12 Heavy chain CDR1
(SEQ ID NO: 7)
GSSLSSSYMS

313R11/313R12/313R14/313R19 Heavy chain CDR2
(SEQ ID NO: 8)
IIGSNGNTYYANWAKG

313R11/313R12/313R14/313R19 Heavy chain CDR3
(SEQ ID NO: 9)
GGYRTSGMDP

313R11/313R12 Light chain CDR1
(SEQ ID NO: 10)
QASQSISSYLNW

313R11/313R12 Light chain CDR2
(SEQ ID NO: 11)
DALKLAS

313R11/313R12 Light chain CDR3
(SEQ ID NO: 12)
QQEHSVGNVDN

313R14/313R19 Heavy chain CDR1
(SEQ ID NO: 13)
GFSLSSSYMS

313R14/313R19 Light chain CDR1 variant1
(SEQ ID NO: 14)
QASQSNIYSDLAW

313R14/313R19 Light chain CDR2
(SEQ ID NO: 15)
RASTLAS

313R14/313R19 Light chain CDR3
(SEQ ID NO: 16)
QQEHLVAWIYN

313R11/313R12 Heavy chain variable region amino acid sequence
(SEQ ID NO: 17)
QVQLESEGGLFKPTDTLTLTCTVSGSSLSSSYMSWVRQAPGKGLEWIGIIGSNGNTYYANWAKGRFTISKTSTTVELKITSPTTED
TATYFCARGGYRTSGMDPWGPGTLVTVSS 313R11/313R12 Light chain variable region amino acid sequence
(SEQ ID NO: 18)
DIVMTQTPASVEVAVGGTVTIKCQASQSISSYLNWYQQKPGQPPKLLIYDALKLASGVPSRFSGSGSGTEYTLTISGVESADAATY
YCQQEHSVGNVDNVFGGGTEVVVKR 313R14 Heavy chain variable region amino acid sequence
(SEQ ID NO: 19)
QVQLQESGPGLVKPSETLSLTCTVSGFSLSSSYMSWIRQPPGKGLEWIGIIGSNGNTYYANWAKGRVTISKTSTTVELKLSSVTAA
DTAVYYCARGGYRTSGMDPWGQGTLVTVSS 313R14/313R19/313R20 Light chain variable region amino acid sequence
(SEQ ID NO: 20)
DIQMTQSPSSLSASVGDRVTITCQASQNIYSDLAWYQQKPGKAPKLLIYRASTLASGVPSRFSGSGSGTDFTLTISSLQPEDFATY
YCQQEHLVAWIYNVFGQGTKVEIKR 313R11 Heavy chain (mIgG1) amino acid sequence with signal sequence underlined
(SEQ ID NO: 21)
<u>MKHLWFFLLLLVAAPRWVLS</u>QVQLESEGGLFKPTDTLTLTCTVSGSSLSSSYMSWVRQAPGKGLEWIGIIGSNGNTYYANWAKGRFT
ISKTSTTVELKITSPTTEDTATYFCARGGYRTSGMDPWGPGTLVTVSSAKTTPPSVYPLAPGSAAQTNSMVTLGCLVKGYFPEPVT
VTWNSGSLSSGVHTFPAVLESDLYTLSSSVTVPSSPRPSETVTCNVAHPASSTKVDKKIVPRDCGCKPCICTVPEVSSVFIFPPKP
KDVLTITLTPKVTCVVVDISKDDPEVQFSWFVDDVEVHTAQTQPREEQFNSTFRSVSELPIMHQDWLNGKEFKCRVNSAAFPAPIE
KTISKTKGRPKAPQVYTIPPPKEQMAKDKVSLTCMITDFFPEDITVEWQWNGQPAENYKNTQPIMNTNGSYFVYSKLNVQKSNWEA
GNTFTCSVLHEGLHNHHTEKSLSHSPGK 313R12 Heavy chain (mIgG2) amino acid sequence with signal sequence underlined
(SEQ ID NO: 22)
<u>MKHLWFFLLLLVAAPRWVLS</u>QVQLESEGGLFKPTDTLTLTCTVSGSSLSSSYMSWVRQAPGKGLEWIGIIGSNGNTYYANWAKGRFT
ISKTSTTVELKITSPTTEDTATYFCARGGYRTSGMDPWGPGTLVTVSSAKTTAPSVYPLAPVCGDTTGSSVTLGCLVKGYFPEPVT
LTWNSGSLSSGVHTFPAVLQSDLYTLSSSVTVTSSTWPSQSITCNVAHPASSTKVDKKIEPRGPTIKPCPPCKCPAPNLLGGPSVF
IFPPKIKDVLMISLSPIVTCVVVDVSEDDPDVQISWFVNNVEVHTAQTQTHREDYNSTLRVVSALPIQHQDWMSGKEFKCKVNNKD
LPAPIERTISKPKGSVRAPQVYVLPPPEEEMTKKQVTLTCMVTDFMPEDIYVEWTNNGKTELNYKNTEPVLDSDGSYFMYSKLRVE
KKNWVERNSYSCSVVHEGLHNHHTTKSFSRTPGK 313R11/313R12 Light chain amino acid sequence with signal sequence underlined
(SEQ ID NO: 23)
<u>MKHLWFFLLLLVAAPRWVLS</u>DIVMTQTPASVEVAVGGTVTIKCQASQSISSYLNWYQQKPGQPPKLLIYDALKLASGVPSRFSGSGS
GTEYTLTISGVESADAATYYCQQEHSVGNVDNVFGGGTEVVVKRTDAAPTVSIFPPSSEQLTSGGASVVCFLNNFYPKDINVKWKI
DGSERQNGVLNSWTDQDSKDSTYSMSSTLTLTKDEYERHNSYTCEATHKTSTSPIVKSFNRNEC 313R14 Heavy chain (hIgG1) amino acid sequence with signal sequence underlined
(SEQ ID NO: 24)
<u>MKHLWFFLLLLVAAPRWVLS</u>QVQLQESGPGLVKPSETLSLTCTVSGFSLSSSYMSWIRQPPGKGLEWIGIIGSNGNTYYANWAKGRV
TISKTSTTVELKLSSVTAADTAVYYCARGGYRTSGMDPWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK 313R14/313R19/313R20 Light chain amino acid sequence with signal sequence underlined
(SEQ ID NO: 25)
<u>MVLQTQVFISLLLWISGAYG</u>DIQMTQSPSSLSASVGDRVTITCQASQNIYSDLAWYQQKPGKAPKLLIYRASTLASGVPSRFSGSG
SGTDFTLTISSLQPEDFATYYCQQEHLVAWIYNVFGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC 313R11 Heavy chain (mIgG1) amino acid sequence without signal sequence
(SEQ ID NO: 26)
QVQLESEGGLFKPTDTLTLTCTVSGSSLSSSYMSWVRQAPGKGLEWIGIIGSNGNTYYANWAKGRFTISKTSTTVELKITSPTTED
TATYFCARGGYRTSGMDPWGPGTLVTVSSAKTTPPSVYPLAPGSAAQTNSMVTLGCLVKGYFPEPVTVTWNSGSLSSGVHTFPAVL
ESDLYTLSSSVTVPSSPRPSETVTCNVAHPASSTKVDKKIVPRDCGCKPCICTVPEVSSVFIFPPKPKDVLTITLTPKVTCVVVDI
SKDDPEVQFSWFVDDVEVHTAQTQPREEQFNSTFRSVSELPIMHQDWLNGKEFKCRVNSAAFPAPIEKTISKTKGRPKAPQVYTIP
PPKEQMAKDKVSLTCMITDFFPEDITVEWQWNGQPAENYKNTQPIMNTNGSYFVYSKLNVQKSNWEAGNTFTCSVLHEGLHNHHTE
KSLSHSPGK 313R12 Heavy chain (mIgG2) amino acid sequence without signal sequence
(SEQ ID NO: 27)
QVQLESEGGLFKPTDTLTLTCTVSGSSLSSSYMSWVRQAPGKGLEWIGIIGSNGNTYYANWAKGRFTISKTSTTVELKITSPTTED
TATYFCARGGYRTSGMDPWGPGTLVTVSSAKTTAPSVYPLAPVCGDTTGSSVTLGCLVKGYFPEPVTLTWNSGSLSSGVHTFPAVL
QSDLYTLSSSVTVTSSTWPSQSITCNVAHPASSTKVDKKIEPRGPTIKPCPPCKCPAPNLLGGPSVFIFPPKIKDVLMISLSPIVT
CVVVDVSEDDPDVQISWFVNNVEVHTAQTQTHREDYNSTLRVVSALPIQHQDWMSGKEFKCKVNNKDLPAPIERTISKPKGSVRAP
QVYVLPPPEEEMTKKQVTLTCMVTDFMPEDIYVEWTNNGKTELNYKNTEPVLDSDGSYFMYSKLRVEKKNWVERNSYSCSVVHEGL
HNHHTTKSFSRTPGK 313R11/313R12 Light chain amino acid sequence without signal sequence
(SEQ ID NO: 28)
DIVMTQTPASVEVAVGGTVTIKCQASQSISSYLNWYQQKPGQPPKLLIYDALKLASGVPSRFSGSGSGTEYTLTISGVESADAATY
YCQQEHSVGNVDNVFGGGTEVVVKRTDAAPTVSIFPPSSEQLTSGGASVVCFLNNFYPKDINVKWKIDGSERQNGVLNSWTDQDSK
DSTYSMSSTLTLTKDEYERHNSYTCEATHKTSTSPIVKSFNRNEC 313R14 Heavy chain (hIgG1) amino acid sequence without signal sequence
(SEQ ID NO: 29)
QVQLQESGPGLVKPSETLSLTCTVSGFSLSSSYMSWIRQPPGKGLEWIGIIGSNGNTYYANWAKGRVTISKTSTTVELKLSSVTAA
DTAVYYCARGGYRTSGMDPWGQGTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQQGNVFSCSVMHEA
LHNHYTQKSLSLSPGK 313R14/313R19/313R20 Light chain amino acid sequence without predicted signal sequence
(SEQ ID NO: 30)
DIQMTQSPSSLSASVGDRVTITCQASQNIYSDLAWYQQKPGKAPKLLIYRASTLASGVPSRFSGSGSGTDFTLTISSLQPEDFATY
YCQQEHLVAWIYNVFGQGTKVEIKRTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC AH-1 peptide
(SEQ ID NO: 31)
SPSYVYHQF 313R19/313R20 Heavy chain variable region amino acid sequence
(SEQ ID NO: 32)
QVQLQESGPGLVKPSETLSLTCTVSGFSLSSSYMSWIRQPPGKGLEWIGIIGSNGNTYYANWAKGRVTISKSSNQVSLKLSSVTAA
DTAVYYCARGGYRTSGMDPWGQGTLVTVSS 313R19 Heavy chain (IgG1) amino acid sequence with signal sequence underlined
(SEQ ID NO: 33)
<u>MKHLWFFLLLVAAPRWVLS</u>QVQLQESGPGLVKPSETLSLTCTVSGFSLSSSYMSWIRQPPGKGLEWIGIIGSNGNTYYANWAKGRV -continued TISKSSNQVSLKLSSVTAADTAVYYCARGGYRTSGMDPWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSNTKVDKRVEPKSCDKTHTCPPCPAPELLGGPSV FLFPPKPKDTLMISRTPEVTCVVVDVSHEDPEVKFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGK

313R19 Heavy chain (IgG1) amino acid sequence without signal sequence
(SEQ ID NO: 34)
QVQLQESGPGLVKPSETLSLTCTVSGFSLSSSYMSWIRQPPGKGLEWIGIIGSNGNTYYANWAKGRVTISKSSNQVSLKLSSVTAA DTAVYYCARGGYRTSGMDPWGQGTLVTVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDGSFFLYSKLTVDKSRWQQGNVFSCSVMHEA

LHNHYTQKSLSLSPGK

Linker
(SEQ ID NO: 35)
ESGGGGVT

Linker
(SEQ ID NO: 36)
LESGGGGVT

Linker
(SEQ ID NO: 37)
GRAQVT

Linker
(SEQ ID NO: 38)
WRAQVT

Linker
(SEQ ID NO: 39)
ARGRAQVT

FLAG Tag
(SEQ ID NO: 40)
DYKDDDDK

Human IgG1 Heavy chain constant region
(SEQ ID NO: 41)
ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEALHNHYTQKSLSLSPGK

Human IgG2 Heavy chain constant region
(SEQ ID NO: 42)
ASTKGPSVFPLAPCSRSTSESTAALGCLVKDYFPEPVTVSWNSGALTSGVHTFPAVLQSSGLYSLSSVVTVPSSNFGTQTYTCNVD HKPSNTKVDKTVERKCCVECPPCPAPPVAGPSVFLFPPKPKDTLMISRTPEVTCVVVDVSHEDPEVQFNWYVDGVEVHNAKTKPRE EQFNSTFRVVSVLTVVHQDWLNGKEYKCKVSNKGLPAPIEKTISKTKGQPREPQVYTLPPSREEMTKNQVSLTCLVKGFYPSDIAV

EWESNGQPENNYKTTPPMLDSDGSFFLYSKLTVDKSRWQQGNVFSCSVMHEALHNHYTQKSLSLSPGK

Human IgG3 Heavy chain constant region
(SEQ ID NO: 43)
ASTKGPSVFPLAPCSRSTSGGTAALGCLVKDYFPEPVTVSWNSGALTSGVHTFPAVLQSSGLYSLSSVVTVPSSSLGTQTYTCNVN HKPSNTKVDKRVELKTPLGDTTHTCPRCPEPKSCDTPPPCPRCPEPKSCDTPPPCPRCPEPKSCDTPPPCPRCPAPELLGGPSVFL FPPKPKDTLMISRTPEVTCVVVDVSHEDPEVQFKWYVDGVEVHNAKTKPREEQYNSTFRVVSVLTVLHQDWLNGKEYKCKVSNKAL PAPIEKTISKTKGQPREPQVYTLPPSREEMTKNQVSLTCLVKGFYPSDIAVEWESSGQPENNYNTTPPMLDSDGSFFLYSKLTVDK

SRWQQGNIFSCSVMHEALHNRFTQKSLSLSPGK

```
Human IgG4 Heavy chain constant region
                                                                           (SEQ ID NO: 44)
ASTKGPSVFPLAPCSRSTSESTAALGCLVKDYFPEPVTVSWNSGALTSGVHTFPAVLQSSGLYSLSSVVTVPSSSLGTKTYTCNVD HKPSNTKVDKRVESKYGPPCPSCPAPEFLGGPSVFLFPPKPKDTLMISRTPEVTCVVVDVSQEDPEVQFNWYVDGVEVHNAKTKPR EEQFNSTYRVVSVLTVLHQDWLNGKEYKCKVSNKGLPSSIEKTISKAKGQPREPQVYTLPPSQEEMTKNQVSLTCLVKGFYPSDIA

VEWESNGQPENNYKTTPPVLDSDGSFFLYSRLTVDKSRWQEGNVFSCSVMHEALHNHYTQKSLSLSLGK

Human IgG1 Fc region (13A Version)
                                                                           (SEQ ID NO: 45)
DKTHTCPPCPAPELLGGPSVFLFPPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDKLTKNQVSLTCLVKGFYPSDIAVEWESNGQPENNYK

TTPPVLKSDGSFFLYSKLTVDKSRWQQGNVFSCSVMHEALHNHYTQKSLSLSPGK

Human IgG1 Fc region (13B Version)
                                                                           (SEQ ID NO: 46)
DKTHTCPPCPAPELLGGPSVFLFPPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDELTKNQVSLTCLVEGFYPSDIAVEWESNGQPENNYK

TTPPVLDSDGSFFLYSELTVDKSRWQQGNVFSCSVMHEALHNHYTQKSLSLSPGK

Human IgG1 Fc region (13A Version)
                                                                           (SEQ ID NO: 47)
EPKSSDKTHTCPPCPAPELLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDKLTKNQVSLTCLVKGFYPSDIAVEWESNGQP

ENNYKTTPPVLKSDGSFFLYSKLTVDKSRWQQGNVFSCSVMHEALHNHYTQKSLSLSPGK

Human IgG1 Fc region (13B Version)
                                                                           (SEQ ID NO: 48)
EPKSSDKTHTCPPCPAPELLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKNQVSLTCLVEGFYPSDIAVEWESNGQP

ENNYKTTPPVLDSDGSFFLYSELTVDKSRWQQGNVFSCSVMHEALHNHYTQKSLSLSPGK

Human IgG2 Fc region (13A Version)
                                                                           (SEQ ID NO: 49)
CVECPPCPAPPVAGPSVFLFPPKPKDTLMISRTPEVTCVVVDVSHEDPEVQFNWYVDGVEVHNAKTKPREEQFNSTFRVVSVLTVV HQDWLNGKEYKCKVSNKGLPAPIEKTISKTKGQPREPQVYTLPPSREKMTKNQVSLTCLVKGFYPSDIAVEWESNGQPENNYKTTP

PMLKSDGSFFLYSKLTVDKSRWQQGNVFSCSVMHEALHNHYTQKSLSLSPGK

Human IgG2 Fc region (13B Version)
                                                                           (SEQ ID NO: 50)
CVECPPCPAPPVAGPSVFLFPPKPKDTLMISRTPEVTCVVVDVSHEDPEVQFNWYVDGVEVHNAKTKPREEQFNSTFRVVSVLTVV HQDWLNGKEYKCKVSNKGLPAPIEKTISKTKGQPREPQVYTLPPSREEMTKNQVSLTCLVEGFYPSDIAVEWESNGQPENNYKTTP

PMLDSDGSFFLYSELTVDKSRWQQGNVFSCSVMHEALHNHYTQKSLSLSPGK

Human IgG2 Fc region (13A Version)
                                                                           (SEQ ID NO: 51)
TKVDKTVERKCCVECPPCPAPPVAGPSVFLFPPKPKDTLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQVYTLPPSREKMTKNQVSLTCLVKGFYPSDIAVEWESN

GQPENNYKTTPPMLKSDGSFFLYSKLTVDKSRWQQGNVFSCSVMHEALHNHYTQKSLSLSPGK

Human IgG2 Fc region (13A Version)
                                                                           (SEQ ID NO: 52)
TKVDKTVERKSCVECPPCPAPPVAGPSVFLFPPKPKDTLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQVYTLPPSREKMTKNQVSLTCLVKGFYPSDIAVEWESN

GQPENNYKTTPPMLKSDGSFFLYSKLTVDKSRWQQGNVFSCSVMHEALHNHYTQKSLSLSPGK

Human IgG2 Fc region (13B Version)
                                                                           (SEQ ID NO: 53)
TKVDKTVERKCCVECPPCPAPPVAGPSVFLFPPKPKDTLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQVYTLPPSREEMTKNQVSLTCLVEGFYPSDIAVEWESN
```

GQPENNYKTTPPMLDSDGSFFLYSELTVDKSRWQQGNVFSCSVMHEALHNHYTQKSLSLSPGK

Human IgG2 Fc region (13B Version)
(SEQ ID NO: 54)
TKVDKTVERKSCVECPPCPAPPVAGPSVFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSREEMTKNQVSLTCLVEGFYPSDIAVEWESN
GQPENNYKTTPPMLDSDGSFFLYSELTVDKSRWQQGNVFSCSVMHEALHNHYTQKSLSLSPGK 313R20 Heavy chain (IgG4) amino acid sequence with signal sequence underlined
(SEQ ID NO: 55)
<u>MKHLWFFLLLLVAAPRWVLS</u>QVQLQESGPGLVKPSETLSLTCTVSGFSLSSSYMSWIRQPPGKGLEWIGIIGSNGNTYYANWAKGRV
TISKSSNQVSLKLSSVTAADTAVYYCARGGYRTSGMDPWGQGTLVTVSSASTKGPSVFPLAPCSRSTSESTAALGCLVKDYFPEPV
TVSWNSGALTSGVHTFPAVLQSSGLYSLSSVVTVPSSSLGTKTYTCNVDHKPSNTKVDKRVESKYGPPCPPCPAPEFLGGPSVFLF
PPKPKDTLMISRTPEVTCVVVDVSQEDPEVQFNWYVDGVEVHNAKTKPREEQFNSTYRVVSVLTVLHQDWLNGKEYKCKVSNKGLP
SSIEKTISKAKGQPREPQVYTLPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK 313R20 Heavy chain (IgG4) amino acid sequence without signal sequence
(SEQ ID NO: 56)
QVQLQESGPGLVKPSETLSLTCTVSGFSLSSSYMSWIRQPPGKGLEWIGIIGSNGNTYYANWAKGRVTISKSSNQVSLKLSSVTAA
DTAVYYCARGGYRTSGMDPWGQGTLVTVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPPCPAPEFLGGPSVFLFPPKPKDTLMISRTPEVTCV
VVDVSQEDPEVQFNWYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEGNVFSCSVMHEALHN
HYTQKSLSLSLGK 313M26/313M32 Heavy chain CDR1
(SEQ ID NO: 57)
TSDYAWN 313M26/313M32 Heavy chain CDR2
(SEQ ID NO: 58)
YISYSGSTSYNPSLRS 313M26/313M32 Heavy chain CDR3
(SEQ ID NO: 59)
ARRQVGLGFAY 313M26/313M32 Light chain CDR1
(SEQ ID NO: 60)
KASQDVSTAVA 313M26/313M32 Light chain CDR2
(SEQ ID NO: 61)
SASYRYT 313M26/313M32 Light chain CDR3
(SEQ ID NO: 62)
QQHYSTP 313M26 Heavy chain variable region amino acid sequence
(SEQ ID NO: 63)
DVQLQESGPGLVKPSQSLSLTCTVTGYSITSDYAWNWVRQFPGNKLEWMGYISYSGSTSYNPSLRSRISITRDTSKNQFFLQLNSV
TTEDTATYYCARRQVGLGFAYWGQGTLVTVSS 313M26 Light chain variable region amino acid sequence
(SEQ ID NO: 64)
DIVMTQSHKFMSTSVGDRVSITCKASQDVSTAVAWYQQKPGQSPKLLIYSASYRYTGVPDRFTGSGSGTDFTFTISSVQAEDLAVY
YCQQHYSTPWTFG 313M26 Heavy chain variable region nucleotide sequence
(SEQ ID NO: 65)
GATGTGCAGCTTCAGGAGTCAGGACCTGGCCTGGTGAAACCTTCTCAGTCTCTGTCCCTCACCTGCACTGTCACTGGCTACTCAAT
CACCAGTGATTATGCCTGGAACTGGGTCCGGCAGTTTCCAGGAAACAAACTGGAGTGGATGGGCTACATAAGCTACAGTGGTAGCA
CTAGCTACAACCCATCTCTCAGAAGTCGAATCTCTATCACTCGAGACACATCCAAGAACCAGTTCTTCCTGCAGTTGAATTCTGTG

```
ACTACTGAGGACACAGCCACATATTACTGTGCAAGGAGACAGGTCGGGCTGGGGTTTGCTTACTGGGGCCAAGGGACTCTGGTCAC

TGTCAGCTCA
```

313M26 Light chain variable region nucleotide sequence (SEQ ID NO: 66)
```
GACATTGTGATGACCCAGTCTCACAAATTCATGTCCACATCAGTTGGAGACAGGGTCAGCATCACCTGCAAGGCCAGTCAGGATGT GAGTACTGCTGTAGCCTGGTATCAACAGAAACCAGGACAATCTCCTAAACTACTGATTTACTCGGCATCCTACCGGTACACTGGAG TCCCTGATCGCTTCACTGGCAGTGGATCTGGGACGGATTTCACTTTCACCATCAGCAGTGTGCAGGCTGAAGACCTGGCAGTTTAT

TACTGTCAGCAACATTATAGTACTCCGTGGACGTTCGGT
```

313M32 Heavy chain variable region amino acid sequence (SEQ ID NO: 67)
```
QVQLQESGPGLVKPSETLSLTCAVSGYSITSDYAWNWIRQPPGKGLEWIGYISYSGSTSYNPSLRSRVTISRDTSKNQFFLKLSSV

TAADTAVYYCARRQVGLGFAYWGQGTLVTVSS
```

313M32 Light chain variable region amino acid sequence (SEQ ID NO: 68)
```
DIQMTQSPSSLSASVGDRVTITCKASQDVSTAVAWYQQKPGKAPKLLIYSASYRYTGVPSRFSGSGSGTDFTFTISSLQPEDIATY

YCQQHYSTPWTFG
```

313M32 Heavy chain (IgG1) amino acid sequence with predicted signal sequence underlined (SEQ ID NO: 69)
```
MDWTWRILFLVAAATGAHSQVQLQESGPGLVKPSETLSLTCAVSGYSITSDYAWNWIRQPPGKGLEWIGYISYSGSTSYNPSLRSR VTISRDTSKNQFFLKLSSVTAADTAVYYCARRQVGLGFAYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKPSNTKVDKRVEPKSCDKTHTCPPCPAPELLGGP SVFLFPPKPKDTLMISRTPEVTCVVVDVSHEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVEWESNGQPENNYKTTPPVLDSDGSFFLYSKL

TVDKSRWQQGNVFSCSVMHEALHNHYTQKSLSLSPGK
```

313M32 Heavy chain (IgG1) amino acid sequence without signal sequence (SEQ ID NO: 70)
```
QVQLQESGPGLVKPSETLSLTCAVSGYSITSDYAWNWIRQPPGKGLEWIGYISYSGSTSYNPSLRSRVTISRDTSKNQFFLKLSSV TAADTAVYYCARRQVGLGFAYWGQGTLVTVSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPVLDSDGSFFLYSKLTVDKSRWQQGNVFSCSVMH

EALHNHYTQKSLSLSPGK
```

313M32 Light chain amino acid sequence with predicted signal sequence underlined (SEQ ID NO: 71)
```
MVLQTQVFISLLLWISGAYGDIQMTQSPSSLSASVGDRVTITCKASQDVSTAVAWYQQKPGKAPKLLIYSASYRYTGVPSRFSGSG SGTDFTFTISSLQPEDIATYYCQQHYSTPWTFGQGTKVEIKRTVAAPSVFIFPPSDEQLKSGTASVVCLLNNFYPREAKVQWKVDN

ALQSGNSQESVTEQDSKDSTYSLSNTLTLSKADYEKHKVYACEVTHQGLSSPVTKSFNRGEC
```

313M32 Light chain amino acid sequence without signal sequence (SEQ ID NO: 72)
```
DIQMTQSPSSLSASVGDRVTITCKASQDVSTAVAWYQQKPGKAPKLLIYSASYRYTGVPSRFSGSGSGTDFTFTISSLQPEDIATY YCQQHYSTPWTFGQGTKVEIKRTVAAPSVFIFPPSDEQLKSGTASVVCLLNNFYPREAKVQWKVDNALQSGNSQESVTEQDSKDST

YSLSNTLTLSKADYEKHKVYACEVTHQGLSSPVTKSFNRGEC
```

313M32 Heavy chain variable region nucleotide sequence (SEQ ID NO: 73)
```
CAGGTCCAGCTGCAGGAGTCTGGCCCAGGACTGGTGAAGCCTTCTGAGACCCTGTCCCTCACCTGCGCTGTCTCTGGTTACTCCAT CACCTCCGATTATGCCTGGAACTGGATTCGGCAGCCCCCAGGGAAGGGGCTGGAGTGGATTGGGTACATAAGCTACTCTGGTAGCA CTAGCTACAACCCCATCTCTCCGGTCACGGGTCACAATATCACGGGACACATCCAAGAACCAGTTCTTCCTGAAGCTGTCCTCTGTG
```

ACCGCCGCTGACACCGCCGTGTATTACTGTGCAAGGAGACAGGTCGGGCTGGGGTTTGCTTACTGGGGCCAAGGAACCCTGGTCAC

CGTCAGCTCA

313M32 Light chain variable region nucleotide sequence (SEQ ID NO: 74)

GACATCCAGATGACCCAGTCTCCATCCTCCCTGTCTGCATCTGTTGGAGACAGAGTCACCATCACTTGCAAGGCTTCTCAGGATGT

GTCTACTGCTGTTGCCTGGTATCAGCAGAAACCAGGGAAAGCCCCTAAGCTCCTGATCTACTCTGCATCCTATCGGTACACTGGGG

TCCCATCAAGGTTCTCCGGATCTGGATCTGGGACAGATTTTACTTTCACCATCAGCAGCCTGCAGCCTGAAGATATTGCAACATAT

TACTGTCAGCAACATTATTCTACTCCTTGGACATTCGGC

313M32 Heavy chain (IgG1) nucleotide sequence (SEQ ID NO: 75)

ATGGACTGGACCTGGAGGATACTCTTTCTCGTGGCTGCAGCCACAGGAGCCCACTCCCAGGTCCAGCTGCAGGAGTCTGGCCCAGG

ACTGGTGAAGCCTTCTGAGACCCTGTCCCTCACCTGCGCTGTCTCTGGTTACTCCATCACCTCCGATTATGCCTGGAACTGGATTC

GGCAGCCCCCAGGGAAGGGGCTGGAGTGGATTGGGTACATAAGCTACTCTGGTAGCACTAGCTACAACCCATCTCTCCGGTCACGG

GTCACAATATCACGGGACACATCCAAGAACCAGTTCTTCCTGAAGCTGTCCTCTGTGACCGCCGCTGACACCGCCGTGTATTACTG

TGCAAGGAGACAGGTCGGGCTGGGGTTTGCTTACTGGGGCCAAGGAACCCTGGTCACCGTCAGCTCAGCCAGCACAAAGGGCCCCT

CCGTGTTCCCTCTGGCCCCTTCCTCCAAGTCCACCTCCGGCGGCACCGCCGCTCTGGGCTGCCTGGTGAAGGACTACTTCCCTGAG

CCTGTGACCGTGTCCTGGAACTCTGGCGCCCTGACCTCTGGCGTGCACACCTTCCCAGCCGTGCTGCAGTCCTCCGGCCTGTACTC

CCTGTCCTCCGTGGTGACCGTGCCTTCCTCCTCCCTGGGCACCCAGACCTACATCTGCAACGTGAACCACAAGCCTTCCAACACCA

AGGTGGACAAGCGGGTGGAGCCTAAGTCCTGCGACAAGACCCACACCTGCCCTCCCTGCCCTGCCCCTGAGCTGCTGGGCGGACCT

TCCGTGTTCCTGTTCCCTCCTAAGCCTAAGGACACCCTGATGATCTCCCGGACCCCTGAGGTGACCTGCGTGGTGGTGGACGTGTC

CCACGAGGATCCTGAGGTGAAGTTCAATTGGTACGTGGACGGCGTGGAGGTGCACAACGCTAAGACCAAGCCAAGGGAGGAGCAGT

ACAACTCCACCTACCGGGTGGTGTCTGTGCTGACCGTGCTGCACCAGGACTGGCTGAACGGCAAAGAATACAAGTGCAAGGTCTCC

AACAAGGCCCTGCCCGCTCCCATCGAGAAAACCATCTCCAAGGCCAAGGGCCAGCCTCGCGAGCCTCAGGTGTACACCCTGCCACC

CAGCCGGGAGGAGATGACCAAGAACCAGGTGTCCCTGACCTGTCTGGTGAAGGGCTTCTACCCTTCCGATATCGCCGTGGAGTGGG

AGTCTAACGGCCAGCCCGAGAACAACTACAAGACCACCCCTCCTGTGCTGGACTCCGACGGCTCCTTCTTCCTGTACTCCAAGCTG

ACCGTGGACAAGTCCCGGTGGCAGCAGGGCAACGTGTTCTCCTGCTCCGTGATGCACGAGGCCCTGCACAACCACTACACCCAGAA

GAGCCTGTCTCTGTCTCCTGGCAAGTGA

313M32 Light chain nucleotide sequence (SEQ ID NO: 76)

ATGGTGCTCCAGACCCAGGTCTTCATTTCCCTGCTGCTCTGGATCAGCGGAGCCTACGGGGACATCCAGATGACCCAGTCTCCATC

CTCCCTGTCTGCATCTGTTGGAGACAGAGTCACCATCACTTGCAAGGCTTCTCAGGATGTGTCTACTGCTGTTGCCTGGTATCAGC

AGAAACCAGGGAAAGCCCCTAAGCTCCTGATCTACTCTGCATCCTATCGGTACACTGGGGTCCCATCAAGGTTCTCCGGATCTGGA

TCTGGGACAGATTTTACTTTCACCATCAGCAGCCTGCAGCCTGAAGATATTGCAACATATTACTGTCAGCAACATTATTCTACTCC

TTGGACATTCGGCCAAGGGACCAAGGTGGAAATCAAACGTACGGTGGCTGCACCATCTGTCTTCATCTTCCCTCCATCTGATGAGC

AGCTCAAATCTGGAACTGCCTCTGTTGTGTGCCTGCTGAATAACTTCTATCCCAGAGAGGCCAAAGTCCAGTGGAAGGTGGATAAC

GCCCTCCAATCCGGCAACTCCCAGGAGAGTGTCACAGAGCAGGACAGCAAGGACAGCACCTACAGCCTCAGCAACACCCTGACACT

GAGCAAAGCAGACTACGAGAAACACAAAGTCTATGCCTGCGAAGTCACCCATCAGGGCCTGTCTTCCCCCGTCACAAAGAGCTTCA

ACAGGGGAGAGTGCTAA

Cynomolgus monkey TIGIT (SEQ ID NO: 77)

MRWCLFLIWAQGLRQAPLASGMMTGTIETTGNISAKKGGSVILQCHLSSTMAQVTQVNWEQHDHSLLAIRNAELGWHIYPAFKDRV

APGPGLGLTLQSLTMNDTGEYFCTYHTYPDGTYRGRIFLEVLESSVAEHSARFQIPLLGAMAMMLVVICIAVIVVVLARKKKSLR

IHSVESGLQRKSTGQEEQIPSAPSPPGSCVQAEAAPAGLCGEQQGDDCAELHDYFNVLSYRSLGSCSFFTETG

Rhesus monkey TIGIT (SEQ ID NO: 78)

MRWCLFLIWAQGLRQAPLASGMMTGTIETTGNISAKKGGSVILQCHLSSTMAQVTQVNWEQHDHSLLAIRNAELGWHIYPAFKDRV

APGPGLGLTLQSLTMNDTGEYFCTYHTYPDGTYRGRIFLEVLESSVAEHSARFQIPLLGAMAMMLVVICIAVIVVVVLARKKKSLR

IHSVESGLQRKSTGQEEQIPSAPSPPGSCVQAEAAPAGLCGEQQGDDCAELHDYFNVLSYRSLGSCSFFTETG

Human TIGITamino acids 55-70

(SEQ ID NO: 79)

TQVNWEQQDQLLAICN

Human TIGITamino acids 105-122

(SEQ ID NO: 80)

EYFCIYHTYPDGTYTGRI

313R14/313R19 Light chain CDR1

(SEQ ID NO: 81)

QASQNIYSDLAW

313M33 Heavy chain (IgG4) amino acid sequence without signal sequence (SEQ ID NO: 82)

QVQLQESGPGLVKPSETLSLTCAVSGYSITSDYAWNWIRQPPGKGLEWIGYISYSGSTSYNPSLRSRVTISRDTSKNQFFLKLSSV

TAADTAVYYCARRQVGLGFAYWGQGTLVTVSSASTKGPSVFPLAPCSRSTSESTAALGCLVKDYFPEPVTVSWNSGALTSGVHTFP

AVLQSSGLYSLSSVVTVPSSSLGTKTYTCNVDHKPSNTKVDKRVESKYGPPCPSCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGSFFLYSRLTVDKSRWQEGNVFSCSVMHEAL

HNHYTQKSLSLSLGK

313M33 Heavy chain (IgG4) amino acid sequence with signal sequence (SEQ ID NO: 83)

MDWTWRILFLVAAATGAHSQVQLQESGPGLVKPSETLSLTCAVSGYSITSDYAWNWIRQPPGKGLEWIGYISYSGSTSYNPSLRSR

VTISRDTSKNQFFLKLSSVTAADTAVYYCARRQVGLGFAYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAKTKPREEQFNSTYRVVSVLTVLHQDWLNGKEYKCKVSNKG

LPSSIEKTISKAKGQPREPQVYTLPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

313M33 Heavy chain (IgG4) nucleotide sequence (SEQ ID NO: 84)

ATGGACTGGACCTGGAGGATACTCTTTCTCGTGGCTGCAGCCACAGGAGCCCACTCCCAGGTCCAGCTGCAGGAGTCTGGCCCAGG

ACTGGTGAAGCCTTCTGAGACCCTGTCCCTCACCTGCGCTGTCTCTGGTTACTCCATCACCTCCGATTATGCCTGGAACTGGATTC

GGCAGCCCCCAGGGAAGGGGCTGGAGTGGATTGGGTACATAAGCTACTCTGGTAGCACTAGCTACAACCCATCTCTCCGGTCACGG

GTCACAATATCACGGGACACATCCAAGAACCAGTTCTTCCTGAAGCTGTCCTCTGTGACCGCCGCTGACACCGCCGTGTATTACTG

TGCAAGGAGACAGGTCGGGCTGGGGTTTGCTTACTGGGGCCAAGGAACCCTGGTCACCGTCAGCTCAGCCAGCACAAAGGGCCCAT

CCGTCTTCCCCCTGGCACCCTGCTCCCGGAGCACCTCCGAGAGCACAGCCGCCCTGGGCTGCCTGGTCAAGGACTACTTCCCCGAA

CCCGTTACCGTGTCTTGGAACTCCGGCGCACTGACCAGCGGCGTGCACACCTTCCCTGCTGTCCTCCAATCCTCTGGACTCTACTC

CCTCTCCTCCGTGGTGACAGTGCCCTCCAGCAGCCTGGGCACTAAGACCTACACCTGCAACGTCGATCACAAGCCCAGCAACACCA

AGGTGGACAAGAGAGTTGAGTCCAAATATGGACCCCCATGCCCACCTTGCCCAGCACCTGAGTTCCTGGGGGGACCATCAGTCTTC

CTGTTCCCCCCAAAACCCAAGGACACTCTCATGATCTCCCGGACCCCTGAGGTCACTTGCGTGGTGGTGGACGTGAGCCAGGAAGA

CCCCGAGGTCCAGTTCAACTGGTATGTGGATGGCGTGGAGGTTCATAATGCCAAGACAAAGCCTCGGGAGGAGCAGTTCAACAGCA

CCTACCGGGTGGTCAGCGTCCTCACCGTCCTGCACCAAGACTGGCTGAACGGCAAGGAGTACAAGTGCAAGGTCTCCAACAAAGGG

CTCCCATCCTCCATCGAGAAAACCATCTCCAAAGCCAAAGGGCAGCCCCGGGAGCCACAGGTGTACACCCTGCCCCCATCCCAAGA

GGAGATGACCAAGAACCAAGTGTCCCTGACCTGCCTGGTCAAAGGCTTCTACCCCAGCGACATCGCCGTGGAGTGGGAGAGCAATG

GGCAGCCTGAGAACAACTACAAGACCACTCCTCCCGTGCTGGACTCCGACGGCTCCTTCTTCCTCTACTCCCGGCTCACCGTGGAC

AAGAGCAGGTGGCAGGAGGGCAATGTCTTCTCCTGCTCCGTGATGCATGAGGCTCTGCACAACCACTACACACAGAAGAGCCTCTC

CCTGTCTCTGGGCAAATGA

What is claimed is:

1. An isolated antibody that specifically binds the extracellular domain of TIGIT, which comprises:
   (a) a heavy chain CDR1 comprising GSSLSSSYMS (SEQ II) NO:7), a heavy chain CDR2 comprising IIGSNGNTYYANWAKG (SEQ ID NO:8), and a heavy chain CDR3 comprising GGYRTSGMDP (SEQ ID NO:9), and a light chain CDR1 comprising QASQSISSYLNW (SEQ ID NO:10), a light chain CDR2 comprising DALKLAS (SEQ ID NO:11), and a light chain CDR3 comprising QQEHSVGNVDN (SEQ ID NO:12);
   (b) a heavy chain CDR1 comprising GFSLSSSYMS (SEQ ID NO:13), a heavy chain CDR2 comprising IIGSNGNTYYANWAKG (SEQ ID NO:8), and a heavy chain CDR3 comprising GGYRTSGMDP (SEQ NO:9); and a light chain CDR1 comprising QASQNIYSDLAW (SEQ ID NO:81), a light chain CDR2 comprising RASTLAS (SEQ ID NO:15), and a light chain CDR3 comprising QQEHLVAWIYN (SEQ ID NO:16); or
   (c) a heavy chain CDR1 comprising TSDYAWN (SEQ ID NO:57), a heavy chain CDR2 comprising YISYSGSTSYNPSLRS (SEQ ID NO:58), and a heavy chain CDR3 comprising ARRQVGLGFAY (SEQ ID NO:59), and a light chain CDR1 comprising KASQDVSTAVA (SEQ ID NO:60), a light chain CDR2 comprising SASYRYT (SEQ ID NO:61), and a light chain CDR3 comprising QQHYSTP (SEQ ID NO:62).

2. The antibody of claim 1, which comprises:
   (a) a heavy chain variable region having at least 90% sequence identity to SEQ ID NO:17 and a light chain variable region having at least 90% sequence identity to SEQ ID NO:18;
   (b) a heavy chain variable region having at least 90% sequence identity to SEQ ID NO:19 and a light chain variable region having at least 90% sequence identity to SEQ ID NO:20;
   (c) a heavy chain variable region having at least 90% sequence identity to SEQ ID NO:32 and a light chain variable region having at least 90% sequence identity to SEQ ID NO:20;
   (d) a heavy chain variable region having at least 95% sequence identity to SEQ ID NO:63 and a light chain variable region having at least 95% sequence identity to SEQ ID NO:64; or
   (e) a heavy chain variable region having at least 95% sequence identity to SEQ ID NO:67 and a light chain variable region having at least 95% sequence identity to SEQ ID NO:68.

3. The antibody of claim 1, which is a monoclonal antibody, a humanized antibody, a chimeric antibody, a bispecific antibody, an IgG1 antibody, an IgG2 antibody, an IgG4 antibody, or an antibody fragment comprising an antigen binding site.

4. The antibody of claim 1, which comprises:
   (a) a heavy chain amino acid sequence of SEQ ID NO:26 and a light chain amino acid sequence of SEQ ID NO:28;
   (b) a heavy chain amino acid sequence of SEQ ID NO:27 and a light chain amino acid sequence of SEQ ID NO:28;
   (c) a heavy chain amino acid sequence of SEQ ID NO:29 and a light chain amino acid sequence of SEQ ID NO:30;
   (d) a heavy chain amino acid sequence of SEQ ID NO:34 and a light chain amino acid sequence of SEQ ID NO:30;
   (e) a heavy chain amino acid sequence of SEQ ID NO:56 and a light chain amino acid sequence of SEQ ID NO:30; or
   (f) a heavy chain amino acid sequence of SEQ ID NO:70 and a light chain amino acid sequence of SEQ ID NO:72.

5. The antibody of claim 1, which:
   (a) inhibits binding of TIGIT to poliovirus receptor (PVR);
   (b) inhibits or blocks the interaction between TIGIT and PVR;
   (c) inhibits TIGIT signaling;
   (d) inhibits TIGIT activation;
   (e) inhibits phosphorylation of TIGIT; and/or
   (f) decreases cell surface expression of TIGIT.

6. The antibody of claim 1, which induces and/or enhances an immune response.

7. The antibody of claim 6, wherein the immune response is directed to a tumor or tumor cell.

8. The antibody of claim 1, which:
   (a) increases cell-mediated immunity;
   (b) increases T-cell activity;
   (c) increases cytolytic (CTL) activity;
   (d) increases natural killer (NK) cell activity;
   (e) increases IL-2 production and/or the number of IL-2-producing cells;
   (f) increases IFN-gamma production and/or the number of IFN-gamma-producing cells;
   (g) increases a Th1-type immune response;
   (h) decreases IL-4 production and/or the number of IL-4-producing cells;
   (i) decreases IL-10 production and/or the number of IL-10-producing cells;
   (j) decreases a Th2-type immune response;
   (k) inhibits and/or decreases the suppressive activity of regulatory T-cells (Tregs); and/or
   (l) inhibits and/or decreases the suppressive activity of myeloid-derived suppressor cells (MDSCs).

9. A heterodimeric agent comprising an antibody of claim 1.

10. A bispecific agent comprising:
   a) a first arm that specifically binds TIGIT, and
   b) a second arm,
   wherein the first arm comprises an antibody of claim 1.

11. A pharmaceutical composition comprising an antibody of claim 1 and a pharmaceutically acceptable carrier.

12. An antibody comprising:
   (a) the heavy chain variable region encoded by the plasmid deposited with ATCC as PTA-122180 and the light chain variable region encoded by the plasmid deposited with ATCC as PTA-122181; or
   (b) the heavy chain variable region encoded by the plasmid deposited with ATCC as PTA-122346 and the light chain variable region encoded by the plasmid deposited with ATCC as PTA-122347.

13. A cell comprising or producing an antibody of claim 1.

14. An isolated polynucleotide molecule comprising a polynucleotide that encodes an antibody of claim 1.

15. An isolated polynucleotide comprising a polynucleotide sequence selected from the group consisting of: SEQ ID NO:65, SEQ ID NO:66, SEQ ID NO:73, SEQ. ID NO:74, SEQ ID NO:75, SEQ ID NO:76, and SEQ ID NO:84.

16. A vector comprising the polynucleotide of claim 14.

17. A polypeptide comprising a sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:55, SEQ ID NO:56, SEQ ID NO:63, SEQ ID NO:67, SEQ ID NO:68, SEQ ID NO:69, SEQ ID NO:70, SEQ ID NO:71, SEQ ID NO:72, SEQ ID NO:82, and SEQ ID NO:83.

\* \* \* \* \*